United States Patent
Schaeffer et al.

(10) Patent No.: US 9,029,325 B2
(45) Date of Patent: *May 12, 2015

(54) AMYLIN ANALOGUES AND PHARMACEUTICAL COMPOSITIONS THEREOF

(71) Applicant: Novo Nordisk A/S, Bagsvaerd (DK)

(72) Inventors: Lauge Schaeffer, Lyngby (DK); Thomas Kruse, Herlev (DK); Henning Thoegersen, Farum (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

This patent is subject to a terminal disclaimer.

(21) Appl. No.: 14/038,265

(22) Filed: Sep. 26, 2013

(65) Prior Publication Data

US 2014/0018286 A1 Jan. 16, 2014

Related U.S. Application Data

(63) Continuation of application No. 13/491,880, filed on Jun. 8, 2012, now Pat. No. 8,575,090.

(60) Provisional application No. 61/496,113, filed on Jun. 13, 2011.

(30) Foreign Application Priority Data

Jun. 10, 2011 (EP) .................................... 11169405

(51) Int. Cl.
| | | |
|---|---|---|
| *A61K 38/22* | (2006.01) | |
| *A61P 1/00* | (2006.01) | |
| *A61P 1/04* | (2006.01) | |
| *A61P 19/10* | (2006.01) | |
| *A61P 25/00* | (2006.01) | |
| *A61P 25/28* | (2006.01) | |
| *A61P 3/00* | (2006.01) | |
| *A61P 3/04* | (2006.01) | |
| *A61P 3/06* | (2006.01) | |
| *A61P 3/08* | (2006.01) | |
| *A61P 3/10* | (2006.01) | |
| *C07K 14/575* | (2006.01) | |
| *A61K 47/48* | (2006.01) | |
| *A61K 45/06* | (2006.01) | |
| *A61K 38/00* | (2006.01) | |

(52) U.S. Cl.
CPC ..... *C07K 14/57527* (2013.01); *A61K 47/48038* (2013.01); *C07K 14/575* (2013.01); *A61K 47/48284* (2013.01); *A61K 38/00* (2013.01); *A61K 45/06* (2013.01); *A61K 38/225* (2013.01); *Y10S 514/909* (2013.01)

(58) Field of Classification Search
CPC ............. A61P 1/00; A61P 1/04; A61P 19/10; A61P 25/00; A61P 25/28; A61P 3/00; A61P 3/04; A61P 3/08; A61P 3/10; A61P 3/14; A61P 9/00; A61P 9/10; A61K 38/22; A61K 38/00; C07K 14/575

See application file for complete search history.

(56) References Cited

U.S. PATENT DOCUMENTS

| | | | |
|---|---|---|---|
| 8,575,090 B2 * | 11/2013 | Schaeffer et al. | ............... 514/1.9 |
| 8,741,836 B2 | 6/2014 | Schaeffer et al. | |
| 2001/0043934 A1 | 11/2001 | L'Italien et al. | |

FOREIGN PATENT DOCUMENTS

| | | | |
|---|---|---|---|
| EP | 2036923 A1 | | 3/2009 |
| WO | WO 9940928 A1 | * | 8/1999 |
| WO | 2007/104789 A2 | | 9/2007 |
| WO | 2009/034119 A1 | | 3/2009 |
| WO | 2009/156473 A1 | | 12/2009 |
| WO | 2010/046357 A1 | | 4/2010 |
| WO | 2011/064282 A1 | | 6/2011 |

OTHER PUBLICATIONS

Demond W. et al. Orthogonal HPLC Methods for Quantitating Related Substances and Degradation Products of Pramlinride. APPS PharmSciTech. 2000. vol. 1(1), Article 6 p. E6, XP002592241, ISSN:1530-9932, 50-59.

Hekman C M et al. Isolation and identification of cyclic imide and deamidation products in heat stressed pramlintide injection drug product. Journal of Pharmaceutical and Biomedical Analysis. 1999. vol. 20(5) pp. 763-772.

Kajava A et al. The Parallel Superpleated Beta-structure as a model for Amyloid Fibrils of Human Amylin. Journal of Molevular Biology. 2005. vol. 348. pp. 247-252.

Meng F et al. Biochemistry. "Rifampicin Does Not Prevent Amloid Fibril Formation by Human Islet Amyloid Polypeptide But does Inhibit Fibril Thiofavint Interactions: Implications for Mechanistic Studies of B Cell Death" 2008. vol. 47(22). pp. 6016-6024.

* cited by examiner

*Primary Examiner* — Julie Ha
*Assistant Examiner* — Kristina M Hellman
(74) *Attorney, Agent, or Firm* — Jianjie Hu

(57) ABSTRACT

The invention relates to polypeptides comprising an amino acid sequence which is an analogue of pramlintide, pharmaceutical compositions comprising these polypeptides, and these polypeptides for use as medicaments.

11 Claims, 1 Drawing Sheet

Figure 1:

α-nitrogen and γ-carboxy group form the amide bonds
to the two neighboring residues

AMYLIN ANALOGUES AND PHARMACEUTICAL COMPOSITIONS THEREOF

CROSS-REFERENCE TO RELATED APPLICATIONS

This application is a continuation of U.S. application Ser. No. 13/491,880, filed Jun. 8, 2012, which claimed priority of European Patent Application 11169405.5, filed Jun. 10, 2011; this application also claims priority under 35 U.S.C. §119(e) of U.S. Provisional application 61/496,113, filed Jun. 13, 2011; the contents of all above-named applications are incorporated herein by reference.

FIELD OF THE INVENTION

The invention relates to polypeptides comprising an amino acid sequence which is an analogue of SEQ ID No: 2 (pramlintide), pharmaceutical compositions comprising these polypeptides, and these polypeptides for use as medicaments.

BACKGROUND OF THE INVENTION

A large and growing number of people suffer from diabetes mellitus and obesity. Diabetes mellitus is a metabolic disorder in which the ability to utilize glucose is partly or completely lost.

A number of treatment regimes target excessive blood glucose whereas others are focused primarily on weight reduction. The most efficient anti-diabetic agent used to lower blood glucose is insulin and analogue(s) thereof. It has been known for a long time that when traditional insulin is used to treat diabetes, it is associated with an increase in body weight. Insulin has to be injected subcutaneously up to several times per day.

Type 2 diabetes is generally treated in the early phases with diet and exercise. As the condition progresses, various oral anti-diabetic agents are added. Injected agents such as GLP-1 analogues may also be used at this stage. In general, these agents are most efficient in patients with functioning beta-cells capable of releasing insulin and amylin.

Human amylin (SEQ ID No: 1) is a 37 amino acid long polypeptide which has physico-chemical properties that make its use as a drug troublesome. In particular, it has a tendency for fibrillogenesis, i.e. the formation of fibrils, in vitro and/or ex vivo and becomes ineffective due to precipitation. Additionally amylin is difficult to formulate as it is chemically unstable and it precipitates at physiologic pH. Therefore it is formulated in acidic solution.

Human amylin binds to two distinct receptor complexes. These two complexes contain the calcitonin receptor plus a receptor activity-modifying proteins, RAMP1 or RAMP3. From the close relationship between the calcitonin receptor and the amylin receptor some cross-reactivity to the calcitonin receptor may be expected of amylin receptor agonist. As an example pramlintide has some affinity to the calcitonin receptor but is 14 times more potent on the amylin receptor.

The calcitonin receptor is found in many tissues throughout the body and it is believed to be involved in regulation of bone metabolism. Salmon calcitonin is currently sold under the tradename Miacalcic®. The product is used against hypercalcaemia, osteoporosis (including post-menopausal osteoporosis and glucocorticoid-related osteoporosis), ostitis derformans (Pagets disease) and is administered once daily either by injection or nasally. The calcitonin is bound to specific receptors in the membrane of the skeleton, the kidneys and in the central nervous system (CNS). The plasma half-life for salmon calcitonin is about 45 minutes.

Polypeptides with activity at the calcitonin receptor could be useful in the treatment of hypercalcaemia, osteoporosis, Pagets disease, obesity or obesity related diseases as well as in the prevention of obesity related diseases. A drawback of the treatment with currently used calcitonin preparations are that, due to the short plasma half-life for salmon calcitonin, the drug has to be administered several times a day and has to be administered immediately before a meal.

Polypeptides with dual activity at both the calcitonin receptor and the amylin receptor may be advantageous.

Pramlintide (SEQ ID No: 2) is a drug product marketed by Amylin Pharmaceuticals as Symlin® for the treatment of diabetes as an add-on to insulin. Pramlintide is an amylin receptor agonist. It is approximately 14 times less active on the calcitonin receptor.

The chemical structure of pramlintide is presented below and also in FIG. 1.

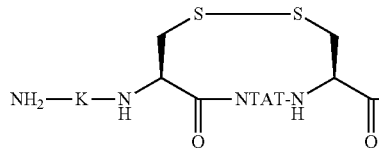
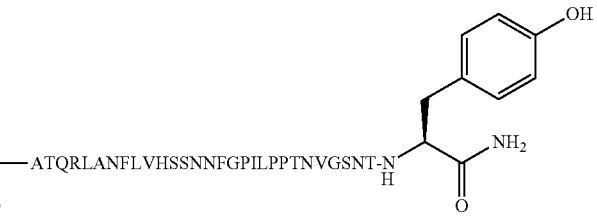

Pramlintide is chemically unstable at neutral pH and it is therefore provided in an acidic solution. Compared to human amylin, the amino acids in position 25, 28 and 29 in pramlintide are substituted with proline. This modification reduces the tendency of the protein for fibrillogenesis. Pramlintide has a very short plasma half-life and therefore has to be injected two to three times daily WO2010046357 and WO2009034119 disclose polypeptides comprising amylin analogues having an albumin binding residue (called amylin derivatives therein). Even though these polypeptides with albumin binding moieties show improved pharmacokinetic (PK) or pharmacodynamic (PD) properties compared to pramlintide, they may still show poor physical stability under certain conditions.

SUMMARY OF THE INVENTION

It has been surprisingly found that polypeptides comprising an amino acid which is an analogue of SEQ ID No: 2 (pramlintide) comprising an amino acid residue at position 37 which is proline can demonstrate increased solubility and/or physical stability.

At least in some embodiments the polypeptides of the present invention have an increased solubility.

At least in some embodiments the polypeptides of the present invention have an increased physical stability.

At least in some embodiments the polypeptides of the present invention have an increased solubility and physical stability.

At least in some embodiments the polypeptides of the present invention display an advantageous pharmacokinetic profile and/or advantageous pharmacological profile. An example of an advantageous pharmacokinetic profile is a long acting profile.

In one broad aspect, the present invention relates to a polypeptide comprising an amino acid sequence which is an analogue of SEQ ID No: 2 wherein said analogue comprises a proline residue at position 37, wherein the amino acid sequence numbering of the analogue corresponds to the amino acid numbering sequence of SEQ ID No: 2. Optionally, the polypeptide has an $EC_{50}$ in a human amylin receptor potency assay, such as that disclosed herein, of about 1800 pM or less. Optionally, the polypeptide has an $EC_{50}$ in a human calcitonin receptor potency assay, such as that disclosed herein, of about 1800 pM or less. Optionally, the polypeptide has a solubility at pH4 of about 100 μM or more in a solubility assay, such as that disclosed herein. Optionally, the polypeptide has a solubility at pH7 of about 100 μM or more in a solubility assay, such as that disclosed herein. Optionally, the polypeptide has a physical stability of about 25 hours or greater in a fibrillogenesis assay (also called a fibrillation assay), such as that disclosed herein. Optionally the polypeptide has at least one substituent attached to at least one of its amino acid residues. The present invention also relates to pharmaceutical formulations comprising same. The present invention also relates to pharmaceutical uses of same. The present invention also relates to the delivery (such as administration) of same to patients in need of treatment of same.

In another broad aspect, the present invention relates to a polypeptide comprising an amino acid sequence which is an analogue of SEQ ID No: 2 wherein said analogue comprises a proline residue at position 37 and a glutamic acid residue at position 14, wherein the amino acid sequence numbering of the analogue corresponds to the amino acid numbering sequence of SEQ ID No: 2. Optionally, the polypeptide has an $EC_{50}$ in a human amylin receptor potency assay (such as that disclosed herein) of about 1800 pM or less. Optionally, the polypeptide has an $EC_{50}$ in a human calcitonin receptor potency assay, such as that disclosed herein, of about 1800 pM or less. Optionally, the polypeptide has a solubility at pH4 of about 100 μM or more in a solubility assay, such as that disclosed herein. Optionally, the polypeptide has a solubility at pH7 of about 100 μM or more in a solubility assay, such as that disclosed herein. Optionally, the polypeptide has a physical stability of about 25 hours or greater in fibrillogenesis assay (also called a fibrillation assay), such as that disclosed herein. Optionally the polypeptide has at least one substituent attached to at least one of its amino acid residues. The present invention also relates to pharmaceutical formulations comprising same. The present invention also relates to pharmaceutical uses of same. The present invention also relates to the delivery (such as administration) of same to patients in need of treatment of same.

In another broad aspect, the present invention relates to a polypeptide comprising an amino acid sequence which is an analogue of SEQ ID No: 2 wherein said analogue comprises a proline residue at position 37, and a histidine or arginine residue at position 17 and a glutamic acid residue at position 14, wherein the amino acid sequence numbering of the analogue corresponds to the amino acid numbering sequence of SEQ ID No: 2. Optionally, the polypeptide has an $EC_{50}$ in a human amylin receptor potency assay (such as that disclosed herein) of about 1800 μM or less. Optionally, the polypeptide has an $EC_{50}$ in a human calcitonin receptor potency assay, such as that disclosed herein, of about 1800 pM or less. Optionally, the polypeptide has a solubility at pH4 of about 100 μM or more in a solubility assay, such as that disclosed herein. Optionally, the polypeptide has a solubility at pH7 of about 100 μM or more in a solubility assay, such as that disclosed herein. Optionally, the polypeptide has a physical stability of about 25 hours or greater in fibrillogenesis assay (also called a fibrillation assay), such as that disclosed herein. Optionally the polypeptide has at least one substituent attached to at least one of its amino acid residues. The present invention also relates to pharmaceutical formulations comprising same. The present invention also relates to pharmaceutical uses of same. The present invention also relates to the delivery (such as administration) of same to patients in need of treatment of same.

In another broad aspect, the present invention relates to a polypeptide comprising an amino acid sequence which is an analogue of SEQ ID No: 2 of Formula (I):

Formula (I)                                                                                                    (SEQ ID No: 3)

$Xaa_1$-Cys-$Xaa_3$-Thr-Ala-Thr-Cys-Ala-Thr-Gln-Arg-Leu-Ala-$Xaa_{14}$-Phe-Leu-$Xaa_{17}$-$Xaa_{18}$-Ser-Ser-$Xaa_{21}$-$Xaa_{22}$-Phe-Gly-Pro-$Xaa_{26}$-Leu-Pro-Pro-Thr-$Xaa_{31}$-Val-Gly-Ser-$Xaa_{35}$-Thr-Pro;

wherein $Xaa_1$ is deleted or independently selected from Ala, Cys, Glu, Gly, His, Arg, Ser and Lys;

$Xaa_3$ is independently selected from Gly, His, Arg, Ser and Asn;

$Xaa_{14}$ is independently selected from Glu and Asn;

$Xaa_{17}$ is independently selected from His, Arg, Lys and Val;

$Xaa_{18}$ is independently selected from Arg, Lys and His;

$Xaa_{21}$ is independently selected from Ala, Lys, Gln, Ser and Asn;

$Xaa_{22}$ is independently selected from Glu, Gln, Ser, Thr and Asn;

$Xaa_{26}$ is independently selected from Pro, Arg and Ile;

$Xaa_{31}$ is independently selected from Ser, Glu, Asp and Asn;

$Xaa_{35}$ is independently selected from His, Arg, Lys, Asp, Gln and Glu;

and where the C-terminal may optionally be derivatized;

optionally, the polypeptide has an $EC_{50}$ in a human amylin receptor potency assay, such as that disclosed herein, of about 1800 pM or less;

optionally, the polypeptide has an $EC_{50}$ in a human calcitonin receptor potency assay, such as that disclosed herein, of about 1800 pM or less.

optionally, the polypeptide has a solubility at pH4 of about 100 μM or more in a solubility assay, such as that disclosed herein;

optionally, the polypeptide has a solubility at pH7 of about 100 μM or more in a solubility assay, such as that disclosed herein;

optionally, the polypeptide has a physical stability of about 25 hours or greater in fibrillogenesis assay (also called a fibrillation assay), such as that disclosed herein; optionally the polypeptide has at least one substituent attached to at least one of its amino acid residues.

The present invention also relates to pharmaceutical formulations comprising same. The present invention also relates to pharmaceutical uses of same. The present invention also relates to the delivery (such as administration) of same to patients in need of treatment of same.

In another aspect, the invention further comprises a pharmaceutical composition comprising the above polypeptide.

In another aspect, the invention further comprises a process for preparing a pharmaceutical composition comprising the above polypeptide.

In another aspect, the invention further comprises the above polypeptide for use as a medicament.

The polypeptides of the present invention are advantageous as they possess improved solubility and/or physical stability.

Suitable assays used to determine the potency at amylin and calcitonin receptors, as well as to determine solubility and physical stability of the polypeptides, are described herein. For example, see Assay (II), (IV) and (III) respectively.

BRIEF DESCRIPTIONS OF THE DRAWINGS

FIG. 1 presents a structure of pramlintide.

Figure 2:
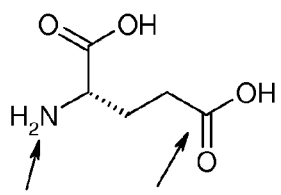

FIG. 2 presents a structure of gammaGlu.

Figure 3:
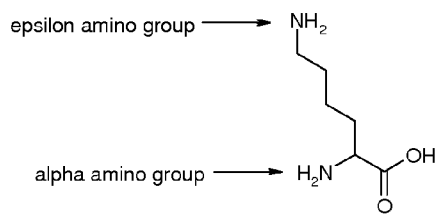

FIG. 3 presents a structure of epsilon amino group and alpha amino group.

Figure 4:

FIG. 4 presents a structure of human amylin.

DEFINITIONS

The term "human amylin" as used herein relates to the polypeptide human amylin having the sequence as depicted in SEQ ID No 1. The term includes, but is not limited to, a human polypeptide hormone of 37 amino acids referred to as amylin, which in nature is co-secreted with insulin from n-cells of the pancreas. Human amylin has the following primary amino acid sequence:

```
                                                          (SEQ ID NO: 1)
Lys-Cys-Asn-Thr-Ala-Thr-Cys-Ala-Thr-Gln-Arg-Leu-Ala-Asn-Phe-Leu-Val-His-Ser-Ser-Asn-

Asn-Phe-Gly-Ala-Ile-Leu-Ser-Ser-Thr-Asn-Val-Gly-Ser-Asn-Thr-Tyr
```

Human amylin has a disulfide bridge between the two Cys residues and a C-terminal amide group. This structure is shown below and also in FIG. 4.

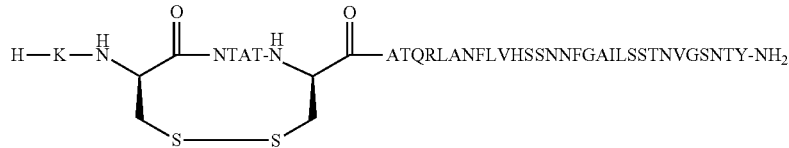

Herein, SEQ ID No: 1 and human amylin may be used interchangeably.

The term "pramlintide" as used herein relates to the synthetic polypeptide having the sequence as depicted in SEQ ID No 2. Pramlintide has the following primary amino acid sequence:

```
                                                          (SEQ ID NO: 2)
Lys-Cys-Asn-Thr-Ala-Thr-Cys-Ala-Thr-Gln-Arg-Leu-Ala-Asn-Phe-Leu-Val-His-Ser-Ser-Asn-

Asn-Phe-Gly-Pro-Ile-Leu-Pro-Pro-Thr-Asn-Val-Gly-Ser-Asn-Thr-Tyr
```

Pramlintide has a disulfide bridge between the two Cys residues and a C-terminal amide group. This structure is shown below and also in FIG. 1.

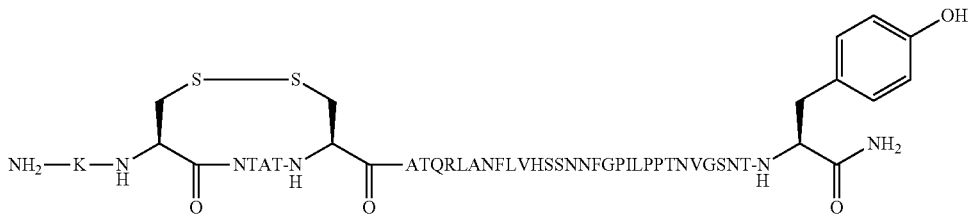

Herein, SEQ ID No: 2 and pramlintide may be used interchangeably.

The term "calcitonin" means salmon calcitonin or human calcitonin.

The term "salmon calcitonin" or "sCT" means the native protein sequence of salmon calcitonin as disclosed in Niall et al (1969), *Biochemistry vol* 64, FIG. 2. Salmon calcitonin is a polypeptide which consists of 32 amino acids. It has a disulphide bridge between the first and seventh amino acids at the amino-terminal end of the polypeptide chain, the disulfide bridge being essential for its biological activity, and a prolinamide group at the carboxyl terminal amino acid.

The term "human calcitonin" means the native protein sequence of human calcitonin as disclosed in Niall et al (1969), *Biochemistry vol* 64, FIG. 2. Human calcitonin is a polypeptide which consists of 32 amino acids. It has a disulphide bridge between the first and seventh amino acids at the amino-terminal end of the polypeptide chain, the disulfide bridge being essential for its biological activity, and a prolinamide group at the carboxyl terminal amino acid.

The term "analogue of amylin" or "amylin analogue" as used herein refers to a variant of SEQ ID No: 1.

The term "analogue of pramlintide" or "pramlintide analogue" as used herein refers to a variant of SEQ ID No: 2.

For instance, said variants include, but are not limited to, one or more substitution and/or one or more deletion and/or one or more addition of any one of the amino acid residues for any natural or unnatural amino acid, synthetic amino acids or peptidomimetics and/or the attachment of a substituent to any one of the natural or unnatural amino acids, synthetic amino acids or peptidomimetics at any available position.

The variant may have the same number of amino acid residues as pramlintide (i.e. 37). Alternatively, the variant may comprise less amino acid residues than pramlintide. Alternatively, the variant may comprise more amino acid residues than pramlintide. In some embodiments, the variant has the same number of amino acid residues as pramlintide (i.e. 37). In some embodiments, the variant includes substitutions of any one of the amino acid residues for any natural or unnatural amino acid, synthetic amino acids or peptidomimetics and/or the attachment of a substituent to any one of the natural or unnatural amino acids, synthetic amino acids or peptidomimetics at any available position.

The polypeptide may comprise one or more amino acid substitutions. Hence, for some embodiments, the number of amino acid substitutions in the amylin analogue may be at least one. Preferably, the number of amino substitutions is between one and fifteen, more preferably between one and twelve, more preferably between one and ten, more preferably between one and five, more preferably between one and three.

The number of amino acid insertions, additions, deletions, or substitutions may be at least 1, but up to 2, 3, 4, 5, 6, 7, 8, 9 or 10 amino acid insertions, additions, deletions, or substitutions may be present. The substitution or addition can be with any natural or unnatural amino acid, synthetic amino acids, peptidomimetics, or other chemical compounds. The addition or deletion of amino acid residues can take place at the N-terminal of the peptide and/or at the C-terminal of the peptide.

When used herein the term "natural amino acid" is an amino acid (with the usual three letter codes & one letter codes in parenthesis) selected from the group consisting of: Glycine (Gly & G), proline (Pro & P), alanine (Ala & A), valine (Val & V), leucine (Leu & L), isoleucine (Ile & I), methionine (Met & M), cysteine (Cys & C), phenylalanine (Phe & F), tyrosine (Tyr & Y), tryptophan (Trp & W), histidine (His & H), lysine (Lys & K), arginine (Arg & R), glutamine (Gln & Q), asparagine (Asn & N), glutamic acid (Glu & E), aspartic acid (Asp & D), serine (Ser & S) and threonine (Thr & T). If, due to typing errors, there are deviations from the commonly used codes, the commonly used codes apply. The amino acids present in the polypeptides of the present invention are, preferably, amino acids which can be coded for by a nucleic acid.

If the analogue contains either more than 37 amino acid residues or less than 37 amino acid residues then the skilled person can still align that sequence with the sequence of pramlintide (SEQ ID No. 2) to determine the placement number of the corresponding, respective amino acid residue. A suitable alignment program is "needle", which is a Needleman-Wunsch alignment. The alogorithm for this alignment program is described in Needleman, S. B. and Wunsch, C. D., (1970), Journal of Molecular Biology, 48: 443-453.

In the numbering sequence of SEQ ID No: 2, and according to established practice in the art, the amino acid residue at the N-terminal (Lys) is assigned no. 1 and subsequent amino acid residues are numbered consecutively, ending at the C-terminal with tyrosine assigned no. 37. Therefore, generally, any reference herein to position number of an amino acid residue provides its location in a 37 amino acid sequence; said 37 amino acid sequence being an analogue of pramlintide. For example, a reference to an analogue modified at position 14 may refer to an analogue wherein the 14th amino residue out of the 37 amino acids in the analogue has been modified.

In other words, the amino acid sequence numbering of the analogue provides the position of each analogue with respect to a 37 amino acid sequence, wherein the numbering is consecutive and ascending in the direction from the N-terminal to the C-terminal.

Analogues may be described by reference to the number of the amino acid residue in pramlintide or human amylin which is modified, i.e. by its position, and the nature of the modification. The following are non-limiting examples of appropriate analogue nomenclature.

For example:

[Pro37]-pramlintide designates an analogue of SEQ ID No: 2 (pramlintide) wherein the change from pramlintide is the substitution of Tyr at position 37 with Pro.

[Glu14,Arg17,Pro37]-pramlintide designates an analogue of SEQ ID No: 2 (pramlintide), in which the Asn at position 14 has been substituted with Glu, the Val at position 17 has been substituted with Arg, and the Tyr at position 37 has been substituted with Pro.

As a still further example, des1 (or Des$^1$) in relation to an analogue of pramlintide refers to an analogue in which the N-terminal amino acid, Lysine, has been deleted. An analogue of pramlintide, where the N-terminal amino acid has been deleted may also be designated des 1 pramlintide.

[Pro25, Pro28, Pro29]-human amylin designates an analogue of SEQ ID No: 1 (human amylin) wherein the modifications from human amylin are that the Ala at position 25 and the Cys at positions 28 and 29 have all been substituted with Pro. This polypeptide is pramlintide. Accordingly, it will be understood that pramlintide is an analogue of human amylin. Thus, 'analogues of pramlintide' and 'analogues of amylin' may be used interchangeably.

As is apparent from the above examples, amino acid residues may be identified by their full name, their one-letter code, and/or their three-letter code. These three ways are fully equivalent.

The expressions "conforms to", "corresponds to", "a position equivalent to" or "corresponding position" as used herein may be used to characterise the site of modification in an analogue of pramlintide by reference to SEQ ID No: 2. Equivalent or corresponding positions are easily deduced, e.g. by simple handwriting and eyeballing; and/or a standard protein or polypeptide alignment program may be used, such as "needle" which is a Needleman-Wunsch alignment. The algorithm is described in Needleman, S. B. and Wunsch, C. D., (1970), Journal of Molecular Biology, 48: 443-453, and the align program by Myers and W. Miller in "Optimal Alignments in Linear Space" CABIOS (computer applications in the biosciences) (1988) 4:11-17. For the alignment, the default scoring matrix BLOSUM62 and the default identity matrix may be used, and the penalty for the first residue in a gap may be set at −10 and the penalties for additional residues in a gap at −0.5.

The polypeptide may comprise one or more substituents on one or more of the amino acid residues. Such polypeptides may also be called pramlintide derivatives or amylin derivatives.

The term "substituent" as used herein means any suitable moiety bonded, in particular covalently bonded, to an amino acid residue, in particular to any available position on an amino acid residue. Typically, the suitable moiety is a chemical moiety.

For some embodiments, the substituent comprises a linker.

For some embodiments, the polypeptide has a substituent on one amino acid residue, which amino acid residue is either the amino acid residue in the N-terminal residue or the amino acid residue is a Lysine.

For some embodiments, the polypeptide has a substituent on the N-terminal amino acid residue bound via the α(alpha)-amino group of the N-terminal amino acid residue.

For some embodiments, the N-terminal amino acid residue is Lysine and the polypeptide has a substituent on the N-terminal amino acid residue bound via the ε(epsilon)-amino group of the lysine amino residue.

For some embodiments, the polypeptide is extended by addition of a Lysine residue at the N-terminal and the polypeptide has a substituent on the N-terminal amino acid residue bound via the ε-amino group of the lysine amino residue.

For some embodiments, the polypeptide is extended by addition of an amino acid residue at the N-terminal and the polypeptide has a substituent on the N-terminal amino acid residue bound via the ε-amino group of the N-terminal amino acid residue.

As used herein, the term "hydrocarbyl" refers to a group comprising at least carbon and hydrogen that may optionally comprise one or more other suitable substituents. Examples of such substituents may include hydroxy, alkyl, halo, alkoxy, haloalkyl, haloalkoxy, amino, aminoalkyl or a cyclic group. In addition to the possibility of the substituents being a cyclic group, a combination of substituents may form a cyclic group. If the hydrocarbyl group comprises more than one carbon atom then those carbon atoms need not necessarily be linked to each other. For example, at least two of the carbon atoms may be linked via a suitable atom or group. Thus, the hydrocarbyl group may contain heteroatoms. Suitable heteroatoms will be apparent to those skilled in the art and include, for instance, sulphur, nitrogen, oxygen, phosphorus and silicon. In one embodiment the hydrocarbyl group is selected from the group consisting of an alkyl group, an alkenyl group, an alkynyl group, an aryl group, a heteroaryl group or a cycloalkyl group, each of which may be optionally substituted. Examples of such substituents may include hydroxy, alkyl, halo, alkoxy, haloalkyl, haloalkoxy, amino, aminoalkyl, or a cycloalkyl group.

As used herein, the term "alkyl" includes both saturated straight chain and branched alkyl groups which may be substituted (mono- or poly-) or unsubstituted. Preferably, the alkyl group is a $C_{1-20}$ alkyl group, more preferably a $C_{1-15}$, more preferably a $C_{1-10}$ alkyl group, more preferably a $C_{1-8}$ alkyl group, more preferably a $C_{1-6}$ alkyl group. Particularly preferred alkyl groups include, for example, methyl, ethyl, n-propyl, iso-propyl, n-butyl, sec-butyl, iso-butyl, tert-butyl, n-pentyl, n-hexyl, n-heptyl and n-octyl. Suitable substituents include, for example, hydroxy, alkyl, halo, alkoxy, haloalkyl, haloalkoxy, amino, aminoalkyl, or a cycloalkyl group.

As used herein, the term "cycloalkyl" refers to a cyclic alkyl group which may be substituted (mono- or poly-) or unsubstituted. Suitable substituents include, for example, hydroxy, alkyl, halo, alkoxy, haloalkyl, haloalkoxy, amino, aminoalkyl, or a cycloalkyl group.

As used herein, the term "alkenyl" refers to a carbon chain containing one or more carbon-carbon double bonds, which may be branched or unbranched, and substituted (mono- or poly-) or unsubstituted. Preferably the alkenyl group is a $C_{2-20}$ alkenyl group, more preferably a $C_{2-15}$ alkenyl group, more preferably a $C_{2-10}$ alkenyl group, more preferably a $C_{2-8}$ alkenyl group, or more preferably a $C_{2-6}$ alkenyl group. Suitable substituents include, for example, hydroxy, alkyl, halo, alkoxy, haloalkyl, haloalkoxy, amino, aminoalkyl, or a cycloalkyl group.

As used herein, the term "alkynyl" refers to a carbon chain containing one or more carbon-carbon triple bonds, which may be branched or unbranched, and substituted (mono- or poly-) or unsubstituted. Preferably the alkynyl group is a $C_{2-20}$ alkynyl group, more preferably a $C_{2-15}$ alkynyl group, more preferably a $C_{2-10}$ alkynyl group, more preferably a $C_{2-8}$ alkynyl group, or more preferably a $C_{2-6}$ alkynyl group. Suitable substituents include, for example, hydroxy, alkyl, halo, alkoxy, haloalkyl, haloalkoxy, amino, aminoalkyl, or a cycloalkyl group.

As used herein, the term "aryl" refers to a $C_{6-10}$ aromatic group which may be substituted (mono- or poly-) or unsubstituted. Typical examples include phenyl and naphthyl etc. Suitable substituents include, for example, hydroxy, alkyl, halo, alkoxy, haloalkyl, haloalkoxy, amino, aminoalkyl, or a cycloalkyl group.

As used herein, the term "heteroaryl" refers to an aryl group as defined above which contains one or more heteroatoms. Suitable heteroatoms will be apparent to those skilled in the art and include, for example, sulphur, nitrogen, oxygen, phosphorus and silicon. Suitable substituents include, for example, hydroxy, alkyl, halo, alkoxy, haloalkyl, haloalkoxy, amino, aminoalkyl, or a cycloalkyl group.

The term "linker" as used herein includes suitable substituents that can join a moiety, such as a chemical moiety, to the polypeptide, such as the polypeptide backbone. Thus, the linker and the chemical moiety become a substituent together. The moiety joined to the linker may be any suitable moiety. Examples include an albumin binding moiety.

In one embodiment the albumin binding moiety has from 6 to 40 carbon atoms, from 8 to 26 carbon atoms or from 14 to 22 carbon atoms for example 16, 17, 18, 19, 20 carbon atoms.

In another embodiment the albumin binding moiety is an acyl group selected from the group comprising $CH_3(CH_2)_rCO-$, wherein r is an integer from 4 to 38, preferably an integer from 4 to 24, more preferably selected from the group comprising $CH_3(CH_2)_6CO-$, $CH_3(CH_2)_8CO-$, $CH_3(CH_2)_{10}CO-$, $CH_3(CH_2)_{12}CO-$, $CH_3(CH_2)_{14}CO-$, $CH_3(CH_2)_{16}CO-$, $CH_3(CH_2)_{18}CO-$, $CH_3(CH_2)_{20}CO-$ and $CH_3(CH_2)_{22}CO-$.

In one embodiment the albumin binding moiety comprises a group which can be negatively charged at pH 7.4.

In one embodiment the albumin binding moiety comprises a carboxylic acid group, such as HOOC(CH₂)ₛCO—, wherein s is an integer from 12 to 22. Preferably s is 16 or 18.

In one embodiment the moiety joined to the linker is an albumin binding moiety.

For example, the linker can comprise one or two amino acids which at one end bind to the moiety—such as an albumin binding moiety—and at the other end bind to any available position on the polypeptide backbone.

In some embodiments, the linker provides a bridge or link between an amino group on the polypeptide backbone and an acyl group on the moiety such as an albumin binding moiety. The linker may be bound to, or near to, the N terminal amino acid residue. Preferably the linker is bound to the amino acid in position 1 of the pramlintide analogue.

Another example of a linker is a combination of at least one amino acid and an amine.

In an embodiment, preferably the amine is the group OEG, wherein the formula of OEG is shown below:

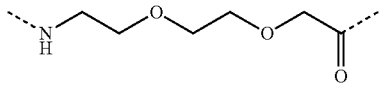

For some embodiments, preferably the linker is selected from the group consisting of γGlu, γGlu-γGlu, γGlu-γGlu-γGlu, γGlu-γGlu-γGlu-γGlu, Glu, Glu-Glu, Glu-γGlu, Glu-Arg, Glu-Glu-Arg, His, His-His, His-γGlu, His-His-γGlu, Gly, Gly-γGlu, Ser, Ser-γGlu, D-Arg-D-Arg, Arg, Arg-Arg, Arg-Arg-γGlu, Ser-Ser,-Gly-Ser-Ser, Ser-Ser,-Gly-Ser-Ser-γGlu, Ser-Ser-Gly-Ser-Ser-Gly and Ser-Ser-Gly-Ser-Ser-Gly-γGlu, γGlu-OEG, γGlu-2xOEG and OEG, preferably the linker is selected from γGlu, γGlu-γGlu, γGlu-OEG, γGlu-2xOEG and OEG, more preferably the linker is γGlu-γGlu.

The linker can contribute to and/or enhance the binding effect of the moiety (for example the albumin binding moiety), e.g. a linker comprising γGlu can enhance the albumin binding effect of the polypeptide.

By using the term "γGlu" or "gGlu" or gammaGlu or gamma-L-Glu is meant an amino acid with the following structure (also shown in FIG. 2):

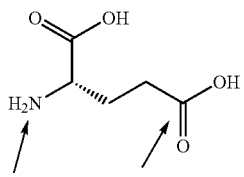

α-nitrogen and γ-carboxy group form the amide bonds to the two neighboring residues By using the term "γGlu-γGlu" is meant moiety with the following structure:

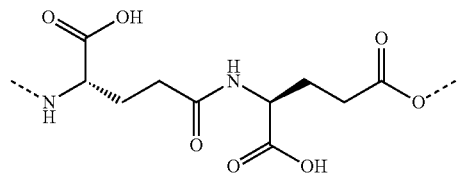

By using the term "γGlu-OEG" is meant a moiety with the following structure:

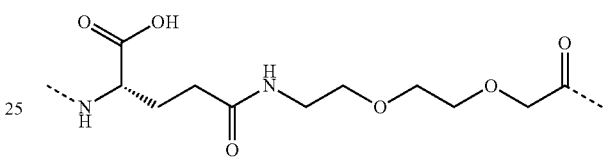

By using the term "γGlu-OEG-OEG" is meant moiety with the following structure:

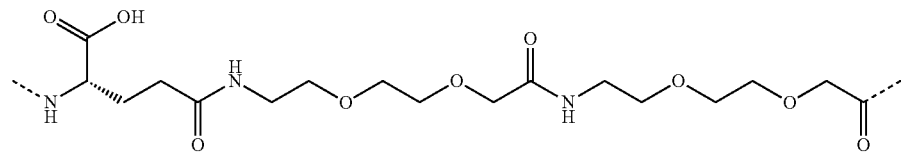

The term "epilson amino group" or "ε-amino group", used herein in relation to lysine, refers to the amino group at the 6 position, using the IUPAC standard numbering conventions. The term "alpha amino group" or "α-amino group" refers to the amino group at the 2 position, using the IUPAC standard numbering conventions. We refer to the following structure (also shown in FIG. 3).

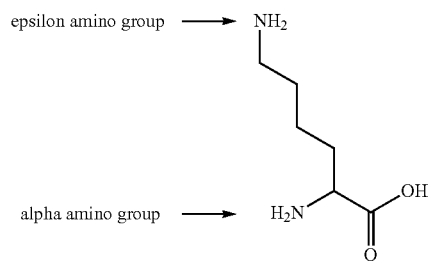

The term "albumin binding moiety" as used herein refers to any chemical group capable of binding to albumin, i.e. has albumin binding affinity. In one embodiment the albumin binding moiety is an acyl group.

In some embodiments, preferably the albumin binding moiety is an acyl group selected from:
(a) $CH_3(CH_2)_rCO—$, wherein r is an integer from 4 to 24;
(b) $HOOC(CH_2)_sCO—$, wherein s is an integer from 14 to 20, for example 16 or 18.

"Albumin binding affinity" may be determined by several methods known within the art. In one method the compound to be measured is radiolabeled with e.g. $^{125}I$ or $^3H$ and incubated with immobilized albumin (Kurtzhals et. al., Biochem. J., 312, 725-731 (1995)). The binding of the compound relative to a standard is calculated. In another method a related compound is radiolabeled and its binding to albumin immobilized on e.g. SPA beads is competed by a dilution series of the compound to be measured. The $EC_{50}$ value for the competition is a measure of the affinity of the compound. In a third method, the receptor affinity or potency of a compound is measured at different concentrations of albumin, and the shift in relative affinity or potency of the compound as a function of albumin concentration reflects its affinity for albumin.

The polypeptides of the present invention exhibit good potency. The term "potency" is used to describe the effect of a given compound in assays where a sigmoidal relationship between log concentration and the effect of a compound has been established. Furthermore, the response should be variable from 0 to 100%. EC(effective concentration)$_{50}$ can be used to describe the concentration of a given compound yielding a response of 50% in the assay, such as in the functional assay.

The polypeptides of the present invention exhibit good activity. The term "activity" refers to the ability to reduce appetite and/or increase satiety. The activity can be measured by the ability to reduce appetite as e.g. described in the Assay (I) herein.

The polypeptides of the present invention exhibit good physical stability. The term "physical stability" of a polypeptide according to the invention, or a formulation thereof refers to the tendency of the polypeptide not to form biologically inactive and/or insoluble aggregates as a result of exposure to thermo-mechanical stresses and/or interaction with interfaces and surfaces that are destabilizing, such as hydrophobic surfaces and interfaces. Physical stability of the aqueous polypeptide formulations may be evaluated by means of visual inspection, ThT fibrillation assay (sometimes referred to as a ThT fibrillogenesis assay) and/or turbidity measurements as described elsewhere herein. Visual inspection of the formulations is performed in a sharp focused light with a dark background. The turbidity of the formulation is characterized by a visual score ranking the degree of turbidity for instance on a scale from 0 to 3 (a formulation showing no turbidity corresponds to a visual score 0, and a formulation showing visual turbidity in daylight corresponds to visual score 3). A formulation is classified physical unstable with respect to protein aggregation, when it shows visual turbidity in daylight. Alternatively, the turbidity of the formulation can be evaluated by simple turbidity measurements well-known to the skilled person.

The polypeptides of the present invention exhibit good chemical stability. The term "chemical stability" of a polypeptide according to the invention or of a formulation thereof refers to no chemical covalent changes in the polypeptide structure hence avoiding the formation of chemical degradation products with potentially less potency and/or potentially increased immunogenic properties compared to the parent (native) polypeptide structure. Various chemical degradation products can be formed depending on the type and nature of the parent polypeptide and the environment to which the polypeptide is exposed. Elimination of chemical degradation can most probably not be completely avoided and increasing amounts of chemical degradation products is often seen during storage and use of the polypeptide formulations as well-known by the person skilled in the art. Most polypeptides are prone to deamidation, a process in which the side chain amide group in glutaminyl or asparaginyl residues is hydrolysed to form a free carboxylic acid. Other degradations pathways involves formation of high molecular weight transformation products where two or more polypeptide molecules are covalently bound to each other through transamidation and/or disulfide interactions leading to formation of covalently bound dimer, oligomer and polymer degradation products (*Stability of Protein Pharmaceuticals*, Ahern. T. J. & Manning M. C., Plenum Press, New York 1992). Oxidation (of for instance methionine residues) can be mentioned as another variant of chemical degradation. The chemical stability of the polypeptide formulation can be evaluated by measuring the amount of the chemical degradation products at various time-points after exposure to different environmental conditions (the formation of degradation products can often be accelerated by for instance increasing temperature). The amount of each individual degradation product is often determined by separation of the degradation products depending on molecule size and/or charge using various chromatography techniques (e.g. SEC-HPLC and/or RP-HPLC).

The term "stabilized formulation" refers to a formulation with increased physical stability, increased chemical stability or increased physical and chemical stability compared to an aqueous solution of the polypeptide.

DESCRIPTION OF THE INVENTION

General Aspects

In one aspect, the present invention relates to polypeptides comprising an amino acid sequence which is an analogue of SEQ ID No: 2 wherein:
said analogue comprises a proline residue at position 37;
wherein the amino acid sequence numbering of the analogue corresponds to the amino acid numbering sequence of SEQ ID No: 2; and
optionally the polypeptide has at least one substituent attached to at least one of its amino acid residues.

In another aspect, the present invention relates to polypeptides comprising an amino acid sequence which is an analogue of SEQ ID No: 2 wherein:
(a) said analogue comprises a proline residue at position 37;
wherein the amino acid sequence numbering of the analogue corresponds to the amino acid numbering sequence of SEQ ID No: 2; and
(b) said analogue has a solubility of about 100 µM or greater at pH4
optionally the polypeptide has at least one substituent attached to at least one of its amino acid residues.

In another aspect, the present invention relates to polypeptides comprising an amino acid sequence which is an analogue of SEQ ID No: 2 wherein:
(a) said analogue comprises a proline residue at position 37;
wherein the amino acid sequence numbering of the analogue corresponds to the amino acid numbering sequence of SEQ ID No: 2; and
(b) said polypeptide has a solubility of about 100 µM or greater at pH7
optionally the polypeptide has at least one substituent attached to at least one of its amino acid residues.

In another aspect, the present invention relates to polypeptides comprising an amino acid sequence which is an analogue of SEQ ID No: 2 wherein:
(a) said analogue comprises a proline residue at position 37;
wherein the amino acid sequence numbering of the analogue corresponds to the amino acid numbering sequence of SEQ ID No: 2; and
(b) said polypeptide has a solubility of about 100 µM or greater at pH4; and
(c) said polypeptide has a solubility of about 100 µM or greater at pH7
optionally the polypeptide has at least one substituent attached to at least one of its amino acid residues.

In another aspect, the present invention relates to polypeptides comprising an amino acid sequence which is an analogue of SEQ ID No: 2 wherein:
(a) said analogue comprises a proline residue at position 37;
wherein the amino acid sequence numbering of the analogue corresponds to the amino acid numbering sequence of SEQ ID No: 2; and
(b) said polypeptide has a solubility of about 100 µM or greater at pH4; and
(c) said polypeptide has a solubility of about 100 µM or greater at pH7; and
(d) said polypeptide has a physical stability of about 25 hours or greater in a fibrillogenesis assay;
optionally the polypeptide has at least one substituent attached to at least one of its amino acid residues.

In another aspect, the present invention relates to polypeptides comprising an amino acid sequence which is an analogue of SEQ ID No: 2 wherein:
(a) said analogue comprises a proline residue at position 37;
(b) said analogue comprises a glutamic acid residue at position 14;
wherein the amino acid sequence numbering of the analogue corresponds to the amino acid numbering sequence of SEQ ID No: 2; and
optionally the polypeptide has at least one substituent attached to at least one of its amino acid residues.

In another aspect, the present invention relates to polypeptides comprising an amino acid sequence which is an analogue of SEQ ID No: 2 wherein:
(a) said analogue comprises a proline residue at position 37;
(b) said analogue comprises a glutamic acid residue at position 14;
wherein the amino acid sequence numbering of the analogue corresponds to the amino acid numbering sequence of SEQ ID No: 2; and
(c) said analogue has a solubility of about 100 µM or greater at pH4
optionally the polypeptide has at least one substituent attached to at least one of its amino acid residues.

In another aspect, the present invention relates to polypeptides comprising an amino acid sequence which is an analogue of SEQ ID No: 2 wherein:
(a) said analogue comprises a proline residue at position 37;
(b) said analogue comprises a glutamic acid residue at position 14;
wherein the amino acid sequence numbering of the analogue corresponds to the amino acid numbering sequence of SEQ ID No: 2; and
(c) said polypeptide has a solubility of about 100 µM or greater at pH7
optionally the polypeptide has at least one substituent attached to at least one of its amino acid residues.

In another aspect, the present invention relates to polypeptides comprising an amino acid sequence which is an analogue of SEQ ID No: 2 wherein:
(a) said analogue comprises a proline residue at position 37;
(b) said analogue comprises a glutamic acid residue at position 14;
wherein the amino acid sequence numbering of the analogue corresponds to the amino acid numbering sequence of SEQ ID No: 2; and
(c) said polypeptide has a solubility of about 100 µM or greater at pH4; and
(d) said polypeptide has a solubility of about 100 µM or greater at pH7
optionally the polypeptide has at least one substituent attached to at least one of its amino acid residues.

In another aspect, the present invention relates to polypeptides comprising an amino acid sequence which is an analogue of SEQ ID No: 2 wherein:
(a) said analogue comprises a proline residue at position 37;
(b) said analogue comprises a glutamic acid residue at position 14;
wherein the amino acid sequence numbering of the analogue corresponds to the amino acid numbering sequence of SEQ ID No: 2; and
(c) said polypeptide has a solubility of about 100 µM or greater at pH4; and
(d) said polypeptide has a solubility of about 100 µM or greater at pH7; and
(e) said polypeptide has a physical stability of about 25 hours or greater in a fibrillogenesis assay;
optionally the polypeptide has at least one substituent attached to at least one of its amino acid residues.

In another aspect, the present invention relates to polypeptides comprising an amino acid sequence which is an analogue of SEQ ID No: 2 wherein:
(a) said analogue comprises a proline residue at position 37;
(b) said analogue comprises a glutamic acid residue at position 14;
(c) said analogue comprises a histidine or arginine residue at position 17;
wherein the amino acid sequence numbering of the analogue corresponds to the amino acid numbering sequence of SEQ ID No: 2; and
optionally the polypeptide has at least one substituent attached to at least one of its amino acid residues.

In another aspect, the present invention relates to a polypeptide comprising an amino acid sequence which is an analogue of SEQ ID No: 2 of Formula (I):

Formula (I) (SEQ ID No: 3)
$Xaa_1$-Cys-$Xaa_3$-Thr-Ala-Thr-Cys-Ala-Thr-Gln-Arg-Leu-Ala-$Xaa_{14}$-Phe-Leu-$Xaa_{17}$-

-continued

Xaa₁₈-Ser-Ser-Xaa₂₁-Xaa₂₂-Phe-Gly-Pro-Xaa₂₆-Leu-Pro-Pro-Thr-Xaa₃₁-Val-Gly-
Ser-Xaa₃₅-Thr-Pro;

wherein
Xaa₁ is deleted or independently selected from Ala, Cys, Glu, Gly, His, Arg, Ser and Lys;
Xaa₃ is independently selected from Gly, His, Arg, Ser and Asn;
Xaa₁₄ is independently selected from Glu and Asn;
Xaa₁₇ is independently selected from His, Arg, Lys and Val;
Xaa₁₈ is independently selected from Arg, Lys and His;
Xaa₂₁ is independently selected from Ala, Lys, Gln, Ser and Asn;
Xaa₂₂ is independently selected from Glu, Gln, Ser, Thr and Asn;
Xaa₂₆ is independently selected from Pro, Arg and Ile;
Xaa₃₁ is independently selected from Ser, Glu, Asp and Asn;
Xaa₃₅ is independently selected from His, Arg, Lys, Asp, Gln and Glu;
and where the C-terminal may optionally be derivatized;
optionally the polypeptide has at least one substituent attached to at least one of its amino acid residues.

In another aspect, the present invention relates to polypeptides comprising an amino acid sequence which is an analogue of SEQ ID No: 2 wherein:
(a) said analogue comprises a glutamic acid residue at position 14;
(b) said analogue comprises an histidine or arginine residue at position 17;
(c) said analogue comprises a histidine residue at position 35;
wherein the amino acid sequence numbering of the analogue corresponds to the amino acid numbering sequence of SEQ ID No: 2; and
(d) said polypeptide has a solubility of about 100 μM or greater at pH4; and
optionally the polypeptide has at least one substituent attached to at least one of its amino acid residues.

In another aspect, the present invention relates to polypeptides comprising an amino acid sequence which is an analogue of SEQ ID No: 2 wherein:
(a) said analogue comprises a glutamic acid residue at position 14;
(b) said analogue comprises an histidine or arginine residue at position 17;
(c) said analogue comprises a histidine residue at position 35;
wherein the amino acid sequence numbering of the analogue corresponds to the amino acid numbering sequence of SEQ ID No: 2; and
(d) said polypeptide has a solubility of about 100 μM or greater at pH7; and
optionally the polypeptide has at least one substituent attached to at least one of its amino acid residues.

In another aspect, the present invention relates to polypeptides comprising an amino acid sequence which is an analogue of SEQ ID No: 2 wherein:
(a) said analogue comprises a glutamic acid residue at position 14;
(b) said analogue comprises an histidine or arginine residue at position 17;
(c) said analogue comprises a histidine residue at position 35;

wherein the amino acid sequence numbering of the analogue corresponds to the amino acid numbering sequence of SEQ ID No: 2; and
(d) said polypeptide has a solubility of about 100 μM or greater at pH4; and
(e) said polypeptide has a solubility of about 100 μM or greater at pH7; and
optionally the polypeptide has at least one substituent attached to at least one of its amino acid residues.

In another aspect, the present invention relates to polypeptides comprising an amino acid sequence which is an analogue of SEQ ID No: 2 wherein:
(a) said analogue comprises a glutamic acid residue at position 14;
(b) said analogue comprises an histidine or arginine residue at position 17;
(c) said analogue comprises a histidine residue at position 35;
wherein the amino acid sequence numbering of the analogue corresponds to the amino acid numbering sequence of SEQ ID No: 2; and
(d) said polypeptide has a physical stability of about 25 hours or greater in a fibrillogenesis assay;
optionally the polypeptide has at least one substituent attached to at least one of its amino acid residues.

In another aspect, the present invention relates to polypeptides comprising an amino acid sequence which is an analogue of SEQ ID No: 2 wherein:
(a) said analogue comprises a glutamic acid residue at position 14;
(b) said analogue comprises an histidine or arginine residue at position 17;
(c) said analogue comprises a histidine residue at position 35;
wherein the amino acid sequence numbering of the analogue corresponds to the amino acid numbering sequence of SEQ ID No: 2; and
(d) said polypeptide has a solubility of about 100 μM or greater at pH4; and
(e) said polypeptide has a solubility of about 100 μM or greater at pH7; and
(f) said polypeptide has a physical stability of about 25 hours or greater in a fibrillogenesis assay;
optionally the polypeptide has at least one substituent attached to at least one of its amino acid residues.

Some Advantages

The polypeptides of the present invention may exhibit improved physical stability.

The polypeptides of the present invention may exhibit improved solubility.

The polypeptides of the present invention may exhibit both improved physical stability and solubility.

Some Preferred Aspects

Suitable assays for measuring human amylin receptor binding and potency, solubility and physical stability are presented herein (For example, see Assays (II), (IV) and (III) respectively).

Preferably Xaa₁₄ is Glu.
Preferably Xaa₁₇ is His or Arg; more preferably Arg.
Preferably Xaa₃₅ is Asn or Gln; more preferably Asn
Preferably Xaa₁₄ is Glu and Xaa₁₇ is Arg.
Preferably Xaa₁₄ is Glu and Xaa₁₇ is His.

In one preferred embodiment of the invention the polypeptide comprising an amino acid sequence which is an analogue of SEQ ID No: 2 is of Formula (I) wherein:
- $Xaa_1$ is Lys;
- $Xaa_3$ is Asn;
- $Xaa_{14}$ is Glu
- $Xaa_{17}$ is His or Arg;
- $Xaa_{18}$ is His;
- $Xaa_{21}$ is Asn;
- $Xaa_{22}$ is Asn;
- $Xaa_{26}$ is Ile;
- $Xaa_{31}$ is Asn;
- $Xaa_{35}$ is Asn.

In one preferred embodiment of the invention the polypeptide comprising an amino acid sequence which is an analogue of SEQ ID No: 2 is of Formula (I) wherein:
- $Xaa_1$ is deleted or independently selected from His, Arg and Lys;
- $Xaa_3$ is independently selected from Gly, His and Asn;
- $Xaa_{14}$ is independently selected from Glu and Asn;
- $Xaa_{17}$ is independently selected from His, Arg and Val;
- $Xaa_{18}$ is independently selected from Arg and His;
- $Xaa_{21}$ is independently selected from Ser and Asn;
- $Xaa_{22}$ is Asn;
- $Xaa_{26}$ is Ile;
- $Xaa_{31}$ is independently selected from Glu and Asn;
- $Xaa_{35}$ is independently selected from His, Arg, Lys, Asp, Gln and Glu.

In one preferred embodiment of the invention the polypeptide comprising an amino acid sequence which is an analogue of SEQ ID No: 2 is of Formula (I) wherein:
- $Xaa_1$ is deleted or independently selected from Gly, His, Arg, Ser and Lys;
- $Xaa_3$ is independently selected from His and Asn;
- $Xaa_{14}$ is independently selected from Glu and Asn;
- $Xaa_{17}$ is independently selected from His, Arg and Val;
- $Xaa_{18}$ is independently selected from Arg and His;
- $Xaa_{21}$ is independently selected from Gln, Ser and Asn;
- $Xaa_{22}$ is Asn;
- $Xaa_{26}$ is independently selected from Pro and Ile;
- $Xaa_{31}$ is Asn;
- $Xaa_{35}$ is Asn.

In one preferred embodiment of the invention the polypeptide comprising an amino acid sequence which is an analogue of SEQ ID No: 2 is of Formula (I) wherein:
- $Xaa_1$ is deleted or independently selected from Ala, Cys, Glu, Gly, His, Arg, Ser and Lys;
- $Xaa_3$ is Asn;
- $Xaa_{14}$ is Glu;
- $Xaa_{17}$ is independently selected from His, Arg and Val;
- $Xaa_{18}$ is independently selected from Arg, Lys and His;
- $Xaa_{21}$ is independently selected from Gln and Asn;
- $Xaa_{22}$ is independently selected from Thr and Asn;
- $Xaa_{26}$ is Ile;
- $Xaa_{31}$ is Asn;
- $Xaa_{35}$ is independently selected from Gln, Gly and Asn.

In one preferred embodiment of the invention the polypeptide comprising an amino acid sequence which is an analogue of SEQ ID No: 2 is of Formula (I) wherein:
- $Xaa_1$ is deleted;
- $Xaa_3$ is independently selected from Gly and Asn;
- $Xaa_{14}$ is Glu;
- $Xaa_{17}$ is independently selected from His, Arg and Val;
- $Xaa_{18}$ is independently selected from Arg and His;
- $Xaa_{21}$ is independently selected from Gln and Asn;
- $Xaa_{22}$ is independently selected from Gln and Asn;
- $Xaa_{26}$ is Ile;
- $Xaa_{31}$ is independently selected from Glu and Asn;
- $Xaa_{35}$ is independently selected from Asn, Gln and Glu.

In one preferred embodiment of the invention the polypeptide comprising an amino acid sequence which is an analogue of SEQ ID No: 2 is of Formula (I) wherein:
- $Xaa_1$ is Lys;
- $Xaa_3$ is Asn;
- $Xaa_{14}$ is Glu;
- $Xaa_{17}$ is independently selected from His, Lys, Arg and Val;
- $Xaa_{18}$ is independently selected from Arg and His;
- $Xaa_{21}$ is independently selected from Ala, Lys, Gln and Ser;
- $Xaa_{22}$ is independently selected from Glu, Gln, Ser, Thr and Asn;
- $Xaa_{26}$ is independently selected from Pro and Ile;
- $Xaa_{31}$ is independently selected from Ser, Glu, Asp and Asn;
- $Xaa_{35}$ is independently selected from Gln, Glu and Asn.

In one embodiment the C-terminal may be derivatized.

In one embodiment, the C-terminal of the polypeptide may be terminated as either an acid or amide. In one aspect, the C-terminal of the polypeptide is an amide.

In one embodiment the C-terminal is derivatized with an amide of Formula (II):

$$C(O)NR^1R^2 \quad (II)$$

wherein $R^1$ and $R^2$ are independently selected from H and alkyl. Preferably $R^1$ and $R^2$ are both H.

In one embodiment, polypeptides of the present invention may have a substituent attached to any available position on one or more of the amino acid residues. Examples of substituents include chemical moieties directly bound to one or more of the amino acid residues, or chemical moieties indirectly bound to one or more of the amino acid residues by means of a linker. Available points of attachment will be known to the skilled person. Examples of available attachment points include the N-terminal of the polypeptide, the C-terminal of the polypeptide, an epsilon-amino group of a Lysine residue, the hydroxyl group of a serine, tyrosine or threonine residue, the amide group of an asparagine or glutamine residue, the carboxyl group of an aspartic acid or glutamic acid residue, the thiol group of a cysteine residue. Preferably, the substituent is attached to the N-terminal of the polypeptide, or the epsilon amino group of a lysine residue.

In another embodiment the substitutent is attached to the N-terminal amino group of the polypeptide wherein the N-terminal amino acid residue corresponds to position 1 of the analogue of SEQ ID No: 2.

In another embodiment the substitutent is attached to the epilson amino group of a lysine residue in position 1 of analogue of SEQ ID No: 2.

In one embodiment, the substituent is selected from a hydrocarbyl substituent group, a hydroxyl group and a halogen atom. Examples of suitable halogen atoms include F, Cl, Br and I. Preferably, the substituent is a hydrocarbyl substituent group.

In another embodiment, the hydrocarbyl substituent group is an alkyl group, or a group of Formula (III):

$$L_n\text{-}Y \quad (III)$$

wherein
- L is a linker;
- n=0 or 1
- Y is a chemical moiety such as an albumin binding moiety.

In one embodiment the linker comprises 1 to 10 amino acids. The linker can further comprise amines.

Examples of suitable amines include:

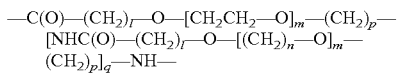

wherein l, m, n, and p independently are 1-7, and q is 0-5.

For example the linker can comprise an amine selected from:

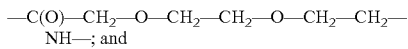

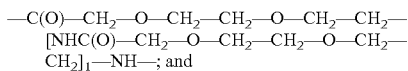

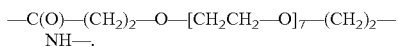

In another embodiment the linker is a combination of amino acid residues and the above mentioned amines, for example:

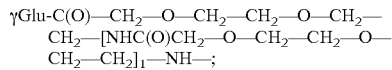

or

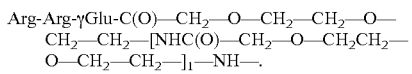

In some embodiments, n=1 and L is selected from the group consisting of γGlu, γGlu-γGlu, γGlu-γGlu-γGlu, γGlu-γGlu-γGlu-γGlu, Glu, Glu-Glu, Glu-γGlu, Glu-Arg, Glu-Arg, His, His-His, His-γGlu, His-His-γGlu, Gly, Gly-γGlu, Ser, Ser-γGlu, D-Arg-D-Arg, Arg, Arg-Arg, Arg-Arg-γGlu, Ser-Ser,-Gly-Ser-Ser, Ser-Ser,-Gly-Ser-Ser-γGlu, Ser-Ser-Gly-Ser-Ser-Gly and Ser-Ser-Gly-Ser-Ser-Gly-γGlu, γGlu-OEG, γGlu-OEG-OEG and OEG.

In some embodiments, n=1 and L is selected from γGlu, γGlu-γGlu, γGlu-OEG, γGlu-OEG-OEG and OEG, more preferably the linker is γGlu-γGlu.

In another embodiment n=0; accordingly there is no linker between the amino acid residues of the polypeptide backbone and chemical moiety, Y i.e. Y is attached to an available position on the polypeptide backbone.

In one embodiment Y is an albumin binding moiety.

In one embodiment the albumin binding moiety is an acyl group.

Preferably the albumin binding moiety is $HOOC(CH_2)_s CO-$, wherein s is an integer from 12 to 22. More preferably s is an integer from 14 to 20, for example 14, 15, 16, 17, 18, 19, or 20. More preferably s is 16 to 18. More preferably s is 18.

In one embodiment the polypeptide of the invention comprises a γGlu linker attached to the N-terminal of the amylin analogue and $HOOC(CH_2)_{18}CO$ or $HOOC(CH_2)_{16}CO-$ as the albumin binding residue and where the sequence of the amylin analogue comprises Glu in position 14, His or Arg in position 17, His in position 35 or Pro in position 37 as compared to SEQ ID NO: 2.

In another embodiment the substituent group and/or group of formula (III) is selected from the following groups presented in Table 1.

TABLE 1

| Abbreviation | Substituent |
|---|---|
| C20diacid |  |
| C20diacid-γGlu |  |
| C20diacid-γGlu-γGlu |  |

TABLE 1-continued

| Abbreviation | Substituent |
| --- | --- |
| C20diacid-γGlu-γGlu-γGlu | (structure) |
| C20diacid-OEG | (structure) |
| C20diacid-γGlu-OEG | (structure) |
| C20diacid-γGlu-OEG-OEG | (structure) |
| C18diacid-γGlu | (structure) |
| C16diacid-γGlu | (structure) |

TABLE 1-continued

| Abbreviation | Substituent |
|---|---|
| C14diacid-γGlu | (structure shown) |

Preferably, the polypeptides of the present invention comprise one substitutent.

Preferably, the polypeptides of the present invention have one substituent attached to the N-terminal amino group of the polypeptide wherein the N-terminal amino acid residue corresponds to position 1 of the analogue of SEQ ID No: 2.

Preferably the substituent is:

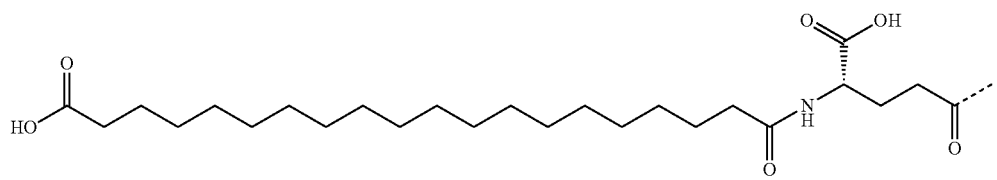

Preferably the substituent

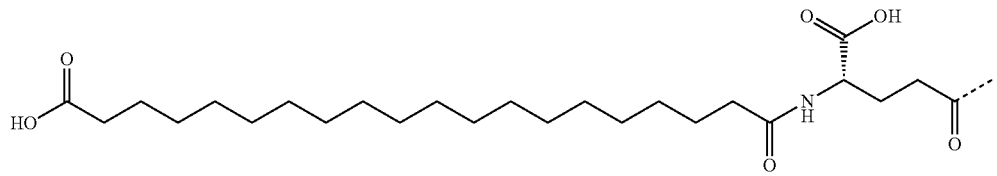

Is attached to the N-terminal amino group of the polypeptide.

For embodiments that comprise an albumin binding moiety, the polypeptides of the present invention can exhibit a protracted pharmacokinetic profile and good pharmacodynamic properties. Therefore the polypeptides according to the present invention do not have to be injected as often as known amylin products.

Further the polypeptides of the invention give a reduction in the food intake. The reduction in food intake is superior over the known amylin products.

In one embodiment the albumin binding moiety binds non-covalently to albumin. Preferably the albumin binding moiety has an albumin binding affinity towards human serum albumin that is below about 10 µM or below about 1 µM.

In one embodiment the polypeptide of the present invention is selected from the following compounds presented in Table 2 (below). Table 2 presents a list of compounds that have a solubility of greater than 100 µM at pH4.

TABLE 2

| Example # | Name | Amylin receptor human $EC_{50}$ (pM) | Solubility pH 4.0 (µM) |
|---|---|---|---|
| 89 | N-alpha-[(S)-4-Carboxy-4-(19-carboxynonadecanoylamino)butyryl]-Gly-[His1, Glu14, Arg17, Pro37]-pramlintide | 25.5 | >200 |
| 90 | N-alpha-[(S)-4-Carboxy-4-(19-carboxynonadecanoylamino)butyryl]-[His1, Glu14, Arg17, Pro37]-pramlintide | 32.5 | >200 |
| 97 | N-alpha-[(S)-4-Carboxy-4-(19-carboxynonadecanoylamino)butyryl]-[Arg1, Pro37]-pramlintide | 34 | >200 |

TABLE 2-continued

| Example # | Name | Amylin receptor human EC$_{50}$ (pM) | Solubility pH 4.0 (μM) |
|---|---|---|---|
| 88 | N-alpha-[(S)-4-Carboxy-4-(19-carboxynonadecanoylamino)butyryl]-[Gly1, Glu14, Arg17, Pro37]-pramlintide | 36 | >200 |
| 166 | N-alpha-[(S)-4-Carboxy-4-(19-carboxynonadecanoylamino)butyryl]-[Glu14, Arg18, Gln21, Ala25, Pro26, Ser28, Ser29, Pro37]-pramlintide | 39 | >200 |
| 143 | N-alpha-[(S)-4-Carboxy-4-(19-carboxynonadecanoylamino)butyryl]-[His1, Glu14, Arg18, Pro37]-pramlintide | 41.5 | >200 |
| 96 | N-alpha-[(S)-4-Carboxy-4-(19-carboxynonadecanoylamino)butyryl]-[Arg1, Glu14, His17, Pro37]-pramlintide | 43 | >200 |
| 121 | N-alpha-(19-carboxynonadecanoyl)-Glu-Glu-Arg-[Glu1, Pro37]-pramlintide | 45 | >200 |
| 102 | N-alpha-[(S)-4-Carboxy-4-(19-carboxynonadecanoylamino)butyryl]-Gly-[Arg1, Glu14, Pro37]-pramlintide | 49.5 | >200 |
| 101 | N-alpha-[(S)-4-Carboxy-4-(19-carboxynonadecanoylamino)butyryl]-Gly-[Arg1, Glu14, His17, Pro37]-pramlintide | 51.5 | >200 |
| 92 | N-alpha-[(S)-4-Carboxy-4-(19-carboxynonadecanoylamino)butyryl]-Gly-[His1, Glu14, Arg17, Pro37]-pramlintide | 52 | >200 |
| 103 | N-alpha-[(S)-4-Carboxy-4-(19-carboxynonadecanoylamino)butyryl]-Gly-[Arg1, Pro37]-pramlintide | 52.5 | >200 |
| 53 | N-alpha-[(S)-4-Carboxy-4-(19-carboxynonadecanoylamino)butyryl]-[Glu14, Arg17, Pro37]-pramlintide | 53 | >200 |
| 91 | N-alpha-[(S)-4-Carboxy-4-(19-carboxynonadecanoylamino)butyryl]-[Gly1, Glu14, His17, Pro37]-pramlintide | 54 | >200 |
| 86 | N-alpha-[(S)-4-Carboxy-4-(19-carboxynonadecanoylamino)butyryl]-[Glu14, Pro37]-pramlintide | 55 | >200 |
| 130 | N-alpha-[(S)-4-Carboxy-4-(19-carboxynonadecanoylamino)butyryl]-[Glu14, His17, Gln21, Pro37]-pramlintide | 55.5 | >200 |
| 52 | N-alpha-[(S)-4-Carboxy-4-(19-carboxynonadecanoylamino)butyryl]-[Glu14, His17, Pro37]-pramlintide | 62 | >200 |
| 106 | N-alpha-[(S)-4-Carboxy-4-(19-carboxynonadecanoylamino)butyryl]-[Ser1, Glu14, His17, Pro37]-pramlintide | 62.5 | >200 |
| 122 | N-alpha-[(S)-4-Carboxy-4-(19-carboxynonadecanoylamino)butyryl]-Glu-Arg-[Glu1, Pro37]-pramlintide | 63 | >200 |
| 168 | N-alpha-[2-(2-{2-[2-(2-{2-[(S)-4-Carboxy-4-(19-carboxyheptadecanoylamino)butyrylamino]ethoxy}ethoxy)acetylamino] ethoxy}ethoxy)acetyl]-[Glu14, His17, Lys21, Pro37]-pramlintide | 71 | >200 |
| 104 | N-alpha-[(S)-4-Carboxy-4-(19-carboxynonadecanoylamino)butyryl]-[des1, Glu14, His17, Pro37]-pramlintide | 79.5 | >200 |
| 145 | N-alpha-[(S)-4-Carboxy-4-(19-carboxynonadecanoylamino)butyryl]-[Lys11, Glu14, His17, Pro37]-pramlintide | 80.5 | >200 |
| 10 | N-alpha-[(S)-4-Carboxy-4-(19-carboxynonadecanoylamino)butyryl]-[Glu1, Glu14, His17, Arg18, Pro37]-pramlintide | 82.3 | >200 |
| 109 | N-alpha-[(S)-4-Carboxy-4-(19-carboxynonadecanoylamino)butyryl]-[His1, Glu14, Pro37]-pramlintide | 84.5 | >200 |
| 108 | N-alpha-[(S)-4-Carboxy-4-(19-carboxynonadecanoylamino)butyryl]-[des1, Glu14, Pro37]-pramlintide | 88 | >200 |
| 124 | N-alpha-[(S)-4-Carboxy-4-(19-carboxynonadecanoylamino)butyryl]-Glu-Arg-[Glu1, Glu14, Arg17, Pro37]-pramlintide | 89.5 | >200 |
| 170 | N-alpha-[(S)-4-Carboxy-4-(19-carboxynonadecanoylamino)butyryl]-[Glu14, Arg18, Ser21, Ser22, Ser28, Ser29, Asp31, Asp35, Pro37]-pramlintide | 90 | >200 |

TABLE 2-continued

| Example # | Name | Amylin receptor human EC$_{50}$ (pM) | Solubility pH 4.0 (μM) |
|---|---|---|---|
| 136 | N-alpha-[(S)-4-Carboxy-4-(19-carboxynonadecanoylamino)butyryl]-[Glu14, His17, Gln21, Gln35, Pro37]-pramlintide | 91 | >200 |
| 146 | N-alpha-[(S)-4-Carboxy-4-(19-carboxynonadecanoylamino)butyryl]-[Glu14, His17, Thr21, Pro37]-pramlintide | 91 | >200 |
| 84 | N-alpha-[(S)-4-Carboxy-4-(19-carboxynonadecanoylamino)butyryl]-[His1, Glu14, Arg17, Pro37]-pramlintide | 92.5 | >200 |
| 135 | N-alpha-[(S)-4-Carboxy-4-(19-carboxynonadecanoylamino)butyryl]-[Glu14, His17, Gln35, Pro37]-pramlintide | 103 | >200 |
| 19 | N-alpha-[(S)-4-Carboxy-4-(19-carboxynonadecanoylamino)butyryl]-His-His-[His1, Glu14, His17, Ala25, Pro26, Ser28, Ser29]-pramlintide | 105.1 | >200 |
| 139 | N-alpha-[(S)-4-Carboxy-4-(19-carboxynonadecanoylamino)butyryl]-[Glu14, Gln21, Gln35, Pro37]-pramlintide | 107.5 | >200 |
| 82 | N-alpha-[2-(2-{2-[2-(2-{2-[(S)-4-Carboxy-4-(17-carboxyheptadecanoylamino)butyrylamino]ethoxy}ethoxy)acetylamino] ethoxy}ethoxy)acetyl]-[Glu1, Glu14, His17, Pro37]-pramlintide | 108.5 | >200 |
| 137 | N-alpha-[(S)-4-Carboxy-4-(19-carboxynonadecanoylamino)butyryl]-[Gly1, Glu14, His17, Gln21, Gln35, Pro37]-pramlintide | 120.5 | >200 |
| 123 | N-alpha-[(S)-4-Carboxy-4-(19-carboxynonadecanoylamino)butyryl]-Glu-Arg-[Glu1, Glu14, His17, Pro37]-pramlintide | 136 | >200 |
| 167 | N-alpha-[2-(2-{2-[2-(2-{2-[(S)-4-Carboxy-4-(19-carboxyheptadecanoylamino)butyrylamino]ethoxy}ethoxy)acetylamino] ethoxy}ethoxy)acetyl]-[Glu14, His17, Glu21, Pro37]-pramlintide | 203 | >200 |
| 151 | N-epsilon1-[(S)-4-Carboxy-4-(19-carboxynonadecanoylamino)butyryl]-[Glu14, His17, Gln21, Ala25, Pro26, Ser28, Ser29, Pro37]-pramlintide | 209 | >200 |
| 161 | N-alpha-[(S)-4-Carboxy-4-(19-carboxynonadecanoylamino)butyryl]-Glu-Arg-[Glu1, Glu14, Arg17, Gln21, Pro37]-pramlintide | 232 | >200 |
| 125 | N-alpha-(19-carboxynonadecanoyl)-Glu-Glu-Arg-[Glu1, Glu14, His17, Pro37]-pramlintide | 288.5 | >200 |
| 155 | N-alpha-[(S)-4-Carboxy-4-(19-carboxynonadecanoylamino)butyryl]-Glu-Glu-[Arg1, Glu14, Arg17, Pro37]-pramlintide | 313 | >200 |
| 162 | N-alpha-[(S)-4-Carboxy-4-(19-carboxynonadecanoylamino)butyryl]-Glu-Arg-[Glu1, Glu14, Arg17, Gln21, Gln35, Pro37]-pramlintide | 411 | >200 |
| 157 | N-alpha-[(S)-4-Carboxy-4-(19-carboxynonadecanoylamino)butyryl]-Glu-Glu-[Arg1, Glu14, Arg17, Gln21, Pro37]-pramlintide | 465 | >200 |
| 163 | N-alpha-[(S)-4-Carboxy-4-(19-carboxynonadecanoylamino)butyryl]-Glu-Arg-[Glu1, Glu14, Arg17, Gln21, Gln31, Gln35, Pro37]-pramlintide | 1059 | >200 |
| 158 | N-alpha-[(S)-4-Carboxy-4-(19-carboxynonadecanoylamino)butyryl]-Glu-Glu-[Arg1, Glu14, Arg17, Gln21, Gln35, Pro37]-pramlintide | 1129 | >200 |
| 138 | N-alpha-[(S)-4-Carboxy-4-(19-carboxynonadecanoylamino)butyryl]-[Glu1, Glu14, Gln21, Gln35, Pro37]-pramlintide | 1512 | >200 |
| 164 | N-alpha-[(S)-4-Carboxy-4-(19-carboxynonadecanoylamino)butyryl]-Glu-Arg-[Glu1, Glu14, Arg17, Gln21, Gln22, Gln31, Gln35, Pro37]-pramlintide | 1713 | >200 |
| 159 | N-alpha-[(S)-4-Carboxy-4-(19-carboxynonadecanoylamino)butyryl]-Glu-Glu-[Arg1, Glu14, Arg17, Gln21, Gln31, Gln35, Pro37]-pramlintide | | >200 |
| 160 | N-alpha-[(S)-4-Carboxy-4-(19-carboxynonadecanoylamino)butyryl]-Glu-Glu-[Arg1, Glu14, Arg17, Gln21, Gln22, Gln31, Gln35, Pro37]-pramlintide | | >200 |
| 169 | N-alpha-[2-(2-{2-[2-(2-{2-[(S)-4-Carboxy-4-(19-carboxyheptadecanoylamino)butyrylamino]ethoxy}ethoxy)acetylamino] ethoxy}ethoxy)acetyl]-[Glu14, His17, Ala21, Pro37]-pramlintide | | >200 |

TABLE 2-continued

| Example # | Name | Amylin receptor human $EC_{50}$ (pM) | Solubility pH 4.0 (μM) |
|---|---|---|---|
| 171 | N-alpha-[(S)-4-Carboxy-4-(19-carboxynonadecanoylamino)butyryl]-[Glu14, Ser21, Ser22, Pro23, Ala25, Pro26, Ser28, Ser29, Asp31, Asp35, Pro37]-pramlintide | | >200 |
| 177 | N-epsilon1-[(S)-4-Carboxy-4-(19-carboxynonadecanoylamino)butyryl]-[Glu14, Arg17, Pro37]-pramlintide | | >200 |
| 178 | N-alpha-[2-(2-{2-[2-(2-{2-[(S)-4-Carboxy-4-(19-carboxyheptadecanoylamino)butyrylamino]ethoxy}ethoxy)acetylamino]ethoxy}ethoxy)acetyl]-[Glu14, Ala21, His35, Pro37]-pramlintide | | >200 |

As demonstrated in the Examples section herein, the polypeptides presented above have a solubility of greater than or equal to 100 μM (micromolar) at pH4.

In one embodiment, the polypeptides of the present invention have a solubility of greater than or equal to 125 μM (micromolar) at pH4.

In one embodiment, the polypeptides of the present invention have a solubility of greater than or equal to 150 μM (micromolar) at pH4.

In one embodiment, the polypeptides of the present invention have a solubility of greater than or equal to 175 μM (micromolar) at pH4.

In one embodiment, the polypeptides of the present invention have a solubility of greater than or equal to 200 μM (micromolar) at pH4.

In one embodiment, the solubility is measured in a solubility assay as presented herein.

In a further embodiment the polypeptide of the present invention is selected from the following compounds presented in Table 3 (below).

Table 3 presents a list of compounds that have a solubility of greater than 100 μM at pH7.

TABLE 3

| Example # | Name | Amylin receptor human $EC_{50}$ (pM) | Solibility pH 7.0 (μM) |
|---|---|---|---|
| 89 | N-alpha-[(S)-4-Carboxy-4-(19-carboxynonadecanoylamino)butyryl]-Gly-[His1, Glu14, Arg17, Pro37]-pramlintide | 25.5 | >200 |
| 90 | N-alpha-[(S)-4-Carboxy-4-(19-carboxynonadecanoylamino)butyryl]-[His1, Glu14, Arg17, Pro37]-pramlintide | 32.5 | >200 |
| 97 | N-alpha-[(S)-4-Carboxy-4-(19-carboxynonadecanoylamino)butyryl]-[Arg1, Pro37]-pramlintide | 34 | >200 |
| 88 | N-alpha-[(S)-4-Carboxy-4-(19-carboxynonadecanoylamino)butyryl]-[Gly1, Glu14, Arg17, Pro37]-pramlintide | 36 | >200 |
| 166 | N-alpha-[(S)-4-Carboxy-4-(19-carboxynonadecanoylamino)butyryl]-[Glu14, Arg18, Gln21, Ala25, Pro26, Ser28, Ser29, Pro37]-pramlintide | 39 | >200 |
| 143 | N-alpha-[(S)-4-Carboxy-4-(19-carboxynonadecanoylamino)butyryl]-[His1, Glu14, Arg18, Pro37]-pramlintide | 41.5 | 165 |
| 96 | N-alpha-[(S)-4-Carboxy-4-(19-carboxynonadecanoylamino)butyryl]-[Arg1, Glu14, His17, Pro37]-pramlintide | 43 | >200 |
| 102 | N-alpha-[(S)-4-Carboxy-4-(19-carboxynonadecanoylamino)butyryl]-Gly-[Arg1, Glu14, Pro37]-pramlintide | 49.5 | >200 |
| 101 | N-alpha-[(S)-4-Carboxy-4-(19-carboxynonadecanoylamino)butyryl]-Gly-[Arg1, Glu14, His17, Pro37]-pramlintide | 51.5 | >200 |
| 92 | N-alpha-[(S)-4-Carboxy-4-(19-carboxynonadecanoylamino)butyryl]-Gly-[His1, Glu14, His17, Pro37]-pramlintide | 52 | >200 |
| 103 | N-alpha-[S]-4-Carboxy-4-(19-carboxynonadecanoylamino)butyryl]-Gly-[Arg1, Pro37]-pramlintide | 52.5 | 199 |
| 53 | N-alpha-[(S)-4-Carboxy-4-(19-carboxynonadecanoylamino)butyryl]-[Glu14, Arg17, Pro37]-pramlintide | 53 | >200 |

TABLE 3-continued

| Example # | Name | Amylin receptor human EC$_{50}$ (pM) | Solibility pH 7.0 (μM) |
|---|---|---|---|
| 91 | N-alpha-[(S)-4-Carboxy-4-(19-carboxynonadecanoylamino)butyryl]-[Gly1, Glu14, His17, Pro37]-pramlintide | 54 | >200 |
| 86 | N-alpha-[(S)-4-Carboxy-4-(19-carboxynonadecanoylamino)butyryl]-[Glu14, Pro37]-pramlintide | 55 | >200 |
| 130 | N-alpha-[(S)-4-Carboxy-4-(19-carboxynonadecanoylamino)butyryl]-[Glu14, His17, Gln21, Pro37]-pramlintide | 55.5 | >200 |
| 52 | N-alpha-[(S)-4-Carboxy-4-(19-carboxynonadecanoylamino)butyryl]-[Glu14, His17, Pro37]-pramlintide | 62 | >200 |
| 106 | N-alpha-[(S)-4-Carboxy-4-(19-carboxynonadecanoylamino)butyryl]-[Ser1, Glu14, His17, Pro37]-pramlintide | 62.5 | >200 |
| 122 | N-alpha-[(S)-4-Carboxy-4-(19-carboxynonadecanoylamino)butyryl]-Glu-Arg-[Glu1, Pro37]-pramlintide | 63 | >200 |
| 168 | N-alpha-[2-(2-{2-[2-(2-{2-[(S)-4-Carboxy-4-(19-carboxyheptadecanoylamino)butyrylamino]ethoxy}ethoxy)acetylamino]ethoxy}ethoxy)acetyl]-[Glu14, His17, Lys21, Pro37]-pramlintide | 71 | >200 |
| 104 | N-alpha-[(S)-4-Carboxy-4-(19-carboxynonadecanoylamino)butyryl]-[des1, Glu14, His17, Pro37]-pramlintide | 79.5 | >200 |
| 145 | N-alpha-[(S)-4-Carboxy-4-(19-carboxynonadecanoylamino)butyryl]-[Lys11, Glu14, His17, Pro37]-pramlintide | 80.5 | >200 |
| 10 | N-alpha-[(S)-4-Carboxy-4-(19-carboxynonadecanoylamino)butyryl]-[Glu1, Glu14, His17, Arg18, Pro37]-pramlintide | 82.3 | >200 |
| 109 | N-alpha-[(S)-4-Carboxy-4-(19-carboxynonadecanoylamino)butyryl]-[His1, Glu14, Pro37]-pramlintide | 84.5 | >200 |
| 108 | N-alpha-[(S)-4-Carboxy-4-(19-carboxynonadecanoylamino)butyryl]-[des1, Glu14, Pro37]-pramlintide | 88 | >200 |
| 124 | N-alpha-[(S)-4-Carboxy-4-(19-carboxynonadecanoylamino)butyryl]-Glu-Arg-[Glu1, Glu14, Arg17, Pro37]-pramlintide | 89.5 | >200 |
| 170 | N-alpha-[(S)-4-Carboxy-4-(19-carboxynonadecanoylamino)butyryl]-[Glu14, Arg18, Ser21, Ser22, Ser28, Ser29, Asp31, Asp35, Pro37]-pramlintide | 90 | >200 |
| 136 | N-alpha-[(S)-4-Carboxy-4-(19-carboxynonadecanoylamino)butyryl]-[Glu14, His17, Gln21, Gln35, Pro37]-pramlintide | 91 | >200 |
| 146 | N-alpha-[(S)-4-Carboxy-4-(19-carboxynonadecanoylamino)butyryl]-[Glu14, His17, Thr21, Pro37]-pramlintide | 91 | >200 |
| 84 | N-alpha-[(S)-4-Carboxy-4-(19-carboxynonadecanoylamino)butyryl]-[His1, Glu14, His17, Pro37]-pramlintide | 92.5 | >200 |
| 135 | N-alpha-[(S)-4-Carboxy-4-(19-carboxynonadecanoylamino)butyryl]-[Glu14, His17, Gln35, Pro37]-pramlintide | 103 | >200 |
| 139 | N-alpha-[(S)-4-Carboxy-4-(19-carboxynonadecanoylamino)butyryl]-[Glu14, Gln21, Gln35, Pro37]-pramlintide | 107.5 | >200 |
| 82 | N-alpha-[2-(2-{2-[2-(2-{2-[(S)-4-Carboxy-4-(17-carboxyheptadecanoylamino)butyrylamino]ethoxy}ethoxy)acetylamino]ethoxy}ethoxy)acetyl]-[Glu1, Glu14, His17, Pro37]-pramlintide | 108.5 | >200 |
| 137 | N-alpha-[(S)-4-Carboxy-4-(19-carboxynonadecanoylamino)butyryl]-[Gly1, Glu14, His17, Gln21, Gln35, Pro37]-pramlintide | 120.5 | >200 |
| 123 | N-alpha-[(S)-4-Carboxy-4-(19-carboxynonadecanoylamino)butyryl]-Glu-Arg-[Glu1, Glu14, His17, Pro37]-pramlintide | 136 | >200 |
| 167 | N-alpha-[2-(2-{2-[2-(2-{2-[S)-4-Carboxy-4-(19-carboxyheptadecanoylamino)butyrylamino]ethoxy}ethoxy)acetylamino]ethoxy}ethoxy)acetyl]-[Glu14, His17, Glu21, Pro37]-pramlintide | 203 | >200 |

TABLE 3-continued

| Example # | Name | Amylin receptor human EC$_{50}$ (pM) | Solubility pH 7.0 (μM) |
|---|---|---|---|
| 151 | N-epsilon1-[(S)-4-Carboxy-4-(19-carboxynonadecanoylamino)butyryl]-[Glu14, His17, Gln21, Ala25, Pro26, Ser28, Ser29, Pro37]-pramlintide | 209 | >200 |
| 161 | N-alpha-[(S)-4-Carboxy-4-(19-carboxynonadecanoylamino)butyryl]-Glu-Arg-[Glu1, Glu14, Arg17, Gln21, Pro37]-pramlintide | 232 | >200 |
| 125 | N-alpha-(19-carboxynonadecanoyl)-Glu-Glu-Arg-[Glu1, Glu14, His17, Pro37]-pramlintide | 288.5 | >200 |
| 155 | N-alpha-[(S)-4-Carboxy-4-(19-carboxynonadecanoylamino)butyryl]-Glu-Glu-[Arg1, Glu14, Arg17, Pro37]-pramlintide | 313 | >200 |
| 162 | N-alpha-[(S)-4-Carboxy-4-(19-carboxynonadecanoylamino)butyryl]-Glu-Arg-[Glu1, Glu14, Arg17, Gln21, Gln35, Pro37]-pramlintide | 411 | >200 |
| 157 | N-alpha-[(S)-4-Carboxy-4-(19-carboxynonadecanoylamino)butyryl]-Glu-Glu-[Arg1, Glu14, Arg17, Gln21, Pro37]-pramlintide | 465 | >200 |
| 163 | N-alpha-[(S)-4-Carboxy-4-(19-carboxynonadecanoylamino)butyryl]-Glu-Arg-[Glu1, Glu14, Arg17, Gln21, Gln31, Gln35, Pro37]-pramlintide | 1059 | >200 |
| 158 | N-alpha-[(S)-4-Carboxy-4-(19-carboxynonadecanoylamino)butyryl]-Glu-Glu-[Arg1, Glu14, Arg17, Gln21, Gln35, Pro37]-pramlintide | 1129 | >200 |
| 138 | N-alpha-[(S)-4-Carboxy-4-(19-carboxynonadecanoylamino)butyryl]-[Glu1, Glu14, Gln21, Gln35, Pro37]-pramlintide | 1512 | >200 |
| 164 | N-alpha-[(S)-4-Carboxy-4-(19-carboxynonadecanoylamino)butyryl]-Glu-Arg-[Glu1, Glu14, Arg17, Gln21, Gln22, Gln31, Gln35, Pro37]-pramlintide | 1713 | >200 |
| 159 | N-alpha-[(S)-4-Carboxy-4-(19-carboxynonadecanoylamino)butyryl]-Glu-Glu-[Arg1, Glu14, Arg17, Gln21, Gln31, Gln35, Pro37]-pramlintide | | >200 |
| 160 | N-alpha-[(S)-4-Carboxy-4-(19-carboxynonadecanoylamino)butyryl]-Glu-Glu-[Arg1, Glu14, Arg17, Gln21, Gln22, Gln31, Gln35, Pro37]-pramlintide | | >200 |
| 169 | N-alpha-[2-(2-{2-[2-(2-{2-[(S)-4-Carboxy-4-(19-carboxyheptadecanoylamino)butyrylamino]ethoxy}ethoxy)acetylamino] ethoxy}ethoxy)acetyl]-[Glu14, His17, Ala21, Pro37]-pramlintide | | >200 |
| 171 | N-alpha-[(S)-4-Carboxy-4-(19-carboxynonadecanoylamino)butyryl]-[Glu14, Ser21, Ser22, Pro23, Ala25, Pro26, Ser28, Ser29, Asp31, Asp35, Pro37]-pramlintide | | >200 |
| 177 | N-epsilon1-[(S)-4-Carboxy-4-(19-carboxynonadecanoylamino)butyryl]-[Glu14, Arg17, Pro37]-pramlintide | | >200 |
| 178 | N-alpha-[2-(2-{2-[2-(2-{2-[(S)-4-Carboxy-4-(19-carboxyheptadecanoylamino)butyrylamino]ethoxy}ethoxy)acetylamino] ethoxy}ethoxy)acetyl]-[Glu14, Ala21, His35, Pro37]-pramlintide | | >200 |

As demonstrated in the Examples section herein, the polypeptides presented above have a solubility of greater than or equal to 100 μM (micromolar) at pH7.

In one embodiment, the polypeptides of the present invention have a solubility of greater than or equal to 125 μM (micromolar) at pH7.

In one embodiment, the polypeptides of the present invention have a solubility of greater than or equal to 150 μM (micromolar) at pH7.

In one embodiment, the polypeptides of the present invention have a solubility of greater than or equal to 175 μM (micromolar) at pH7.

In one embodiment, the polypeptides of the present invention have a solubility of greater than or equal to 200 μM (micromolar) at pH7.

In one embodiment, the solubility is measured in a solubility assay as presented herein.

Table 4 presents a list of compounds that have a solubility of greater than 100 μM at both pH 4 and pH7.

TABLE 4

| Example # | Name | Amylin receptor human EC$_{50}$ (pM) | Solubility pH 4.0 (μM) | Solubility pH 7.0 (μM) |
|---|---|---|---|---|
| 89 | N-alpha-[(S)-4-Cardoxy-4-(19-carboxynonadecanoylamino)butyryl]-Gly-[His1, Glu14, Arg17, Pro37]-pramlintide | 25.5 | >200 | >200 |
| 90 | N-alpha-[(S)-4-Carboxy-4-(19-carboxynonadecanoylamino)butyryl]-[His1, Glu14, Arg17, Pro37]-pramlintide | 32.5 | >200 | >200 |
| 97 | N-alpha-[(S)-4-Carboxy-4-(19-carboxynonadecanoylamino)butyryl]-[Arg1, Pro37]-pramlintide | 34 | >200 | >200 |
| 88 | N-alpha-[(S)-4-Carboxy-4-(19-carboxynonadecanoylamino)butyryl]-[Gly1, Glu14, Arg17, Pro37]-pramlintide | 36 | >200 | >200 |
| 166 | N-alpha-[(S)-4-Carboxy-4-(19-carboxynonadecanoylamino)butyryl]-[Glu14, Arg18, Gln21, Ala25, Pro26, Ser28, Ser29, Pro37]-pramlintide | 39 | >200 | >200 |
| 143 | N-alpha-[(S)-4-Carboxy-4-(19-carboxynonadecanoylamino)butyryl]-[His1, Glu14, Arg18, Pro37]-pramlintide | 41.5 | >200 | 165 |
| 96 | N-alpha-[(S)-4-Carboxy-4-(19-carboxynonadecanoylamino)butyryl]-[Arg1, Glu14, His17, Pro37]-pramlintide | 43 | >200 | >200 |
| 102 | N-alpha-[(S)-4-Carboxy-4-(19-carboxynonadecanoylamino)butyryl]-Gly-[Arg1, Glu14, Pro37]-pramlintide | 49.5 | >200 | >200 |
| 101 | N-alpha-[(S)-4-Carboxy-4-(19-carboxynonadecanoylamino)butyryl]-Gly-[Arg1, Glu14, His17, Pro37]-pramlintide | 51.5 | >200 | >200 |
| 92 | N-alpha-[(S)-4-Carboxy-4-(19-carboxynonadecanoylamino)butyryl]-Gly-[His1, Glu14, His17, Pro37]-pramlintide | 52 | >200 | >200 |
| 103 | N-alpha-[(S)-4-Carboxy-4-(19-carboxynonadecanoylamino)butyryl]-Gly-[Arg1, Pro37]-pramlintide | 52.5 | >200 | 199 |
| 53 | N-alpha-[(S)-4-Carboxy-4-(19-carboxynonadecanoylamino)butyryl]-[Glu14, Arg17, Pro37]-pramlintide | 53 | >200 | >200 |
| 91 | N-alpha-[(S)-4-Carboxy-4-(19-carboxynonadecanoylamino)butyryl]-[Gly1, Glu14, His17, Pro37]-pramlintide | 54 | >200 | >200 |
| 86 | N-alpha-[(S)-4-Carboxy-4-(19-carboxynonadecanoylamino)butyryl]-[Glu14, Pro37]-pramlintide | 55 | >200 | >200 |
| 130 | N-alpha-[(S)-4-Carboxy-4-(19-carboxynonadecanoylamino)butyryl]-[Glu14, His17, Gln21, Pro37]-pramlintide | 55.5 | >200 | >200 |
| 52 | N-alpha-[(S)-4-Carboxy-4-(19-carboxynonadecanoylamino)butyryl]-[Glu14, His17, Pro37]-pramlintide | 62 | >200 | >200 |
| 106 | N-alpha-[(S)-4-Carboxy-4-(19-carboxynonadecanoylamino)butyryl]-[Ser1, Glu14, His17, Pro37]-pramlintide | 62.5 | >200 | >200 |
| 122 | N-alpha-[(S)-4-Carboxy-4-(19-carboxynonadecanoylamino)butyryl]-Glu-Arg-[Glu1, Pro37]-pramlintide | 63 | >200 | >200 |
| 168 | N-alpha-[2-(2-{2-[2-(2-{2-[(S)-4-Carboxy-4-(19-carboxyheptadecanoylamino)butyrylamino]ethoxy}ethoxy)acetylamino]ethoxy}ethoxy)acetyl]-[Glu14, His17, Lys21, Pro37]-pramlintide | 71 | >200 | >200 |
| 42 | N-alpha-[(S)-4-Carboxy-4-(17-carboxyheptadecanoylamino)butyryl]-Glu-[Glu14, His17]-pramlintide | 73.9 | >200 | >200 |
| 104 | N-alpha-[(S)-4-Carboxy-4-(19-carboxynonadecanoylamino)butyryl]-[des1, Glu14, His17, Pro37]-pramlintide | 79.5 | >200 | >200 |
| 145 | N-alpha-[(S)-4-Carboxy-4-(19-carboxynonadecanoylamino)butyryl]-[Lys11, Glu14, His17, Pro37]-pramlintide | 80.5 | >200 | >200 |
| 10 | N-alpha-[(S)-4-Carboxy-4-(19-carboxynonadecanoylamino)butyryl]-[Glu1, Glu14, His17, Arg18, Pro37]-pramlintide | 82.3 | >200 | >200 |
| 109 | N-alpha-[(S)-4-Carboxy-4-(19-carboxynonadecanoylamino)butyryl]-[His1, Glu14, Pro37]-pramlintide | 84.5 | >200 | >200 |

TABLE 4-continued

| Example # | Name | Amylin receptor human EC$_{50}$ (pM) | Solubility pH 4.0 (µM) | Solubility pH 7.0 (µM) |
|---|---|---|---|---|
| 108 | N-alpha-[(S)-4-Carboxy-4-(19-carboxynonadecanoylamino)butyryl]-[des1, Glu14, Pro37]-pramlintide | 88 | >200 | >200 |
| 72 | N-epsilon25-[2-(2-{2-[2-(2-{2-[(S)-4-Carboxy-4-(17-carboxyheptadecanoylamino)butyrylamino]ethoxy}ethoxy)acetylamino] ethoxy}ethoxy)acetyl]-[Glu14, Ser21, Lys25]-pramlintide | 89 | >200 | 126 |
| 124 | N-alpha-[(S)-4-Carboxy-4-(19-carboxynonadecanoylamino)butyryl]-Glu-Arg-[Glu1, Glu14, Arg17, Pro37]-pramlintide | 89.5 | >200 | >200 |
| 170 | N-alpha-[(S)-4-Carboxy-4-(19-carboxynonadecanoylamino)butyryl]-[Glu14, Arg18, Ser21, Ser22, Ser28, Ser29, Asp31, Asp35, Pro37]-pramlintide | 90 | >200 | >200 |
| 136 | N-alpha-[(S)-4-Carboxy-4-(19-carboxynonadecanoylamino)butyryl]-[Glu14, His17, Gln21, Gln35, Pro37]-pramlintide | 91 | >200 | >200 |
| 146 | N-alpha-[(S)-4-Carboxy-4-(19-carboxynonadecanoylamino)butyryl]-[Glu14, His17, Thr21, Pro37]-pramlintide | 91 | >200 | >200 |
| 84 | N-alpha-[(S)-4-Carboxy-4-(19-carboxynonadecanoylamino)butyryl]-[His1, Glu14, His17, Pro37]-pramlintide | 92.5 | >200 | >200 |
| 135 | N-alpha-[(S)-4-Carboxy-4-(19-carboxynonadecanoylamino)butyryl]-[Glu14, His17, Gln35, Pro37]-pramlintide | 103 | >200 | >200 |
| 139 | N-alpha-[(S)-4-Carboxy-4-(19-carboxynonadecanoylamino)butyryl]-[Glu14, Gln21, Gln35, Pro37]-pramlintide | 107.5 | >200 | >200 |
| 82 | N-alpha-[2-(2-{2-[2-(2-{2-[(S)-4-Carboxy-4-(17-carboxyheptadecanoylamino)butyrylamino]ethoxy}ethoxy)acetylamino] ethoxy}ethoxy)acetyl]-[Glu1, Glu14, His17, Pro37]-pramlintide | 108.5 | >200 | >200 |
| 137 | N-alpha-[(S)-4-Carboxy-4-(19-carboxynonadecanoylamino)butyryl]-[Gly1, Glu14, His17, Gln21, Gln35, Pro37]-pramlintide | 120.5 | >200 | >200 |
| 123 | N-alpha-[(S)-4-Carboxy-4-(19-carboxynonadecanoylamino)butyryl]-Glu-Arg-[Glu1, Glu14, His17, Pro37]-pramlintide | 136 | >200 | >200 |
| 167 | N-alpha-[2-(2-{2-[2-(2-{2-[(S)-4-Carboxy-4-(19-carboxyheptadecanoylamino)butyrylamino]ethoxy}ethoxy)acetylamino] ethoxy}ethoxy)acetyl]-[Glu14, His17, Glu21, Pro37]-pramlintide | 203 | >200 | >200 |
| 151 | N-epsilon1-[(S)-4-Carboxy-4-(19-carboxynonadecanoylamino)butyryl]-[Glu14, His17, Gln21, Ala25, Pro26, Ser28, Ser29, Pro37]-pramlintide | 209 | >200 | >200 |
| 161 | N-alpha-[(S)-4-Carboxy-4-(19-carboxynonadecanoylamino)butyryl]-Glu-Arg-[Glu1, Glu14, Arg17, Gln21, Pro37]-pramlintide | 232 | >200 | >200 |
| 40 | N-alpha-[(S)-4-Carboxy-4-(19-carboxynonadecanoylamino)butyryl]-Glu-[His1, Glu14, His17]-pramlintide | 248 | >200 | >200 |
| 125 | N-alpha-(19-carboxynonadecanoyl)-Glu-Glu-Arg-[Glu1, Glu14, His17, Pro37]-pramlintide | 288.5 | >200 | >200 |
| 155 | N-alpha-[(S)-4-Carboxy-4-(19-carboxynonadecanoylamino)butyryl]-Glu-Glu-[Arg1, Glu14, Arg17, Pro37]-pramlintide | 313 | >200 | >200 |
| 162 | N-alpha-[(S)-4-Carboxy-4-(19-carboxynonadecanoylamino)butyryl]-Glu-Arg-[Glu1, Glu14, Arg17, Gln21, Gln35, Pro37]-pramlintide | 411 | >200 | >200 |
| 157 | N-alpha-[(S)-4-Carboxy-4-(19-carboxynonadecanoylamino)butyryl]-Glu-Glu-[Arg1, Glu14, Arg17, Gln21, Pro37]-pramlintide | 465 | >200 | >200 |
| 163 | N-alpha-[(S)-4-Carboxy-4-(19-carboxynonadecanoylamino)butyryl]-Glu-Arg-[Glu1, Glu14, Arg17, Gln21, Gln31, Gln35, Pro37]-pramlintide | 1059 | >200 | >200 |
| 158 | N-alpha-[(S)-4-Carboxy-4-(19-carboxynonadecanoylamino)butyryl]-Glu-Glu-[Arg1, Glu14, Arg17, Gln21 ,Gln35, Pro37]-pramlintide | 1129 | >200 | >200 |
| 138 | N-alpha-[(S)-4-Carboxy-4-(19-carboxynonadecanoylamino)butyryl]-[Glu1, Glu14, Gln21, Gln35, Pro37]-pramlintide | 1512 | >200 | >200 |

TABLE 4-continued

| Example # | Name | Amylin receptor human EC$_{50}$ (pM) | Solubility pH 4.0 (μM) | Solubility pH 7.0 (μM) |
|---|---|---|---|---|
| 164 | N-alpha-[(S)-4-Carboxy-4-(19-carboxynonadecanoylamino)butyryl]-Glu-Arg-[Glu1, Glu14, Arg17, Gln21, Gln22, Gln31, Gln35, Pro37]-pramlintide | 1713 | >200 | >200 |
| 159 | N-alpha-[(S)-4-Carboxy-4-(19-carboxynonadecanoylamino)butyryl]-Glu-Glu-[Arg1, Glu14, Arg17, Gln21, Gln31, Gln35, Pro37]-pramlintide | | >200 | >200 |
| 160 | N-alpha-[(S)-4-Carboxy-4-(19-carboxynonadecanoylamino)butyryl]-Glu-Glu-[Arg1, Glu14, Arg17, Gln21, Gln22, Gln31, Gln35, Pro37]-pramlintide | | >200 | >200 |
| 169 | N-alpha-[2-(2-{2-[2-(2-{2-[(S)-4-Carboxy-4-(19-carboxyheptadecanoylamino)butyrylamino]ethoxy}ethoxy)acetylamino] ethoxy}ethoxy)acetyl]-[Glu14, His17, Ala21, Pro37]-pramlintide | | >200 | >200 |
| 171 | N-alpha-[(S)-4-Carboxy-4-(19-carboxynonadecanoylamino)butyryl]-[Glu14, Ser21, Ser22, Pro23, Ala25, Pro26, Ser28, Ser29, Asp31, Asp35, Pro37]-pramlintide | | >200 | >200 |
| 177 | N-epsilon1-[(S)-4-Carboxy-4-(19-carboxynonadecanoylamino)butyryl]-[Glu14, Arg17, Pro37]-pramlintide | | >200 | >200 |
| 178 | N-alpha-[2-(2-{2-[2-(2-{2-[(S)-4-Carboxy-4-(19-carboxyheptadecanoylamino)butyrylamino]ethoxy}ethoxy)acetylamino] ethoxy}ethoxy)acetyl]-[Glu14, Ala21, His35, Pro37]-pramlintide | | >200 | >200 |

As demonstrated in the Examples section herein, the polypeptides presented above have a solubility of greater than or equal to 100 μM (micromolar) at both pH 4 and pH7.

In one embodiment, the polypeptides of the present invention have a solubility of greater than or equal to 125 μM (micromolar) at both pH 4 and pH7.

In one embodiment, the polypeptides of the present invention have a solubility of greater than or equal to 150 μM (micromolar) at both pH 4 and pH7.

In one embodiment, the polypeptides of the present invention have a solubility of greater than or equal to 175 μM (micromolar) at both pH 4 and pH7.

In one embodiment, the polypeptides of the present invention have a solubility of greater than or equal to 200 μM (micromolar) at both pH 4 and pH7.

In one embodiment, the solubility is measured in a solubility assay as presented herein.

Table 5 presents a list of compounds that have physical stability of greater than or equal to 25 hours in a fibrillogenesis assay.

TABLE 5

| Example # | Name | Amylin receptor human EC$_{50}$ (pM) | Th T pH 4.0 lag time (h) | Th T pH 4.0 recovery (%) |
|---|---|---|---|---|
| 89 | N-alpha-[(S)-4-Carboxy-4-(19-carboxynonadecanoylamino)butyryl]-Gly-[His1, Glu14, Arg17, Pro37]-pramlintide | 25.5 | >45 | 91 |
| 90 | N-alpha-[(S)-4-Carboxy-4-(19-carboxynonadecanoylamino)butyryl]-[His1, Glu14, Arg17, Pro37]-pramlintide | 32.5 | >45 | 93 |
| 88 | N-alpha-[(S)-4-Carboxy-4-(19-carboxynonadecanoylamino)butyryl]-[Gly1, Glu14, Arg17, Pro37]-pramlintide | 36 | >45 | 87 |
| 96 | N-alpha-[(S)-4-Carboxy-4-(19-carboxynonadecanoylamino)butyryl]-[Arg1, Glu14, His17, Pro37]-pramlintide | 43 | >45 | 92 |
| 101 | N-alpha-[(S)-4-Carboxy-4-(19-carboxynonadecanoylamino)butyryl]-Gly-[Arg1, Glu14, His17, Pro37]-pramlintide | 51.5 | >45 | 98 |
| 53 | N-alpha-[(S)-4-Carboxy-4-(19-carboxynonadecanoylamino)butyryl]-[Glu14, Arg17, Pro37]-pramlintide | 53 | >45 | 96.2 |
| 91 | N-alpha-[(S)-4-Carboxy-4-(19-carboxynonadecanoylamino)butyryl]-[Gly1, Glu14, His17, Pro37]-pramlintide | 54 | 29 | 0 |

TABLE 5-continued

| Example # | Name | Amylin receptor human EC$_{50}$ (pM) | Th T pH 4.0 lag time (h) | Th T pH 4.0 recovery (%) |
|---|---|---|---|---|
| 130 | N-alpha-[(S)-4-Carboxy-4-(19-carboxynonadecanoylamino)butyryl]-[Glu14, His17, Gln21, Pro37]-pramlintide | 55.5 | >45 | 93 |
| 52 | N-alpha-[(S)-4-Carboxy-4-(19-carboxynonadecanoylamino)butyryl]-[Glu14, His17, Pro37]-pramlintide | 62 | >45 | 92.3 |
| 145 | N-alpha-[(S)-4-Carboxy-4-(19-carboxynonadecanoylamino)butyryl]-[Lys11, Glu14, His17, Pro37]-pramlintide | 80.5 | >45 | 91 |
| 124 | N-alpha-[(S)-4-Carboxy-4-(19-carboxynonadecanoylamino)butyryl]-Glu-Arg-[Glu1, Glu14, Arg17, Pro37]-pramlintide | 89.5 | >45 | 9.3 |
| 170 | N-alpha-[(S)-4-Carboxy-4-(19-carboxynonadecanoylamino)butyryl]-[Glu14, Arg18, Ser21, Ser22, Ser28, Ser29, Asp31, Asp35, Pro37]-pramlintide | 90 | >45 | 94 |
| 136 | N-alpha-[(S)-4-Carboxy-4-(19-carboxynonadecanoylamino)butyryl]-[Glu14, His17, Gln21, Gln35, Pro37]-pramlintide | 91 | >45 | 100 |
| 146 | N-alpha-[(S)-4-Carboxy-4-(19-carboxynonadecanoylamino)butyryl]-[Glu14, His17, Thr21, Pro37]-pramlintide | 91 | >45 | 87 |
| 84 | N-alpha-[(S)-4-Carboxy-4-(19-carboxynonadecanoylamino)butyryl]-[His1, Glu14, His17, Pro37]-pramlintide | 92.5 | 25.6 | 100 |
| 135 | N-alpha-[(S)-4-Carboxy-4-(19-carboxynonadecanoylamino)butyryl]-[Glu14, His17, Gln35, Pro37]-pramlintide | 103 | >45 | 100 |
| 137 | N-alpha-[(S)-4-Carboxy-4-(19-carboxynonadecanoylamino)butyryl]-[Gly1, Glu14, His17, Gln21, Gln35, Pro37]-pramlintide | 120.5 | 29 | 23 |
| 161 | N-alpha-[(S)-4-Carboxy-4-(19-carboxynonadecanoylamino)butyryl]-Glu-Arg-[Glu1, Glu14, Arg17, Gln21, Pro37]-pramlintide | 232 | >45 | 96 |
| 162 | N-alpha-[(S)-4-Carboxy-4-(19-carboxynonadecanoylamino)butyryl]-Glu-Arg-[Glu1, Glu14, Arg17, Gln21, Gln35, Pro37]-pramlintide | 411 | >45 | 98 |
| 163 | N-alpha-[(S)-4-Carboxy-4-(19-carboxynonadecanoylamino)butyryl]-Glu-Arg-[Glu1, Glu14, Arg17, Gln21, Gln31, Gln35, Pro37]-pramlintide | 1059 | >45 | 95 |
| 164 | N-alpha-[(S)-4-Carboxy-4-(19-carboxynonadecanoylamino)butyryl]-Glu-Arg-[Glu1, Glu14, Arg17, Gln21, Gln22, Gln31, Gln35, Pro37]-pramlintide | 1713 | >45 | 95 |
| 156 | N-alpha-[(S)-4-Carboxy-4-(19-carboxynonadecanoylamino)butyryl]-Glu-[Arg1, Glu14, Arg17, Pro37]-pramlintide | 66 | >45 | 99 |

As demonstrated in the Examples section herein, the polypeptides presented above have a physical stability of greater than or equal to 25 hours in a fibrillogenesis assay.

In one embodiment, the polypeptides of the present invention have a physical stability of greater than or equal to 30 hours.

In one embodiment, the polypeptides of the present invention have a physical stability of greater than or equal to 35 hours.

In one embodiment, the polypeptides of the present invention have a physical stability of greater than or equal to 40 hours.

In one embodiment, the polypeptides of the present invention have a physical stability of greater than or equal to 45 hours.

In one embodiment, the physical stability is measured in a fibrillogenesis assay as presented herein.

Table 6 presents a list of compounds that have a human amylin receptor EC$_{50}$ value of 1800 pM (picomolar) or less.

TABLE 6

| Example # | Name | Amylin receptor human EC$_{50}$ (pM) |
|---|---|---|
| 89 | N-alpha-[(S)-4-Carboxy-4-(19-carboxynonadecanoylamino)butyryl]-Gly-[His1, Glu14, Arg17, Pro37]-pramlintide | 25.5 |
| 90 | N-alpha-[(S)-4-Carboxy-4-(19-carboxynonadecanoylamino)butyryl]-[His1, Glu14, Arg17, Pro37]-pramlintide | 32.5 |

TABLE 6-continued

| Example # | Name | Amylin receptor human EC$_{50}$ (pM) |
|---|---|---|
| 97 | N-alpha-[(S)-4-Carboxy-4-(19-carboxynonadecanoylamino)butyryl]-[Arg1, Pro37]-pramlintide | 34 |
| 88 | N-alpha-[(S)-4-Carboxy-4-(19-carboxynonadecanoylamino)butyryl]-[Gly1, Glu14, Arg17, Pro37]-pramlintide | 36 |
| 166 | N-alpha-[(S)-4-Carboxy-4-(19-carboxynonadecanoylamino)butyryl]-[Glu14, Arg18, Gln21, Ala25, Pro26, Ser28, Ser29, Pro37]-pramlintide | 39 |
| 143 | N-alpha-[(S)-4-Carboxy-4-(19-carboxynonadecanoylamino)butyryl]-[His1, Glu14, Arg18, Pro37]-pramlintide | 41.5 |
| 96 | N-alpha-[(S)-4-Carboxy-4-(19-carboxynonadecanoylamino)butyryl]-[Arg1, Glu14, His17, Pro37]-pramlintide | 43 |
| 121 | N-alpha-(19-carboxynonadecanoyl)-Glu-Glu-Arg-[Glu1, Pro37]-pramlintide | 45 |
| 102 | N-alpha-[(S)-4-Carboxy-4-(19-carboxynonadecanoylamino)butyryl]-Gly-[Arg1, Glu14, Pro37]-pramlintide | 49.5 |
| 101 | N-alpha-[(S)-4-Carboxy-4-(19-carboxynonadecanoylamino)butyryl]-Gly-[Arg1, Glu14, His17, Pro37]-pramlintide | 51.5 |
| 92 | N-alpha-[(S)-4-Carboxy-4-(19-carboxynonadecanoylamino)butyryl]-Gly-[His1, Glu14, His17, Pro37]-pramlintide | 52 |
| 103 | N-alpha-[(S)-4-Carboxy-4-(19-carboxynonadecanoylamino)butyryl]-Gly-[Arg1, Pro37]-pramlintide | 52.5 |
| 53 | N-alpha-[(S)-4-Carboxy-4-(19-carboxynonadecanoylamino)butyryl]-[Glu14, Arg17, Pro37]-pramlintide | 53 |
| 91 | N-alpha-[(S)-4-Carboxy-4-(19-carboxynonadecanoylamino)butyryl]-[Gly1, Glu14, His17, Pro37]-pramlintide | 54 |
| 86 | N-alpha-[(S)-4-Carboxy-4-(19-carboxynonadecanoylamino)butyryl]-[Glu14, Pro37]-pramlintide | 55 |
| 130 | N-alpha-[(S)-4-Carboxy-4-(19-carboxynonadecanoylamino)butyryl]-[Glu14, His17, Gln21, Pro37]-pramlintide | 55.5 |
| 52 | N-alpha-[(S)-4-Carboxy-4-(19-carboxynonadecanoylamino)butyryl]-[Glu14, His17, Pro37]-pramlintide | 62 |
| 45 | N-alpha-[(S)-4-Carboxy-4-(17-carboxyheptadecanoylamino)butyryl]-His-His-[His1, Glu14, His17]-pramlintide | 62.4 |
| 106 | N-alpha-[(S)-4-Carboxy-4-(19-carboxynonadecanoylamino)butyryl]-[Ser1, Glu14, His17, Pro37]-pramlintide | 62.5 |
| 122 | N-alpha-[(S)-4-Carboxy-4-(19-carboxynonadecanoylamino)butyryl]-Glu-Arg-[Glu1, Pro37]-pramlintide | 63 |
| 168 | N-alpha-[2-(2-{2-[2-(2-{2-[(S)-4-Carboxy-4-(19-carboxyheptadecanoylamino)butyrylamino]ethoxy}ethoxy)acetylamino]ethoxy}ethoxy)acetyl]-[Glu14, His17, Lys21, Pro37]-pramlintide | 71 |
| 104 | N-alpha-[(S)-4-Carboxy-4-(19-carboxynonadecanoylamino)butyryl]-[des1, Glu14, His17, Pro37]-pramlintide | 79.5 |
| 145 | N-alpha-[(S)-4-Carboxy-4-(19-carboxynonadecanoylamino)butyryl]-[Lys11, Glu14, His17, Pro37]-pramlintide | 80.5 |
| 10 | N-alpha-[(S)-4-Carboxy-4-(19-carboxynonadecanoylamino)butyryl]-[Glu1, Glu14, His17, Arg18, Pro37]-pramlintide | 82.3 |
| 109 | N-alpha-[(S)-4-Carboxy-4-(19-carboxynonadecanoylamino)butyryl]-[His1, Glu14, Pro37]-pramlintide | 84.5 |
| 108 | N-alpha-[(S)-4-Carboxy-4-(19-carboxynonadecanoylamino)butyryl]-[des1, Glu14, Pro37]-pramlintide | 88 |
| 124 | N-alpha-[(S)-4-Carboxy-4-(19-carboxynonadecanoylamino)butyryl]-Glu-Arg-[Glu1, Glu14, Arg17, Pro37]-pramlintide | 89.5 |
| 170 | N-alpha-[(S)-4-Carboxy-4-(19-carboxynonadecanoylamino)butyryl]-[Glu14, Arg18, Ser21, Ser22, Ser28, Ser29, Asp31, Asp35, Pro37]-pramlintide | 90 |
| 136 | N-alpha-[(S)-4-Carboxy-4-(19-carboxynonadecanoylamino)butyryl]-[Glu14, His17, Gln21, Gln35, Pro37]-pramlintide | 91 |
| 146 | N-alpha-[(S)-4-Carboxy-4-(19-carboxynonadecanoylamino)butyryl]-[Glu14, His17, Thr21, Pro37]-pramlintide | 91 |
| 84 | N-alpha-[(S)-4-Carboxy-4-(19-carboxynonadecanoylamino)butyryl]-[His1, Glu14, His17, Pro37]-pramlintide | 92.5 |
| 135 | N-alpha-[(S)-4-Carboxy-4-(19-carboxynonadecanoylamino)butyryl]-[Glu14, His17, Gln35, Pro37]-pramlintide | 103 |
| 19 | N-alpha-[(S)-4-Carboxy-4-(19-carboxynonadecanoylamino)butyryl]-His-His-[His1, Glu14, His17, Ala25, Pro26, Ser28, Ser29]-pramlintide | 105.1 |
| 139 | N-alpha-[(S)-4-Carboxy-4-(19-carboxynonadecanoylamino)butyryl]-[Glu14, Gln21, Gln35, Pro37]-pramlintide | 107.5 |
| 82 | N-alpha-[2-(2-{2-[2-(2-{2-[(S)-4-Carboxy-4-(17-carboxyheptadecanoylamino)butyrylamino]ethoxy}ethoxy)acetylamino]ethoxy}ethoxy)acetyl]-[Glu1, Glu14, His17, Pro37]-pramlintide | 108.5 |
| 137 | N-alpha-[(S)-4-Carboxy-4-(19-carboxynonadecanoylamino)butyryl]-[Gly1, Glu14, His17, Gln21, Gln35, Pro37]-pramlintide | 120.5 |
| 123 | N-alpha-[(S)-4-Carboxy-4-(19-carboxynonadecanoylamino)butyryl]-Glu-Arg-[Glu1, Glu14, His17, Pro37]-pramlintide | 136 |
| 167 | N-alpha-[2-(2-{2-[2-(2-{2-[(S)-4-Carboxy-4-(19-carboxyheptadecanoylamino)butyrylamino]ethoxy}ethoxy)acetylamino]ethoxy}ethoxy)acetyl]-[Glu14, His17, Glu21, Pro37]-pramlintide | 203 |

TABLE 6-continued

| Example # | Name | Amylin receptor human EC$_{50}$ (pM) |
|---|---|---|
| 151 | N-epsilon1-[(S)-4-Carboxy-4-(19-carboxynonadecanoylamino)butyryl]-[Glu14, His17, Gln21, Ala25, Pro26, Ser28, Ser29, Pro37]-pramlintide | 209 |
| 161 | N-alpha-[(S)-4-Carboxy-4-(19-carboxynonadecanoylamino)butyryl]-Glu-Arg-[Glu1, Glu14, Arg17, Gln21, Pro37]-pramlintide | 232 |
| 125 | N-alpha-(19-carboxynonadecanoyl)-Glu-Glu-Arg-[Glu1, Glu14, His17, Pro37]-pramlintide | 288.5 |
| 155 | N-alpha-[(S)-4-Carboxy-4-(19-carboxynonadecanoylamino)butyryl]-Glu-Glu-[Arg1, Glu14, Arg17, Pro37]-pramlintide | 313 |
| 162 | N-alpha-[(S)-4-Carboxy-4-(19-carboxynonadecanoylamino)butyryl]-Glu-Arg-[Glu1, Glu14, Arg17, Gln21, Gln35, Pro37]-pramlintide | 411 |
| 157 | N-alpha-[(S)-4-Carboxy-4-(19-carboxynonadecanoylamino)butyryl]-Glu-Glu-[Arg1, Glu14, Arg17, Gln21, Pro37]-pramlintide | 465 |
| 163 | N-alpha-[(S)-4-Carboxy-4-(19-carboxynonadecanoylamino)butyryl]-Glu-Arg-[Glu1, Glu14, Arg17, Gln21, Gln31, Gln35, Pro37]-pramlintide | 1059 |
| 158 | N-alpha-[(S)-4-Carboxy-4-(19-carboxynonadecanoylamino)butyryl]-Glu-Glu-[Arg1, Glu14, Arg17, Gln21, Gln35, Pro37]-pramlintide | 1129 |
| 138 | N-alpha-[(S)-4-Carboxy-4-(19-carboxynonadecanoylamino)butyryl]-[Glu1, Glu14, Gln21, Gln35, Pro37]-pramlintide | 1512 |
| 164 | N-alpha-[(S)-4-Carboxy-4-(19-carboxynonadecanoylamino)butyryl]-Glu-Arg-[Glu1, Glu14, Arg17, Gln21, Gln22, Gln31, Gln35, Pro37]-pramlintide | 1713 |
| 153 | N-alpha-[(S)-4-Carboxy-4-(19-carboxynonadecanoylamino)butyryl]-Gly-[Arg1, Glu14, Arg17, Pro37]-pramlintide | 43 |
| 154 | N-alpha-[(S)-4-Carboxy-4-(19-carboxynonadecanoylamino)butyryl]-[Arg17, Pro37]-pramlintide | 53 |
| 156 | N-alpha-[(S)-4-Carboxy-4-(19-carboxynonadecanoylamino)butyryl]-Glu-[Arg1, Glu14, Arg17, Pro37]-pramlintide | 66 |
| 152 | N-alpha-[(S)-4-Carboxy-4-(19-carboxynonadecanoylamino)butyryl]-[Arg14, Arg17, Pro37]-pramlintide | 129 |

As demonstrated in the Examples section herein, the polypeptides presented above have a human amylin EC$_{50}$ value of 1800 pM (picomolar) or less.

In one embodiment, the polypeptides of the present invention have a human amylin EC$_{50}$ value of 1500 pM (picomolar) or less.

In one embodiment, the polypeptides of the present invention have a human amylin EC$_{50}$ value of 1200 pM (picomolar) or less.

In one embodiment, the polypeptides of the present invention have a human amylin EC$_{50}$ value of 1000 pM (picomolar) or less.

In one embodiment, the polypeptides of the present invention have a human amylin EC$_{50}$ value of 800 pM (picomolar) or less.

In one embodiment, the polypeptides of the present invention have a human amylin EC$_{50}$ value of 600 pM (picomolar) or less.

In one embodiment, the polypeptides of the present invention have a human amylin EC$_{50}$ value of 400 pM (picomolar) or less.

In one embodiment, the polypeptides of the present invention have a human amylin EC$_{50}$ value of 200 pM (picomolar) or less.

In one embodiment, the polypeptides of the present invention have a human amylin EC$_{50}$ value of 100 pM (picomolar) or less.

In one embodiment, the polypeptides of the present invention have a human amylin EC$_{50}$ value of 75 pM (picomolar) or less.

In one embodiment, the polypeptides of the present invention have a human amylin EC$_{50}$ value of 60 pM (picomolar) or less.

In one embodiment, the human amylin EC$_{50}$ is measured in an assay as presented herein.

Table 7 presents a list of compounds that have a human amylin receptor EC$_{50}$ value of 1800 pM (picomolar) or less.

TABLE 7

| Example # | Name | Amylin receptor human EC$_{50}$ (pM) | CTa receptor human EC$_{50}$ (pM) |
|---|---|---|---|
| 89 | N-alpha-[(S)-4-Carboxy-4-(19-carboxynonadecanoylamino)butyryl]-Gly-[His1, Glu14, Arg17, Pro37]-pramlintide | 25.5 | 39.5 |
| 90 | N-alpha-[(S)-4-Carboxy-4-(19-carboxynonadecanoylamino)butyryl]-pramlintide | 32.5 | 47.5 |
| 97 | N-alpha-[(S)-4-Carboxy-4-(19-carboxynonadecanoylamino)butyryl-[Arg1, Pro37]-pramlintide | 34 | 38.5 |
| 88 | N-alpha-[(S)-4-Carboxy-4-(19-carboxynonadecanoylamino)butyryl]-[Gly1, Glu14, Arg17, Pro37]-pramlintide | 36 | 55 |
| 166 | N-alpha-[(S)-4-Carboxy-4-(19-carboxynonadecanoylamino)butyryl]- | 39 | 34 |

TABLE 7-continued

| Example # | Name | Amylin receptor human EC$_{50}$ (pM) | CTa receptor human EC$_{50}$ (pM) |
|---|---|---|---|
| | [Glu14, Arg18, Gln21, Ala25, Pro26, Ser28, Ser29, Pro37]-pramlintide | | |
| 143 | N-alpha-[(S)-4-Carboxy-4-(19-carboxynonadecanoylamino)butyryl]-[His1, Glu14, Arg18, Pro37]-pramlintide | 41.5 | 22 |
| 96 | N-alpha-[(S)-4-Carboxy-4-(19-carboxynonadecanoylamino)butyryl]-[Arg1, Glu14, His17, Pro37]-pramlintide | 43 | 55 |
| 121 | N-alpha-(19-carboxynonadecanoyl)-Glu-Glu-Arg-[Glu1, Pro37]-pramlintide | 45 | 61.5 |
| 102 | N-alpha-[(S)-4-Carboxy-4-(19-carboxynonadecanoylamino)butyryl]-Gly-[Arg1, Glu14, Pro37]-pramlintide | 49.5 | 50.5 |
| 101 | N-alpha-[(S)-4-Carboxy-4-(19-carboxynonadecanoylamino)butyryl]-Gly-[Arg1, Glu14, His17, Pro37]-pramlintide | 51.5 | 45.5 |
| 92 | N-alpha-[(S)-4-Carboxy-4-(19-carboxynonadecanoylamino)butyryl]-Gly-[His1, Glu14, His17, Pro37]-pramlintide | 52 | 49 |
| 103 | N-alpha-[(S)-4-Carboxy-4-(19-carboxynonadecanoylamino)butyryl]-Gly-[Arg1, Pro37]-pramlintide | 52.5 | 75 |
| 53 | N-alpha-[(S)-4-Carboxy-4-(19-carboxynonadecanoylamino)butyryl]-[Glu14, Arg17, Pro37]-pramlintide | 53 | 79.7 |
| 91 | N-alpha-[(S)-4-Carboxy-4-(19-carboxynonadecanoylamino)butyryl]-[Gly1, Glu14, His17, Pro37]-pramlintide | 54 | 52 |
| 86 | N-alpha-[(S)-4-Carboxy-4-(19-carboxynonadecanoylamino)butyryl]-[Glu14, Pro37]-pramlintide | 55 | 52.5 |
| 130 | N-alpha-[(S)-4-Carboxy-4-(19-carboxynonadecanoylamino)butyryl]-[Glu14, His17, Gln21, Pro37]-pramlintide | 55.5 | 31.5 |
| 52 | N-alpha-[(S)-4-Carboxy-4-(19-carboxynonadecanoylamino)butyryl]-[Glu14, His17, Pro37]-pramlintide | 62 | 53.7 |
| 106 | N-alpha-[(S)-4-Carboxy-4-(19-carboxynonadecanoylamino)butyryl]-[Ser1, Glu14, His17, Pro37]-pramlintide | 62.5 | 70.5 |
| 122 | N-alpha-[(S)-4-Carboxy-4-(19-carboxynonadecanoylamino)butyryl]-Glu-Arg-[Glu1, Pro37]-pramlintide | 63 | 61 |
| 168 | N-alpha-[2-(2-{2-[2-(2-{2-[(S)-4-Carboxy-4-(19-carboxyheptadecanoylamino)butyrylamino]ethoxy}ethoxy)acetylamino]ethoxy}ethoxy)acetyl]-[Glu14, His17, Lys21, Pro37]-pramlintide | 71 | 85 |
| 104 | N-alpha-[(S)-4-Carboxy-4-(19-carboxynonadecanoylamino)butyryl]-[des1, Glu14, His17, Pro37]-pramlintide | 79.5 | 106.5 |
| 145 | N-alpha-[(S)-4-Carboxy-4-(19-carboxynonadecanoylamino)butyryl]-[Lys11, Glu14, His17, Pro37]-pramlintide | 80.5 | 83 |
| 10 | N-alpha-[(S)-4-Carboxy-4-(19-carboxynonadecanoylamino)butyryl]-[Glu1, Glu14, His17, Arg18, Pro37]-pramlintide | 82.3 | 86.4 |
| 109 | N-alpha-[(S)-4-Carboxy-4-(19-carboxynonadecanoylamino)butyryl]-[His1, Glu14, Pro37]-pramlintide | 84.5 | 72.5 |
| 108 | N-alpha-[(S)-4-Carboxy-4-(19-carboxynonadecanoylamino)butyryl]-[des1, Glu14, Pro37]-pramlintide | 88 | 73.5 |
| 124 | N-alpha-[S)-4-Carboxy-4-(19-carboxynonadecanoylamino)butyryl]-Glu-Arg-[Glu1, Glu14, Arg17, Pro37]-pramlintide | 89.5 | 367 |
| 170 | N-alpha-[(S)-4-Carboxy-4-(19-carboxynonadecanoylamino)butyryl]-[Glu14, Arg18, Ser21, Ser22, Ser28, Ser29, Asp31, Asp35, Pro37]-pramlintide | 90 | 76 |
| 136 | N-alpha-[(S)-4-Carboxy-4-(19-carboxynonadecanoylamino)butyryl]-[Glu14, His17, Gln21, Gln35, Pro37]-pramlintide | 91 | 45 |
| 146 | N-alpha-[(S)-4-Carboxy-4-(19-carboxynonadecanoylamino)butyryl]-[Glu14, His17, Thr21, Pro37]-pramlintide | 91 | 59.5 |

TABLE 7-continued

| Example # | Name | Amylin receptor human EC$_{50}$ (pM) | CTa receptor human EC$_{50}$ (pM) |
|---|---|---|---|
| 84 | N-alpha-[(S)-4-Carboxy-4-(19-carboxynonadecanoylamino)butyryl]-[His1, Glu14, His17, Pro37]-pramlintide | 92.5 | 67 |
| 135 | N-alpha-[(S)-4-Carboxy-4-(19-carboxynonadecanoylamino)butyryl]-[Glu14, His17, Gln35, Pro37]-pramlintide | 103 | 97 |
| 139 | N-alpha-[(S)-4-Carboxy-4-(19-carboxynonadecanoylamino)butyryl]-[Glu14, Gln21, Gln35, Pro37]-pramlintide | 107.5 | 58.5 |
| 82 | N-alpha-[2-(2-{2-[2-(2-{2-[(S)-4-Carboxy-4-(17-carboxyheptadecanoylamino)butyrylamino]ethoxy}ethoxy)acetylamino] ethoxy}ethoxy)acetyl]-[Glu1, Glu14, His17, Pro37]-pramlintide | 108.5 | 288.5 |
| 137 | N-alpha-[(S)-4-Carboxy-4-(19-carboxynonadecanoylamino)butyryl]-[Gly1, Glu14, His17, Gln21, Gln35, Pro37]-pramlintide | 120.5 | 72 |
| 123 | N-alpha-[(S)-4-Carboxy-4-(19-carboxynonadecanoylamino)butyryl]-Glu-Arg-[Glu1, Glu14, His17, Pro37]-pramlintide | 136 | 377.5 |
| 167 | N-alpha-[2-(2-{2-[2-(2-{2-[(S)-4-Carboxy-4-(19-carboxyheptadecanoylamino)butyrylamino]ethoxy}ethoxy)acetylamino] ethoxy}ethoxy)acetyl]-[Glu14, His17, Glu21, Pro37]-pramlintide | 203 | 113 |
| 151 | N-epsilon1-[(S)-4-Carboxy-4-(19-carboxynonadecanoylamino)butyryl]-[Glu14, His17, Gln21, Ala25, Pro26, Ser28, Ser29, Pro37]-pramlintide | 209 | 67.5 |
| 161 | N-alpha-[(S)-4-Carboxy-4-(19-carboxynonadecanoylamino)butyryl]-Glu-Arg-[Glu1, Glu14, Arg17, Gln21, Pro37]-pramlintide | 232 | 1133 |
| 125 | N-alpha-(19-carboxynonadecanoyl)-Glu-Glu-Arg-[Glu1, Glu14, His17, Pro37]-pramlintide | 288.5 | 443 |
| 155 | N-alpha-[(S)-4-Carboxy-4-(19-carboxynonadecanoylamino)butyryl]-Glu-Glu-[Arg1, Glu14, Arg17, Pro37]-pramlintide | 313 | 526 |
| 157 | N-alpha-[(S)-4-Carboxy-4-(19-carboxynonadecanoylamino)butyryl]-Glu-Glu-[Arg1, Glu14, Arg17, Gln21, Pro37]-pramlintide | 465 | 547 |
| 158 | N-alpha-[(S)-4-Carboxy-4-(19-carboxynonadecanoylamino)butyryl]-Glu-Glu-[Arg1, Glu14, Arg17, Gln21, Gln35, Pro37]-pramlintide | 1129 | 1188 |
| 138 | N-alpha-[(S)-4-Carboxy-4-(19-carboxynonadecanoylamino)butyryl]-[Glu1, Glu14, Gln21, Gln35, Pro37]-pramlintide | 1512 | 496.5 |
| 153 | N-alpha-[(S)-4-Carboxy-4-(19-carboxynonadecanoylamino)butyryl]-Gly-[Arg1, Glu14, Arg17, Pro37]-pramlintide | 43 | 41 |
| 154 | N-alpha-[(S)-4-Carboxy-4-(19-carboxynonadecanoylamino)butyryl]-[Arg17, Pro37]-pramlintide | 53 | 57 |
| 156 | N-alpha-[(S)-4-Carboxy-4-(19-carboxynonadecanoylamino)butyryl]-Glu-[Arg1, Glu14, Arg17, Pro37]-pramlintide | 66 | 168 |
| 152 | N-alpha-[(S)-4-Carboxy-4-(19-carboxynonadecanoylamino)butyryl]-[Arg14, Arg17, Pro37]-pramlintide | 129 | 453 |

As demonstrated in the Examples section herein, the polypeptides presented above have a human calcitonin EC$_{50}$ value of 1800 pM (picomolar) or less.

In one embodiment, the polypeptides of the present invention have a human calcitonin EC$_{50}$ value of 1500 pM (picomolar) or less.

In one embodiment, the polypeptides of the present invention have a human calcitonin EC$_{50}$ value of 1200 pM (picomolar) or less.

In one embodiment, the polypeptides of the present invention have a human calcitonin EC$_{50}$ value of 1000 pM (picomolar) or less.

In one embodiment, the polypeptides of the present invention have a human calcitonin EC$_{50}$ value of 800 pM (picomolar) or less.

In one embodiment, the polypeptides of the present invention have a human calcitonin EC$_{50}$ value of 600 pM (picomolar) or less.

In one embodiment, the polypeptides of the present invention have a human calcitonin EC$_{50}$ value of 400 pM (picomolar) or less.

In one embodiment, the polypeptides of the present invention have a human calcitonin EC$_{50}$ value of 200 pM (picomolar) or less.

In one embodiment, the polypeptides of the present invention have a human calcitonin EC$_{50}$ value of 100 pM (picomolar) or less.

In one embodiment, the polypeptides of the present invention have a human calcitonin EC$_{50}$ value of 80 pM (picomolar) or less.

In one embodiment, the human calcitonin $EC_{50}$ is measured in an assay as presented herein.

Table 8 presents a list of compounds that have a human amylin receptor $EC_{50}$ value of 1800 pM (picomolar) or less, a solubility of 150 µM or more at pH7 and a physical stability of 25 hours or more in a fibrillogensis assay.

TABLE 8

| Example # | Name | Amylin receptor human $EC_{50}$ (pM) | Solubility pH 7.0 (M) | ThT pH 4.0 Lag time (h) |
|---|---|---|---|---|
| 89 | N-alpha-[(S)-4-Carboxy-4-(19-carboxynonadecanoylamino)butyryl]-Gly-[His1, Glu14, Arg17, Pro37]-pramlintide | 25.5 | >200 | >45 |
| 90 | N-alpha-[(S)-4-Carboxy-4-(19-carboxynonadecanoylamino)butyryl]-[His1, Glu14, Arg17, Pro37]-pramlintide | 32.5 | >200 | >45 |
| 88 | N-alpha-[(S)-4-Carboxy-4-(19-carboxynonadecanoylamino)butyryl]-[Gly1, Glu14, Arg17, Pro37]-pramlintide | 36 | >200 | >45 |
| 96 | N-alpha-[(S)-4-Carboxy-4-(19-carboxynonadecanoylamino)butyryl]-[Arg1, Glu14, His17, Pro37]-pramlintide | 43 | >200 | >45 |
| 101 | N-alpha-[(S)-4-Carboxy-4-(19-carboxynonadecanoylamino)butyryl]-Gly-[Arg1, Glu14, His17, Pro37]-pramlintide | 51.5 | >200 | >45 |
| 53 | N-alpha-[(S)-4-Carboxy-4-(19-carboxynonadecanoylamino)butyryl]-[Glu14, Arg17, Pro37]-pramlintide | 53 | >200 | >45 |
| 91 | N-alpha-[(S)-4-Carboxy-4-(19-carboxynonadecanoylamino)butyryl]-[Gly1, Glu14, His17, Pro37]-pramlintide | 54 | >200 | 29 |
| 130 | N-alpha-[(S)-4-Carboxy-4-(19-carboxynonadecanoylamino)butyryl]-[Glu14, His17, Gln21, Pro37]-pramlintide | 55.5 | >200 | >45 |
| 52 | N-alpha-[(S)-4-Carboxy-4-(19-carboxynonadecanoylamino)butyryl]-[Glu14, His17, Pro37]-pramlintide | 62 | >200 | >45 |
| 145 | N-alpha-[(S)-4-Carboxy-4-(19-carboxynonadecanoylamino)butyryl]-[Lys11, Glu14, His17, Pro37]-pramlintide | 80.5 | >200 | >45 |
| 124 | N-alpha-[(S)-4-Carboxy-4-(19-carboxynonadecanoylamino)butyryl]-Glu-Arg-[Glu1, Glu14, Arg17, Pro37]-pramlintide | 89.5 | >200 | >45 |
| 170 | N-alpha-[(S)-4-Carboxy-4-(19-carboxynonadecanoylamino)butyryl]-[Glu14, Arg18, Ser21, Ser22, Ser28, Ser29, Asp31, Asp35, Pro37]-pramlintide | 90 | >200 | >45 |
| 136 | N-alpha-[(S)-4-Carboxy-4-(19-carboxynonadecanoylamino)butyryl]-[Glu14, His17, Gln21, Gln35, Pro37]-pramlintide | 91 | >200 | >45 |
| 146 | N-alpha-[(S)-4-Carboxy-4-(19-carboxynonadecanoylamino)butyryl]-[Glu14, His17, Thr21, Pro37]-pramlintide | 91 | >200 | >45 |
| 84 | N-alpha-[(S)-4-Carboxy-4-(19-carboxynonadecanoylamino)butyryl]-[His1, Glu14, His17, Pro37]-pramlintide | 92.5 | >200 | 25.6 |
| 135 | N-alpha-[(S)-4-Carboxy-4-(19-carboxynonadecanoylamino)butyryl]-[Glu14, His17, Gln35, Pro37]-pramlintide | 103 | >200 | >45 |
| 137 | N-alpha-[(S)-4-Carboxy-4-(19-carboxynonadecanoylamino)butyryl]-[Gly1, Glu14, His17, Gln21, Gln35, Pro37]-pramlintide | 120.5 | >200 | 29 |
| 161 | N-alpha-[(S)-4-Carboxy-4-(19-carboxynonadecanoylamino)butyryl]-Glu-Arg-[Glu1, Glu14, Arg17, Gln21, Pro37]-pramlintide | 232 | >200 | >45 |
| 162 | N-alpha-[(S)-4-Carboxy-4-(19-carboxynonadecanoylamino)butyryl]-Glu-Arg-[Glu1, Glu14, Arg17, Gln21, Gln35, Pro37]-pramlintide | 411 | >200 | >45 |
| 163 | N-alpha-[(S)-4-Carboxy-4-(19-carboxynonadecanoylamino)butyryl]-Glu-Arg-[Glu1, Glu14, Arg17, Gln21, Gln31, Gln35, Pro37]-pramlintide | 1059 | >200 | >45 |
| 164 | N-alpha-[(S)-4-Carboxy-4-(19-carboxynonadecanoylamino)butyryl]-Glu-Arg-[Glu1, Glu14, Arg17, Gln21, Gln22, Gln31, Gln35, Pro37]-pramlintide | 1713 | >200 | >45 |

In one embodiment, the polypeptides of the present invention have a human amylin $EC_{50}$ value of 1800 pM (picomolar) or less, and a solubility of greater than 150 µM at pH7, and a physical stability of greater than or equal to 25 hours in a fibrillogenesis assay.

In one embodiment, the human amylin $EC_{50}$, solubility at pH7 and physical stability is measured in assays as presented herein.

Table 9 presents a list of compounds that have a human amylin receptor $EC_{50}$ value of 1800 pM (picomolar) or less, a solubility of 200 µM or more at pH7 and a physical stability of 45 hours or more in a fibrillogensis assay.

TABLE 9

| Example # | Name | Amylin receptor human $EC_{50}$ (pM) | Solubility pH 7.0 (µM) | Solubility pH 7.5 (µM) | ThT pH 4.0 lag time (hr) |
|---|---|---|---|---|---|
| 89 | N-alpha-[(S)-4-Carboxy-4-(19-carboxynonadecanoylamino)butyryl]-Gly-[His1, Glu14, Arg17, Pro37]-pramlintide | 25.5 | >200 | >200 | >45 |
| 90 | N-alpha-[(S)-4-Carboxy-4-(19-carboxynonadecanoylamino)butyryl]-[His1, Glu14, Arg17, Pro37]-pramlintide | 32.5 | >200 | >200 | >45 |

TABLE 9-continued

| Example # | Name | Amylin receptor human EC$_{50}$ (pM) | Solubility pH 7.0 (μM) | Solubility pH 7.5 (μM) | ThT pH 4.0 lag time (hr) |
|---|---|---|---|---|---|
| 88 | N-alpha-[S)-4-Carboxy-4-(19-carboxynonadecanoylamino)butyryl]-[Gly1, Glu14, Arg17, Pro37]-pramlintide | 36 | >200 | >200 | >45 |
| 96 | N-alpha-[(S)-4-Carboxy-4-(19-carboxynonadecanoylamino)butyryl]-[Arg1, Glu14, His17, Pro37]-pramlintide | 43 | >200 | >200 | >45 |
| 101 | N-alpha-[(S)-4-Carboxy-4-(19-carboxynonadecanoylamino)butyryl]-Gly-[Arg1, Glu14, His17, Pro37]-pramlintide | 51.5 | >200 | >200 | >45 |
| 53 | N-alpha-[(S)-4-Carboxy-4-(19-carboxynonadecanoylamino)butyryl]-[Glu14, Arg17, Pro37]-pramlintide | 53 | >200 | >200 | >45 |
| 130 | N-alpha-[(S)-4-Carboxy-4-(19-carboxynonadecanoylamino)butyryl]-[Glu14, His17, Gln21, Pro37]-pramlintide | 55.5 | >200 | >200 | >45 |
| 52 | N-alpha-[(S)-4-Carboxy-4-(19-carboxynonadecanoylamino)butyryl]-[Glu14, His17, Pro37]-pramlintide | 62 | >200 | >200 | >45 |
| 145 | N-alpha-[(S)-4-Carboxy-4-(19-carboxynonadecanoylamino)butyryl]-[Lys11, Glu14, His17, Pro37]-pramlintide | 80.5 | >200 | >200 | >45 |
| 124 | N-alpha-[(S)-4-Carboxy-4-(19-carboxynonadecanoylamino)butyryl]-Glu-Arg-[Glu1, Glu14, Arg17, Pro37]-pramlintide | 89.5 | >200 | >200 | >45 |
| 170 | N-alpha-[(S)-4-Carboxy-4-(19-carboxynonadecanoylamino)butyryl]-[Glu14, Arg18, Ser21, Ser22, Ser28, Ser29, Asp31, Asp35, Pro37]-pramlintide | 90 | >200 | >200 | >45 |
| 136 | N-alpha-[(S)-4-Carboxy-4-(19-carboxynonadecanoylamino)butyryl]-[Glu14, His17, Gln21, Gln35, Pro37]-pramlintide | 91 | >200 | >200 | >45 |
| 146 | N-alpha-[(S)-4-Carboxy-4-(19-carboxynonadecanoylamino)butyryl]-[Glu14, His17, Thr21, Pro37]-pramlintide | 91 | >200 | >200 | >45 |
| 135 | N-alpha-[(S)-4-Carboxy-4-(19-carboxynonadecanoylamino)butyryl]-[Glu14, His17, Gln35, Pro37]-pramlintide | 103 | >200 | >200 | >45 |
| 161 | N-alpha-[(S)-4-Carboxy-4-(19-carboxynonadecanoylamino)butyryl]-Glu-Arg-[Glu1, Glu14, Arg17, Gln21, Pro37]-pramlintide | 232 | >200 | >200 | >45 |
| 162 | N-alpha-[(S)-4-Carboxy-4-(19-carboxynonadecanoylamino)butyryl]-Glu-Arg-[Glu1, Glu14, Arg17, Gln21, Gln35, Pro37]-pramlintide | 411 | >200 | >200 | >45 |
| 163 | N-alpha-[(S)-4-Carboxy-4-(19-carboxynonadecanoylamino)butyryl]-Glu-Arg-[Glu1, Glu14, Arg17, Gln21, Gln31, Gln35, Pro37]-pramlintide | 1059 | >200 | >200 | >45 |
| 164 | N-alpha-[(S)-4-Carboxy-4-(19-carboxynonadecanoylamino)butyryl]-Glu-Arg-[Glu1, Glu14, Arg17, Gln21, Gln22, Gln31, Gln35, Pro37]-pramlintide | 1713 | >200 | >200 | >45 |

In one embodiment, the polypeptides of the present invention have a human amylin EC$_{50}$ value of 1800 pM (picomolar) or less, and a solubility of greater than 200 μM at pH7, and a physical stability of greater than or equal to 45 hours in a fibrillogenesis assay.

In one embodiment, the human amylin EC$_{50}$, solubility at pH7 and physical stability is measured in assays as presented herein.

In one aspect of the invention the amylin derivatives are selected from the group consisting of: N-alpha-[(S)-4-Carboxy-4-(19-carboxynonadecanoylamino)butyryl]-[His1,Glu14,His17,Arg18]-pramlintide, N-alpha-[(S)-4-Carboxy-4-(19-carboxynonadecanoylamino)butyryl]-[His1,Glu8,Glu14,His17,Arg18]-pramlintide, N-alpha-[(S)-4-Carboxy-4-(19-carboxynonadecanoylamino)butyryl]-[des1,Gly3,Glu14,His17,Arg18,Glu31,Gly35]-pramlintide, N-alpha-[(S)-4-Carboxy-4-(19-carboxynonadecanoylamino)butyryl]-[des1,Gly3,Glu14,His17,Arg18,Gln21,Gln22,Glu31,Gly35]-pramlintide, N-alpha-[(S)-4-Carboxy-4-(19-carboxynonadecanoylamino)butyryl]-[Glu1,Glu14,His17,Arg18]-pramlintide, N-alpha-[(S)-4-Carboxy-4-(19-carboxynonadecanoylamino)butyryl]-[His1,Glu14,His17,Arg18,Ala25,Pro26,Ser28,Ser29]-pramlintide, N-alpha-[(S)-4-Carboxy-4-(19-carboxynonadecanoylamino)butyryl]-[His1,Glu14,His17,Arg18,Glu25,Ser28,Arg29]-pramlintide, N-alpha-[(S)-4-Carboxy-4-(19-carboxynonadecanoylamino)butyryl]-[His1,Glu14,His17,Arg18,Glu22,Ala25,Arg26,Ser28,Ser29]-pramlintide,
N-alpha-[(S)-4-Carboxy-4-(19-carboxynonadecanoylamino)butyryl]-[His1,Glu14,His17,Arg18,Ser21,Ser22,Asp31,Asp35]-pramlintide,
N-alpha-[(S)-4-Carboxy-4-(19-carboxynonadecanoylamino)butyryl]-[Glu1,Glu14,His17,Arg18,Pro37]-pramlintide,
N-alpha-[(S)-4-Carboxy-4-(19-carboxynonadecanoylamino)butyryl]-His-His-[His1,Glu14,His17]-pramlintide,
N-alpha-[(S)-4-Carboxy-4-(19-carboxynonadecanoylamino)butyryl]-His-His-[His1,Glu14,Arg17]-pramlintide,
N-epsilon21-[2-(2-{2-[2-(2-{2-[(S)-4-Carboxy-4-(19-carboxyheptadecanoylamino)butyrylamino]ethoxy}ethoxy)acetylamino]ethoxy}ethoxy)acetyl]-[Arg1,Glu14,His17,Arg18,Lys21]-pramlintide,
N-alpha-[(S)-4-Carboxy-4-(19-carboxynonadecanoylamino)butyryl]-[His1,Glu14,Arg18]-pramlintide,
N-alpha-[(S)-4-Carboxy-4-(19-carboxynonadecanoylamino)butyryl]-[His1,Gly3,Glu14,His17,Arg18,Ser21,Ser22,Glu31,Glu35]-pramlintide,
N-alpha-[(S)-4-Carboxy-4-(19-carboxynonadecanoylamino)butyryl]-His-[His1,Glu14,His17]-pramlintide,
N-alpha-[(S)-4-Carboxy-4-(19-carboxynonadecanoylamino)butyryl]-[His1,Glu14,His17]-pramlintide,
N-alpha-[(S)-4-Carboxy-4-(19-carboxynonadecanoylamino)butyryl]-His-His-[His1,Glu14,His17,Ala25,Pro26,Ser28,Ser29]-pramlintide,
N-alpha-[(S)-4-Carboxy-4-(19-carboxynonadecanoylamino)butyryl]-His-His-[His1,Glu14]-pramlintide,
N-alpha-[(S)-4-Carboxy-4-(19-carboxynonadecanoylamino)butyryl]-His-His-[His1,Glu14,His17,Arg35]-pramlintide,
N-alpha-[(S)-4-Carboxy-4-(19-carboxynonadecanoylamino)butyryl]-His-His- [His1,Arg3,Glu14,His17]-pramlintide,
N-alpha-[2-(2-{2-[2-(2-{2-[(S)-4-Carboxy-4-(19-carboxyheptadecanoylamino)butyrylamino]ethoxy}ethoxy)acetylamino]ethoxy}ethoxy)acetyl]-[His1,Glu14,His17,Arg18,Ala19,Thr20,Gln21,Glu22,Leu23]-pramlintide
N-alpha-[(S)-4-Carboxy-4-(19-carboxynonadecanoylamino)butyryl]-[Glu1,Gly3,Glu14,Arg18,Ser21,Ser22,Ala25,Pro26,Ser28,Ser29,Glu31,Arg35]-pramlintide
N-alpha-[(S)-4-Carboxy-4-(19-carboxynonadecanoylamino)butyryl]-Glu-[Arg1,Glu14,His17]-pramlintide,
N-alpha-[(S)-4-Carboxy-4-(19-carboxynonadecanoylamino)butyryl]-Glu-[Glu14,His17]-pramlintide,
N-alpha-[(S)-4-Carboxy-4-(19-carboxynonadecanoylamino)butyryl]-[Glu14,His17]-pramlintide,
N-alpha-[(S)-4-Carboxy-4-(19-carboxynonadecanoylamino)butyryl]-[des1,Glu14,His17]-pramlintide,
N-alpha-[(S)-4-Carboxy-4-(19-carboxynonadecanoylamino)butyryl]-[Glu1,Glu14,His17]-pramlintide,
N-alpha-[(S)-4-Carboxy-4-(19-carboxynonadecanoylamino)butyryl]-[Glu1,Glu14,His17,Arg18]-pramlintide,
N-alpha-[(S)-4-Carboxy-4-(19-carboxynonadecanoylamino)butyryl]-His-His-[His1,Glu14,His17,His35]-pramlintide,
N-alpha-[(S)-4-Carboxy-4-(19-carboxynonadecanoylamino)butyryl]-His-His-[His1,His3,Glu14,His17,His 35]-pramlintide,
N-alpha-[(S)-4-Carboxy-4-(19-carboxynonadecanoylamino)butyryl]-His-His-[His1,His3,Glu14,His17,His 29,His35]-pramlintide,
N-alpha-[(S)-4-Carboxy-4-(19-carboxynonadecanoylamino)butyryl]-His-His-[His1,Glu14,His17,His 29,His 35]-pramlintide,
N-alpha-[(S)-4-Carboxy-4-(19-carboxynonadecanoylamino)butyryl]-His-His-[His1,His3,Glu14,His17]-pramlintide,
N-alpha-[(S)-4-Carboxy-4-(19-carboxynonadecanoylamino)butyryl]-His-His-[His1,Glu14,His17,His29]-pramlintide,
N-alpha-[2-(2-{2-[2-(2-{2-[(S)-4-Carboxy-4-(19-carboxyheptadecanoylamino)butyrylamino]ethoxy}ethoxy)acetylamino]ethoxy}ethoxy)acetyl]-D-Arg-D-Arg-[Glu14,His17,Arg18]-pramlintide,
N-alpha-[2-(2-{2-[2-(2-{2-[(S)-4-Carboxy-4-(19-carboxyheptadecanoylamino)butyrylamino]ethoxy}ethoxy)acetylamino]ethoxy}ethoxy)acetyl]-D-Arg-D-Arg-[Glu14,His17,Arg18,Ala21,Ser35]-pramlintide,
N-alpha-[(S)-4-Carboxy-4-(19-carboxynonadecanoylamino)butyryl]-Ser-Ser-Gly-Ser-Ser-[Gly1,Glu14,His17]-pramlintide,
N-alpha-[(S)-4-Carboxy-4-(19-carboxynonadecanoylamino)butyryl]-Glu-[His1,Glu14,His17]-pramlintide,
N-alpha-[(S)-4-Carboxy-4-(19-carboxynonadecanoylamino)butyryl]-Glu-Glu-[Glu14,His17]-pramlintide,
N-alpha-[(S)-4-Carboxy-4-(17-carboxyheptadecanoylamino)butyryl]-Glu-[Glu14,His17]-pramlintide,
N-alpha-[2-(2-{2-[2-(2-{2-[(S)-4-Carboxy-4-(19-carboxyheptadecanoylamino)butyrylamino]ethoxy}ethoxy)acetylamino]ethoxy}ethoxy)acetyl]-[des1,Glu14,His17]-pramlintide,
N-alpha-[(S)-4-Carboxy-4-(19-carboxynonadecanoylamino)butyryl]-Ser-Ser-Gly-Ser-Ser-Gly-[His1,Glu14,His17]-pramlintide,
N-alpha-[(S)-4-Carboxy-4-(17-carboxyheptadecanoylamino)butyryl]-His-His-[His1,Glu14,His17]-pramlintide,
N-alpha-[(S)-4-Carboxy-4-(17-carboxyheptadecanoylamino)butyryl]-[Glu14,His17]-pramlintide,
N-alpha-[(S)-4-Carboxy-4-(17-carboxyheptadecanoylamino)butyryl]-His-[His1,Glu14,His17]-pramlintide,
N-alpha-[(S)-4-Carboxy-4-(17-carboxyheptadecanoylamino)butyryl]-[His1,Glu14,His17]-pramlintide,
N-alpha-{(S)-4-Carboxy-4-[(S)-4-Carboxy-4-(17-carboxyheptadecanoylamino)butyrylamino]butyryl}-[des1,Glu14,His17]-pramlintide,
N-alpha-[(S)-4-Carboxy-4-(19-carboxynonadecanoylamino)butyryl]-[Glu14,Arg17]-pramlintide,
N-alpha-[(S)-4-Carboxy-4-(17-carboxyheptadecanoylamino)butyryl]-[Glu14,Arg17]-pramlintide,
N-alpha-[(S)-4-Carboxy-4-(19-carboxynonadecanoylamino)butyryl]-[Glu14,His17,Pro37]-pramlintide,
N-alpha-[(S)-4-Carboxy-4-(19-carboxynonadecanoylamino)butyryl]-[Glu14,Arg17,Pro37]-pramlintide,
N-alpha-[(S)-4-Carboxy-4-(19-carboxynonadecanoylamino)butyryl]-[Glu10,Glu14,His17]-pramlintide,
N-alpha-[(S)-4-Carboxy-4-(19-carboxynonadecanoylamino)butyryl]-[Glu14,His17,His 35]-pramlintide,
N-alpha-[(S)-4-Carboxy-4-(19-carboxynonadecanoylamino)butyryl]-Glu-[Glu14,His17,His 35]-pramlintide,
N-alpha-[(S)-4-Carboxy-4-(19-carboxynonadecanoylamino)butyryl]-[Glu14,Arg17,His35]-pramlintide,
N-alpha-[(S)-4-Carboxy-4-(19-carboxynonadecanoylamino)butyryl]-Glu-[Glu14,Arg17,His35]-pramlintide,
N-alpha-[(S)-4-Carboxy-4-(17-carboxyheptadecanoylamino)butyryl]-[Glu14,His17,His 35]-pramlintide,
N-alpha-[(S)-4-Carboxy-4-(17-carboxyheptadecanoylamino)butyryl]-Glu-[Glu14,His17,His 35]-pramlintide, N-alpha-[(S)-4-Carboxy-4-(17-carboxyheptadecanoylamino)butyryl]-[Glu14,Arg17,His35]-pramlintide,
N-alpha-[(S)-4-Carboxy-4-(17-carboxyheptadecanoylamino)butyryl]-Glu-[Glu14,Arg17,His35]-pramlintide,
N-alpha-[(S)-4-Carboxy-4-(19-carboxynonadecanoylamino)butyryl]-His-His-[His1,Glu14,His17,Ser21,Glu35]-pramlintide,
N-alpha-[(S)-4-Carboxy-4-(19-carboxynonadecanoylamino)butyryl]-[Glu14,His17,Ala25,Pro26,Ser28,Ser29,His35]-pramlintide,
N-alpha-[(S)-4-Carboxy-4-(19-carboxynonadecanoylamino)butyryl]-[Glu14,Arg17,Ala25,Pro26,Ser28,Ser29,His35]-pramlintide,
N-alpha-[(S)-4-Carboxy-4-(19-carboxynonadecanoylamino)butyryl]-His-[Glu14,His17,His 35]-pramlintide,
N-alpha-[(S)-4-Carboxy-4-(19-carboxynonadecanoylamino)butyryl]-His-His-[Glu14,His17,His 35]-pramlintide,
N-alpha-[(S)-4-Carboxy-4-(19-carboxynonadecanoylamino)butyryl]-His-[Glu14,Arg17,His35]-pramlintide,
N-alpha-[(S)-4-Carboxy-4-(19-carboxynonadecanoylamino)butyryl]-His-His-[Glu14,Arg17,His35]-pramlintide,
N-alpha-[(S)-4-Carboxy-4-(17-carboxyheptadecanoylamino)butyryl]-His-[Glu14,His17,His 35]-pramlintide,
N-alpha-[(S)-4-Carboxy-4-(17-carboxyheptadecanoylamino)butyryl]-His-[Glu14,Arg17,His35]-pramlintide,
N-epsilon25-[2-(2-{2-[2-(2-{2-[(S)-4-Carboxy-4-(17-carboxyheptadecanoylamino)butyrylamino]ethoxy}ethoxy)acetylamino]ethoxy}ethoxy)acetyl]-[Glu14,Ser21,Lys25]-pramlintide,
N-epsilon25-[2-(2-{2-[2-(2-{2-[(S)-4-Carboxy-4-(17-carboxyheptadecanoylamino)butyrylamino]ethoxy}ethoxy)acetylamino]ethoxy}ethoxy)acetyl]-[Glu14,His17,Lys25]-pramlintide,
N-epsilon21-[2-(2-{2-[2-(2-{2-[(S)-4-Carboxy-4-(17-carboxyheptadecanoylamino)butyrylamino]ethoxy}ethoxy)acetylamino]ethoxy}ethoxy)acetyl]-[Glu14,His17,Lys21,Glu35]-pramlintide,
N-alpha-[(S)-4-Carboxy-4-(19-carboxynonadecanoylamino)butyryl]-[des1,Glu14,His17,His35]-pramlintide,
N-alpha-[(S)-4-Carboxy-4-(19-carboxynonadecanoylamino)butyryl]-[His1,Glu14,His17,His35]-pramlintide,
N-alpha-[(S)-4-Carboxy-4-(19-carboxynonadecanoylamino)butyryl]-[His1,Glu14,His17,Arg18,His35]-pramlintide,
N-alpha-[(S)-4-Carboxy-4-(19-carboxynonadecanoylamino)butyryl]-[Glu14,His17,Arg18,His35]-pramlintide,
N-alpha-[(S)-4-Carboxy-4-(19-carboxynonadecanoylamino)butyryl]-[Glu14,His17,Arg18]-pramlintide,
N-epsilon17-[2-(2-{2-[2-(2-{2-[(S)-4-Carboxy-4-(17-carboxyheptadecanoylamino)butyrylamino]ethoxy}ethoxy)acetylamino]ethoxy}ethoxy)acetyl]-[Glu14,Lys17]-pramlintide,
N-alpha-[(S)-4-Carboxy-4-(19-carboxynonadecanoylamino)butyryl]-Gly-[Glu14,His17,His 35]-pramlintide,
N-alpha-[2-(2-{2-[2-(2-{2-[(S)-4-Carboxy-4-(17-carboxyheptadecanoylamino)butyrylamino]ethoxy}ethoxy)acetylamino]ethoxy}ethoxy)acetyl]-[Glu1,Glu14,His17,Pro37]-pramlintide,
N-epsilon17-[2-(2-{2-[2-(2-{2-[(S)-4-Carboxy-4-(17-carboxyheptadecanoylamino)butyrylamino]ethoxy}ethoxy)acetylamino]ethoxy}ethoxy)acetyl]-[Glu14,Lys17,Ser21,Glu35]-pramlintide,
N-alpha-[(S)-4-Carboxy-4-(19-carboxynonadecanoylamino)butyryl]-[His1,Glu14,His17,Pro37]-pramlintide,
N-alpha-[(S)-4-Carboxy-4-(19-carboxynonadecanoylamino)butyryl]-Ser-[Glu14,His17,His35]-pramlintide,
N-alpha-[(S)-4-Carboxy-4-(19-carboxynonadecanoylamino)butyryl]-[Glu14, Pro37]-pramlintide,
N-epsilon1-[(S)-4-Carboxy-4-(19-carboxynonadecanoylamino)butyryl]-[Glu14,His17,His35]-pramlintide,
N-alpha-[(S)-4-Carboxy-4-(19-carboxynonadecanoylamino)butyryl]-[Gly1,Glu14,Arg17,Pro37]-pramlintide,
N-alpha-[(S)-4-Carboxy-4-(19-carboxynonadecanoylamino)butyryl]-Gly-[His1,Glu14,Arg17,Pro37]-pramlintide,
N-alpha-[(S)-4-Carboxy-4-(19-carboxynonadecanoylamino)butyryl]-[His1,Glu14,Arg17,Pro37]-pramlintide,
N-alpha-[(S)-4-Carboxy-4-(19-carboxynonadecanoylamino)butyryl]-[Gly1,Glu14,His17,Pro37]-pramlintide,
N-alpha-[(S)-4-Carboxy-4-(19-carboxynonadecanoylamino)butyryl]-Gly-[His1,Glu14,His17,Pro37]-pramlintide,
N-alpha-[(S)-4-Carboxy-4-(19-carboxynonadecanoylamino)butyryl]-[Glu14, His35]-pramlintide,
N-epsilon1-[(S)-4-Carboxy-4-(17-carboxyheptadecanoylamino)butyryl]-[Glu14,His17,His35]-pramlintide,
N-alpha-[(S)-4-Carboxy-4-(19-carboxynonadecanoylamino)butyryl]-[Arg1,Glu14,His17,His 35]-pramlintide,
N-alpha-[(S)-4-Carboxy-4-(19-carboxynonadecanoylamino)butyryl]-[Arg1,Glu14,His17,Pro37]-pramlintide,
N-alpha-[(S)-4-Carboxy-4-(19-carboxynonadecanoylamino)butyryl]-[Arg1, Pro37]-pramlintide,
N-alpha-[(S)-4-Carboxy-4-(19-carboxynonadecanoylamino)butyryl]-[Arg1, His35]-pramlintide,
N-alpha-[(S)-4-Carboxy-4-(19-carboxynonadecanoylamino)butyryl]-Gly-[Arg1,His35]-pramlintide,
N-alpha-[(S)-4-Carboxy-4-(19-carboxynonadecanoylamino)butyryl]-Gly-[Arg1,Glu14,His17,His 35]-pramlintide,
N-alpha-[(S)-4-Carboxy-4-(19-carboxynonadecanoylamino)butyryl]-Gly-[Arg1,Glu14,His17,Pro37]-pramlintide,
N-alpha-[(S)-4-Carboxy-4-(19-carboxynonadecanoylamino)butyryl]-Gly-[Arg1,Glu14,Pro37]-pramlintide,
N-alpha-[(S)-4-Carboxy-4-(19-carboxynonadecanoylamino)butyryl]-Gly-[Arg1,Pro37]-pramlintide,
N-alpha-[(S)-4-Carboxy-4-(19-carboxynonadecanoylamino)butyryl]-[des1,Glu14,His17,Pro37]-pramlintide,
N-alpha-[(S)-4-Carboxy-4-(19-carboxynonadecanoylamino)butyryl]-[Gly1,Glu14,His17,His35]-pramlintide,
N-alpha-[(S)-4-Carboxy-4-(19-carboxynonadecanoylamino)butyryl]-[Ser1,Glu14,His17,Pro37]-pramlintide,
N-alpha-[(S)-4-Carboxy-4-(19-carboxynonadecanoylamino)butyryl]-[Ser1,Glu14,His17,His 35]-pramlintide,
N-alpha-[(S)-4-Carboxy-4-(19-carboxynonadecanoylamino)butyryl]-[des1,Glu14,Pro37]-pramlintide,
N-alpha-[(S)-4-Carboxy-4-(19-carboxynonadecanoylamino)butyryl]-[His1,Glu14,Pro37]-pramlintide,
N-alpha-[(S)-4-Carboxy-4-(19-carboxynonadecanoylamino)butyryl]-[His1,Glu14,Ser21,Ser28,Ser29,His35]-pramlintide,
N-alpha-[(S)-4-Carboxy-4-(19-carboxynonadecanoylamino)butyryl]-[His1,Glu14,Arg17,Ser21,Ser28,Ser29,His35]-pramlintide,
N-alpha-[(S)-4-Carboxy-4-(19-carboxynonadecanoylamino)butyryl]-[Glu14,His17,Arg35]-pramlintide,
N-alpha-[(S)-4-Carboxy-4-(19-carboxynonadecanoylamino)butyryl]-[Glu14,His17,Lys35]-pramlintide,
N-alpha-[(S)-4-Carboxy-4-(19-carboxynonadecanoylamino)butyryl]-[Glu14,His17,His36]-pramlintide, N-alpha-[(S)-4-Carboxy-4-(19-carboxynonadecanoylamino)butyryl]-[Glu14,His17,His34]-pramlintide,
N-alpha-[(S)-4-Carboxy-4-(19-carboxynonadecanoylamino)butyryl]-[Glu14,His17,His32]-pramlintide,
N-alpha-[(S)-4-Carboxy-4-(19-carboxynonadecanoylamino)butyryl]-[Glu14,His17,Gln21,His35)-pramlintide,
N-alpha-[2-(2-{2-[2-(2-{2-[(S)-4-Carboxy-4-(19-carboxyheptadecanoylamino)butyrylamino]ethoxy}ethoxy)acetylamino]ethoxy}ethoxy)acetyl]-[Glu14,His17,Ser21,His35]-pramlintide,
N-alpha-[2-(2-{2-[2-(2-{2-[(S)-4-Carboxy-4-(19-carboxyheptadecanoylamino)butyrylamino]ethoxy}ethoxy)acetylamino]ethoxy}ethoxy)acetyl]-[His1,Glu14,His17,Ser21,His35]-pramlintide,
N-alpha-[2-(2-{2-[2-(2-{2-[(S)-4-Carboxy-4-(17-carboxyheptadecanoylamino)butyrylamino]ethoxy}ethoxy)acetylamino]ethoxy}ethoxy)acetyl]-D-Arg-D-Arg-[Orn1,Glu14,His17,Arg18]-pramlintide,
N-alpha-(19-carboxynonadecanoyl)-Glu-Glu-Arg-[Glu1,Pro37]-pramlintide
N-alpha-[(S)-4-Carboxy-4-(19-carboxynonadecanoylamino)butyryl]-Glu-Arg-[Glu1,Pro37]-pramlintide,
N-alpha-[(S)-4-Carboxy-4-(19-carboxynonadecanoylamino)butyryl]-Glu-Arg-[Glu1,Glu14,His17,Pro37]-pramlintide,
N-alpha-[(S)-4-Carboxy-4-(19-carboxynonadecanoylamino)butyryl]-Glu-Arg-[Glu1,Glu14,Arg17,Pro37]-pramlintide,
N-alpha-(19-carboxynonadecanoyl)-Glu-Glu-Arg-[Glu1,Glu14,His17,Pro37]-pramlintide,
N-epsilon25-[2-(2-{2-[2-(2-{2-[(S)-4-Carboxy-4-(17-carboxyheptadecanoylamino)butyrylamino]ethoxy}ethoxy)acetylamino]ethoxy}ethoxy)acetyl]-[Glu14,Lys25]-pramlintide,
N-epsilon21-[2-(2-{2-[2-(2-{2-[(S)-4-Carboxy-4-(19-carboxyheptadecanoylamino)butyrylamino]ethoxy}ethoxy)acetylamino]ethoxy}ethoxy)acetyl]-[Glu14,Lys21,Ser29,His35]-pramlintide,
N-alpha-[(S)-4-Carboxy-4-(19-carboxynonadecanoylamino)butyryl]-[Glu14,His17,Asp21,His35]-pramlintide,
N-alpha-[(S)-4-Carboxy-4-(19-carboxynonadecanoylamino)butyryl]-Glu-[Glu14,His17,Gln21,His35]-pramlintide,
N-alpha-[(S)-4-Carboxy-4-(19-carboxynonadecanoylamino)butyryl]-[Glu14,His17,Gln21,Pro37]-pramlintide,
N-epsilon21-[2-(2-{2-[2-(2-{2-[(S)-4-Carboxy-4-(19-carboxyheptadecanoylamino)butyrylamino]ethoxy}ethoxy)acetylamino]ethoxy}ethoxy)acetyl]-[Glu14,Lys21,Ser28,Ser29,His35]-pramlintide,
N-epsilon21-[2-(2-{2-[2-(2-{2-[(S)-4-Carboxy-4-(19-carboxyheptadecanoylamino)butyrylamino]ethoxy}ethoxy)acetylamino]ethoxy}ethoxy)acetyl]-[Glu14,Lys21,His35]-pramlintide,
N-epsilon25-[2-(2-{2-[2-(2-{2-[(S)-4-Carboxy-4-(19-carboxyheptadecanoylamino)butyrylamino]ethoxy}ethoxy)acetylamino]ethoxy}ethoxy)acetyl]-[Glu14,His17,Ser21,Lys25,Ser28,Ser29.His35]-pramlintide,
N-epsilon25-[2-(2-{2-[2-(2-{2-[(S)-4-Carboxy-4-(19-carboxyheptadecanoylamino)butyrylamino]ethoxy}ethoxy)acetylamino]ethoxy}ethoxy)acetyl]-[His17,His21,Lys25,Ser28,Ser29.His35]-pramlintide,
N-alpha-[(S)-4-Carboxy-4-(19-carboxynonadecanoylamino)butyryl]-[Glu14,His17,Gln35,Pro37]-pramlintide,
N-alpha-[(S)-4-Carboxy-4-(19-carboxynonadecanoylamino)butyryl]-[Glu14,His17,Gln21,Gln35,Pro37]-pramlintide,
N-alpha-[(S)-4-Carboxy-4-(19-carboxynonadecanoylamino)butyryl]-[Gly1,Glu14,His17,Gln21,Gln35,Pro37]-pramlintide,
N-alpha-[(S)-4-Carboxy-4-(19-carboxynonadecanoylamino)butyryl]-[Glu1,Glu14,Gln21,Gln35,Pro37]-pramlintide,
N-alpha-[(S)-4-Carboxy-4-(19-carboxynonadecanoylamino)butyryl]-[Glu14,Gln21,Gln35,Pro37]-pramlintide,
N-epsilon25-[2-(2-{2-[2-(2-{2-[(S)-4-Carboxy-4-(19-carboxyheptadecanoylamino)butyrylamino]ethoxy}ethoxy)acetylamino]ethoxy}ethoxy)acetyl]-[His17,Lys25,Ser28,Ser29,His35]-pramlintide,
N-epsilon21-[2-(2-{2-[2-(2-{2-[(S)-4-Carboxy-4-(19-carboxyheptadecanoylamino)butyrylamino]ethoxy}ethoxy)acetylamino]ethoxy}ethoxy)acetyl]-[His17,Lys21,Ser28,His35]-pramlintide,
N-epsilon25-[2-(2-{2-[2-(2-{2-[(S)-4-Carboxy-4-(19-carboxyheptadecanoylamino)butyrylamino]ethoxy}ethoxy)acetylamino]ethoxy}ethoxy)acetyl]-[Glu14,His17,Lys25,Ser28,Ser29,His35]-pramlintide,
N-alpha-[(S)-4-Carboxy-4-(19-carboxynonadecanoylamino)butyryl]-[His1,Glu14,Arg18,Pro37]-pramlintide,
N-epsilon21-[2-(2-{2-[2-(2-{2-[(S)-4-Carboxy-4-(19-carboxyheptadecanoylamino)butyrylamino]ethoxy}ethoxy)acetylamino]ethoxy}ethoxy)acetyl]-[Glu14,His17,Lys21,Ser28,His35]-pramlintide,
N-alpha-[(S)-4-Carboxy-4-(19-carboxynonadecanoylamino)butyryl]-[Lys11,Glu14,His17,Pro37]-pramlintide,
N-alpha-[(S)-4-Carboxy-4-(19-carboxynonadecanoylamino)butyryl]-[Glu14,His17,Thr21,Pro37]-pramlintide,
N-epsilon21-[2-(2-{2-[2-(2-{2-[(S)-4-Carboxy-4-(19-carboxyheptadecanoylamino)butyrylamino]ethoxy}ethoxy)acetylamino]ethoxy}ethoxy)acetyl]-[Glu14,Lys21,Ser28,Arg29,His35]-pramlintide,
N-epsilon21-[2-(2-{2-[2-(2-{2-[(S)-4-Carboxy-4-(19-carboxyheptadecanoylamino)butyrylamino]ethoxy}ethoxy)acetylamino]ethoxy}ethoxy)acetyl]-[Glu14,His17,Lys21,Ser28,Ser29,His35]-pramlintide,
N-epsilon1-[(S)-4-Carboxy-4-(19-carboxynonadecanoylamino)butyryl]-Arg-[Glu14,Arg17,His35,Pro37]-pramlintide,
N-epsilon21-[2-(2-{2-[2-(2-{2-[(S)-4-Carboxy-4-(19-carboxyheptadecanoylamino)butyrylamino]ethoxy}ethoxy)acetylamino]ethoxy}ethoxy)acetyl]-[Glu14,Arg18,Lys21,Ser28,Arg29,Arg35]-pramlintide,
N-epsilon1-[(S)-4-Carboxy-4-(19-carboxynonadecanoylamino)butyryl]-[Glu14,His17,Gln21,Ala25,Pro26,Ser28,Ser29,Pro37]-pramlintide,
N-alpha-[(S)-4-Carboxy-4-(19-carboxynonadecanoylamino)butyryl]-[Arg14,Arg17,Pro37]-pramlintide,
N-alpha-[(S)-4-Carboxy-4-(19-carboxynonadecanoylamino)butyryl]-Gly-[Arg1,Glu14,Arg17,Pro37]-pramlintide,
N-alpha-[(S)-4-Carboxy-4-(19-carboxynonadecanoylamino)butyryl]-[Arg17,Pro37]-pramlintide,
N-alpha-[(S)-4-Carboxy-4-(19-carboxynonadecanoylamino)butyryl]-Glu-Glu-[Arg1,Glu14,Arg17,Pro37]-pramlintide,
N-alpha-[(S)-4-Carboxy-4-(19-carboxynonadecanoylamino)butyryl]-Glu-[Arg1,Glu14,Arg17,Pro37]-pramlintide, N-alpha-[(S)-4-Carboxy-4-(19-carboxynonadecanoy-lamino)butyryl]-Glu-Glu-[Arg1,Glu14,Arg17,Gln21,Pro37]-pramlintide,
N-alpha-[(S)-4-Carboxy-4-(19-carboxynonadecanoy-lamino)butyryl]-Glu-Glu-[Arg1,Glu14,Arg17,Gln21,Gln35,Pro37]-pramlintide,
N-alpha-[(S)-4-Carboxy-4-(19-carboxynonadecanoy-lamino)butyryl]-Glu-Glu-[Arg1,Glu14,Arg17,Gln21,Gln31,Gln35,Pro37]-pramlintide,
N-alpha-[(S)-4-Carboxy-4-(19-carboxynonadecanoy-lamino)butyryl]-Glu-Glu-[Arg1,Glu14,Arg17,Gln21,Gln22,Gln31,Gln35,Pro37]-pramlintide,
N-alpha-[(S)-4-Carboxy-4-(19-carboxynonadecanoy-lamino)butyryl]-Glu-Arg-[Glu1,Glu14,Arg17,Gln21,Pro37]-pramlintide,
N-alpha-[(S)-4-Carboxy-4-(19-carboxynonadecanoy-lamino)butyryl]-Glu-Arg-[Glu1,Glu14,Arg17,Gln21,Gln35,Pro37]-pramlintide,
N-alpha-[(S)-4-Carboxy-4-(19-carboxynonadecanoy-lamino)butyryl]-Glu-Arg-[Glu1,Glu14,Arg17,Gln21,Gln31,Gln35,Pro37]-pramlintide,
N-alpha-[(S)-4-Carboxy-4-(19-carboxynonadecanoy-lamino)butyryl]-Glu-Arg-[Glu1,Glu14,Arg17,Gln21,Gln22,Gln31,Gln35,Pro37]-pramlintide,
N-alpha-[(S)-4-Carboxy-4-(19-carboxynonadecanoy-lamino)butyryl]-Glu-Glu-[Glu1,Glu14,Arg17,Pro37]-pramlintide,
N-alpha-[(S)-4-Carboxy-4-(19-carboxynonadecanoy-lamino)butyryl]-[Glu14,Arg18,Gln21,Ala25,Pro26,Ser28,Ser29,Pro37]-pramlintide,
N-alpha-[2-(2-{2-[2-(2-{2-[(S)-4-Carboxy-4-(19-carboxy-heptadecanoylamino)butyrylamino]ethoxy}ethoxy)acety-lamino]ethoxy}ethoxy)acetyl]-[Glu14,His17,Glu21,Pro37]-pramlintide,
N-alpha-[2-(2-{2-[2-(2-{2-[(S)-4-Carboxy-4-(19-carboxy-heptadecanoylamino)butyrylamino]ethoxy}ethoxy)acety-lamino]ethoxy}ethoxy)acetyl]-[Glu14,His17,Lys21,Pro37]-pramlintide,
N-alpha-[2-(2-{2-[2-(2-{2-[(S)-4-Carboxy-4-(19-carboxy-heptadecanoylamino)butyrylamino]ethoxy}ethoxy)acety-lamino]ethoxy}ethoxy)acetyl]-[Glu14,His17,Ala21,Pro37]-pramlintide,
N-alpha-[(S)-4-Carboxy-4-(19-carboxynonadecanoy-lamino)butyryl]-[Glu14,Arg18,Ser21,Ser22,Ser28,Ser29,Asp31,Asp35,Pro37]-pramlintide,
N-alpha-[(S)-4-Carboxy-4-(19-carboxynonadecanoy-lamino)butyryl]-[Glu14,Ser21,Ser22,Pro23,Ala25,Pro26,Ser28,Ser29,Asp31,Asp35,Pro37]-pramlintide,
N-alpha-[(S)-4-Carboxy-4-(19-carboxynonadecanoy-lamino)butyryl]-[Glu14,Arg17,Asp21,Pro37]-pramlintide,
N-alpha-[(S)-4-Carboxy-4-(19-carboxynonadecanoy-lamino)butyryl]-[Glu14,Arg17,Asp35,Pro37]-pramlintide,
N-alpha-[(S)-4-Carboxy-4-(19-carboxynonadecanoy-lamino)butyryl]-[Glu14,Arg17,Asp31,Pro37]-pramlintide,
N-alpha-[(S)-4-Carboxy-4-(19-carboxynonadecanoy-lamino)butyryl]-[Glu14,Arg17,Asp22,Pro37]-pramlintide,
N-alpha-[(S)-4-Carboxy-4-(19-carboxynonadecanoy-lamino)butyryl]-[Asp3,Glu14,Arg17,Pro37]-pramlintide,
N-epsilon1-[(S)-4-Carboxy-4-(19-carboxynonadecanoy-lamino)butyryl]-[Glu14,Arg17,Pro37]-pramlintide,
N-alpha-[2-(2-{2-[2-(2-{2-[(S)-4-Carboxy-4-(19-carboxy-heptadecanoylamino)butyrylamino]ethoxy}ethoxy)acety-lamino]ethoxy}ethoxy)acetyl]-[Glu14,Ala21,His35,Pro37]-pramlintide.

For some embodiments, the polypeptide of the present invention has a protracted pharmacokinetic profile compared to pramlintide as measured by Assay (IX) as described in the section Assays.

For some embodiments, the polypeptide of the present invention has a plasma T½ of at least 30 hour.
For some embodiments, the polypeptide of the present invention has a plasma T½ of at least 40 hour.
For some embodiments, the polypeptide of the present invention has a plasma T½ of at least 50 hours.
For some embodiments, the polypeptide of the present invention has a plasma T½ of at least 60 hours.
For some embodiments, the polypeptide of the present invention has a plasma T½ of at least 70 hours.
For some embodiments, the polypeptide of the present invention has a plasma T½ of at least 75 hours.
For some embodiments, the polypeptide of the present invention has a plasma T½ of at least 80 hours.
For some embodiments, the polypeptide of the present invention has a plasma T½ of at least 85 hours.
For some embodiments, the polypeptide of the present invention has a plasma T½ of at least 90 hours.
For some embodiments, the polypeptide of the present invention has a plasma T½ of at least 95 hours.
For some embodiments, the polypeptide of the present invention has a plasma T½ of at least 100 hours.

Process

The production of polypeptides such as amylin or analogues thereof is well known in the art. The polypeptides of the invention can thus be produced by classical polypeptide synthesis, e.g. solid phase polypeptide synthesis using t-Boc or Fmoc chemistry or other well established techniques, see e.g. Greene and Wuts, "Protective Groups in Organic Synthesis", John Wiley & Sons, 1999. The polypeptides may also be produced by a method which comprises culturing a host cell containing a DNA sequence encoding the polypeptide and capable of expressing the polypeptide in a suitable nutrient medium under conditions permitting the expression of the polypeptide. For polypeptides comprising non-natural amino acid residues, the recombinant cell should be modified such that the non-natural amino acids are incorporated into the polypeptide, for instance by use of tRNA mutants.

Pharmaceutical Compositions

In one aspect the invention concerns a pharmaceutical composition comprising a polypeptide according of the invention, and a pharmaceutically acceptable excipient. The compositions are suited for parenteral administration.

In one embodiment the polypeptide is present in the formulation at a concentration of from about 0.1 mg/ml to about 25 mg/ml. In another aspect, the polypeptide is present in the formulation at a concentration of from about 1 mg/ml to about 10 mg/ml.

In another embodiment, the formulation has a pH from 2.0 to 10.0. In another embodiment, the formulation has a pH from 2.0 to 7.0. In another embodiment, the formulation has a pH from 2.5 to 4.5. In another embodiment, the formulation has a pH from 3.5 to 4.5.

Pharmaceutical compositions containing a polypeptide according to the present invention may be prepared by conventional techniques, e.g. as described in Remington's *Pharmaceutical Sciences,* 1985 or in Remington: *The Science and Practice of Pharmacy,* 19$^{th}$ edition, 1995.

The formulation may further comprise a buffer system, preservative(s), isotonicity agent(s), chelating agent(s), stabilizers and/or surfactants. The use of such excipients in pharmaceutical compositions is well-known to the skilled person. For convenience reference is made to Remington: *The Science and Practice of Pharmacy*, 19th edition, 1995.

In one embodiment the pharmaceutical formulation is an aqueous formulation, i.e. formulation comprising water. Such formulation is typically a solution or a suspension. In a further embodiment of the invention the pharmaceutical formulation is an aqueous solution.

The term "aqueous formulation" is defined as a formulation comprising at least 50% w/w water.

Likewise, the term "aqueous solution" is defined as a solution comprising at least 50% w/w water, and the term "aqueous suspension" is defined as a suspension comprising at least 50% w/w water.

In another embodiment the pharmaceutical formulation is a freeze-dried formulation, whereto the physician or the patient adds solvents and/or diluents prior to use. In another embodiment the pharmaceutical formulation is a dried formulation (e.g. freeze-dried or spray-dried) ready for use without any prior dissolution.

By "dried form" is intended the liquid pharmaceutical composition or formulation is dried either by freeze drying (i.e., lyophilization; see, for example, Williams and Polli (1984) J. Parenteral Sci. Technol. 38:48-59), spray drying (see Masters (1991) in Spray-Drying Handbook (5th ed; Longman Scientific and Technical, Essez, U.K.), pp. 491-676; Broadhead et al. (1992) Drug Devel. Ind. Pharm. 18:1169-1206; and Mumenthaler et al. (1994) Pharm. Res. 11:12-20), or air drying (Carpenter and Crowe (1988) Cryobiology 25:459-470; and Roser (1991) Biopharm. 4:47-53).

In a further embodiment of the invention the buffer is selected from the group consisting of acetate, carbonate, citrate, glycylglycine, histidine, glycine, lysine, arginine, dihydrogen phosphate, hydrogen phosphate, phosphate, and tris (hydroxymethyl)-aminomethan, bicine, tricine, malic acid, lactic acid, succinate, maleic acid, fumaric acid, tartaric acid, aspartic acid or mixtures thereof. Each one of these specific buffers constitutes an alternative embodiment of the invention.

In another embodiment of the invention the formulation further comprises a pharmaceutically acceptable preservative. In a further embodiment of the invention the formulation further comprises an isotonic agent, e.g. propylene glycol, mannitol or glycerol. In a further embodiment of the invention the formulation further comprises a chelating agent.

In another embodiment of the invention the formulation further comprises a stabilizer. The use of a stabilizer in pharmaceutical compositions is well-known to the skilled person. For convenience reference is made to Remington: *The Science and Practice of Pharmacy*, 19th edition, 1995.

Aggregate formation by a polypeptide during storage of a liquid pharmaceutical composition can adversely affect biological activity of that polypeptide, resulting in loss of therapeutic efficacy of the pharmaceutical composition. Furthermore, aggregate formation may cause other problems such as blockage of tubing, membranes, or pumps when the polypeptide-containing pharmaceutical composition is administered using an infusion system.

Compositions of the invention are stabilized liquid pharmaceutical compositions whose therapeutically active components include a polypeptide that possibly exhibits aggregate formation during storage in liquid pharmaceutical formulations.

By "aggregate formation" is intended a physical interaction between the polypeptide molecules that results in formation of oligomers, which may remain soluble, or large visible aggregates that precipitate from the solution.

By "during storage" is intended a liquid pharmaceutical composition or formulation once prepared, is not immediately administered to a subject. Rather, following preparation, it is packaged for storage, either in a liquid form, in a frozen state, or in a dried form for later reconstitution into a liquid form or other form suitable for administration to a subject.

The pharmaceutical compositions of the invention may further comprise an amount of an amino acid base sufficient to decrease aggregate formation by the polypeptide during storage of the composition.

By "amino acid base" is intended an amino acid or a combination of amino acids, where any given amino acid is present either in its free base form or in its salt form. Where a combination of amino acids is used, all of the amino acids may be present in their free base forms, all may be present in their salt forms, or some may be present in their free base forms while others are present in their salt forms. In one embodiment, amino acids used in preparing the compositions of the invention are those carrying a charged side chain, such as arginine, lysine, aspartic acid, and glutamic acid. Any stereoisomer (i.e., L, D, or a mixture thereof) of a particular amino acid (e.g. methionine, histidine, imidazole, arginine, lysine, isoleucine, aspartic acid, tryptophan, threonine and mixtures thereof) or combinations of these stereoisomers, may be present in the pharmaceutical compositions of the invention so long as the particular amino acid is present either in its free base form or its salt form. In one embodiment the L-stereoisomer is used. Compositions of the invention may also be formulated with derivatives of these amino acids. Suitable arginine derivatives include, for example, aminoguanidine, ornithine and N-monoethyl L-arginine, suitable methionine derivatives include ethionine and buthionine and suitable cysteine derivatives include S-methyl-L cysteine. As with the other amino acids, the amino acid derivatives are incorporated into the compositions in either their free base form or their salt form. In a another embodiment of the invention the amino acids or amino acid derivatives thereof are used in a concentration, which is sufficient to prevent or delay aggregation of the protein.

In another embodiment of the invention the formulation further comprises a surfactant. In another embodiment of the invention the formulation further comprises protease inhibitors. The use of a protease inhibitor is particular useful in pharmaceutical compositions comprising zymogens of proteases in order to inhibit autocatalysis.

It is possible that other ingredients may be present in the polypeptide pharmaceutical formulation of the present invention. Such additional ingredients may include wetting agents, emulsifiers, antioxidants, bulking agents, tonicity modifiers, chelating agents, metal ions, oleaginous vehicles, proteins (e.g., human serum albumin, gelatine or proteins) and a zwitterion (e.g., an amino acid such as betaine, taurine, arginine, glycine, lysine and histidine). Such additional ingredients, of course, should not adversely affect the overall stability of the pharmaceutical formulation of the present invention.

Pharmaceutical compositions containing a polypeptide according to the present invention may be administered to a patient in need of such treatment at several sites, for example, at topical sites, for example, skin and mucosal sites, at sites which bypass absorption, for example, administration in an artery, in a vein, in the heart, and at sites which involve absorption, for example, administration in the skin, under the skin, in a muscle or in the abdomen.

Administration of pharmaceutical compositions according to the invention may be through several routes of administration, for example, lingual, sublingual, buccal, in the mouth, oral, in the stomach and intestine, nasal, pulmonary, for example, through the bronchioles and alveoli or a combination thereof, epidermal, dermal, transdermal, vaginal, rectal, ocular, for examples through the conjunctiva, uretal, and parenteral to patients in need of such a treatment.

Compositions of the current invention may be administered in several dosage forms, for example, as solutions, suspensions, emulsions, microemulsions, multiple emulsion, foams, salves, pastes, plasters, ointments, tablets, coated tablets, rinses, capsules, for example, hard gelatine capsules and soft gelatine capsules, suppositories, rectal capsules, drops, gels, sprays, powder, aerosols, inhalants, eye drops, ophthalmic ointments, ophthalmic rinses, vaginal pessaries, vaginal rings, vaginal ointments, injection solution, in situ transforming solutions, for example in situ gelling, in situ setting, in situ precipitating, in situ crystallization, infusion solution, and implants.

Compositions of the invention may further be compounded in, or attached to, for example through covalent, hydrophobic and electrostatic interactions, a drug carrier, drug delivery system and advanced drug delivery system in order to further enhance stability of the derivative of an amylin analogue thereof increase bioavailability, increase solubility, decrease adverse effects, achieve chronotherapy well known to those skilled in the art, and increase patient compliance or any combination thereof.

Compositions of the current invention are useful in the formulation of solids, semisolids, powder and solutions for pulmonary administration of the derivative of an amylin analogue, using, for example a metered dose inhaler, dry powder inhaler and a nebulizer, all being devices well known to those skilled in the art.

Compositions of the current invention are useful in the formulation of controlled, sustained, protracting, retarded, and slow release drug delivery systems.

Parenteral administration may be performed by subcutaneous, intramuscular, intraperitoneal or intravenous injection by means of a syringe, optionally a pen-like syringe. Alternatively, parenteral administration can be performed by means of an infusion pump. A further option is a composition which may be a solution or suspension for the administration of the derivative of an amylin analogue in the form of a nasal or pulmonal spray. As a still further option, the pharmaceutical compositions containing the polypeptide of the invention can also be adapted to transdermal administration, e.g. by needle-free injection or from a patch, optionally an iontophoretic patch, or transmucosal, e.g. buccal, administration.

The polypeptide of the invention can be administered via the pulmonary route in a vehicle, as a solution, suspension or dry powder using any of known types of devices suitable for pulmonary drug delivery. Examples of these comprise of, but are not limited to, the three general types of aerosol-generating for pulmonary drug delivery, and may include jet or ultrasonic nebulizers, metered-dose inhalers, or dry powder inhalers (cf. Yu J, Chien Y W. Pulmonary drug delivery: Physiologic and mechanistic aspects. Crit. Rev Ther Drug Carr Sys 14(4) (1997) 395-453).

In one embodiment of the invention the pharmaceutical formulation comprising the polypeptide of the invention is stable for more than 6 weeks of usage and for more than 3 years of storage.

In another embodiment of the invention the pharmaceutical formulation comprising the polypeptide of the invention is stable for more than 4 weeks of usage and for more than 3 years of storage.

In another embodiment of the invention the pharmaceutical formulation comprising the derivative of an amylin analogue is stable for more than 4 weeks of usage and for more than two years of storage.

In another embodiment of the invention the pharmaceutical formulation comprising the derivative of an amylin analogue is stable for more than 2 weeks of usage and for more than two years of storage.

In one aspect a process for preparing a pharmaceutical composition comprising the derivative according to the invention comprises mixing a derivative according to the invention with at least one pharmaceutically acceptable excipient.

Therapeutic Indications

In one aspect the polypeptide according to the invention can be used as a medicament.

In one aspect the polypeptide according to the invention can be used as a medicament for the treatment or prevention of hyperglycemia, type 2 diabetes, impaired glucose tolerance, type 1 diabetes, obesity, hypertension, syndrome X, dyslipidemia, cognitive disorders, atherosclerosis, myocardial infarction, coronary heart disease and other cardiovascular disorders, stroke, inflammatory bowel syndrome, dyspepsia and gastric ulcers.

In one aspect the polypeptide is for use in delaying or preventing disease progression in type 2 diabetes.

In one aspect the polypeptide according to the invention can be used as a medicament for the treatment of or prevention of obesity.

In one aspect the polypeptide according to the invention can be used as a medicament for the treatment or prevention of hypercalcaemia, osteoporosis or ostitis derformans. In one aspect the polypeptide can be used as a medicament for reducing body weight. In one aspect the polypeptide can be used as a medicament for the treatment or prevention of obesity, or as a medicament for preventing body weight increase. In one aspect the polypeptide can be used as a medicament for modifying the food intake, such as reducing the food intake.

In one aspect the medicament can be used for decreasing food intake, decreasing n-cell apoptosis, increasing n-cell function and n-cell mass, and/or for restoring glucose sensitivity to n-cells.

In one aspect the polypeptide according to the invention can be used for the preparation of a medicament.

In one aspect the polypeptide can be used for the preparation of a medicament for the treatment or prevention of hyperglycemia, type 2 diabetes, impaired glucose tolerance, type 1 diabetes, obesity, hypertension, syndrome X, dyslipidemia, cognitive disorders, atherosclerosis, myocardial infarction, coronary heart disease and other cardiovascular disorders, stroke, inflammatory bowel syndrome, dyspepsia and gastric ulcers.

In one aspect, the polypeptide can be used for the preparation of a medicament for delaying or preventing disease progression in type 2 diabetes.

In one aspect the polypeptide can be used for the preparation of a medicament for decreasing food intake, decreasing n-cell apoptosis, increasing n-cell function and n-cell mass, and/or for restoring glucose sensitivity to n-cells.

The treatment with a polypeptide according to the present invention may also be combined with a second or more pharmacologically active substances, e.g. selected from antidiabetic agents, antiobesity agents, appetite regulating agents, antihypertensive agents, agents for the treatment and/or prevention of complications resulting from or associated with diabetes and agents for the treatment and/or prevention of complications and disorders resulting from or associated with obesity. Examples of these pharmacologically active substances are: Insulin, insulin derivative, insulin analogues, GLP-1, GLP-1 derivatives, GLP-1 analogues, oxyntomodulin derivatives, sulphonylureas, biguanides, meglitinides, glucosidase inhibitors, glucagon antagonists, DPP-IV (dipeptidyl peptidase-IV) inhibitors, inhibitors of hepatic enzymes involved in stimulation of gluconeogenesis and/or glycogenolysis, glucose uptake modulators, compounds modifying the lipid metabolism such as antihyperlipidemic agents as HMG CoA inhibitors (statins), compounds lowering food intake, RXR agonists and agents acting on the ATP-dependent potassium channel of the β-cells; Cholestyramine, colestipol, clofibrate, gemfibrozil, lovastatin, pravastatin, simvastatin, probucol, dextrothyroxine, neteglinide, repaglinide; β-blockers such as alprenolol, atenolol, timolol, pindolol, propranolol and metoprolol, ACE (angiotensin converting enzyme) inhibitors such as benazepril, captopril, enalapril, fosinopril, lisinopril, alatriopril, quinapril and ramipril, calcium channel blockers such as nifedipine, felodipine, nicardipine, isradipine, nimodipine, diltiazem and verapamil, and α-blockers such as doxazosin, urapidil, prazosin and terazosin; CART (cocaine amphetamine regulated transcript) agonists, NPY (neuropeptide Y) antagonists, MC4 (melanocortin 4) agonists, orexin antagonists, TNF (tumor necrosis factor) agonists, CRF (corticotropin releasing factor) agonists, CRF BP (corticotropin releasing factor binding protein) antagonists, urocortin agonists, β3 agonists, MSH (melanocyte-stimulating hormone) agonists, MCH (melanocyte-concentrating hormone) antagonists, CCK (cholecystokinin) agonists, serotonin re-uptake inhibitors, serotonin and noradrenaline re-uptake inhibitors, mixed serotonin and noradrenergic compounds, 5HT (serotonin) agonists, bombesin agonists, galanin antagonists, growth hormone, growth hormone releasing compounds, TRH (thyrotropin releasing hormone) agonists, UCP 2 or 3 (uncoupling protein 2 or 3) modulators, leptin agonists, DA agonists (bromocriptin, doprexin), lipase/amylase inhibitors, RXR (retinoid X receptor) modulators, TR β agonists; histamine H3 antagonists, gastrin and gastrin analogs.

It should be understood that any suitable combination of the polypeptides according to the invention with one or more of the above-mentioned compounds and optionally one or more further pharmacologically active substances are considered to be within the scope of the present invention.

The invention will be further summarised in the paragraphs below:
1. A polypeptide selected from:
   (i) A polypeptide comprising an amino acid sequence which is an analogue of SEQ ID No: 2 wherein:
       said analogue comprises a proline residue at position 37;
       wherein the amino acid sequence numbering of the analogue corresponds to the amino acid numbering sequence of SEQ ID No: 2; and
       optionally the polypeptide has at least one substituent attached to at least one of its amino acid residues.
   (ii) A polypeptide comprising an amino acid sequence which is an analogue of SEQ ID No: 2 wherein:
       (a) said analogue comprises a proline residue at position 37;
       wherein the amino acid sequence numbering of the analogue corresponds to the amino acid numbering sequence of SEQ ID No: 2; and
       (b) said polypeptide has a solubility of about 100 μM or greater at pH4
       optionally the polypeptide has at least one substituent attached to at least one of its amino acid residues.
   (iii) A polypeptide comprising an amino acid sequence which is an analogue of SEQ ID No: 2 wherein:
       (a) said analogue comprises a proline residue at position 37;
       wherein the amino acid sequence numbering of the analogue corresponds to the amino acid numbering sequence of SEQ ID No: 2; and
       (b) said polypeptide has a solubility of about 100 μM or greater at pH7; and
       optionally the polypeptide has at least one substituent attached to at least one of its amino acid residues.
   (iv) A polypeptide comprising an amino acid sequence which is an analogue of SEQ ID No: 2 wherein:
       (a) said analogue comprises a proline residue at position 37;
       wherein the amino acid sequence numbering of the analogue corresponds to the amino acid numbering sequence of SEQ ID No: 2; and
       (b) said polypeptide has a solubility of about 100 μM or greater at pH4; and
       (c) said polypeptide has a solubility of about 100 μM or greater at pH7; and
       optionally the polypeptide has at least one substituent attached to at least one of its amino acid residues.
   (v) A polypeptide comprising an amino acid sequence which is an analogue of SEQ ID No: 2 wherein:
       (a) said analogue comprises a proline residue at position 37;
       wherein the amino acid sequence numbering of the analogue corresponds to the amino acid numbering sequence of SEQ ID No: 2; and
       (b) said polypeptide has a solubility of about 100 μM or greater at pH4; and
       (c) said polypeptide has a solubility of about 100 μM or greater at pH7; and
       (d) said polypeptide has a physical stability of about 25 hours or greater in a fibrillogenesis assay; and
       optionally the polypeptide has at least one substituent attached to at least one of its amino acid residues.
2. The polypeptide according to paragraph 1 wherein said analogue comprises a residue at position 14 which is independently selected from any one of asparagine and glutamic acid; preferably glutamic acid.
3. The polypeptide according to any one of paragraphs 1 and 2 wherein said analogue comprises a residue at position 17 which is independently selected from any one of histidine, arginine, lysine and valine; preferably histidine and arginine; more preferably arginine.
4. The polypeptide according to any preceding paragraph wherein said analogue comprises a residue at position 35 which is independently selected from any one of histidine, arginine, lysine, aspartic acid, glutamic acid, asparagine and glutamine; preferably histidine, asparagine, glutamine and glutamic acid; more preferably histidine, glutamine and asparagine; more preferably asparagine.
5. The polypeptide according to any preceding paragraph wherein said analogue comprises a residue at position 1 which is deleted or independently selected from any one of alanine, cysteine, glutamic acid, glycine, histidine, arginine, serine and lysine; preferably glycine, histidine, arginine and lysine; more preferably lysine.

6. The polypeptide according to any preceding paragraph wherein said analogue comprises a residue at position 3 which is independently selected from any one of glycine, histidine, arginine, serine and asparagine; preferably asparagine.
7. The polypeptide according to any preceding paragraph wherein said analogue comprises a residue at position 18 which is independently selected from any one of arginine, lysine and histidine; preferably histidine.
8. The polypeptide according to any preceding paragraph wherein said analogue comprises a residue at position 21 which is independently selected from any one of alanine, lysine, glutamine, serine, threonine and asparagine; preferably glutamine and asparagine; more preferably asparagine.
9. The polypeptide according to any preceding paragraph wherein said analogue comprises a residue at position 22 which is independently selected from any one of glutamic acid, glutamine, serine, threonine and asparagine; preferably serine and asparagine; more preferably asparagine.
10. The polypeptide according to any preceding paragraph wherein said analogue comprises a residue at position 26 which is independently selected from any one of proline, arginine and isoleucine; preferably asparagine.
11. The polypeptide according to any preceding paragraph wherein said analogue comprises a residue at position 31 which is independently selected from any one of serine, glutamic acid, aspartic acid and asparagine; preferably aspartic acid and asparagine; more preferably asparagine.
12. The polypeptide according to any preceding claim wherein the analogue comprises an amino acid residue at position 14 which is glutamic acid, a residue at position 17 which is arginine and a residue at position 37 which is proline.
13. The polypeptide according to paragraphs 1 to 11 wherein the analogue comprises an amino acid residue at position 14 which is glutamic acid, a residue at position 17 which is histidine and a residue at position 37 which is proline.
14. The polypeptide according to paragraphs 1 to 11 wherein the analogue comprises an amino acid residue at position 14 which is glutamic acid, a residue at position 17 which is histidine and a residue at position 35 which is glutamine and a residue at position 37 which is proline.
15. The polypeptides according to any preceding claims wherein the remaining residues are the same as in SEQ ID No: 2.
16. The polypeptides according to any preceding claims wherein the analogue comprises the same amino acid residues at positions 2, 4 to 16, 19, 20, 23 to 25, 27 to 30, 32 to 34 and 36 as the residues at positions 2, 4 to 16, 19, 20, 23 to 25, 27 to 30, 32 to 34 and 36 of SEQ ID No: 2.
17. A polypeptide according to paragraph 1 comprising an amino acid sequence which is an analogue of SEQ ID No: 2 of Formula (I):

wherein
$Xaa_1$ is deleted or independently selected from Ala, Cys, Glu, Gly, His, Arg, Ser and Lys;
$Xaa_3$ is independently selected from Gly, His, Arg, Ser and Asn; $Xaa_{14}$ is independently selected from Glu and Asn;
$Xaa_{17}$ is independently selected from His, Arg, Lys and Val;
$Xaa_{18}$ is independently selected from Arg, Lys and His;
$Xaa_{21}$ is independently selected from Ala, Lys, Gln, Ser and Asn;
$Xaa_{22}$ is independently selected from Glu, Gln, Ser, Thr and Asn;
$Xaa_{26}$ is independently selected from Pro, Arg and Ile;
$Xaa_{31}$ is independently selected from Ser, Glu, Asp and Asn;
$Xaa_{35}$ is independently selected from His, Arg, Lys, Asp, Gln and Glu;
and where the C-terminal may optionally be derivatized;
18. A polypeptide according to paragraph 17 wherein $Xaa_{14}$ is Glu.
19. A polypeptide according to any one of paragraphs 17 and 18, wherein $Xaa_{17}$ is Arg or His.
20. A polypeptide according to any one of paragraphs 17 to 19 wherein $Xaa_{35}$ is Asn or Gln
21. A polypeptide according to any one of paragraphs 17 to 19 wherein:
$Xaa_1$ is Lys;
$Xaa_3$ is Asn;
$Xaa_{14}$ is Glu
$Xaa_{17}$ is His or Arg;
$Xaa_{18}$ His;
$Xaa_{21}$ Asn;
$Xaa_{22}$ is Asn;
$Xaa_{26}$ is Ile;
$Xaa_{31}$ is Asn;
$Xaa_{35}$ is Asn.
22. A polypeptide according to paragraph 17, wherein
$Xaa_1$ is deleted or independently selected from His, Arg and Lys;
$Xaa_3$ is independently selected from Gly, His and Asn;
$Xaa_{14}$ is independently selected from Glu and Asn;
$Xaa_{17}$ is independently selected from His, Arg and Val;
$Xaa_{18}$ is independently selected from Arg and His;
$Xaa_{21}$ is independently selected from Ser and Asn;
$Xaa_{22}$ is Asn;
$Xaa_{26}$ is Ile;
$Xaa_{31}$ is independently selected from Glu and Asn;
$Xaa_{35}$ is independently selected from His, Arg, Lys, Asp, Gln and Glu.
23. A polypeptide according to any of paragraph 17 wherein
$Xaa_1$ is deleted or independently selected from Gly, His, Arg, Ser and Lys;
$Xaa_3$ is independently selected from His and Asn;
$Xaa_{14}$ is independently selected from Glu and Asn;
$Xaa_{17}$ is independently selected from His, Arg and Val;
$Xaa_{18}$ is independently selected from Arg and His;
$Xaa_{21}$ is independently selected from Gln, Ser and Asn;

Formula (I) (SEQ ID No: 3)
$Xaa_1$-Cys-$Xaa_3$-Thr-Ala-Thr-Cys-Ala-Thr-Gln-Arg-Leu-Ala-$Xaa_{14}$-Phe-Leu-$Xaa_{17}$-$Xaa_{18}$-Ser-Ser-$Xaa_{21}$-$Xaa_{22}$-Phe-Gly-Pro-$Xaa_{26}$-Leu-Pro-Pro-Thr-$Xaa_{31}$-Val-Gly-Ser-$Xaa_{35}$-Thr-Pro;

Xaa$_{22}$ is Asn;
Xaa$_{26}$ is independently selected from Pro and Ile;
Xaa$_{31}$ is Asn;
Xaa$_{35}$ is Asn;
24. A polypeptide according to paragraph 17, wherein
Xaa$_1$ is deleted or independently selected from Ala, Cys, Glu, Gly, His, Arg, Ser and Lys;
Xaa$_3$ is Asn;
Xaa$_{14}$ is Glu;
Xaa$_{17}$ is independently selected from His, Arg and Val;
Xaa$_{18}$ is independently selected from Arg, Lys and His;
Xaa$_{21}$ is independently selected from Gln and Asn;
Xaa$_{22}$ is independently selected from Thr and Asn;
Xaa$_{26}$ is Ile;
Xaa$_{31}$ is Asn;
Xaa$_{35}$ is independently selected from Gln, Gly and Asn;
25. A polypeptide according to any of paragraph 17, wherein
Xaa$_1$ is deleted;
Xaa$_3$ is independently selected from Gly and Asn;
Xaa$_{14}$ is Glu;
Xaa$_{17}$ is independently selected from His, Arg and Val;
Xaa$_{18}$ is independently selected from Arg and His;
Xaa$_{21}$ is independently selected from Gln and Asn;
Xaa$_{22}$ is independently selected from Gln and Asn;
Xaa$_{26}$ is Ile;
Xaa$_{31}$ is independently selected from Glu and Asn;
Xaa$_{35}$ is independently selected from Asn, Gln and Glu.
26. A polypeptide according to paragraph 17, wherein
Xaa$_1$ is Lys;
Xaa$_3$ is Asn;
Xaa$_{14}$ is Glu;
Xaa$_{17}$ is independently selected from His, Lys, Arg and Val;
Xaa$_{18}$ is independently selected from Arg and His;
Xaa$_{21}$ is independently selected from Ala, Lys, Gln and Ser;
Xaa$_{22}$ is independently selected from Glu, Gln, Ser, Thr and Asn;
Xaa$_{26}$ is independently selected from Pro and Ile;
Xaa$_{31}$ is independently selected from Ser, Glu, Asp and Asn;
Xaa$_{35}$ is independently selected from Gln, Glu and Asn.
27. The polypeptide according to any one of the preceding paragraphs comprising a C-terminal amide.
28. The polypeptide according to paragraph 27 wherein the C-terminal amide is of Formula (II):

C(O)NR$^1$R$^2$ (II)

wherein R$^1$ and R$^2$ are independently selected from H and alkyl. Preferably R$^1$ and R$^2$ are both H.
29. The polypeptide according to paragraph 28 wherein R$^1$ and R$^2$ are both H.
30. The polypeptide according to any one of the preceding paragraphs wherein at least one substituent is attached to one of the amino acid residues.
31. The polypeptide according to paragraph 30 wherein the substituent is selected from a hydrocarbyl group, a hydroxyl group and a halogen atom.
32. The polypeptide according any one of paragraphs 30 and 31 wherein the substituent group is of formula (II):

L$_n$-Y (II)

wherein
L is a linker;
n=0 or 1
Y is an albumin binding moiety.

33. The polypeptide according to paragraph 32 wherein the albumin binding moiety is an acyl group selected from:
(a) CH$_3$(CH$_2$)$_r$CO—, wherein r is an integer from 12 to 20;
(b) HOOC(CH$_2$)$_s$CO—, wherein s is an integer from 12 to 22 or s is an integer from 12 to 18, or s is 16 to 18 or preferably s is 18.
34. The polypeptide according to any one of paragraphs 32 and 33 wherein the linker is selected from the group consisting of γGlu, γGlu-γGlu, γGlu-γGlu-γGlu, γGlu-γGlu-γGlu-γGlu, Glu, Glu-Glu, Glu-γGlu, Glu-Arg, Glu-Glu-Arg, His, His-His, His-γGlu, His-His-γGlu, Gly, Gly-γGlu, Ser, Ser-γGlu, D-Arg-D-Arg, Arg, Arg-Arg, Arg-Arg-γGlu, Ser-Ser,-Gly-Ser-Ser, Ser-Ser,-Gly-Ser-Ser-γGlu, Ser-Ser-Gly-Ser-Ser-Gly and Ser-Ser-Gly-Ser-Ser-Gly-γGlu, γGlu-OEG, γGlu-OEG-OEG and OEG, preferably the linker is selected from γGlu, γGlu-γGlu, γGlu-OEG, γGlu-OEG-OEG and OEG, more preferably the linker is γGlu.
35. The polypeptide according to any preceding paragraph wherein the substituent group is selected from the groups presented in Table 1 (presented earlier).
36. The polypeptide according to any preceding paragraph wherein a substituent is attached to the α-amino group of the N-terminal amino acid residue or to a Lys residue.
37. The polypeptide according any preceding paragraph wherein a substituent is attached to the amino acid residue at position 1 only.
38. The polypeptide according to any preceding paragraphs selected from the group consisting of any of the polypeptides presented in Table 2 (presented earlier); or from the group consisting of any of the polypeptides presented in Table 3 (presented earlier); or from the group consisting of any of the polypeptides presented in Table 4 (presented earlier); or from the group consisting of any of the polypeptides presented in Table 5 (presented earlier); or from the group consisting of any of the polypeptides presented in Table 6 (presented earlier); or from the group consisting of any of the polypeptides presented in Table 7 (presented earlier); or from the group consisting of any of the polypeptides presented in Table 8 (presented earlier); or from the group consisting of any of the polypeptides presented in Table 9 (presented earlier); or from the group consisting of any of the polypeptides presented in Table 10 (presented later); or from the group consisting of any of the polypeptides presented in Table 11 (presented later); or from the group consisting of any of the polypeptides presented in Table 12 (presented later); or from the group consisting of any of the polypeptides presented in Table 13 (presented later); or from the group consisting of any of the polypeptides presented in Table 14 (presented later); or from the group consisting of any of the polypeptides presented in Table 15 (presented later).
39. The polypeptide according to any preceding paragraphs selected from the group consisting of any of the polypeptides presented in Table 8 (presented earlier)
40. The polypeptide according to any preceding paragraphs selected from the group consisting of any of the polypeptides presented in Table 9 (presented earlier)
41. The polypeptide according to any preceding paragraph wherein the polypeptide is:
N-alpha-[(S)-4-Carboxy-4-(19-carboxynonadecanoylamino)butyryl]-[Glu14,Arg17,Pro37]-pramlintide [example 53]
42. A pharmaceutical composition comprising a polypeptide according to any of the preceding paragraphs and a pharmaceutically acceptable excipient.

43. The pharmaceutical composition according to paragraph 42, which is suited for parenteral administration.
44. A process for preparing a pharmaceutical composition according to paragraph 42 or paragraph 43 comprising mixing a polypeptide according to any preceding paragraph with at least one pharmaceutically acceptable excipient.
45. A polypeptide according to any of the preceding paragraphs for use as a medicament.
46. A polypeptide according to any one of the preceding paragraphs for use in the treatment or prevention of hyperglycemia, type 2 diabetes, impaired glucose tolerance, type 1 diabetes, obesity, hypertension, syndrome X, dyslipidemia, cognitive disorders, atherosclerosis, myocardial infarction, coronary heart disease and other cardiovascular disorders, stroke, inflammatory bowel syndrome, dyspepsia and gastric ulcers.
47. A polypeptide according to any one of the preceding paragraphs for use in delaying or preventing disease progression in type 2 diabetes.
48. A polypeptide according to any one of the preceding paragraphs for use in preventing or treating obesity.
49. A polypeptide according to any one of the preceding paragraphs for use in decreasing food intake, decreasing β-cell apoptosis, increasing β-cell function and β-cell mass, and/or for restoring glucose sensitivity to β-cells.
50. A polypeptide according to any one of the preceding paragraphs for use in the treatment or prevention of hypercalcaemia, osteoporosis or ostitis derformans.
51. A method of treating or preventing hyperglycemia, type 2 diabetes, impaired glucose tolerance, type 1 diabetes, obesity, hypertension, syndrome X, dyslipidemia, cognitive disorders, atherosclerosis, myocardial infarction, coronary heart disease and other cardiovascular disorders, stroke, inflammatory bowel syndrome, dyspepsia and gastric ulcers by administering a polypeptide according to any preceding paragraph to an animal.
52. A method of delaying or preventing disease progression in type 2 diabetes by administering a polypeptide according to any preceding paragraph to an animal.
53. A method of decreasing food intake, decreasing n-cell apoptosis, increasing n-cell function and n-cell mass, and/or for restoring glucose sensitivity to n-cells by administering a polypeptide according to any preceding paragraph to an animal.
54. A method of treating or preventing hypercalcaemia, osteoporosis or ostitis derformans by administering a polypeptide according to any preceding paragraph to an animal.
55. The polypeptide according to any one of the preceding paragraphs wherein said polypeptide has an $EC_{50}$ at the human amylin receptor of about 1800 pM or less.
56. The polpeptide according to any one of the preceding paragraphs wherein said polypeptide has an $EC_{50}$ at the human calcitonin receptor of about 1800 pM or less.

The invention will be further summarised in the further paragraphs below:

1. A derivative of amylin, which is an amylin analogue having up to ten amino acid residues modifications as compared to SEQ ID NO: 2 and having a substituent attached to the α-amino group of the N-terminal amino acid residue or to a Lys residue in the amylin analogue, wherein said substituent comprises an albumin binding moiety and wherein
    a. the amino acid residue in position 14 of the amylin analogue is Glu or
    b. the amino acid residue in position 35 of the amylin analogue is His, Arg, Lys, Asp or Glu or
    c. the amino acid residue in position 37 of the amylin analogue is Pro
2. A derivative according to paragraph 1, wherein the amino acid residue in position 14 is Glu.
3. A derivative according to paragraphs 1-2, wherein
    a. the amino acid residue in position 14 is Glu and the amino acid in position 35 is His, Arg, Lys, Asp or Glu or
    b. the amino acid residue in position 14 is Glu and the amino acid in position 37 is Pro
4. A derivative according to paragraphs 1-3, wherein
    a. the amino acid residue in position 14 is Glu and the amino acid in position 35 is His.
5. A derivative according to paragraphs 1-4, wherein the amino acid residue in position 17 is His.
6. A derivative according to paragraphs 1-5, wherein the amylin analogue comprises 1, 2, 3, 4, 5 or 6 substitutions.
7. A derivative according to paragraphs 1-6 wherein the amino acid in position 1 of the amylin analogue is substituted or is deleted.
8. A derivative according to paragraphs 1-7 wherein the amino acid in position 1 is selected from the group consisting of Lys, Glu, Arg, Ala, Ser, Cys, Gly and His.
9. A derivative according to paragraphs 1-8, wherein the substituent comprises a linker.
10. A derivative according to paragraphs 1-9, wherein the linker comprises 1-10 amino acids which are attached to the α-amino group of the N-terminal amino acid residue or to a Lys residue in the amylin analogue.
11. A derivative according to paragraph 10, wherein the amino acids are selected from the group consisting of γGlu, γGlu-γGlu, γGlu-γGlu-γGlu, γGlu-γGlu-γGlu-γGlu, Glu, Glu-Glu, Glu-Arg, Glu-Glu-Arg, His, His-His, His-γGlu, His His γGlu, Gly, Gly γGlu, Ser, Ser-γGlu, D-Arg-D-Arg, Arg, Arg-Arg, Arg-Arg-γGlu, Ser-Ser,-Gly-Ser-Ser, Ser-Ser,-Gly-Ser-Ser-γGlu, Ser-Ser-Gly-Ser-Ser-Gly and Ser-Ser-Gly-Ser-Ser-Gly-γGlu.
12. A derivative according to paragraphs 1-11, wherein the linker comprises —C(O)—$(CH_2)_l$—O—[$CH_2CH_2$—O]$_m$—$(CH_2)_p$—[NHC(O)—$(CH_2)_l$—O—[$(CH_2)_n$—O]$_m$—$(CH_2)_q$]$_q$—NH—wherein l, m, n, and p independently are 1-7, and q is 0-5.
13. A derivative according to paragraphs 1-12, wherein the linker is selected from the group consisting of —C(O)—$CH_2$—O—$CH_2$—$CH_2$—O—$CH_2$—$CH_2$—NH— or —C(O)$CH_2$—O—$CH_2CH_2$—O—$CH_2$—$CH_2$—[NHC(O)$CH_2$O—$CH_2$—$CH_2$O—$CH_2$—$CH_2$—]$_1$—NH— and —C(O)—$(CH_2)_2$—O—[$CH_2CH_2$—O]$_7$—$(CH_2)_2$—NH—.
14. A derivative according to paragraphs 1-13, wherein the linker is selected from the group consisting of γGlu-C(O)—$CH_2$—O—$CH_2$—$CH_2$—O—$CH_2$—$CH_2$—[NHC(O)—$CH_2$—O—$CH_2$—$CH_2$—O—$CH_2$—$CH_2$—]$_1$—NH— and Arg-Arg-γGlu-C(O)—$CH_2$—$CH_2$—$CH_2$—O—$CH_2$—$CH_2$—[NHC(O)—$CH_2$O—$CH_2$—$CH_2$—O—$CH_2$—$CH_2$—]$_1$—NH—.
15. A derivative according to any of paragraphs 1-14, wherein the albumin binding residue is an acyl group selected from the group comprising $HOOC(CH_2)_s CO$—, wherein s is an integer from 14 to 20, for example 16 or 18.
16. A derivative according to paragraphs 1-15, wherein the derivative comprises a γGlu linker attached to the N-terminal of the amylin analogue and $HOOC(CH_2)_{18}CO$ or HOOC(CH$_2$)$_{16}$CO— as the albumin binding residue and where the sequence of the amylin analogue comprises:
  a. Glu in position 14
  b. His or Arg in position 17
  c. His in position 35 or Pro in position 37,
17. A derivative according to paragraph 1, where the amylin analogue comprises an amino acid sequence of formula 1:

Formula (1)                                                             (SEQ ID No: 3)
Xaa$_1$-Cys-Xaa$_3$-Thr-Ala-Thr-Cys-Ala-Thr-Gln-Arg-Leu-Ala-Glu-Phe-Leu-Xaa$_{17}$-Xaa$_{18}$-

Ser-Ser-Xaa$_{21}$-Xaa$_{22}$-Phe-Gly-Pro-Xaa$_{26}$-Leu-Pro-Pro-Thr-Xaa$_{31}$-Val-Gly-Ser-Xaa$_{35}$-

Thr-Xaa$_{37}$ wherein
Xaa$_1$ is deleted or independently selected from Ala, Cys, Glu, Gly, His, Arg, Ser and Lys;
Xaa$_3$ is independently selected from Gly, His, Arg, Ser and Asn;
Xaa$_{17}$ is independently selected from His, Arg, Lys and Val;
Xaa$_{18}$ is independently selected from Arg, Lys and His;
Xaa$_{21}$ is independently selected from Ala, Lys, Gln, Ser and Asn;
Xaa$_{22}$ is independently selected from Glu, Gln, Ser, Thr and Asn;
Xaa$_{26}$ is independently selected from Pro, Arg and Ile;
Xaa$_{31}$ is independently selected from Ser, Glu, Asp and Asn;
Xaa$_{35}$ is independently selected from His, Arg, Lys, Asp and Glu;
Xaa$_{37}$ is independently selected from Pro and Tyr;
and where the C-terminal may optionally be derivatized as an amide.
18. A derivative according to paragraphs 1 and 17, wherein
Xaa$_1$ is deleted or independently selected from His, Arg and Lys;
Xaa$_3$ is independently selected from Gly, His and Asn;
Xaa$_{17}$ is independently selected from His, Arg and Val;
Xaa$_{18}$ is independently selected from Arg and His;
Xaa$_{21}$ is independently selected from Ser and Asn;
Xaa$_{22}$ is Asn;
Xaa$_{26}$ is Ile;
Xaa$_{31}$ is independently selected from Glu and Asn;
Xaa$_{35}$ is independently selected from His, Arg, Lys, Asp and Glu;
Xaa$_{37}$ is independently selected from Pro and Tyr.
19. A derivative according to any of paragraphs 1 and 17 wherein
Xaa$_1$ is deleted or independently selected from Gly, His, Arg, Ser and Lys;
Xaa$_3$ is independently selected from His and Asn;
Xaa$_{17}$ is independently selected from His, Arg and Val;
Xaa$_{18}$ is independently selected from Arg and His;
Xaa$_{21}$ is independently selected from Gln, Ser and Asn;
Xaa$_{22}$ is Asn;
Xaa$_{26}$ is independently selected from Pro and Ile;
Xaa$_{31}$ is Asn;
Xaa$_{35}$ is His;
Xaa$_{37}$ is Tyr.
20. A derivative according to paragraphs 1 and 17, wherein
Xaa$_1$ is deleted or independently selected from Ala, Cys, Glu, Gly, His, Arg, Ser and Lys;
Xaa$_3$ is Asn;
Xaa$_{17}$ is independently selected from His, Arg and Val;
Xaa$_{18}$ is independently selected from Arg, Lys and His;
Xaa$_{21}$ is independently selected from Gln and Asn;
Xaa$_{22}$ is independently selected from Thr and Asn;
Xaa$_{26}$ is Ile;
Xaa$_{31}$ is Asn;
Xaa$_{35}$ is independently selected from Gly and Asn;
Xaa$_{37}$ is Pro.
21. A derivative according to any of paragraphs 1 and 17, wherein
Xaa$_1$ is deleted;
Xaa$_3$ is independently selected from Gly and Asn;
Xaa$_{17}$ is independently selected from His, Arg and Val;
Xaa$_{18}$ is independently selected from Arg and His;
Xaa$_{21}$ is independently selected from Gln and Asn;
Xaa$_{22}$ is independently selected from Gln and Asn;
Xaa$_{26}$ is Ile;
Xaa$_{31}$ is independently selected from Glu and Asn;
Xaa$_{35}$ is independently selected from His and Ser;
Xaa$_{37}$ is independently selected from Pro and Tyr.
22. A derivative according to paragraphs 1 and 17, wherein
Xaa$_1$ is Lys;
Xaa$_3$ is Asn;
Xaa$_{17}$ is independently selected from His, Lys, Arg and Val;
Xaa$_{18}$ is independently selected from Arg and His;
Xaa$_{21}$ is independently selected from Ala, Lys, Gln and Ser;
Xaa$_{22}$ is independently selected from Glu, Gln, Ser, Thr and Asn;
Xaa$_{26}$ is independently selected from Pro and Ile;
Xaa$_{31}$ is independently selected from Ser, Glu, Asp and Asn;
Xaa$_{35}$ is independently selected from His, Glu and Asn;
Xaa$_{37}$ is independently selected from Pro and Tyr.
23. A derivative according to paragraphs 1 and 17-22, wherein the albumin binding residue binds non-covalently to albumin.
24. A derivative according to any of paragraphs 1 and 17-23, wherein the albumin binding residue has a binding affinity towards human serum albumin that is below about 10 µM or below about 1 µM.
25. A derivative according to any of paragraphs 1 and 17-24, wherein the albumin binding residue comprises a group which can be negatively charged at pH 7.4.
26. A derivative according to any of paragraphs 1 and 17-25, wherein the albumin binding residue comprises a carboxylic acid group.
27. A derivative according to any of paragraphs 1 and 17-26, wherein the albumin binding residue is an acyl group selected from the group comprising HOOC (CH$_2$)$_s$ CO—, wherein s is an integer from 12 to 22, for example 17, 18, 19, 20, 21 or 22.
28. A derivative according to paragraphs 1 and 27, wherein s is 16 or 18.
29. A derivative according to paragraphs 1 and 17-28, wherein the substituent comprises a linker
30. A derivative according to paragraphs 1 and 17-29, wherein the linker comprises 1-10 amino acids which are attached to the α-amino group of the N-terminal amino acid residue or to a Lys residue in the amylin analogue.

31. A derivative according to paragraphs 1 and 17-30, wherein the amino acids are selected from the group consisting of A derivative according to paragraph 10, wherein the amino acids are selected from the group consisting of γGlu, γGlu-γGlu, γGlu-γGlu-γGlu, γGlu-γGlu-γGlu-γGlu, Glu, Glu-Glu, Glu-γGlu, Glu-Arg, Glu-Glu-Arg, His, His-His, His-γGlu, His-His-γGlu, Gly, Gly-γGlu, Ser, Ser-γGlu, D-Arg-D-Arg, Arg, Arg-Arg, Arg-Arg-γGlu, Ser-Ser,-Gly-Ser-Ser, Ser-Ser,-Gly-Ser-Ser-γGlu, Ser-Ser-Gly-Ser-Ser-Gly and Ser-Ser-Gly-Ser-Ser-Gly-γGlu.

32. A derivative according to paragraphs 1 and 17-31, wherein the linker comprises γGlu.

33. A derivative according to paragraphs 1 and 17-32, wherein the linker comprises —C(O)—$(CH_2)_l$—O—$[CH_2CH_2—O]_m$—$(CH_2)_p$—[NHC(O)—$(CH_2)_l$—O—$[(CH_2)_n—O]_m$—$(CH_2)_p]_q$—NH— wherein l, m, n, and p independently are 1-7, and q is 0-5.

34. A derivative according to paragraphs 1 and 17-33, wherein the linker is selected from the group consisting of —C(O)—$CH_2$—O—$CH_2$—$CH_2$—O—$CH_2$—$CH_2$—NH— or —C(O)—$CH_2$—O—$CH_2$—$CH_2$—O—$CH_2$—$CH_2$—[NHC(O)—$CH_2$—O—$CH_2$—$CH_2$—O—$CH_2$—$CH_2$—]$_1$ —NH— and —C(O)—$(CH_2)_2$—O—$[CH_2CH_2—O]_7$—$(CH_2)_2$—NH—.

35. A derivative according to paragraphs 1 and 17-34, wherein the linker is selected from the group consisting of γGlu-C(O)—$CH_2$—O—$CH_2$—$CH_2$—O—$CH_2$—$CH_2$—[NHC(O)—$CH_2O$—$CH_2$—$CH_2$—O—$CH_2$—$CH_2]_1$—NH— and Arg-Arg-γGlu-C(O)—$CH_2$—O—$CH_2$—$CH_2$—O—$CH_2$—$CH_2$—[NHC(O)—$CH_2O$—$CH_2$—$CH_2O$—$CH_2$—$CH_2]_1$—NH—.

36. A derivative according to paragraphs 1 and 17-28, wherein the linker is γGlu-γGlu-γGlu-γGlu-C(O)—$CH_2$—O—$CH_2$—$CH_2O$—$CH_2$—$CH_2$—[NHC(O)—$CH_2O$—$CH_2$—$CH_2$—O—$CH_2$—$CH_2]_1$—NH—.

37. A derivative according to paragraph 1, wherein the derivative is selected from the group consisting of:

N-alpha-[(S)-4-Carboxy-4-(19-carboxynonadecanoylamino)butyryl]-[His1,Glu14,His17,Arg18]-pramlintide, N-alpha-[(S)-4-Carboxy-4-(19-carboxynonadecanoylamino)butyryl]-[His1,Glu8,Glu14,His17,Arg18]-pramlintide, N-alpha-[(S)-4-Carboxy-4-(19-carboxynonadecanoylamino)butyryl]-[des1,Gly3,Glu14,His17,Arg18,Glu31,Gly35]-pramlintide, N-alpha-[(S)-4-Carboxy-4-(19-carboxynonadecanoylamino)butyryl]-[des1,Gly3,Glu14,His17,Arg18,Gln21,Gln22,Glu31,Gly35]-pramlintide, N-alpha-[(S)-4-Carboxy-4-(19-carboxynonadecanoylamino)butyryl]-[Glu1,Glu14,His17,Arg18]-pramlintide, N-alpha-[(S)-4-Carboxy-4-(19-carboxynonadecanoylamino)butyryl]-[His1,Glu14,His17,Arg18,Ala25,Pro26,Ser28,Ser29]-pramlintide, N-alpha-[(S)-4-Carboxy-4-(19-carboxynonadecanoylamino)butyryl]-[His1,Glu14,His17,Arg18,Glu25,Ser28,Arg29]-pramlintide, N-alpha-[(S)-4-Carboxy-4-(19-carboxynonadecanoylamino)butyryl]-[His1,Glu14,His17,Arg18,Glu22,Ala25,Arg26,Ser28,Ser29]-pramlintide, N-alpha-[(S)-4-Carboxy-4-(19-carboxynonadecanoylamino)butyryl]-[His1,Glu14,His17,Arg18,Ser21,Ser22,Asp31,Asp35]-pramlintide, N-alpha-[(S)-4-Carboxy-4-(19-carboxynonadecanoylamino)butyryl]-[Glu1,Glu14,His17,Arg18,Pro37]-pramlintide, N-alpha-[(S)-4-Carboxy-4-(19-carboxynonadecanoylamino)butyryl]-His-His-[His1,Glu14,His17]-pramlintide, N-alpha-[(S)-4-Carboxy-4-(19-carboxynonadecanoylamino)butyryl]-His-His- [His1,Glu14,Arg17]-pramlintide, N-epsilon21-[2-(2-{2-[2-(2-{2-[(S)-4-Carboxy-4-(19-carboxyheptadecanoylamino)butyrylamino]ethoxy}ethoxy)acetylamino]ethoxy}ethoxy)acetyl]-[Arg1,Glu14,His17,Arg18,Lys21]-pramlintide, N-alpha-[(S)-4-Carboxy-4-(19-carboxynonadecanoylamino)butyryl]-[His1,Glu14,Arg18]-pramlintide, N-alpha-[(S)-4-Carboxy-4-(19-carboxynonadecanoylamino)butyryl]-[His1,Gly3,Glu14,His17,Arg18,Ser21,Ser22,Glu31,Glu35]-pramlintide, N-alpha-[(S)-4-Carboxy-4-(19-carboxynonadecanoylamino)butyryl]-His-[His1,Glu14,His17]-pramlintide, N-alpha-[(S)-4-Carboxy-4-(19-carboxynonadecanoylamino)butyryl]-[His1,Glu14,His17]-pramlintide, N-alpha-[(S)-4-Carboxy-4-(19-carboxynonadecanoylamino)butyryl]-His-His-[His1,Glu14,His17,Ala25,Pro26,Ser28,Ser29]-pramlintide, N-alpha-[(S)-4-Carboxy-4-(19-carboxynonadecanoylamino)butyryl]-His-His-[His1,Glu14]-pramlintide, N-alpha-[(S)-4-Carboxy-4-(19-carboxynonadecanoylamino)butyryl]-His-His-[His1,Glu14,His17,Arg35]-pramlintide, N-alpha-[(S)-4-Carboxy-4-(19-carboxynonadecanoylamino)butyryl]-His-His- [His1,Arg3,Glu14,His17]-pramlintide, N-alpha-[2-(2-{2-[2-(2-{2-[(S)-4-Carboxy-4-(19-carboxyheptadecanoylamino)butyrylamino]ethoxy}ethoxy)acetylamino]ethoxy}ethoxy)acetyl]-[His1,Glu14,His17,Arg18,Ala19,Thr20,Gln21,Glu22,Leu23]-pramlintide N-alpha-[(S)-4-Carboxy-4-(19-carboxynonadecanoylamino)butyryl]-[Glu1,Gly3,Glu14,Arg18,Ser21,Ser22,Ala25,Pro26,Ser28,Ser29,Glu31,Arg35]-pramlintide N-alpha-[(S)-4-Carboxy-4-(19-carboxynonadecanoylamino)butyryl]-Glu-[Arg1,Glu14,His17]-pramlintide, N-alpha-[(S)-4-Carboxy-4-(19-carboxynonadecanoylamino)butyryl]-Glu-[Glu14,His17]-pramlintide, N-alpha-[(S)-4-Carboxy-4-(19-carboxynonadecanoylamino)butyryl]-[Glu14,His17]-pramlintide, N-alpha-[(S)-4-Carboxy-4-(19-carboxynonadecanoylamino)butyryl]-[des1,Glu14,His17]-pramlintide, N-alpha-[(S)-4-Carboxy-4-(19-carboxynonadecanoylamino)butyryl]-[Glu1,Glu14,His17]-pramlintide, N-alpha-[(S)-4-Carboxy-4-(19-carboxynonadecanoylamino)butyryl]-[Glu1,Glu14,His17,Arg18]-pramlintide, N-alpha-[(S)-4-Carboxy-4-(19-carboxynonadecanoylamino)butyryl]-His-His-[His1,Glu14,His17,His35]-pramlintide, N-alpha-[(S)-4-Carboxy-4-(19-carboxynonadecanoylamino)butyryl]-His-His-[His1,His3,Glu14,His17,His35]-pramlintide, N-alpha-[(S)-4-Carboxy-4-(19-carboxynonadecanoylamino)butyryl]-His-His-[His1,His3,Glu14,His17,His29,His35]-pramlintide, N-alpha-[(S)-4-Carboxy-4-(19-carboxynonadecanoylamino)butyryl]-His-His-[His1,Glu14,His17,His 29,His 35]-pramlintide, N-alpha-[(S)-4-Carboxy-4-(19-carboxynonadecanoylamino)butyryl]-His-His-[His1,His3,Glu14,His17]-pramlintide, N-alpha-[(S)-4-Carboxy-4-(19-carboxynonadecanoylamino)butyryl]-His-His-[His1,Glu14,His17,His29]-pramlintide,
N-alpha-[2-(2-{2-[2-(2-{2-[(S)-4-Carboxy-4-(19-carboxyheptadecanoylamino)butyrylamino]ethoxy}ethoxy)acetylamino]ethoxy}ethoxy)acetyl]-D-Arg-D-Arg-[Glu14,His17,Arg18]-pramlintide,
N-alpha-[2-(2-{2-[2-(2-{2-[(S)-4-Carboxy-4-(19-carboxyheptadecanoylamino)butyrylamino]ethoxy}ethoxy)acetylamino]ethoxy}ethoxy)acetyl]-D-Arg-D-Arg-[Glu14,His17,Arg18,Ala21,Ser35]-pramlintide,
N-alpha-[(S)-4-Carboxy-4-(19-carboxynonadecanoylamino)butyryl]-Ser-Ser-Gly-Ser-Ser-[Gly1,Glu14,His17]-pramlintide,
N-alpha-[(S)-4-Carboxy-4-(19-carboxynonadecanoylamino)butyryl]-Glu-[His1,Glu14,His17]-pramlintide,
N-alpha-[(S)-4-Carboxy-4-(19-carboxynonadecanoylamino)butyryl]-Glu-Glu-[Glu14,His17]-pramlintide,
N-alpha-[(S)-4-Carboxy-4-(17-carboxyheptadecanoylamino)butyryl]-Glu-[Glu14,His17]-pramlintide,
N-alpha-[2-(2-{2-[2-(2-{2-[(S)-4-Carboxy-4-(19-carboxyheptadecanoylamino)butyrylamino]ethoxy}ethoxy)acetylamino]ethoxy}ethoxy)acetyl]-[des1,Glu14,His17]-pramlintide,
N-alpha-[(S)-4-Carboxy-4-(19-carboxynonadecanoylamino)butyryl]-Ser-Ser-Gly-Ser-Ser-Gly-[His1,Glu14,His17]-pramlintide,
N-alpha-[(S)-4-Carboxy-4-(17-carboxyheptadecanoylamino)butyryl]-His-His-[His1,Glu14,His17]-pramlintide,
N-alpha-[(S)-4-Carboxy-4-(17-carboxyheptadecanoylamino)butyryl]-[Glu14,His17]-pramlintide,
N-alpha-[(S)-4-Carboxy-4-(17-carboxyheptadecanoylamino)butyryl]-His-[His1,Glu14,His17]-pramlintide,
N-alpha-[(S)-4-Carboxy-4-(17-carboxyheptadecanoylamino)butyryl]-[His1,Glu14,His17]-pramlintide,
N-alpha-{(S)-4-Carboxy-4-[(S)-4-Carboxy-4-(17-carboxyheptadecanoylamino)butyrylamino]butyryl}-[des1,Glu14,His17]-pramlintide,
N-alpha-[(S)-4-Carboxy-4-(19-carboxynonadecanoylamino)butyryl]-[Glu14,Arg17]-pramlintide,
N-alpha-[(S)-4-Carboxy-4-(17-carboxyheptadecanoylamino)butyryl]-[Glu14,Arg17]-pramlintide,
N-alpha-[(S)-4-Carboxy-4-(19-carboxynonadecanoylamino)butyryl]-[Glu14,His17,Pro37]-pramlintide,
N-alpha-[(S)-4-Carboxy-4-(19-carboxynonadecanoylamino)butyryl]-[Glu14,Arg17,Pro37]-pramlintide,
N-alpha-[(S)-4-Carboxy-4-(19-carboxynonadecanoylamino)butyryl]-[Glu10,Glu14,His17]-pramlintide,
N-alpha-[(S)-4-Carboxy-4-(19-carboxynonadecanoylamino)butyryl]-[Glu14,His17,His 35]-pramlintide,
N-alpha-[(S)-4-Carboxy-4-(19-carboxynonadecanoylamino)butyryl]-Glu-[Glu14,His17,His 35]-pramlintide,
N-alpha-[(S)-4-Carboxy-4-(19-carboxynonadecanoylamino)butyryl]-[Glu-14,Arg17,His35]-pramlintide,
N-alpha-[(S)-4-Carboxy-4-(19-carboxynonadecanoylamino)butyryl]-Glu-[Glu14,Arg17,His35]-pramlintide,
N-alpha-[(S)-4-Carboxy-4-(17-carboxyheptadecanoylamino)butyryl]-[Glu14,His17,His 35]-pramlintide,
N-alpha-[(S)-4-Carboxy-4-(17-carboxyheptadecanoylamino)butyryl]-[Glu14,His17,His 35]-pramlintide,
N-alpha-[(S)-4-Carboxy-4-(17-carboxyheptadecanoylamino)butyryl]-[Glu14,Arg17,His35]-pramlintide,
N-alpha-[(S)-4-Carboxy-4-(17-carboxyheptadecanoylamino)butyryl]-Glu-[Glu-14,Arg17,His35]-pramlintide,
N-alpha-[(S)-4-Carboxy-4-(19-carboxynonadecanoylamino)butyryl]-His-His-[His1,Glu14,His17,Ser21,Glu35]-pramlintide,
N-alpha-[(S)-4-Carboxy-4-(19-carboxynonadecanoylamino)butyryl]-[Glu-14,His17,Ala25,Pro26,Ser28,Ser29,His35]-pramlintide,
N-alpha-[(S)-4-Carboxy-4-(19-carboxynonadecanoylamino)butyryl]-[Glu-14,Arg17,Ala25,Pro26,Ser28,Ser29,His35]-pramlintide,
N-alpha-[(S)-4-Carboxy-4-(19-carboxynonadecanoylamino)butyryl]-His-[Glu-14,His17,His 35]-pramlintide,
N-alpha-[(S)-4-Carboxy-4-(19-carboxynonadecanoylamino)butyryl]-His-His-[Glu14,His17,His 35]-pramlintide,
N-alpha-[(S)-4-Carboxy-4-(19-carboxynonadecanoylamino)butyryl]-His-[Glu14,Arg17,His35]-pramlintide,
N-alpha-[(S)-4-Carboxy-4-(19-carboxynonadecanoylamino)butyryl]-His-His-[Glu14,Arg17,His35]-pramlintide,
N-alpha-[(S)-4-Carboxy-4-(17-carboxyheptadecanoylamino)butyryl]-His-[Glu14,His17,His 35]-pramlintide,
N-alpha-[(S)-4-Carboxy-4-(17-carboxyheptadecanoylamino)butyryl]-His-[Glu14,Arg17,His35]-pramlintide,
N-epsilon25-[2-(2-{2-[2-(2-{2-[(S)-4-Carboxy-4-(17-carboxyheptadecanoylamino)butyrylamino]ethoxy}ethoxy)acetylamino]ethoxy}ethoxy)acetyl]-[Glu14,Ser21,Lys25]-pramlintide,
N-epsilon25-[2-(2-{2-[2-(2-{2-[(S)-4-Carboxy-4-(17-carboxyheptadecanoylamino)butyrylamino]ethoxy}ethoxy)acetylamino]ethoxy}ethoxy)acetyl]-[Glu14,His17,Lys25]-pramlintide,
N-epsilon21-[2-(2-{2-[2-(2-{2-[(S)-4-Carboxy-4-(17-carboxyheptadecanoylamino)butyrylamino]ethoxy}ethoxy)acetylamino]ethoxy}ethoxy)acetyl]-[Glu14,His17,Lys21,Glu35]-pramlintide,
N-alpha-[(S)-4-Carboxy-4-(19-carboxynonadecanoylamino)butyryl]-[des1,Glu14,His17,His35]-pramlintide,
N-alpha-[(S)-4-Carboxy-4-(19-carboxynonadecanoylamino)butyryl]-[His1,Glu14,His17,His35]-pramlintide,
N-alpha-[(S)-4-Carboxy-4-(19-carboxynonadecanoylamino)butyryl]-[His1,Glu14,His17,Arg18,His35]-pramlintide,
N-alpha-[(S)-4-Carboxy-4-(19-carboxynonadecanoylamino)butyryl]-[Glu14,His17,Arg18,His35]-pramlintide,
N-alpha-[(S)-4-Carboxy-4-(19-carboxynonadecanoylamino)butyryl]-[Glu14,His17,Arg18]-pramlintide,
N-epsilon17-[2-(2-{2-[2-(2-{2-[(S)-4-Carboxy-4-(17-carboxyheptadecanoylamino)butyrylamino]ethoxy}ethoxy)acetylamino]ethoxy}ethoxy)acetyl]-[Glu14,Lys17]-pramlintide,
N-alpha-[(S)-4-Carboxy-4-(19-carboxynonadecanoylamino)butyryl]-Gly-[Glu14,His17,His 35]-pramlintide,
N-alpha-[2-(2-{2-[2-(2-{2-[(S)-4-Carboxy-4-(17-carboxyheptadecanoylamino)butyrylamino]ethoxy}ethoxy)acetylamino]ethoxy}ethoxy)acetyl]-[Glu1,Glu14,His17,Pro37]-pramlintide,
N-epsilon17-[2-(2-{2-[2-(2-{2-[(S)-4-Carboxy-4-(17-carboxyheptadecanoylamino)butyrylamino]ethoxy}ethoxy)acetylamino]ethoxy}ethoxy)acetyl]-[Glu14,Lys17,Ser21,Glu35]-pramlintide,
N-alpha-[(S)-4-Carboxy-4-(19-carboxynonadecanoylamino)butyryl]-[His1,Glu14,His17,Pro37]-pramlintide,
N-alpha-[(S)-4-Carboxy-4-(19-carboxynonadecanoylamino)butyryl]-Ser-[Glu14,His17,His35]-pramlintide,
N-alpha-[(S)-4-Carboxy-4-(19-carboxynonadecanoylamino)butyryl]-[Glu14,Pro37]-pramlintide, N-epsilon1-[(S)-4-Carboxy-4-(19-carboxynonadecanoylamino)butyryl]-[Glu14,His17,His35]-pramlintide,
N-alpha-[(S)-4-Carboxy-4-(19-carboxynonadecanoylamino)butyryl]-[Gly1,Glu14,Arg17,Pro37]-pramlintide,
N-alpha-[(S)-4-Carboxy-4-(19-carboxynonadecanoylamino)butyryl]-Gly-[His1,Glu14,Arg17,Pro37]-pramlintide,
N-alpha-[(S)-4-Carboxy-4-(19-carboxynonadecanoylamino)butyryl]-[His1,Glu14,Arg17,Pro37]-pramlintide,
N-alpha-[(S)-4-Carboxy-4-(19-carboxynonadecanoylamino)butyryl]-[Gly1,Glu14,His17,Pro37]-pramlintide,
N-alpha-[(S)-4-Carboxy-4-(19-carboxynonadecanoylamino)butyryl]-Gly-[His1,Glu14,His17,Pro37]-pramlintide,
N-alpha-[(S)-4-Carboxy-4-(19-carboxynonadecanoylamino)butyryl]-[Glu14,His35]-pramlintide,
N-epsilon1-[(S)-4-Carboxy-4-(17-carboxyheptadecanoylamino)butyryl]-[Glu14,His17,His35]-pramlintide,
N-alpha-[(S)-4-Carboxy-4-(19-carboxynonadecanoylamino)butyryl]-[Arg1,Glu14,His17,His 35]-pramlintide,
N-alpha-[(S)-4-Carboxy-4-(19-carboxynonadecanoylamino)butyryl]-[Arg1,Glu14,His17,Pro37]-pramlintide,
N-alpha-[(S)-4-Carboxy-4-(19-carboxynonadecanoylamino)butyryl]-[Arg1,Pro37]-pramlintide,
N-alpha-[(S)-4-Carboxy-4-(19-carboxynonadecanoylamino)butyryl]-[Arg1,His35]-pramlintide,
N-alpha-[(S)-4-Carboxy-4-(19-carboxynonadecanoylamino)butyryl]-Gly-[Arg1,His35]-pramlintide,
N-alpha-[(S)-4-Carboxy-4-(19-carboxynonadecanoylamino)butyryl]-Gly-[Arg1,Glu14,His17,His 35]-pramlintide,
N-alpha-[(S)-4-Carboxy-4-(19-carboxynonadecanoylamino)butyryl]-Gly-[Arg1,Glu14,His17,Pro37]-pramlintide,
N-alpha-[(S)-4-Carboxy-4-(19-carboxynonadecanoylamino)butyryl]-Gly-[Arg1,Glu14,Pro37]-pramlintide,
N-alpha-[(S)-4-Carboxy-4-(19-carboxynonadecanoylamino)butyryl]-Gly-[Arg1,Pro37]-pramlintide,
N-alpha-[(S)-4-Carboxy-4-(19-carboxynonadecanoylamino)butyryl]-[des1,Glu14,His17,Pro37]-pramlintide,
N-alpha-[(S)-4-Carboxy-4-(19-carboxynonadecanoylamino)butyryl]-[Gly1,Glu14,His17,His35]-pramlintide,
N-alpha-[(S)-4-Carboxy-4-(19-carboxynonadecanoylamino)butyryl]-[Ser1,Glu14,His17,Pro37]-pramlintide,
N-alpha-[(S)-4-Carboxy-4-(19-carboxynonadecanoylamino)butyryl]-[Ser1,Glu14,His17,His 35]-pramlintide,
N-alpha-[(S)-4-Carboxy-4-(19-carboxynonadecanoylamino)butyryl]-[des1,Glu14,Pro37]-pramlintide,
N-alpha-[(S)-4-Carboxy-4-(19-carboxynonadecanoylamino)butyryl]-[His1,Glu14,Pro37]-pramlintide,
N-alpha-[(S)-4-Carboxy-4-(19-carboxynonadecanoylamino)butyryl]-[His1,Glu14,Ser21,Ser28,Ser29,His 35]-pramlintide,
N-alpha-[(S)-4-Carboxy-4-(19-carboxynonadecanoylamino)butyryl]-[His1,Glu14,Arg17,Ser21,Ser28,Ser29,His35]-pramlintide,
N-alpha-[(S)-4-Carboxy-4-(19-carboxynonadecanoylamino)butyryl]-[Glu14,His17,Arg35]-pramlintide,
N-alpha-[(S)-4-Carboxy-4-(19-carboxynonadecanoylamino)butyryl]-[Glu14,His17,Lys35]-pramlintide,
N-alpha-[(S)-4-Carboxy-4-(19-carboxynonadecanoylamino)butyryl]-[Glu14,His17,His36]-pramlintide,
N-alpha-[(S)-4-Carboxy-4-(19-carboxynonadecanoylamino)butyryl]-[Glu14,His17,His34]-pramlintide,
N-alpha-[(S)-4-Carboxy-4-(19-carboxynonadecanoylamino)butyryl]-[Glu14,His17,His32]-pramlintide,
N-alpha-[(S)-4-Carboxy-4-(19-carboxynonadecanoylamino)butyryl]-[Glu14,His17,Gln21,His 35)-pramlintide,
N-alpha-[2-(2-{2-[2-(2-{2-[(S)-4-Carboxy-4-(19-carboxyheptadecanoylamino)butyrylamino]ethoxy}ethoxy)acetylamino]ethoxy}ethoxy)acetyl]-[Glu14,His17,Ser21,His35]-pramlintide,
N-alpha-[2-(2-{2-[2-(2-{2-[(S)-4-Carboxy-4-(19-carboxyheptadecanoylamino)butyrylamino]ethoxy}ethoxy)acetylamino]ethoxy}ethoxy)acetyl]-[His1,Glu14,His17,Ser21,His35]-pramlintide,
N-alpha-[2-(2-{2-[2-(2-{2-[(S)-4-Carboxy-4-(17-carboxyheptadecanoylamino)butyrylamino]ethoxy}ethoxy)acetylamino]ethoxy}ethoxy)acetyl]-D-Arg-D-Arg-[Orn1,Glu14,His17,Arg18]-pramlintide,
N-alpha-(19-carboxynonadecanoyl)-Glu-Glu-Arg-[Glu1,Pro37]-pramlintide
N-alpha-[(S)-4-Carboxy-4-(19-carboxynonadecanoylamino)butyryl]-Glu-Arg-[Glu1,Pro37]-pramlintide,
N-alpha-[(S)-4-Carboxy-4-(19-carboxynonadecanoylamino)butyryl]-Glu-Arg-[Glu1,Glu14,His17,Pro37]-pramlintide,
N-alpha-[(S)-4-Carboxy-4-(19-carboxynonadecanoylamino)butyryl]-Glu-Arg-[Glu1,Glu14,Arg17,Pro37]-pramlintide,
N-alpha-(19-carboxynonadecanoyl)-Glu-Glu-Arg-[Glu1,Glu14,His17,Pro37]-pramlintide,
N-epsilon25-[2-(2-{2-[2-(2-{2-[(S)-4-Carboxy-4-(17-carboxyheptadecanoylamino)butyrylamino]ethoxy}ethoxy)acetylamino]ethoxy}ethoxy)acetyl]-[Glu14,Lys25]-pramlintide,
N-epsilon21-[2-(2-{2-[2-(2-{2-[(S)-4-Carboxy-4-(19-carboxyheptadecanoylamino)butyrylamino]ethoxy}ethoxy)acetylamino]ethoxy}ethoxy)acetyl]-[Glu14,Lys21,Ser29,His35]-pramlintide,
N-alpha-[(S)-4-Carboxy-4-(19-carboxynonadecanoylamino)butyryl]-[Glu14,His17,Asp21,His35]-pramlintide,
N-alpha-[(S)-4-Carboxy-4-(19-carboxynonadecanoylamino)butyryl]-Glu-[Glu14,His17,Gln21,His35]-pramlintide,
N-alpha-[(S)-4-Carboxy-4-(19-carboxynonadecanoylamino)butyryl]-[Glu14,His17,Gln21,Pro37]-pramlintide,
N-epsilon21-[2-(2-{2-[2-(2-{2-[(S)-4-Carboxy-4-(19-carboxyheptadecanoylamino)butyrylamino]ethoxy}ethoxy)acetylamino]ethoxy}ethoxy)acetyl]-[Glu14,Lys21,Ser28,Ser29,His35]-pramlintide,
N-epsilon21-[2-(2-{2-[2-(2-{2-[(S)-4-Carboxy-4-(19-carboxyheptadecanoylamino)butyrylamino]ethoxy}ethoxy)acetylamino]ethoxy}ethoxy)acetyl]-[Glu14,Lys21,His35]-pramlintide,
N-epsilon25-[2-(2-{2-[2-(2-{2-[(S)-4-Carboxy-4-(19-carboxyheptadecanoylamino)butyrylamino]ethoxy}ethoxy)acetylamino]ethoxy}ethoxy)acetyl]-[Glu14,His17,Ser21,Lys25,Ser28,Ser29.His35]-pramlintide,
N-epsilon25-[2-(2-{2-[2-(2-{2-[(S)-4-Carboxy-4-(19-carboxyheptadecanoylamino)butyrylamino]ethoxy}ethoxy)acetylamino]ethoxy}ethoxy)acetyl]-[His17,His21,Lys25,Ser28,Ser29.His35]-pramlintide,
N-alpha-[(S)-4-Carboxy-4-(19-carboxynonadecanoylamino)butyryl]-[Glu14,His17,Gln35,Pro37]-pramlintide,
N-alpha-[(S)-4-Carboxy-4-(19-carboxynonadecanoylamino)butyryl]-[Glu14,His17,Gln21,Gln35,Pro37]-pramlintide, N-alpha-[(S)-4-Carboxy-4-(19-carboxynonadecanoylamino)butyryl]-[Gly1,Glu14,His17,Gln21,Gln35,Pro37]-pramlintide,
N-alpha-[(S)-4-Carboxy-4-(19-carboxynonadecanoylamino)butyryl]-[Glu1,Glu14,Gln21,Gln35,Pro37]-pramlintide,
N-alpha-[(S)-4-Carboxy-4-(19-carboxynonadecanoylamino)butyryl]-[Glu14,Gln21,Gln35,Pro37]-pramlintide,
N-epsilon25-[2-(2-{2-[2-(2-{2-[(S)-4-Carboxy-4-(19-carboxyheptadecanoylamino)butyrylamino]ethoxy}ethoxy)acetylamino]ethoxy}ethoxy)acetyl]-[His17,Lys25,Ser28,Ser29,His35]-pramlintide,
N-epsilon21-[2-(2-{2-[2-(2-{2-[(S)-4-Carboxy-4-(19-carboxyheptadecanoylamino)butyrylamino]ethoxy}ethoxy)acetylamino]ethoxy}ethoxy)acetyl]-[His17,Lys21,Ser28,His35]-pramlintide,
N-epsilon25-[2-(2-{2-[2-(2-{2-[(S)-4-Carboxy-4-(19-carboxyheptadecanoylamino)butyrylamino]ethoxy}ethoxy)acetylamino]ethoxy}ethoxy)acetyl]-[Glu14,His17,Lys25,Ser28,Ser29,His35]-pramlintide,
N-alpha-[(S)-4-Carboxy-4-(19-carboxynonadecanoylamino)butyryl]-[His1,Glu14,Arg18,Pro37]-pramlintide,
N-epsilon21-[2-(2-{2-[2-(2-{2-[(S)-4-Carboxy-4-(19-carboxyheptadecanoylamino)butyrylamino]ethoxy}ethoxy)acetylamino]ethoxy}ethoxy)acetyl]-[Glu14,His17,Lys21,Ser28,His35]-pramlintide,
N-alpha-[(S)-4-Carboxy-4-(19-carboxynonadecanoylamino)butyryl]-[Lys11,Glu14,His17,Pro37]-pramlintide,
N-alpha-[(S)-4-Carboxy-4-(19-carboxynonadecanoylamino)butyryl]-[Glu14,His17,Thr21,Pro37]-pramlintide,
N-epsilon21-[2-(2-{2-[2-(2-{2-[(S)-4-Carboxy-4-(19-carboxyheptadecanoylamino)butyrylamino]ethoxy}ethoxy)acetylamino]ethoxy}ethoxy)acetyl]-[Glu14,Lys21,Ser28,Arg29,His35]-pramlintide,
N-epsilon21-[2-(2-{2-[2-(2-{2-[(S)-4-Carboxy-4-(19-carboxyheptadecanoylamino)butyrylamino]ethoxy}ethoxy)acetylamino]ethoxy}ethoxy)acetyl]-[Glu14,His17,Lys21,Ser28,Ser29,His35]-pramlintide,
N-epsilon1-[(S)-4-Carboxy-4-(19-carboxynonadecanoylamino)butyryl]-Arg-[Glu14,Arg17,His35,Pro37]-pramlintide,
N-epsilon21-[2-(2-{2-[2-(2-{2-[(S)-4-Carboxy-4-(19-carboxyheptadecanoylamino)butyrylamino]ethoxy}ethoxy)acetylamino]ethoxy}ethoxy)acetyl]-[Glu14,Arg18,Lys21,Ser28,Arg29,Arg35]-pramlintide,
N-epsilon1-[(S)-4-Carboxy-4-(19-carboxynonadecanoylamino)butyryl]-[Glu14,His17,Gln21,Ala25,Pro26,Ser28,Ser29,Pro37]-pramlintide,
N-alpha-[(S)-4-Carboxy-4-(19-carboxynonadecanoylamino)butyryl]-[Arg14,Arg17,Pro37]-pramlintide,
N-alpha-[(S)-4-Carboxy-4-(19-carboxynonadecanoylamino)butyryl]-Gly-[Arg1,Glu14,Arg17,Pro37]-pramlintide,
N-alpha-[(S)-4-Carboxy-4-(19-carboxynonadecanoylamino)butyryl]-[Arg17,Pro37]-pramlintide,
N-alpha-[(S)-4-Carboxy-4-(19-carboxynonadecanoylamino)butyryl]-Glu-Glu-[Arg1,Glu14,Arg17,Pro37]-pramlintide,
N-alpha-[(S)-4-Carboxy-4-(19-carboxynonadecanoylamino)butyryl]-Glu-[Arg1,Glu14,Arg17,Pro37]-pramlintide,
N-alpha-[(S)-4-Carboxy-4-(19-carboxynonadecanoylamino)butyryl]-Glu-Glu-[Arg1,Glu14,Arg17,Gln21,Pro37]-pramlintide,
N-alpha-[(S)-4-Carboxy-4-(19-carboxynonadecanoylamino)butyryl]-Glu-Glu-[Arg1,Glu14,Arg17,Gln21,Gln35,Pro37]-pramlintide,
N-alpha-[(S)-4-Carboxy-4-(19-carboxynonadecanoylamino)butyryl]-Glu-Glu-[Arg1,Glu14,Arg17,Gln21,Gln31,Gln35,Pro37]-pramlintide,
N-alpha-[(S)-4-Carboxy-4-(19-carboxynonadecanoylamino)butyryl]-Glu-Glu-[Arg1,Glu14,Arg17,Gln21,Gln22,Gln31,Gln35,Pro37]-pramlintide,
N-alpha-[(S)-4-Carboxy-4-(19-carboxynonadecanoylamino)butyryl]-Glu-Arg-[Glu1,Glu14,Arg17,Gln21,Pro37]-pramlintide,
N-alpha-[(S)-4-Carboxy-4-(19-carboxynonadecanoylamino)butyryl]-Glu-Arg-[Glu1,Glu14,Arg17,Gln21,Gln35,Pro37]-pramlintide,
N-alpha-[(S)-4-Carboxy-4-(19-carboxynonadecanoylamino)butyryl]-Glu-Arg-[Glu1,Glu14,Arg17,Gln21,Gln31,Gln35,Pro37]-pramlintide,
N-alpha-[(S)-4-Carboxy-4-(19-carboxynonadecanoylamino)butyryl]-Glu-Arg-[Glu1,Glu14,Arg17,Gln21,Gln22,Gln31,Gln35,Pro37]-pramlintide,
N-alpha-[(S)-4-Carboxy-4-(19-carboxynonadecanoylamino)butyryl]-Glu-Glu-[Glu1,Glu14,Arg17,Pro37]-pramlintide,
N-alpha-[(S)-4-Carboxy-4-(19-carboxynonadecanoylamino)butyryl]-[Glu14,Arg18,Gln21,Ala25,Pro26,Ser28,Ser29,Pro37]-pramlintide,
N-alpha-[2-(2-{2-[2-(2-{2-[(S)-4-Carboxy-4-(19-carboxyheptadecanoylamino)butyrylamino]ethoxy}ethoxy)acetylamino]ethoxy}ethoxy)acetyl]-[Glu14,His17,Glu21,Pro37]-pramlintide,
N-alpha-[2-(2-{2-[2-(2-{2-[(S)-4-Carboxy-4-(19-carboxyheptadecanoylamino)butyrylamino]ethoxy}ethoxy)acetylamino]ethoxy}ethoxy)acetyl]-[Glu14,His17,Lys21,Pro37]-pramlintide,
N-alpha-[2-(2-{2-[2-(2-{2-[(S)-4-Carboxy-4-(19-carboxyheptadecanoylamino)butyrylamino]ethoxy}ethoxy)acetylamino]ethoxy}ethoxy)acetyl]-[Glu14,His17,Ala21,Pro37]-pramlintide,
N-alpha-[(S)-4-Carboxy-4-(19-carboxynonadecanoylamino)butyryl]-[Glu14,Arg18,Ser21,Ser22,Ser28,Ser29,Asp31,Asp35,Pro37]-pramlintide,
N-alpha-[(S)-4-Carboxy-4-(19-carboxynonadecanoylamino)butyryl]-[Glu14,Ser21,Ser22,Pro23,Ala25,Pro26,Ser28,Ser29,Asp31,Asp35,Pro37]-pramlintide,
N-alpha-[(S)-4-Carboxy-4-(19-carboxynonadecanoylamino)butyryl]-[Glu14,Arg17,Asp21,Pro37]-pramlintide,
N-alpha-[(S)-4-Carboxy-4-(19-carboxynonadecanoylamino)butyryl]-[Glu14,Arg17,Asp35,Pro37]-pramlintide,
N-alpha-[(S)-4-Carboxy-4-(19-carboxynonadecanoylamino)butyryl]-[Glu14,Arg17,Asp31,Pro37]-pramlintide,
N-alpha-[(S)-4-Carboxy-4-(19-carboxynonadecanoylamino)butyryl]-[Glu14,Arg17,Asp22,Pro37]-pramlintide,
N-alpha-[(S)-4-Carboxy-4-(19-carboxynonadecanoylamino)butyryl]-[Asp3,Glu14,Arg17,Pro37]-pramlintide,
N-epsilon1-[(S)-4-Carboxy-4-(19-carboxynonadecanoylamino)butyryl]-[Glu14,Arg17,Pro37]-pramlintide,
N-alpha-[2-(2-{2-[2-(2-{2-[(S)-4-Carboxy-4-(19-carboxyheptadecanoylamino)butyrylamino]ethoxy}ethoxy)acetylamino]ethoxy}ethoxy)acetyl]-[Glu14,Ala21,His35,Pro37]-pramlintide.

38. A pharmaceutical composition comprising a derivative according to any of paragraphs 1-37, and a pharmaceutically acceptable excipient.
39. The pharmaceutical composition according to paragraph 38, which is suited for parenteral administration.
40. A derivative according to any one of the paragraphs 1-37 for use as a medicament.
41. A derivative according to any one of the paragraphs 1-37 for use as a medicament for the treatment or prevention of hyperglycemia, type 2 diabetes, impaired glucose tolerance, type 1 diabetes, obesity, hypertension, syndrome X, dyslipidemia, cognitive disorders, atherosclerosis, myocardial infarction, coronary heart disease and other cardiovascular disorders, stroke, inflammatory bowel syndrome, dyspepsia and gastric ulcers.
42. A derivative according to any one of the paragraphs 1-37 for use as a medicament for delaying or preventing disease progression in type 2 diabetes.
43. A derivative according to any one of the paragraphs 1-37 for use as a medicament for decreasing food intake, decreasing n-cell apoptosis, increasing n-cell function and n-cell mass, and/or for restoring glucose sensitivity to n-cells.
44. Use of a derivative according to any one of the paragraphs 1-37 for the preparation of a medicament.
45. Use of a derivative according to any one of the paragraphs 1-37 for the preparation of a medicament for the treatment or prevention of hyperglycemia, type 2 diabetes, impaired glucose tolerance, type 1 diabetes, obesity, hypertension, syndrome X, dyslipidemia, cognitive disorders, atherosclerosis, myocardial infarction, coronary heart disease and other cardiovascular disorders, stroke, inflammatory bowel syndrome, dyspepsia and gastric ulcers.
46. Use of a derivative according to any one of the paragraphs 1-37 for the preparation of a medicament for delaying or preventing disease progression in type 2 diabetes.
47. Use of a derivative according to any one of the paragraphs 1-37 for the preparation of a medicament for treating obesity, decreasing food intake, decreasing β-cell apoptosis, increasing β-cell function and β-cell mass, and/or for restoring glucose sensitivity to β-cells.
48. A process for preparing a pharmaceutical composition according to paragraphs 38-39 comprising mixing a derivative according to any one of paragraphs 1-37 with at least one pharmaceutically acceptable excipient.
49. Derivative of amylin according to the examples The invention will be further summarised in the further paragraphs below:

1. A derivative of amylin, which is an amylin analogue having up to ten amino acid residues modifications as compared to SEQ ID NO: 2 and having a substituent attached to the α-amino group of the N-terminal amino acid residue or to a Lys residue in the amylin analogue, wherein said substituent comprises an albumin binding moiety and wherein
   a. the amino acid residue in position 14 of the amylin analogue is Glu or
   b. the amino acid residue in position 35 of the amylin analogue is His, Arg, Lys, Asp or Glu or
   c. the amino acid residue in position 37 of the amylin analogue is Pro
2. A derivative according to paragraph 1, wherein the amino acid residue in position 14 is Glu.
3. A derivative according to paragraphs 1-2, wherein
   c. the amino acid residue in position 14 is Glu and the amino acid in position 35 is His, Arg, Lys, Asp or Glu or
   d. the amino acid residue in position 14 is Glu and the amino acid in position 37 is Pro
4. A derivative according to paragraphs 1-4, wherein the amino acid residue in position 17 is His.
5. A derivative according to paragraph 1, where the amylin analogue comprises an amino acid sequence of formula I:

```
Formula (1)                                                    (SEQ ID No: 3)
Xaa₁-Cys-Xaa₃-Thr-Ala-Thr-Cys-Ala-Thr-Gln-Arg-Leu-Ala-Glu-Phe-Leu-Xaa₁₇-Xaa₁₈-

Ser-Ser-Xaa₂₁-Xaa₂₂-Phe-Gly-Pro-Xaa₂₆-Leu-Pro-Pro-Thr-Xaa₃₁-Val-Gly-Ser-Xaa₃₅-

Thr-Xaa₃₇
``` wherein
$Xaa_1$ is deleted or independently selected from Ala, Cys, Glu, Gly, His, Arg, Ser and Lys;
$Xaa_3$ is independently selected from Gly, His, Arg, Ser and Asn;
$Xaa_{17}$ is independently selected from His, Arg, Lys and Val;
$Xaa_{18}$ is independently selected from Arg, Lys and His;
$Xaa_{21}$ is independently selected from Ala, Lys, Gln, Ser and Asn;
$Xaa_{22}$ is independently selected from Glu, Gln, Ser, Thr and Asn;
$Xaa_{26}$ is independently selected from Pro, Arg and Ile;
$Xaa_{31}$ is independently selected from Ser, Glu, Asp and Asn;
$Xaa_{35}$ is independently selected from His, Arg, Lys, Asp and Glu;
$Xaa_{37}$ is independently selected from Pro and Tyr;
and where the C-terminal may optionally be derivatized as an amide.

6. A derivative according to paragraphs 1-5, wherein the substituent comprises a linker having 1-10 amino acids which are attached to the α-amino group of the N-terminal amino acid residue or to a Lys residue in the amylin analogue.
7. A derivative according to paragraphs 1-6, wherein the linker comprises γGlu.
8. A derivative according to paragraphs 1-7, wherein the linker is selected from the group consisting of γGlu-C(O)CH₂—O—CH₂—CH₂—O—CH₂—CH₂—[NHC(O)—CH₂—O—CH₂—CH₂—O—CH₂—CH₂—]₁—NH— and Arg-Arg-γGlu-C(O)CH₂—O—CH₂—CH₂—O—CH₂—CH₂—[NHC(O)—CH₂—O—CH₂—CH₂—O—CH₂—CH₂—]₁—NH—.
9. A derivative according to paragraphs 1-8, wherein the derivative comprises a γGlu linker attached to the N-terminal of the amylin analogue and HOOC(CH₂)₁₈CO or HOOC(CH₂)₁₆CO— as the albumin binding residue and where the sequence of the amylin analogue comprises:

a. Glu in position 14
b. His or Arg in position 17
c. His in position 35 or Pro in position 37, 10. A derivative according to paragraph 1, wherein the derivative is selected from the group consisting of:

N-alpha-[(S)-4-Carboxy-4-(19-carboxynonadecanoylamino)butyryl]-[His1,Glu14,His17,Arg18]-pramlintide,
N-alpha-[(S)-4-Carboxy-4-(19-carboxynonadecanoylamino)butyryl]-[His1,Glu8,Glu14,His17,Arg18]-pramlintide,
N-alpha-[(S)-4-Carboxy-4-(19-carboxynonadecanoylamino)butyryl]-[des1,Gly3,Glu14,His17,Arg18,Glu31,Gly35]-pramlintide,
N-alpha-[(S)-4-Carboxy-4-(19-carboxynonadecanoylamino)butyryl]-[des1,Gly3,Glu14,His17,Arg18,Gln21,Gln22,Glu31,Gly35]-pramlintide,
N-alpha-[(S)-4-Carboxy-4-(19-carboxynonadecanoylamino)butyryl]-[Glu1,Glu14,His17,Arg18]-pramlintide,
N-alpha-[(S)-4-Carboxy-4-(19-carboxynonadecanoylamino)butyryl]-[His1,Glu14,His17,Arg18,Ala25,Pro26,Ser28,Ser29]-pramlintide,
N-alpha-[(S)-4-Carboxy-4-(19-carboxynonadecanoylamino)butyryl]-[His1,Glu14,His17,Arg18,Glu25,Ser28,Arg29]-pramlintide,
N-alpha-[(S)-4-Carboxy-4-(19-carboxynonadecanoylamino)butyryl]-[His1,Glu14,His17,Arg18,Glu22,Ala25,Arg26,Ser28,Ser29]-pramlintide,
N-alpha-[(S)-4-Carboxy-4-(19-carboxynonadecanoylamino)butyryl]-[His1,Glu14,His17,Arg18,Ser21,Ser22,Asp31,Asp35]-pramlintide,
N-alpha-[(S)-4-Carboxy-4-(19-carboxynonadecanoylamino)butyryl]-[Glu1,Glu14,His17,Arg18,Pro37]-pramlintide,
N-alpha-[(S)-4-Carboxy-4-(19-carboxynonadecanoylamino)butyryl]-His-His-[His1,Glu14,His17]-pramlintide,
N-alpha-[(S)-4-Carboxy-4-(19-carboxynonadecanoylamino)butyryl]-His-His-[His1,Glu14,Arg17]-pramlintide,
N-epsilon21-[2-(2-{2-[2-(2-{2-[(S)-4-Carboxy-4-(19-carboxyheptadecanoylamino)butyrylamino]ethoxy}ethoxy)acetylamino]ethoxy}ethoxy)acetyl]-[Arg1,Glu14,His17,Arg18,Lys21]-pramlintide,
N-alpha-[(S)-4-Carboxy-4-(19-carboxynonadecanoylamino)butyryl]-[His1,Glu14,Arg18]-pramlintide,
N-alpha-[(S)-4-Carboxy-4-(19-carboxynonadecanoylamino)butyryl]-[His1,Gly3,Glu14,His17,Arg18,Ser21,Ser22,Glu31,Glu35]-pramlintide,
N-alpha-[(S)-4-Carboxy-4-(19-carboxynonadecanoylamino)butyryl]-His-[His1,Glu14,His17]-pramlintide,
N-alpha-[(S)-4-Carboxy-4-(19-carboxynonadecanoylamino)butyryl]-[His1,Glu14,His17]-pramlintide,
N-alpha-[(S)-4-Carboxy-4-(19-carboxynonadecanoylamino)butyryl]-His-His-[His1,Glu14,His17,Ala25,Pro26,Ser28,Ser29]-pramlintide,
N-alpha-[(S)-4-Carboxy-4-(19-carboxynonadecanoylamino)butyryl]-His-His-[His1,Glu14]-pramlintide,
N-alpha-[(S)-4-Carboxy-4-(19-carboxynonadecanoylamino)butyryl]-His-His-[His1,Glu14,His17,Arg35]-pramlintide,
N-alpha-[(S)-4-Carboxy-4-(19-carboxynonadecanoylamino)butyryl]-His-His-[[His1,Arg3,Glu14,His17]-pramlintide,
N-alpha-[2-(2-{2-[2-(2-{2-[(S)-4-Carboxy-4-(19-carboxyheptadecanoylamino)butyrylamino]ethoxy}ethoxy)acetylamino]ethoxy}ethoxy)acetyl]-[His1,Glu14,His17,Arg18,Ala19,Thr20,Gln21,Glu22,Leu23]-pramlintide
N-alpha-[(S)-4-Carboxy-4-(19-carboxynonadecanoylamino)butyryl]-[Glu1,Gly3,Glu14,Arg18,Ser21,Ser22,Ala25,Pro26,Ser28,Ser29,Glu31,Arg35]-pramlintide,
N-alpha-[(S)-4-Carboxy-4-(19-carboxynonadecanoylamino)butyryl]-Glu-[Arg1,Glu14,His17]-pramlintide,
N-alpha-[(S)-4-Carboxy-4-(19-carboxynonadecanoylamino)butyryl]-Glu-[Glu14,His17]-pramlintide,
N-alpha-[(S)-4-Carboxy-4-(19-carboxynonadecanoylamino)butyryl]-[Glu14,His17]-pramlintide,
N-alpha-[(S)-4-Carboxy-4-(19-carboxynonadecanoylamino)butyryl]-[des1,Glu14,His17]-pramlintide,
N-alpha-[(S)-4-Carboxy-4-(19-carboxynonadecanoylamino)butyryl]-[Glu1,Glu14,His17]-pramlintide,
N-alpha-[(S)-4-Carboxy-4-(19-carboxynonadecanoylamino)butyryl]-[Glu1,Glu14,His17,Arg18]-pramlintide,
N-alpha-[(S)-4-Carboxy-4-(19-carboxynonadecanoylamino)butyryl]-His-His-[His1,Glu14,His17,His35]-pramlintide,
N-alpha-[(S)-4-Carboxy-4-(19-carboxynonadecanoylamino)butyryl]-His-His-[His1,His3,Glu14,His17,His35]-pramlintide,
N-alpha-[(S)-4-Carboxy-4-(19-carboxynonadecanoylamino)butyryl]-His-His-[His1,His3,Glu14,His17,His29,His35]-pramlintide,
N-alpha-[(S)-4-Carboxy-4-(19-carboxynonadecanoylamino)butyryl]-His-His-[His1,Glu14,His17,His 29,His 35]-pramlintide,
N-alpha-[(S)-4-Carboxy-4-(19-carboxynonadecanoylamino)butyryl]-His-His-[His1,His3,Glu14,His17]-pramlintide,
N-alpha-[(S)-4-Carboxy-4-(19-carboxynonadecanoylamino)butyryl]-His-His-[His1,Glu14,His17,His29]-pramlintide,
N-alpha-[2-(2-{2-[2-(2-{2-[(S)-4-Carboxy-4-(19-carboxyheptadecanoylamino)butyrylamino]ethoxy}ethoxy)acetylamino]ethoxy}ethoxy)acetyl]-D-Arg-D-Arg-[Glu14,His17,Arg18]-pramlintide,
N-alpha-[2-(2-{2-[2-(2-{2-[(S)-4-Carboxy-4-(19-carboxyheptadecanoylamino)butyrylamino]ethoxy}ethoxy)acetylamino]ethoxy}ethoxy)acetyl]-D-Arg-D-Arg-[Glu14,His17,Arg18,Ala21,Ser35]-pramlintide,
N-alpha-[(S)-4-Carboxy-4-(19-carboxynonadecanoylamino)butyryl]-Ser-Ser-Gly-Ser-Ser-[Gly1,Glu14,His17]-pramlintide,
N-alpha-[(S)-4-Carboxy-4-(19-carboxynonadecanoylamino)butyryl]-Glu-[His1,Glu14,His17]-pramlintide,
N-alpha-[(S)-4-Carboxy-4-(19-carboxynonadecanoylamino)butyryl]-Glu-Glu-[Glu14,His17]-pramlintide,
N-alpha-[(S)-4-Carboxy-4-(17-carboxyheptadecanoylamino)butyryl]-Glu-[Glu14,His17]-pramlintide,
N-alpha-[2-(2-{2-[2-(2-{2-[(S)-4-Carboxy-4-(19-carboxyheptadecanoylamino)butyrylamino]ethoxy}ethoxy)acetylamino]ethoxy}ethoxy)acetyl]-[des1,Glu14,His17]-pramlintide,
N-alpha-[(S)-4-Carboxy-4-(19-carboxynonadecanoylamino)butyryl]-Ser-Ser-Gly-Ser-Ser-Gly-[His1,Glu14,His17]-pramlintide,
N-alpha-[(S)-4-Carboxy-4-(17-carboxyheptadecanoylamino)butyryl]-His-His-[His1,Glu14,His17]-pramlintide,
N-alpha-[(S)-4-Carboxy-4-(17-carboxyheptadecanoylamino)butyryl]-[Glu14,His17]-pramlintide,
N-alpha-[(S)-4-Carboxy-4-(17-carboxyheptadecanoylamino)butyryl]-His-[His1,Glu14,His17]-pramlintide,
N-alpha-[(S)-4-Carboxy-4-(17-carboxyheptadecanoylamino)butyryl]-[His1,Glu14,His17]-pramlintide, N-alpha-{(S)-4-Carboxy-4-[(S)-4-Carboxy-4-(17-carboxyheptadecanoylamino)butyrylamino]butyryl}-des1,Glu14,His17]-pramlintide,
N-alpha-[(S)-4-Carboxy-4-(19-carboxynonadecanoylamino)butyryl]-[Glu14,Arg17]-pramlintide,
N-alpha-[(S)-4-Carboxy-4-(17-carboxyheptadecanoylamino)butyryl]-[Glu14,Arg17]-pramlintide,
N-alpha-[(S)-4-Carboxy-4-(19-carboxynonadecanoylamino)butyryl]-[Glu14,His17,Pro37]-pramlintide,
N-alpha-[(S)-4-Carboxy-4-(19-carboxynonadecanoylamino)butyryl]-[Glu14,Arg17,Pro37]-pramlintide,
N-alpha-[(S)-4-Carboxy-4-(19-carboxynonadecanoylamino)butyryl]-[Glu10,Glu14,His17]-pramlintide,
N-alpha-[(S)-4-Carboxy-4-(19-carboxynonadecanoylamino)butyryl]-[Glu14,His17,His35]-pramlintide,
N-alpha-[(S)-4-Carboxy-4-(19-carboxynonadecanoylamino)butyryl]-Glu-[Glu14,His17,His35]-pramlintide,
N-alpha-[(S)-4-Carboxy-4-(19-carboxynonadecanoylamino)butyryl]-[Glu14,Arg17,His35]-pramlintide,
N-alpha-[(S)-4-Carboxy-4-(19-carboxynonadecanoylamino)butyryl]-Glu-[Glu14,Arg17,His35]-pramlintide,
N-alpha-[(S)-4-Carboxy-4-(17-carboxyheptadecanoylamino)butyryl]-[Glu14,His17,His35]-pramlintide,
N-alpha-[(S)-4-Carboxy-4-(17-carboxyheptadecanoylamino)butyryl]-Glu-[Glu14,His17,His35]-pramlintide,
N-alpha-[(S)-4-Carboxy-4-(17-carboxyheptadecanoylamino)butyryl]-[Glu14,Arg17,His35]-pramlintide,
N-alpha-[(S)-4-Carboxy-4-(17-carboxyheptadecanoylamino)butyryl]-Glu-[Glu14,Arg17,His35]-pramlintide,
N-alpha-[(S)-4-Carboxy-4-(19-carboxynonadecanoylamino)butyryl]-His-His-[His1,Glu14,His17,Ser21,Glu35]-pramlintide,
N-alpha-[(S)-4-Carboxy-4-(19-carboxynonadecanoylamino)butyryl]-[Glu14,His17,Ala25,Pro26,Ser28,Ser29,His35]-pramlintide,
N-alpha-[(S)-4-Carboxy-4-(19-carboxynonadecanoylamino)butyryl]-[Glu14,Arg17,Ala25,Pro26,Ser28,Ser29,His35]-pramlintide,
N-alpha-[(S)-4-Carboxy-4-(19-carboxynonadecanoylamino)butyryl]-His-[Glu14,His17,His35]-pramlintide,
N-alpha-[(S)-4-Carboxy-4-(19-carboxynonadecanoylamino)butyryl]-His-His-[Glu14,His17,His 35]-pramlintide,
N-alpha-[(S)-4-Carboxy-4-(19-carboxynonadecanoylamino)butyryl]-His-[Glu14,Arg17,His35]-pramlintide,
N-alpha-[(S)-4-Carboxy-4-(19-carboxynonadecanoylamino)butyryl]-His-His-[Glu14,Arg17,His35]-pramlintide,
N-alpha-[(S)-4-Carboxy-4-(17-carboxyheptadecanoylamino)butyryl]-His-[Glu14,His17,His 35]-pramlintide,
N-alpha-[(S)-4-Carboxy-4-(17-carboxyheptadecanoylamino)butyryl]-His-[Glu14,Arg17,His35]-pramlintide,
N-epsilon25-[2-(2-{2-[2-(2-{2-[(S)-4-Carboxy-4-(17-carboxyheptadecanoylamino)butyrylamino]ethoxy}ethoxy)acetylamino]ethoxy}ethoxy)acetyl]-[Glu14,Ser21,Lys25]-pramlintide,
N-epsilon25-[2-(2-{2-[2-(2-{2-[(S)-4-Carboxy-4-(17-carboxyheptadecanoylamino)butyrylamino]ethoxy}ethoxy)acetylamino]ethoxy}ethoxy)acetyl]-[Glu14,His17,Lys25]-pramlintide,
N-epsilon21-[2-(2-{2-[2-(2-{2-[(S)-4-Carboxy-4-(17-carboxyheptadecanoylamino)butyrylamino]ethoxy}ethoxy)acetylamino]ethoxy}ethoxy)acetyl]-[Glu14,His17,Lys21,Glu35]-pramlintide,
N-alpha-[(S)-4-Carboxy-4-(19-carboxynonadecanoylamino)butyryl]-[des1,Glu14,His17,His35]-pramlintide,
N-alpha-[(S)-4-Carboxy-4-(19-carboxynonadecanoylamino)butyryl]-[His1,Glu14,His17,His35]-pramlintide,
N-alpha-[(S)-4-Carboxy-4-(19-carboxynonadecanoylamino)butyryl]-[His1,Glu14,His17,Arg18,His35]-pramlintide,
N-alpha-[(S)-4-Carboxy-4-(19-carboxynonadecanoylamino)butyryl]-[Glu14,His17,Arg18,His35]-pramlintide,
N-alpha-[(S)-4-Carboxy-4-(19-carboxynonadecanoylamino)butyryl]-[Glu14,His17,Arg18]-pramlintide,
N-epsilon17-[2-(2-{2-[2-(2-{2-[(S)-4-Carboxy-4-(17-carboxyheptadecanoylamino)butyrylamino]ethoxy}ethoxy)acetylamino]ethoxy}ethoxy)acetyl]-[Glu14,Lys17]-pramlintide,
N-alpha-[(S)-4-Carboxy-4-(19-carboxynonadecanoylamino)butyryl]-Gly-[Glu14,His17,His 35]-pramlintide,
N-alpha-[2-(2-{2-[2-(2-{2-[(S)-4-Carboxy-4-(17-carboxyheptadecanoylamino)butyrylamino]ethoxy}ethoxy)acetylamino]ethoxy}ethoxy)acetyl]-[Glu1,Glu14,His17,Pro37]-pramlintide,
N-epsilon17-[2-(2-{2-[2-(2-{2-[(S)-4-Carboxy-4-(17-carboxyheptadecanoylamino)butyrylamino]ethoxy}ethoxy)acetylamino]ethoxy}ethoxy)acetyl]-[Glu14,Lys17,Ser21,Glu35]-pramlintide,
N-alpha-[(S)-4-Carboxy-4-(19-carboxynonadecanoylamino)butyryl]-[His1,Glu14,His17,Pro37]-pramlintide,
N-alpha-[(S)-4-Carboxy-4-(19-carboxynonadecanoylamino)butyryl]-Ser-[Glu14,His17,His 35]-pramlintide,
N-alpha-[(S)-4-Carboxy-4-(19-carboxynonadecanoylamino)butyryl]-[Glu14,Pro37]-pramlintide,
N-epsilon1-[(S)-4-Carboxy-4-(19-carboxynonadecanoylamino)butyryl]-[Glu14,His17,His35]-pramlintide,
N-alpha-[(S)-4-Carboxy-4-(19-carboxynonadecanoylamino)butyryl]-[Gly1,Glu14,Arg17,Pro37]-pramlintide,
N-alpha-[(S)-4-Carboxy-4-(19-carboxynonadecanoylamino)butyryl]-Gly-[His1,Glu14,Arg17,Pro37]-pramlintide,
N-alpha-[(S)-4-Carboxy-4-(19-carboxynonadecanoylamino)butyryl]-[His1,Glu14,Arg17,Pro37]-pramlintide,
N-alpha-[(S)-4-Carboxy-4-(19-carboxynonadecanoylamino)butyryl]-[Gly1,Glu14,His17,Pro37]-pramlintide,
N-alpha-[(S)-4-Carboxy-4-(19-carboxynonadecanoylamino)butyryl]-Gly-[His1,Glu14,His17,Pro37]-pramlintide,
N-alpha-[(S)-4-Carboxy-4-(19-carboxynonadecanoylamino)butyryl]-[Glu14,His35]-pramlintide,
N-epsilon1-[(S)-4-Carboxy-4-(17-carboxyheptadecanoylamino)butyryl]-[Glu14,His17,His35]-pramlintide,
N-alpha-[(S)-4-Carboxy-4-(19-carboxynonadecanoylamino)butyryl]-[Arg1,Glu14,His17,His 35]-pramlintide,
N-alpha-[(S)-4-Carboxy-4-(19-carboxynonadecanoylamino)butyryl]-[Arg1,Glu14,His17,Pro37]-pramlintide,
N-alpha-[(S)-4-Carboxy-4-(19-carboxynonadecanoylamino)butyryl]-[Arg1, Pro37]-pramlintide,
N-alpha-[(S)-4-Carboxy-4-(19-carboxynonadecanoylamino)butyryl]-[Arg1, His35]-pramlintide,
N-alpha-[(S)-4-Carboxy-4-(19-carboxynonadecanoylamino)butyryl]-Gly-[Arg1,His35]-pramlintide,
N-alpha-[(S)-4-Carboxy-4-(19-carboxynonadecanoylamino)butyryl]-Gly-[Arg1,Glu14,His17,His 35]-pramlintide,
N-alpha-[(S)-4-Carboxy-4-(19-carboxynonadecanoylamino)butyryl]-Gly-[Arg1,Glu14,His17,Pro37]-pramlintide,
N-alpha-[(S)-4-Carboxy-4-(19-carboxynonadecanoylamino)butyryl]-Gly-[Arg1,Glu14,Pro37]-pramlintide, N-alpha-[(S)-4-Carboxy-4-(19-carboxynonadecanoylamino)butyryl]-Gly-[Arg1,Pro37]-pramlintide,
N-alpha-[(S)-4-Carboxy-4-(19-carboxynonadecanoylamino)butyryl]-[des1,Glu14,His17,Pro37]-pramlintide,
N-alpha-[(S)-4-Carboxy-4-(19-carboxynonadecanoylamino)butyryl]-[Gly1,Glu14,His17,His35]-pramlintide,
N-alpha-[(S)-4-Carboxy-4-(19-carboxynonadecanoylamino)butyryl]-[Ser1,Glu14,His17,Pro37]-pramlintide,
N-alpha-[(S)-4-Carboxy-4-(19-carboxynonadecanoylamino)butyryl]-[Ser1,Glu14,His17,His 35]-pramlintide,
N-alpha-[(S)-4-Carboxy-4-(19-carboxynonadecanoylamino)butyryl]-[des1,Glu14,Pro37]-pramlintide,
N-alpha-[(S)-4-Carboxy-4-(19-carboxynonadecanoylamino)butyryl]-[His1,Glu14,Pro37]-pramlintide,
N-alpha-[(S)-4-Carboxy-4-(19-carboxynonadecanoylamino)butyryl]-[His1,Glu14,Ser21,Ser28,Ser29,His 35]-pramlintide,
N-alpha-[(S)-4-Carboxy-4-(19-carboxynonadecanoylamino)butyryl]-[His1,Glu14,Arg17,Ser21,Ser28,Ser29,His35]-pramlintide,
N-alpha-[(S)-4-Carboxy-4-(19-carboxynonadecanoylamino)butyryl]-[Glu14,His17,Arg35]-pramlintide,
N-alpha-[(S)-4-Carboxy-4-(19-carboxynonadecanoylamino)butyryl]-[Glu14,His17,Lys35]-pramlintide,
N-alpha-[(S)-4-Carboxy-4-(19-carboxynonadecanoylamino)butyryl]-[Glu14,His17,His36]-pramlintide,
N-alpha-[(S)-4-Carboxy-4-(19-carboxynonadecanoylamino)butyryl]-[Glu14,His17,His34]-pramlintide,
N-alpha-[(S)-4-Carboxy-4-(19-carboxynonadecanoylamino)butyryl]-[Glu14,His17,His32]-pramlintide,
N-alpha-[(S)-4-Carboxy-4-(19-carboxynonadecanoylamino)butyryl]-[Glu14,His17,Gln21,His35)-pramlintide,
N-alpha-[2-(2-{2-[2-(2-{2-[(S)-4-Carboxy-4-(19-carboxyheptadecanoylamino)butyrylamino]ethoxy}ethoxy)acetylamino]ethoxy}ethoxy)acetyl]-[Glu14,His17,Ser21,His35]-pramlintide,
N-alpha-[2-(2-{2-[2-(2-{2-[(S)-4-Carboxy-4-(19-carboxyheptadecanoylamino)butyrylamino]ethoxy}ethoxy)acetylamino]ethoxy}ethoxy)acetyl]-[His1,Glu14,His17,Ser21,His35]-pramlintide,
N-alpha-[2-(2-{2-[2-(2-{2-[(S)-4-Carboxy-4-(17-carboxyheptadecanoylamino)butyrylamino]ethoxy}ethoxy)acetylamino]ethoxy}ethoxy)acetyl]-D-Arg-D-Arg-[Orn1,Glu14,His17,Arg18]-pramlintide,
N-alpha-(19-carboxynonadecanoyl)-Glu-Glu-Arg-[Glu1,Pro37]-pramlintide
N-alpha-[(S)-4-Carboxy-4-(19-carboxynonadecanoylamino)butyryl]-Glu-Arg-[Glu1,Pro37]-pramlintide,
N-alpha-[(S)-4-Carboxy-4-(19-carboxynonadecanoylamino)butyryl]-Glu-Arg-[Glu1,Glu14,His17,Pro37]-pramlintide,
N-alpha-[(S)-4-Carboxy-4-(19-carboxynonadecanoylamino)butyryl]-Glu-Arg-[Glu1,Glu14,Arg17,Pro37]-pramlintide,
N-alpha-(19-carboxynonadecanoyl)-Glu-Glu-Arg-[Glu1,Glu14,His17,Pro37]-pramlintide,
N-epsilon25-[2-(2-{2-[2-(2-{2-[(S)-4-Carboxy-4-(17-carboxyheptadecanoylamino)butyrylamino]ethoxy}ethoxy)acetylamino]ethoxy}ethoxy)acetyl]-[Glu14,Lys25]-pramlintide,
N-epsilon21-[2-(2-{2-[2-(2-{2-[(S)-4-Carboxy-4-(19-carboxyheptadecanoylamino)butyrylamino]ethoxy}ethoxy)acetylamino]ethoxy}ethoxy)acetyl]-[Glu14,Lys21,Ser29,His35]-pramlintide,
N-alpha-[(S)-4-Carboxy-4-(19-carboxynonadecanoylamino)butyryl]-[Glu14,His17,Asp21,His35]-pramlintide,
N-alpha-[(S)-4-Carboxy-4-(19-carboxynonadecanoylamino)butyryl]-Glu-[Glu14,His17,Gln21,His35]-pramlintide,
N-alpha-[(S)-4-Carboxy-4-(19-carboxynonadecanoylamino)butyryl]-[Glu14,His17,Gln21,Pro37]-pramlintide,
N-epsilon21-[2-(2-{2-[2-(2-{2-[(S)-4-Carboxy-4-(19-carboxyheptadecanoylamino)butyrylamino]ethoxy}ethoxy)acetylamino]ethoxy}ethoxy)acetyl]-[Glu14,Lys21,Ser28,Ser29,His35]-pramlintide,
N-epsilon21-[2-(2-{2-[2-(2-{2-[(S)-4-Carboxy-4-(19-carboxyheptadecanoylamino)butyrylamino]ethoxy}ethoxy)acetylamino]ethoxy}ethoxy)acetyl]-[Glu14,Lys21,His35]-pramlintide,
N-epsilon25-[2-(2-{2-[2-(2-{2-[(S)-4-Carboxy-4-(19-carboxyheptadecanoylamino)butyrylamino]ethoxy}ethoxy)acetylamino]ethoxy}ethoxy)acetyl]-[Glu14,His17,Ser21,Lys25,Ser28,Ser29.His35]-pramlintide,
N-epsilon25-[2-(2-{2-[2-(2-{2-[(S)-4-Carboxy-4-(19-carboxyheptadecanoylamino)butyrylamino]ethoxy}ethoxy)acetylamino]ethoxy}ethoxy)acetyl]-[His17,His21,Lys25,Ser28,Ser29.His35]-pramlintide,
N-alpha-[(S)-4-Carboxy-4-(19-carboxynonadecanoylamino)butyryl]-[Glu14,His17,Gln35,Pro37]-pramlintide,
N-alpha-[(S)-4-Carboxy-4-(19-carboxynonadecanoylamino)butyryl]-[Glu14,His17,Gln21,Gln35,Pro37]-pramlintide,
N-alpha-[(S)-4-Carboxy-4-(19-carboxynonadecanoylamino)butyryl]-[Gly1,Glu14,His17,Gln21,Gln35,Pro37]-pramlintide,
N-alpha-[(S)-4-Carboxy-4-(19-carboxynonadecanoylamino)butyryl]-[Glu1,Glu14,Gln21,Gln35,Pro37]-pramlintide,
N-alpha-[(S)-4-Carboxy-4-(19-carboxynonadecanoylamino)butyryl]-[Glu14,Gln21,Gln35,Pro37]-pramlintide,
N-epsilon25-[2-(2-{2-[2-(2-{2-[(S)-4-Carboxy-4-(19-carboxyheptadecanoylamino)butyrylamino]ethoxy}ethoxy)acetylamino]ethoxy}ethoxy)acetyl]-[His17,Lys25,Ser28,Ser29,His35]-pramlintide,
N-epsilon21-[2-(2-{2-[2-(2-{2-[(S)-4-Carboxy-4-(19-carboxyheptadecanoylamino)butyrylamino]ethoxy}ethoxy)acetylamino]ethoxy}ethoxy)acetyl]-[His17,Lys21,Ser28,His35]-pramlintide,
N-epsilon25-[2-(2-{2-[2-(2-{2-[(S)-4-Carboxy-4-(19-carboxyheptadecanoylamino)butyrylamino]ethoxy}ethoxy)acetylamino]ethoxy}ethoxy)acetyl]-[Glu14,His17,Lys25,Ser28,Ser29,His35]-pramlintide,
N-alpha-[(S)-4-Carboxy-4-(19-carboxynonadecanoylamino)butyryl]-[His1,Glu14,Arg18,Pro37]-pramlintide,
N-epsilon21-[2-(2-{2-[2-(2-{2-[(S)-4-Carboxy-4-(19-carboxyheptadecanoylamino)butyrylamino]ethoxy}ethoxy)acetylamino]ethoxy}ethoxy)acetyl]-[Glu14,His17,Lys21,Ser28,His35]-pramlintide,
N-alpha-[(S)-4-Carboxy-4-(19-carboxynonadecanoylamino)butyryl]-[Lys11,Glu14,His17,Pro37]-pramlintide,
N-alpha-[(S)-4-Carboxy-4-(19-carboxynonadecanoylamino)butyryl]-[Glu14,His17,Thr21,Pro37]-pramlintide,
N-epsilon21-[2-(2-{2-[2-(2-{2-[(S)-4-Carboxy-4-(19-carboxyheptadecanoylamino)butyrylamino]ethoxy}ethoxy)acetylamino]ethoxy}ethoxy)acetyl]-[Glu14,Lys21,Ser28,Arg29,His35]-pramlintide, N-epsilon21-[2-(2-{2-[2-(2-{2-[(S)-4-Carboxy-4-(19-carboxyheptadecanoylamino)butyrylamino]ethoxy}ethoxy)acetylamino]ethoxy}ethoxy)acetyl]-[Glu14,His17,Lys21,Ser28,Ser29,His35]-pramlintide, N-epsilon1-[(S)-4-Carboxy-4-(19-carboxynonadecanoylamino)butyryl]-Arg-[Glu14,Arg17,His35,Pro37]-pramlintide, N-epsilon21-[2-(2-{2-[2-(2-{2-[(S)-4-Carboxy-4-(19-carboxyheptadecanoylamino)butyrylamino]ethoxy}ethoxy)acetylamino]ethoxy}ethoxy)acetyl]-[Glu14,Arg18,Lys21,Ser28,Arg29,Arg35]-pramlintide, N-epsilon1-[(S)-4-Carboxy-4-(19-carboxynonadecanoylamino)butyryl]-[Glu14,His17,Gln21,Ala25,Pro26,Ser28,Ser29,Pro37]-pramlintide, N-alpha-[(S)-4-Carboxy-4-(19-carboxynonadecanoylamino)butyryl]-[Arg14,Arg17,Pro37]-pramlintide, N-alpha-[(S)-4-Carboxy-4-(19-carboxynonadecanoylamino)butyryl]-Gly-[Arg1,Glu14,Arg17,Pro37]-pramlintide, N-alpha-[(S)-4-Carboxy-4-(19-carboxynonadecanoylamino)butyryl]-[Arg17,Pro37]-pramlintide, N-alpha-[(S)-4-Carboxy-4-(19-carboxynonadecanoylamino)butyryl]-Glu-Glu-[Arg1,Glu14,Arg17,Pro37]-pramlintide, N-alpha-[(S)-4-Carboxy-4-(19-carboxynonadecanoylamino)butyryl]-Glu-[Arg1,Glu14,Arg17,Pro37]-pramlintide, N-alpha-[(S)-4-Carboxy-4-(19-carboxynonadecanoylamino)butyryl]-Glu-Glu-[Arg1,Glu14,Arg17,Gln21,Pro37]-pramlintide, N-alpha-[(S)-4-Carboxy-4-(19-carboxynonadecanoylamino)butyryl]-Glu-Glu-[Arg1,Glu14,Arg17,Gln21,Gln35,Pro37]-pramlintide, N-alpha-[(S)-4-Carboxy-4-(19-carboxynonadecanoylamino)butyryl]-Glu-Glu-[Arg1,Glu14,Arg17,Gln21,Gln31,Gln35,Pro37]-pramlintide, N-alpha-[(S)-4-Carboxy-4-(19-carboxynonadecanoylamino)butyryl]-Glu-Glu-[Arg1,Glu14,Arg17,Gln21,Gln22,Gln31,Gln35,Pro37]-pramlintide, N-alpha-[(S)-4-Carboxy-4-(19-carboxynonadecanoylamino)butyryl]-Glu-Arg-[Glu1,Glu14,Arg17,Gln21,Pro37]-pramlintide, N-alpha-[(S)-4-Carboxy-4-(19-carboxynonadecanoylamino)butyryl]-Glu-Arg-[Glu1,Glu14,Arg17,Gln21,Gln35,Pro37]-pramlintide, N-alpha-[(S)-4-Carboxy-4-(19-carboxynonadecanoylamino)butyryl]-Glu-Arg-[Glu1,Glu14,Arg17,Gln21,Gln31,Gln35,Pro37]-pramlintide, N-alpha-[(S)-4-Carboxy-4-(19-carboxynonadecanoylamino)butyryl]-Glu-Arg-[Glu1,Glu14,Arg17,Gln21,Gln22,Gln31,Gln35,Pro37]-pramlintide, N-alpha-[(S)-4-Carboxy-4-(19-carboxynonadecanoylamino)butyryl]-Glu-Glu-[Glu1,Glu14,Arg17,Pro37]-pramlintide, N-alpha-[(S)-4-Carboxy-4-(19-carboxynonadecanoylamino)butyryl]-[Glu14,Arg18,Gln21,Ala25,Pro26,Ser28,Ser29,Pro37]-pramlintide, N-alpha-[2-(2-{2-[2-(2-{2-[(S)-4-Carboxy-4-(19-carboxyheptadecanoylamino)butyrylamino]ethoxy}ethoxy)acetylamino]ethoxy}ethoxy)acetyl]-[Glu14,His17,Glu21,Pro37]-pramlintide, N-alpha-[2-(2-{2-[2-(2-{2-[(S)-4-Carboxy-4-(19-carboxyheptadecanoylamino)butyrylamino]ethoxy}ethoxy)acetylamino]ethoxy}ethoxy)acetyl]-[Glu14,His17,Lys21,Pro37]-pramlintide, N-alpha-[2-(2-{2-[2-(2-{2-[(S)-4-Carboxy-4-(19-carboxyheptadecanoylamino)butyrylamino]ethoxy}ethoxy)acetylamino]ethoxy}ethoxy)acetyl]-[Glu14,His17,Ala21,Pro37]-pramlintide, N-alpha-[(S)-4-Carboxy-4-(19-carboxynonadecanoylamino)butyryl]-[Glu14,Arg18,Ser21,Ser22,Ser28,Ser29,Asp31,Asp35,Pro37]-pramlintide, N-alpha-[(S)-4-Carboxy-4-(19-carboxynonadecanoylamino)butyryl]-[Glu14,Ser21,Ser22,Pro23,Ala25,Pro26,Ser28,Ser29,Asp31,Asp35,Pro37]-pramlintide, N-alpha-[(S)-4-Carboxy-4-(19-carboxynonadecanoylamino)butyryl]-[Glu14,Arg17,Asp21,Pro37]-pramlintide, N-alpha-[(S)-4-Carboxy-4-(19-carboxynonadecanoylamino)butyryl]-[Glu14,Arg17,Asp35,Pro37]-pramlintide, N-alpha-[(S)-4-Carboxy-4-(19-carboxynonadecanoylamino)butyryl]-[Glu14,Arg17,Asp31,Pro37]-pramlintide, N-alpha-[(S)-4-Carboxy-4-(19-carboxynonadecanoylamino)butyryl]-[Glu14,Arg17,Asp22,Pro37]-pramlintide, N-alpha-[(S)-4-Carboxy-4-(19-carboxynonadecanoylamino)butyryl]-[Asp3,Glu14,Arg17,Pro37]-pramlintide, N-epsilon1-[(S)-4-Carboxy-4-(19-carboxynonadecanoylamino)butyryl]-[Glu14,Arg 17, Pro37]-pramlintide, N-alpha-[2-(2-{2-[2-(2-{2-[(S)-4-Carboxy-4-(19-carboxyheptadecanoylamino)butyrylamino]ethoxy}ethoxy)acetylamino]ethoxy}ethoxy)acetyl]-[Glu14,Ala21,His35,Pro37]-pramlintide.

11. A pharmaceutical composition comprising a derivative according to any of paragraphs 1-10, and a pharmaceutically acceptable excipient.

12. A derivative according to any one of the paragraphs 1-10 for use as a medicament.

13. A derivative according to any one of the paragraphs 1-10 for use as a medicament for treating obesity, for decreasing food intake, decreasing β-cell apoptosis, increasing β-cell function and β-cell mass, and/or for restoring glucose sensitivity to β-cells.

14. Use of a derivative according to any one of the paragraphs 1-10 for the preparation of a medicament.

15. A process for preparing a pharmaceutical composition comprising mixing a derivative according to any one of paragraphs 1-10 with at least one pharmaceutically acceptable excipient.

The present invention will now be described only by way of examples.

EXAMPLES

The polypeptides prepared are shown in Table 10.

TABLE 10

| Example # | Name |
|---|---|
| 1 | N-alpha-[(S)-4-Carboxy-4-(19-carboxynonadecanoylamino)butyryl]-[His1,Glu14,His17,Arg18]-pramlintide |

TABLE 10-continued

| Example # | Name |
|---|---|
| 2 | N-alpha-[(S)-4-Carboxy-4-(19-carboxynonadecanoylamino)butyryl]-[His1,Glu8,Glu14,His17,Arg18]-pramlintide |
| 3 | N-alpha-[(S)-4-Carboxy-4-(19-carboxynonadecanoylamino)butyryl]-[des1,Gly3,Glu14,His17,Arg18,Glu31,Gly35]-pramlintide |
| 4 | N-alpha-[(S)-4-Carboxy-4-(19-carboxynonadecanoylamino)butyryl]-[des1,Gly3,Glu14,His17,Arg18,Gln21,Gln22,Glu31,Gly35]-pramlintide |
| 5 | N-alpha-[(S)-4-Carboxy-4-(19-carboxynonadecanoylamino)butyryl]-[Glu1,Glu14,His17,Arg18]-pramlintide |
| 6 | N-alpha-[(S)-4-Carboxy-4-(19-carboxynonadecanoylamino)butyryl]-[His1,Glu14,His17,Arg18,Ala25,Pro26,Ser28,Ser29]-pramlintide |
| 7 | N-alpha-[(S)-4-Carboxy-4-(19-carboxynonadecanoylamino)butyryl]-[His1,Glu14,His17,Arg18,Glu25,Ser28,Arg29]-pramlintide |
| 8 | N-alpha-[(S)-4-Carboxy-4-(19-carboxynonadecanoylamino)butyryl]-[His1,Glu14,His17,Arg18,Glu22,Ala25,Arg26,Ser28,Ser29]-pramlintide |
| 9 | N-alpha-[(S)-4-Carboxy-4-(19-carboxynonadecanoylamino)butyryl]-[His1,Glu14,His17,Arg18,Ser21,Ser22,Asp31,Asp35]-pramlintide |
| 10 | N-alpha-[(S)-4-Carboxy-4-(19-carboxynonadecanoylamino)butyryl]-[Glu1,Glu14,His17,Arg18,Pro37]-pramlintide |
| 11 | N-alpha-[(S)-4-Carboxy-4-(19-carboxynonadecanoylamino)butyryl]-His-His-[His1,Glu14,His17]-pramlintide |
| 12 | N-alpha-[(S)-4-Carboxy-4-(19-carboxynonadecanoylamino)butyryl]-His-His-[His1,Glu14,Arg17]-pramlinte |
| 14 | N-epsilon21-[2-(2-{2-[2-(2-{2-[(S)-4-Carboxy-4-(19-carboxyheptadecanoylamino)butyrylamino]ethoxy}ethoxy)acetylamino]ethoxy}ethoxy)acetyl]-[Arg1,Glu14,His17,Arg18,Lys21]-pramlintide |
| 15 | N-alpha-[(S)-4-Carboxy-4-(19-carboxynonadecanoylamino)butyryl]-[His1,Glu14,Arg18]-pramlintide |
| 16 | N-alpha-[(S)-4-Carboxy-4-(19-carboxynonadecanoylamino)butyryl]-[His1,Gly3,Glu14,His17,Arg18,Ser21,Ser,22,Glu31,Glu35]-pramlintide |
| 17 | N-alpha-[(S)-4-Carboxy-4-(19-carboxynonadecanoylamino)butyryl]-His-[His1,Glu14,His17]-pramlintide |
| 18 | N-alpha-[(S)-4-Carboxy-4-(19-carboxynonadecanoylamino)butyryl]-[His1,Glu14,His17]-pramlintide |
| 19 | N-alpha-[(S)-4-Carboxy-4-(19-carboxynonadecanoylamino)butyryl]-His-His-[His1,Glu14,His17,Ala25,Pro26,Ser28,Ser29]-pramlintide |
| 20 | N-alpha-[(S)-4-Carboxy-4-(19-carboxynonadecanoylamino)butyryl]-His-His-[His1,Glu14]-pramlintide |
| 21 | N-alpha-[(S)-4-Carboxy-4-(19-carboxynonadecanoylamino)butyryl]-His-His-[His1,Glu14,His17,Arg35]-pramlintide |
| 22 | N-alpha-[(S)-4-Carboxy-4-(19-carboxynonadecanoylamino)butyryl]-His-His-[His1,Arg3,Glu14,His17]-pramlintide |
| 23 | N-alpha-[2-(2-{2-[2-(2-{2-[(S)-4-Carboxy-4-(19-carboxyheptadecanoylamino)butyrylamino]ethoxy}ethoxy)acetylamino]ethoxy}ethoxy)acetyl]-[His1,Glu14,His17,Arg18,Ala19,Thr20,Gln21,Glu22,Leu23]-pramlintide |
| 24 | N-alpha-[(S)-4-Carboxy-4-(19-carboxynonadecanoylamino)butyryl]-[Glu1,Gly3,Glu14,Arg18,Ser21,Ser22,Ala25,Pro26,Ser28,Ser29,Glu31,Arg35]-pramlintide |
| 25 | N-alpha-[(S)-4-Carboxy-4-(19-carboxynonadecanoylamino)butyryl]-Glu-[Arg1,Glu14,His17]-pramlintide |
| 26 | N-alpha-[(S)-4-Carboxy-4-(19-carboxynonadecanoylamino)butyryl]-Glu-[Glu14,His17]-pramlintide |
| 27 | N-alpha-[(S)-4-Carboxy-4-(19-carboxynonadecanoylamino)butyryl]-[Glu14,His17]-pramlintide |
| 28 | N-alpha-[(S)-4-Carboxy-4-(19-carboxynonadecanoylamino)butyryl]-[des1,Glu14,His17]-pramlintide |
| 29 | N-alpha-[(S)-4-Carboxy-4-(19-carboxynonadecanoylamino)butyryl]-[Glu1,Glu14,His17]-pramlintide |
| 30 | N-alpha-[(S)-4-Carboxy-4-(19-carboxynonadecanoylamino)butyryl]-[Glu1,Glu14,His17,Arg18]-pramlintide |
| 31 | N-alpha-[(S)-4-Carboxy-4-(19-carboxynonadecanoylamino)butyryl]-His-His-[His1,Glu14,His17,His35]-pramlintide |
| 32 | N-alpha-[(S)-4-Carboxy-4-(19-carboxynonadecanoylamino)butyryl]-His-His-[His1,His3,Glu14,His17,His35]-pramlintide |
| 33 | N-alpha-[(S)-4-Carboxy-4-(19-carboxynonadecanoylamino)butyryl]-His-His-[His1,His3,Glu14,His17,His29,His35]-pramlintide |
| 34 | N-alpha-[(S)-4-Carboxy-4-(19-carboxynonadecanoylamino)butyryl]-His-His-[His1,Glu14,His17,His29,His35]-pramlintide |
| 35 | N-alpha-[(S)-4-Carboxy-4-(19-carboxynonadecanoylamino)butyryl]-His-His-[His1,His3,Glu14,His17]-pramlintide |
| 36 | N-alpha-[(S)-4-Carboxy-4-(19-carboxynonadecanoylamino)butyryl]-His-His-[His1,Glu14,His17,His29]-pramlintide |
| 37 | N-alpha-[2-(2-{2-[2-(2-{2-[(S)-4-Carboxy-4-(19-carboxyheptadecanoylamino)butyrylamino]ethoxy}ethoxy)acetylamino]ethoxy}ethoxy)acetyl]-D-Arg-D-Arg-[Glu14,His17,Arg18]-pramlintide |

TABLE 10-continued

| Example # | Name |
|---|---|
| 38 | N-alpha-[2-(2-{2-[2-(2-{2-[(S)-4-Carboxy-4-(19-carboxyheptadecanoylamino)butyrylamino]ethoxy}ethoxy)acetylamino]ethoxy}ethoxy)acetyl]-D-Arg-D-Arg-[Glu14,His17,Arg18,Ala21,Ser35]-pramlintide |
| 39 | N-alpha-[(S)-4-Carboxy-4-(19-carboxynonadecanoylamino)butyryl]-Ser-Ser-Gly-Ser-Ser-[Gly1,Glu14,His17]-pramlintide |
| 40 | N-alpha-[(S)-4-Carboxy-4-(19-carboxynonadecanoylamino)butyryl]-Glu-[His1,Glu14,His17]-pramlintide |
| 41 | N-alpha-[(S)-4-Carboxy-4-(19-carboxynonadecanoylamino)butyryl]-Glu-Glu-[Glu14,His17]-pramlintide |
| 42 | N-alpha-[(S)-4-Carboxy-4-(17-carboxyheptadecanoylamino)butyryl]-Glu-[Glu14,His17]-pramlintide |
| 43 | N-alpha-[2-(2-{2-[2-(2-{2-[(S)-4-Carboxy-4-(19-carboxyheptadecanoylamino)butyrylamino]ethoxy}ethoxy)acetylamino]ethoxy}ethoxy)acetyl]-[des1,Glu14,His17]-pramlintide |
| 44 | N-alpha-[(S)-4-Carboxy-4-(19-carboxynonadecanoylamino)butyryl]-Ser-Ser-Gly-Ser-Ser-Gly-[His1,Glu14,His17]-pramlintide |
| 45 | N-alpha-[(S)-4-Carboxy-4-(17-carboxyheptadecanoylamino)butyryl]-His-His-[His1,Glu14,His17]-pramlintide |
| 46 | N-alpha-[(S)-4-Carboxy-4-(17-carboxyheptadecanoylamino)butyryl]-[Glu14,His17]-pramlintide |
| 47 | N-alpha-[(S)-4-Carboxy-4-(17-carboxyheptadecanoylamino)butyryl]-His-[His1,Glu14,His17]-pramlintide |
| 48 | N-alpha-[(S)-4-Carboxy-4-(17-carboxyheptadecanoylamino)butyryl]-[His1,Glu14,His17]-pramlintide |
| 49 | N-alpha-{(S)-4-Carboxy-4-[(S)-4-Carboxy-4-(17-carboxyheptadecanoylamino)butyrylamino]butyryl}-[des1,Glu14,His17]-pramlintide |
| 50 | N-alpha-[(S)-4-Carboxy-4-(19-carboxynonadecanoylamino)butyryl]-[Glu14,Arg17]-pramlintide |
| 51 | N-alpha-[(S)-4-Carboxy-4-(17-carboxyheptadecanoylamino)butyryl]-[Glu14,Arg17]-pramlintide |
| 52 | N-alpha-[(S)-4-Carboxy-4-(19-carboxynonadecanoylamino)butyryl]-[Glu14,His17,Pro37]-pramlintide |
| 53 | N-alpha-[(S)-4-Carboxy-4-(19-carboxynonadecanoylamino)butyryl]-[Glu14,Arg17,Pro37]-pramlintide |
| 54 | N-alpha-[(S)-4-Carboxy-4-(19-carboxynonadecanoylamino)butyryl]-[Glu10,Glu14,His17]-pramlintide |
| 55 | N-alpha-[(S)-4-Carboxy-4-(19-carboxynonadecanoylamino)butyryl]-[Glu14,His17,His35]-pramlintide |
| 56 | N-alpha-[(S)-4-Carboxy-4-(19-carboxynonadecanoylamino)butyryl]-Glu-[Glu14,His17,His35]-pramlintide |
| 57 | N-alpha-[(S)-4-Carboxy-4-(19-carboxynonadecanoylamino)butyryl]-[Glu14,Arg17,His35]-pramlintide |
| 58 | N-alpha-[(S)-4-Carboxy-4-(19-carboxynonadecanoylamino)butyryl]-Glu-[Glu14,Arg17,His35]-pramlintide |
| 59 | N-alpha-[(S)-4-Carboxy-4-(17-carboxyheptadecanoylamino)butyryl]-[Glu14,His17,His35]-pramlintide |
| 60 | N-alpha-[(S)-4-Carboxy-4-(17-carboxyheptadecanoylamino)butyryl]-Glu-[Glu14,His17,His35]-pramlintide |
| 61 | N-alpha-[(S)-4-Carboxy-4-(17-carboxyheptadecanoylamino)butyryl]-[Glu14,Arg17,His35]-pramlintide |
| 62 | N-alpha-[(S)-4-Carboxy-4-(17-carboxyheptadecanoylamino)butyryl]-Glu-[Glu14,Arg17,His35]-pramlintide |
| 63 | N-alpha-[(S)-4-Carboxy-4-(19-carboxynonadecanoylamino)butyryl]-His-His-[His1,Glu14,His17,Ser21,Glu35]-pramlintide |
| 64 | N-alpha-[(S)-4-Carboxy-4-(19-carboxynonadecanoylamino)butyryl]-[Glu14,His17,Ala25,Pro26,Ser28,Ser29,His35]-pramlintide |
| 65 | N-alpha-[(S)-4-Carboxy-4-(19-carboxynonadecanoylamino)butyryl]-[Glu14,Arg17,Ala25,Pro26,Ser28,Ser29,His35]-pramlintide |
| 66 | N-alpha-[(S)-4-Carboxy-4-(19-carboxynonadecanoylamino)butyryl]-His-[Glu14,His17,His35]-pramlintide |
| 67 | N-alpha-[(S)-4-Carboxy-4-(19-carboxynonadecanoylamino)butyryl]-His-His-[Glu14,His17,His35]-pramlintide |
| 68 | N-alpha-[(S)-4-Carboxy-4-(19-carboxynonadecanoylamino)butyryl]-His-[Glu14,Arg17,His35]-pramlintide |
| 69 | N-alpha-[(S)-4-Carboxy-4-(19-carboxynonadecanoylamino)butyryl]-His-His-[Glu14,Arg17,His35]-pramlintide |
| 70 | N-alpha-[(S)-4-Carboxy-4-(17-carboxyheptadecanoylamino)butyryl]-His-[Glu14,His17,His35]-pramlintide |
| 71 | N-alpha-[(S)-4-Carboxy-4-(17-carboxyheptadecanoylamino)butyryl]-His-[Glu14,Arg17,His35]-pramlintide |
| 72 | N-epsilon25-[2-(2-{2-[2-(2-{2-[(S)-4-Carboxy-4-(17-carboxyheptadecanoylamino)butyrylamino]ethoxy}ethoxy)acetylamino]ethoxy}ethoxy)acetyl]-[Glu14,Ser21,Lys25]-pramlintide |
| 73 | N-epsilon25-[2-(2-{2-[2-(2-{2-[(S)-4-Carboxy-4-(17-carboxyheptadecanoylamino)butyrylamino]ethoxy}ethoxy)acetylamino]ethoxy}ethoxy)acetyl]-[Glu14,His17,Lys25]-pramlintide |

TABLE 10-continued

| Example # | Name |
|---|---|
| 74 | N-epsilon21-[2-(2-{2-[2-(2-{2-[(S)-4-Carboxy-4-(17-carboxyheptadecanoylamino)butyrylamino]ethoxy}ethoxy)acetylamino]ethoxy}ethoxy)acetyl]-[Glu14,His17,Lys21,Glu35]-pramlintide |
| 75 | N-alpha-[(S)-4-Carboxy-4-(19-carboxynonadecanoylamino)butyryl]-[des1,Glu14,His17,His35]-pramlintide |
| 76 | N-alpha-[(S)-4-Carboxy-4-(19-carboxynonadecanoylamino)butyryl]-[His1,Glu14,His17,His35]-pramlintide |
| 77 | N-alpha-[(S)-4-Carboxy-4-(19-carboxynonadecanoylamino)butyryl]-[His1,Glu14,His17,Arg18,His35]-pramlintide |
| 78 | N-alpha-[(S)-4-Carboxy-4-(19-carboxynonadecanoylamino)butyryl]-[Glu14,His17,Arg18,His35]-pramlintide |
| 79 | N-alpha-[(S)-4-Carboxy-4-(19-carboxynonadecanoylamino)butyryl-[Glu14,His17,Arg18]-pramlintide |
| 80 | N-epsilon17-[2-(2-{2-[2-(2-{2-[(S)-4-Carboxy-4-(17-carboxyheptadecanoylamino)butyrylamino]ethoxy}ethoxy)acetylamino]ethoxy}ethoxy)acetyl]-[Glu14,Lys17]-pramlintide |
| 81 | N-alpha-[(S)-4-Carboxy-4-(19-carboxynonadecanoylamino)butyryl]-Gly-[Glu14,His17,His35]-pramlintide |
| 82 | N-alpha-[2-(2-{2-[2-(2-{2-[(S)-4-Carboxy-4-(17-carboxyheptadecanoylamino)butyrylamino]ethoxy}ethoxy)acetylamino]ethoxy}ethoxy)acetyl]-[Glu1,Glu14,His17,Pro37]-pramlintide |
| 83 | N-epsilon17-[2-(2-{2-[2-(2-{2-[(S)-4-Carboxy-4-(17-carboxyheptadecanoylamino)butyrylamino]ethoxy}ethoxy)acetylamino]ethoxy}ethoxy)acetyl]-[Glu14,Lys17,Ser21,Glu35]-pramlintide |
| 84 | N-alpha-[(S)-4-Carboxy-4-(19-carboxynonadecanoylamino)butyryl]-[His1,Glu14,His17,Pro37]-pramlintide |
| 85 | N-alpha-[(S)-4-Carboxy-4-(19-carboxynonadecanoylamino)butyryl]-Ser-[Glu14,His17,His35]-pramlintide |
| 86 | N-alpha-[(S)-4-Carboxy-4-(19-carboxynonadecanoylamino)butyryl]-[Glu14,Pro37]-pramlintide |
| 87 | N-epsilon1-[(S)-4-Carboxy-4-(19-carboxynonadecanoylamino)butyryl]-[Glu14,His17,His35]-pramlintide |
| 88 | N-alpha-[(S)-4-Carboxy-4-(19-carboxynonadecanoylamino)butyryl]-[Gly1,Glu14,Arg17,Pro37]-pramlintide |
| 89 | N-alpha-[(S)-4-Carboxy-4-(19-carboxynonadecanoylamino)butyryl]-Gly-[Gly1,Glu14,Arg17,Pro37]-pramlintide |
| 90 | N-alpha-[(S)-4-Carboxy-4-(19-carboxynonadecanoylamino)butyryl]-[His1,Glu14,Arg17,Pro37]-pramlintide |
| 91 | N-alpha-[(S)-4-Carboxy-4-(19-carboxynonadecanoylamino)butyryl]-[Gly1,Glu14,His17,Pro37]-pramlintide |
| 92 | N-alpha-[(S)-4-Carboxy-4-(19-carboxynonadecanoylamino)butyryl]-Gly-[His1,Glu14,His17,Pro37]-pramlintide |
| 93 | N-alpha-[(S)-4-Carboxy-4-(19-carboxynonadecanoylamino)butyryl]-[Glu14,His35]-pramlintide |
| 94 | N-epsilon1-[(S)-4-Carboxy-4-(17-carboxyheptadecanoylamino)butyryl]-[Glu14,His17,His35]-pramlintide |
| 95 | N-alpha-[(S)-4-Carboxy-4-(19-carboxynonadecanoylamino)butyryl]-[Arg1,G1u14,His17,His35]-pramlintide |
| 96 | N-alpha-[(S)-4-Carboxy-4-(19-carboxynonadecanoylamino)butyryl]-[Arg1,Glu14,His17,Pro37]-pramlintide |
| 97 | N-alpha-[(S)-4-Carboxy-4-(19-carboxynonadecanoylamino)butyryl]-[Arg1,Pro37]-pramlintide |
| 98 | N-alpha-[(S)-4-Carboxy-4-(19-carboxynonadecanoylamino)butyryl]-[Arg1,His35]-pramlintide |
| 99 | N-alpha-[(S)-4-Carboxy-4-(19-carboxynonadecanoylamino)butyryl]-Gly-[Arg1,His35]-pramlintide |
| 100 | N-alpha-[(S)-4-Carboxy-4-(19-carboxynonadecanoylamino)butyryl]-Gly-[Arg1,Glu14,His17,His35]-pramlintide |
| 101 | N-alpha-[(S)-4-Carboxy-4-(19-carboxynonadecanoylamino)butyryl]-Gly-[Arg1,Glu14,His17,Pro37]-pramlintide |
| 102 | N-alpha-[(S)-4-Carboxy-4-(19-carboxynonadecanoylamino)butyryl]-Gly-[Arg1,Glu14,Pro37]-pramlintide |
| 103 | N-alpha-[(S)-4-Carboxy-4-(19-carboxynonadecanoylamino)butyryl]-Gly-[Arg1,Pro37]-pramlintide |
| 104 | N-alpha-[(S)-4-Carboxy-4-(19-carboxynonadecanoylamino)butyryl]-[des1,Glu14,His17,Pro37]-pramlintide |
| 105 | N-alpha-[(S)-4-Carboxy-4-(19-carboxynonadecanoylamino)butyryl]-[Gly1,Glu14,His17,His35]-pramlintide |
| 106 | N-alpha-[(S)-4-Carboxy-4-(19-carboxynonadecanoylamino)butyryl]-[Ser1,Glu14,His17,Pro37]-pramlintide |
| 107 | N-alpha-[(S)-4-Carboxy-4-(19-carboxynonadecanoylamino)butyryl]-[Ser1,Glu14,His17,His35]-pramlintide |
| 108 | N-alpha-[(S)-4-Carboxy-4-(19-carboxynonadecanoylamino)butyryl]-[des1,Glu14,Pro37]-pramlintide |
| 109 | N-alpha-[(S)-4-Carboxy-4-(19-carboxynonadecanoylamino)butyryl]-[His1,Glu14,Pro37]-pramlintide |

TABLE 10-continued

| Example # | Name |
|---|---|
| 110 | N-alpha-[(S)-4-Carboxy-4-(19-carboxynonadecanoylamino)butyryl]-[His1,Glu14,Ser21,Ser28,Ser29,His35]-pramlintide |
| 111 | N-alpha-[(S)-4-Carboxy-4-(19-carboxynonadecanoylamino)butyryl]-[His1,Glu14,Arg17,Ser21,Ser28,Ser29,His35]-pramlintide |
| 112 | N-alpha-[(S)-4-Carboxy-4-(19-carboxynonadecanoylamino)butyryl]-[Glu14,His17,Arg35]-pramlintide |
| 113 | N-alpha-[(S)-4-Carboxy-4-(19-carboxynonadecanoylamino)butyryl]-[Glu14,His17,Lys35]-pramlintide |
| 114 | N-alpha-[(S)-4-Carboxy-4-(19-carboxynonadecanoylamino)butyryl]-[Glu14,His17,His36]-pramlintide |
| 115 | N-alpha-[(S)-4-Carboxy-4-(19-carboxynonadecanoylamino)butyryl]-[Glu14,His17,His34]-pramlintide |
| 116 | N-alpha-[(S)-4-Carboxy-4-(19-carboxynonadecanoylamino)butyryl]-[Glu14,His17,His32]-pramlintide |
| 117 | N-alpha-[(S)-4-Carboxy-4-(19-carboxynonadecanoylamino)butyryl]-[Glu14,His17,Gln21,His35]-pramlintide |
| 118 | N-alpha-[2-(2-{2-[2-(2-{2-[(S)-4-Carboxy-4-(19-carboxyheptadecanoylamino)butyrylamino]ethoxy}ethoxy)acetylamino]ethoxy}ethoxy)acetyl]-[Glu14,His17,Ser21,His35]-pramlintide |
| 119 | N-alpha-[2-(2-{2-[2-(2-{2-[(S)-4-Carboxy-4-(19-carboxyheptadecanoylamino)butyrylamino]ethoxy}ethoxy)acetylamino]ethoxy}ethoxy)acetyl]-[His1,Glu14,His17,Ser21,His35]-pramlintide |
| 120 | N-alpha-[2-(2-{2-[2-(2-{2-[(S)-4-Carboxy-4-(17-carboxyheptadecanoylamino)butyrylamino]ethoxy}ethoxy)acetylamino]ethoxy}ethoxy)acetyl]-D-Arg-D-Arg-[Orn1,Glu14,His17,Arg18]-pramlintide |
| 121 | N-alpha-(19-carboxynonadecanoyl)-Glu-Glu-Arg-[Glu1,Pro37]-pramlintide |
| 122 | N-alpha-[(S)-4-Carboxy-4-(19-carboxynonadecanoylamino)butyryl]-Glu-Arg-[Glu1,Pro37]-pramlintide |
| 123 | N-alpha-[(S)-4-Carboxy-4-(19-carboxynonadecanoylamino)butyryl]-Glu-Arg-[Glu1,Glu14,His17,Pro37]-pramlintide |
| 124 | N-alpha-[(S)-4-Carboxy-4-(19-carboxynonadecanoylamino)butyryl]-Glu-Arg-[Glu1,Glu14,Arg17,Pro37]-pramlintide |
| 125 | N-alpha-(19-carboxynonadecanoyl)-Glu-Glu-Arg-[Glu1,Glu14,His17,Pro37]-pramlintide |
| 126 | N-epsilon25-[2-(2-{2-[2-(2-{2-[(S)-4-Carboxy-4-(17-carboxyheptadecanoylamino)butyrylamino]ethoxy}ethoxy)acetylamino]ethoxy}ethoxy)acetyl]-[Glu14,Lys25]-pramlintide |
| 127 | N-epsilon21-[2-(2-{2-[2-(2-{2-[(S)-4-Carboxy-4-(19-carboxyheptadecanoylamino)butyrylamino]ethoxy}ethoxy)acetylamino]ethoxy}ethoxy)acetyl]-[Glu14,Lys21,Ser29,His35]-pramlintide |
| 128 | N-alpha-[(S)-4-Carboxy-4-(19-carboxynonadecanoylamino)butyryl]-[Glu14,His17,Asp21,His35]-pramlintide |
| 129 | N-alpha-[(S)-4-Carboxy-4-(19-carboxynonadecanoylamino)butyryl]-Glu-[Glu14,His17,Gln21,His35]-pramlintide |
| 130 | N-alpha-[(S)-4-Carboxy-4-(19-carboxynonadecanoylamino)butyryl]-[Glu14,His17,Gln21,Pro37]-pramlintide |
| 131 | N-epsilon21-[2-(2-{2-[2-(2-{2-[(S)-4-Carboxy-4-(19-carboxyheptadecanoylamino)butyrylamino]ethoxy}ethoxy)acetylamino]ethoxy}ethoxy)acetyl]-[Glu14,Lys21,Ser28,Ser29,His35]-pramlintide |
| 132 | N-epsilon21-[2-(2-{2-[2-(2-{2-[(S)-4-Carboxy-4-(19-carboxyheptadecanoylamino)butyrylamino]ethoxy}ethoxy)acetylamino]ethoxy}ethoxy)acetyl]-[Glu14,Lys21,His35]-pramlintide |
| 133 | N-epsilon25-[2-(2-{2-[2-(2-{2-[(S)-4-Carboxy-4-(19-carboxyheptadecanoylamino)butyrylamino]ethoxy}ethoxy)acetylamino]ethoxy}ethoxy)acetyl]-[Glu14,His17,Ser21,Lys25,Ser28,Ser29.His35]-pramlintide |
| 134 | N-epsilon25-[2-(2-{2-[2-(2-{2-[(S)-4-Carboxy-4-(19-carboxyheptadecanoylamino)butyrylamino]ethoxy}ethoxy)acetylamino]ethoxy}ethoxy)acetyl]-[His17,His21,Lys25,Ser28,Ser29.His35]-pramlintide |
| 135 | N-alpha-[(S)-4-Carboxy-4-(19-carboxynonadecanoylamino)butyryl]-[Glu14,His17,Gln35,Pro37]-pramlintide |
| 136 | N-alpha-[(S)-4-Carboxy-4-(19-carboxynonadecanoylamino)butyryl]-[Glu14,His17,Gln21,Gln35,Pro37]-pramlintide |
| 137 | N-alpha-[(S)-4-Carboxy-4-(19-carboxynonadecanoylamino)butyryl]-[Gly1,Glu14,His17,Gln21,Gln35,Pro37]-pramlintide |
| 138 | N-alpha-[(S)-4-Carboxy-4-(19-carboxynonadecanoylamino)butyryl]-[Glu1,Glu14,Gln21,Gln35,Pro37]-pramlintide |
| 139 | N-alpha-[(S)-4-Carboxy-4-(19-carboxynonadecanoylamino)butyryl]-[Glu14,Gln21,Gln35,Pro37]-pramlintide |
| 140 | N-epsilon25-[2-(2-{2-[2-(2-{2-[(S)-4-Carboxy-4-(19-carboxyheptadecanoylamino)butyrylamino]ethoxy}ethoxy)acetylamino]ethoxy}ethoxy)acetyl]-[His17,Lys25,Ser28,Ser29,His35]-pramlintide |
| 141 | N-epsilon21-[2-(2-{2-[2-(2-{2-[(S)-4-Carboxy-4-(19-carboxyheptadecanoylamino)butyrylamino]ethoxy}ethoxy)acetylamino]ethoxy}ethoxy)acetyl]-[His17,Lys21,Ser28,His35]-pramlintide |
| 142 | N-epsilon25-[2-(2-{2-[2-(2-{2-[(S)-4-Carboxy-4-(19-carboxyheptadecanoylamino)butyrylamino]ethoxy}ethoxy)acetylamino]ethoxy}ethoxy)acetyl]-[Glu14,His17,Lys25,Ser28,Ser29,His35]-pramlintide |

TABLE 10-continued

| Example # | Name |
|---|---|
| 143 | N-alpha-[(S)-4-Carboxy-4-(19-carboxynonadecanoylamino)butyryl]-[His1,Glu14,Arg18,Pro37]-pramlintide |
| 144 | N-epsilon21-[2-(2-{2-[2-(2-{2-[(S)-4-Carboxy-4-(19-carboxyheptadecanoylamino)butyrylamino]ethoxy}ethoxy)acetylamino]ethoxy}ethoxy)acetyl]-[Glu14,His17,Lys21,Ser28,His35]-pramlintide |
| 145 | N-alpha-[(S)-4-Carboxy-4-(19-carboxynonadecanoylamino)butyryl]-[Lys11,Glu14,His17,Pro37]-pramlintide |
| 146 | N-alpha-[(S)-4-Carboxy-4-(19-carboxynonadecanoylamino)butyryl]-[Glu14,His17,Thr21,Pro37]-pramlintide |
| 147 | N-epsilon21-[2-(2-{2-[2-(2-{2-[(S)-4-Carboxy-4-(19-carboxyheptadecanoylamino)butyrylamino]ethoxy}ethoxy)acetylamino]ethoxy}ethoxy)acetyl]-[Glu14,Lys21,Ser28,Arg29,His35]-pramlintide |
| 148 | N-epsilon21-[2-(2-{2-[2-(2-{2-[(S)-4-Carboxy-4-(19-carboxyheptadecanoylamino)butyrylamino]ethoxy}ethoxy)acetylamino]ethoxy}ethoxy)acetyl]-[Glu14,His17,Lys21,Ser28,Ser29,His35]-pramlintide |
| 149 | N-epsilon1-[(S)-4-Carboxy-4-(19-carboxynonadecanoylamino)butyryl]-Arg-[Glu14,Arg17,His35,Pro37]-pramlintide |
| 150 | N-epsilon21-[2-(2-{2-[2-(2-{2-[(S)-4-Carboxy-4-(19-carboxyheptadecanoylamino)butyrylamino]ethoxy}ethoxy)acetylamino]ethoxy}ethoxy)acetyl]-[Glu14,Arg18,Lys21,Ser28,Arg29,Arg35]-pramlintide |
| 151 | N-epsilon1-[(S)-4-Carboxy-4-(19-carboxynonadecanoylamino)butyryl]-[Glu14,His17,Gln21,Ala25,Pro26,Ser28,Ser29,Pro37]-pramlintide |
| 152 | N-alpha-[(S)-4-Carboxy-4-(19-carboxynonadecanoylamino)butyryl]-[Arg14,Arg17,Pro37]-pramlintide |
| 153 | N-alpha-[(S)-4-Carboxy-4-(19-carboxynonadecanoylamino)butyryl]-Gly-[Arg1,Glu14,Arg17,Pro37]-pramlintide |
| 154 | N-alpha-[(S)-4-Carboxy-4-(19-carboxynonadecanoylamino)butyryl]-[Arg17,Pro37]-pramlintide |
| 155 | N-alpha-[(S)-4-Carboxy-4-(19-carboxynonadecanoylamino)butyryl]-Glu-Glu-[Arg1,Glu14,Arg17,Pro37]-pramlintide |
| 156 | N-alpha-[(S)-4-Carboxy-4-(19-carboxynonadecanoylamino)butyryl]-Glu-[Arg1,Glu14,Arg17,Pro37]-pramlintide |
| 157 | N-alpha-[(S)-4-Carboxy-4-(19-carboxynonadecanoylamino)butyryl]-Glu-Glu-[Arg1,Glu14,Arg17,Gln21,Pro37]-pramlintide |
| 158 | N-alpha-[(S)-4-Carboxy-4-(19-carboxynonadecanoylamino)butyryl]-Glu-Glu-[Arg1,Glu14,Arg17,Gln21,Gln35,Pro37]-pramlintide |
| 159 | N-alpha-[(S)-4-Carboxy-4-(19-carboxynonadecanoylamino)butyryl]-Glu-Glu-[Arg1,Glu14,Arg17,Gln21,Gln31,Gln35,Pro37]-pramlintide |
| 160 | N-alpha-[(S)-4-Carboxy-4-(19-carboxynonadecanoylamino)butyryl]-Glu-Glu-[Arg1,Glu14,Arg17,Gln21,Gln22,Gln31,Gln35,Pro37]-pramlintide |
| 161 | N-alpha-[(S)-4-Carboxy-4-(19-carboxynonadecanoylamino)butyryl]-Glu-Arg-[Glu1,Glu14,Arg17,Gln21,Pro37]-pramlintide |
| 162 | N-alpha-[(S)-4-Carboxy-4-(19-carboxynonadecanoylamino)butyryl]-Glu-Arg-[Glu1,Glu14,Arg17,Gln21,Gln35,Pro37]-pramlintide |
| 163 | N-alpha-[(S)-4-Carboxy-4-(19-carboxynonadecanoylamino)butyryl]-Glu-Arg-[Glu1,Glu14,Arg17,Gln21,Gln31,Gln35,Pro37]-pramlintide |
| 164 | N-alpha-[(S)-4-Carboxy-4-(19-carboxynonadecanoylamino)butyryl]-Glu-Arg-[Glu1,Glu14,Arg17,Gln21,Gln22,Gln31,Gln35,Pro37]-pramlintide |
| 165 | N-alpha-[(S)-4-Carboxy-4-(19-carboxynonadecanoylamino)butyryl]-Glu-Glu-[Glu1,Glu14,Arg17,Pro37]-pramlintide |
| 166 | N-alpha-[(S)-4-Carboxy-4-(19-carboxynonadecanoylamino)butyryl]-[Glu14,Arg18,Gln21,Ala25,Pro26,Ser28,Ser29,Pro37]-pramlintide |
| 167 | N-alpha-[2-(2-{2-[2-(2-{2-[(S)-4-Carboxy-4-(19-carboxyheptadecanoylamino)butyrylamino]ethoxy}ethoxy)acetylamino]ethoxy}ethoxy)acetyl]-[Glu14,His17,Glu21,Pro37]-pramlintide |
| 168 | N-alpha-[2-(2-{2-[2-(2-{2-[(S)-4-Carboxy-4-(19-carboxyheptadecanoylamino)butyrylamino]ethoxy}ethoxy)acetylamino]ethoxy}ethoxy)acetyl]-[Glu14,His17,Lys21,Pro37]-pramlintide |
| 169 | N-alpha-[2-(2-{2-[2-(2-{2-[(S)-4-Carboxy-4-(19-carboxyheptadecanoylamino)butyrylamino]ethoxy}ethoxy)acetylamino]ethoxy}ethoxy)acetyl]-[Glu14,His17,Ala21,Pro37]-pramlintide |
| 170 | N-alpha-[(S)-4-Carboxy-4-(19-carboxynonadecanoylamino)butyryl]-[Glu14,Arg18,Ser21,Ser22,Ser28,Ser29,Asp31,Asp35,Pro37]-pramlintide |
| 171 | N-alpha-[(S)-4-Carboxy-4-(19-carboxynonadecanoylamino)butyryl]-[Glu14,Ser21,Ser22,Pro23,Ala25,Pro26,Ser28,Ser29,Asp31,Asp35,Pro37]-pramlintide |
| 172 | N-alpha-[(S)-4-Carboxy-4-(19-carboxynonadecanoylamino)butyryl]-[Glu14,Arg17,Asp21,Pro37]-pramlintide |
| 173 | N-alpha-[(S)-4-Carboxy-4-(19-carboxynonadecanoylamino)butyryl]-[Glu14,Arg17,Asp35,Pro37]-pramlintide |
| 174 | N-alpha-[(S)-4-Carboxy-4-(19-carboxynonadecanoylamino)butyryl]-[Glu14,Arg17,Asp31,Pro37]-pramlintide |
| 175 | N-alpha-[(S)-4-Carboxy-4-(19-carboxynonadecanoylamino)butyryl]-[Glu14,Arg17,Asp22,Pro37]-pramlintide |
| 176 | N-alpha-[(S)-4-Carboxy-4-(19-carboxynonadecanoylamino)butyryl]-[Asp3,Glu14,Arg17,Pro37]-pramlintide |
| 177 | N-epsilon1-[(S)-4-Carboxy-4-(19-carboxynonadecanoylamino)butyryl]-[Glu14,Arg17,Pro37]-pramlintide |

TABLE 10-continued

| Example # | Name |
|---|---|
| 178 | N-alpha-[2-(2-{2-[2-(2-{2-[(S)-4-Carboxy-4-(19-carboxyheptadecanoylamino)butyrylamino]ethoxy}ethoxy)acetylamino]ethoxy}ethoxy)acetyl]-[Glu14,Ala21,His35,Pro37]-pramlintide |

The in vitro potency of the polypeptides vs. amylin receptors and calcitonin receptors from rats and humans (as described in Assay (II)) is shown in Table 11

TABLE 11

| Example # | Amylin receptor rat $EC_{50}$ (pM) | CTa receptor rat $EC_{50}$ (pM) | Amylin receptor human $EC_{50}$ (pM) | CTa receptor human $EC_{50}$ (pM) |
|---|---|---|---|---|
| 1 | 64.5 | 379 | 93.4 | 149.7 |
| 2 | | | 602 | 4300.5 |
| 3 | | | 164 | 222 |
| 4 | | | 253.3 | 284.3 |
| 5 | | | 353.5 | 1650 |
| 6 | | | 114.7 | 239.8 |
| 7 | | | 77.9 | 131 |
| 8 | | | 126.5 | 278.5 |
| 9 | 330.5 | 1734 | 211.6 | 207.6 |
| 10 | 374.5 | 806.5 | 82.3 | 86.4 |
| 11 | 88.5 | 962 | 85.3 | 208.3 |
| 12 | 82 | 6764 | 77.5 | 408.5 |
| 14 | | | 99.4 | 469 |
| 15 | | | 83 | 125 |
| 16 | | | 313 | 197.5 |
| 17 | 147 | 221 | 111.3 | 166.4 |
| 18 | 187 | 1165 | 130.7 | 125.5 |
| 19 | 132 | 824 | 105.1 | 309.7 |
| 20 | | | 150.6 | 740.2 |
| 21 | 133 | 1342 | 192 | 429.2 |
| 22 | 261 | 1288 | 98.5 | 157.2 |
| 23 | | | 385 | 492 |
| 24 | 4512 | 1753 | 1441.5 | 672 |
| 25 | | | 118.8 | 184 |
| 26 | 475.5 | 1393 | 130 | 214.1 |
| 27 | 188 | 539 | 121.4 | 106.8 |
| 28 | | | 179.1 | 259 |
| 29 | | | 377.4 | 656.6 |
| 30 | | | 174.2 | 753.4 |
| 31 | 200 | 1309 | 163.5 | 155.5 |
| 32 | 401 | 4873 | 603 | 543 |
| 33 | | | 1032.5 | 484 |
| 34 | | | 271.5 | 198 |
| 35 | | | 286 | 801.5 |
| 36 | | | 167 | 190.5 |
| 37 | 132 | 1890 | 83.2 | 641.9 |
| 38 | 233 | 4479 | 148.8 | 1109.7 |
| 39 | | | 253 | 432.5 |
| 40 | | | 248 | 439 |
| 41 | | | 402 | 798.5 |
| 42 | 134.5 | 2432.5 | 73.9 | 273.5 |
| 43 | | | 333.5 | 672 |
| 44 | | | 305.5 | 669 |
| 45 | | | 62.4 | 264.5 |
| 46 | 122 | 433 | 46.9 | 79.2 |
| 47 | | | 59 | 258 |
| 48 | 15 | 375 | 42.5 | 112 |
| 49 | | | 151 | 527 |
| 50 | | | 100.9 | 458.5 |
| 51 | | | 61 | 600 |
| 52 | 159.5 | 76 | 62 | 53.7 |
| 53 | 348 | 287 | 53 | 79.7 |
| 54 | | | 129.5 | 199.5 |
| 55 | 262 | 673 | 151.6 | 163.2 |
| 56 | 643 | 4974 | 299 | 352 |
| 57 | 510.5 | 2842.5 | 111 | 387 |
| 58 | 63 | 2233 | 116.5 | 605.5 |
| 59 | 23 | 148 | 56 | 60.5 |
| 60 | | | 101.5 | 168.5 |
| 61 | 38 | 2360 | 67.5 | 334.5 |
| 62 | 281 | 17580 | 172 | 1073 |

TABLE 11-continued

| Example # | Amylin receptor rat $EC_{50}$ (pM) | CTa receptor rat $EC_{50}$ (pM) | Amylin receptor human $EC_{50}$ (pM) | CTa receptor human $EC_{50}$ (pM) |
|---|---|---|---|---|
| 63 | | | 558.5 | 631.5 |
| 64 | | | 153 | 94.5 |
| 65 | 1334 | 5353 | 217 | 341.5 |
| 66 | 305 | 656 | 182.5 | 210 |
| 67 | | | 96.5 | 114.5 |
| 68 | | | 93.5 | 430 |
| 69 | | | 101 | 614.5 |
| 70 | | | 58.5 | 99 |
| 71 | | | 79.5 | 946.5 |
| 72 | | | 89 | 100.5 |
| 73 | 52 | 167 | 38.5 | 45 |
| 74 | 504 | 2062 | 184 | 216 |
| 75 | | | 365.5 | 286 |
| 76 | 224 | 1043 | 121.5 | 85.5 |
| 77 | | | 66 | 110 |
| 78 | | | 68.5 | 96.5 |
| 79 | | | 56.5 | 77 |
| 80 | | | 455.5 | 4302.5 |
| 81 | | | 95.5 | 70.5 |
| 82 | | | 108.5 | 288.5 |
| 83 | | | 1748.5 | 8430 |
| 84 | 121 | 109 | 92.5 | 67 |
| 85 | | | 132.5 | 153 |
| 86 | | | 55 | 52.5 |
| 87 | 106 | 437 | 142 | 228 |
| 88 | 300 | 370 | 36 | 55 |
| 89 | 151 | 114 | 25.5 | 39.5 |
| 90 | 217 | 128 | 32.5 | 47.5 |
| 91 | | | 54 | 52 |
| 92 | | | 52 | 49 |
| 93 | 138 | 215 | 135.5 | 180 |
| 94 | | | 119.5 | 285.5 |
| 95 | | | 82 | 174.5 |
| 96 | 88 | 58 | 43 | 55 |
| 97 | | | 34 | 38.5 |
| 98 | | | 74.5 | 193 |
| 99 | | | 45 | 87.5 |
| 100 | | | 67.5 | 89.5 |
| 101 | 75 | 44 | 51.5 | 45.5 |
| 102 | | | 49.5 | 50.5 |
| 103 | | | 52.5 | 75 |
| 104 | | | 79.5 | 106.5 |
| 105 | | | 207.5 | 160.5 |
| 106 | | | 62.5 | 70.5 |
| 107 | | | 225 | 171 |
| 108 | | | 88 | 73.5 |
| 109 | | | 84.5 | 72.5 |
| 110 | | | 921 | 349 |
| 111 | | | 393.5 | 569.5 |
| 112 | | | 98 | 104 |
| 113 | | | 134 | 130 |
| 114 | | | 381.5 | 112.5 |
| 115 | | | 129 | 114.5 |
| 116 | | | 487 | 124 |
| 117 | | | 156 | 169 |
| 118 | | | 434.5 | 277 |
| 119 | | | 938 | 1076 |
| 120 | 33 | 2569 | 29.5 | 690.5 |
| 121 | | | 45 | 61.5 |
| 122 | | | 63 | 61 |
| 123 | | | 136 | 377.5 |
| 124 | | | 89.5 | 367 |
| 125 | | | 288.5 | 443 |
| 126 | | | 76 | 101 |
| 127 | | | 1093.5 | 480.5 |
| 128 | | | 291 | 265.5 |
| 129 | | | 391 | 247.5 |
| 130 | | | 55.5 | 31.5 |
| 131 | | | 858 | 336 |
| 132 | | | 998.5 | 601 |
| 133 | | | 416 | 142 |
| 134 | | | 390 | 193.5 |
| 135 | | | 103 | 97 |
| 136 | | | 91 | 45 |
| 137 | | | 120.5 | 72 |
| 138 | | | 1512 | 496.5 |
| 139 | | | 107.5 | 58.5 |

TABLE 11-continued

| Example # | Amylin receptor rat $EC_{50}$ (pM) | CTa receptor rat $EC_{50}$ (pM) | Amylin receptor human $EC_{50}$ (pM) | CTa receptor human $EC_{50}$ (pM) |
|---|---|---|---|---|
| 140 | | | 198.5 | 114 |
| 141 | | | 482.5 | 889 |
| 142 | | | 301 | 110.5 |
| 143 | | | 41.5 | 22 |
| 144 | | | 625 | 347 |
| 145 | | | 80.5 | 83 |
| 146 | | | 91 | 59.5 |
| 147 | | | 540.5 | 229 |
| 148 | | | 1031 | 319 |
| 150 | | | 344 | 731.5 |
| 151 | | | 209 | 67.5 |
| 152 | | | 129 | 453 |
| 153 | | | 43 | 41 |
| 154 | | | 53 | 57 |
| 155 | | | 313 | 526 |
| 156 | | | 66 | 168 |
| 157 | | | 465 | 547 |
| 158 | | | 1129 | 1188 |
| 161 | | | 232 | 1133 |
| 162 | | | 411 | 2195 |
| 163 | | | 1059 | 3707 |
| 164 | | | 1713 | 3568 |
| 166 | | | 39 | 34 |
| 167 | | | 203 | 113 |
| 168 | | | 71 | 85 |
| 170 | | | 90 | 76 |

The solubility of the polypeptides was tested as described in Assay (IV) and results shown in Table 12.

TABLE 12

| Example # | Solubility (μM) | | | | | | | |
|---|---|---|---|---|---|---|---|---|
| | pH 3.0 | pH 4.0 | pH 5.0 | pH 6.0 | pH 6.5 | pH 7.0 | pH 7.5 | pH 8.0 |
| 1 | >200 | >200 | >200 | 52 | 16 | 15 | 58 | 138 |
| 3 | >200 | >200 | 68 | >200 | >200 | >200 | >200 | >200 |
| 4 | >200 | 120 | 0 | 42 | 82 | 146 | 183 | 190 |
| 5 | >200 | >200 | 62 | 164 | 181 | >200 | >200 | >200 |
| 6 | >200 | 163 | 168 | 12 | 4 | 7 | 18 | 48 |
| 7 | >200 | >200 | 13 | 69 | 32 | 42 | 89 | 155 |
| 8 | 178 | 93 | 2 | 1 | 1 | 1 | 1 | 3 |
| 9 | >200 | 116 | 5 | >200 | >200 | >200 | >200 | >200 |
| 10 | >200 | >200 | >200 | >200 | >200 | >200 | >200 | >200 |
| 11 | >200 | >200 | >200 | >200 | 44 | 29 | 157 | >200 |
| 12 | >200 | >200 | >200 | >200 | 45 | 9 | 26 | 69 |
| 14 | >200 | >200 | >200 | 192 | 102 | 13 | 7 | 47 |
| 15 | >200 | >200 | 10 | 1 | 1 | 10 | 56 | 134 |
| 16 | 179 | 80 | 1 | 34 | 12 | 104 | 122 | 129 |
| 17 | >200 | >200 | >200 | 160 | 66 | 88 | >200 | >200 |
| 18 | >200 | >200 | >200 | >200 | 153 | 191 | >200 | >200 |
| 19 | >200 | >200 | 155 | 175 | 35 | 6 | 61 | 158 |
| 20 | >200 | >200 | >200 | 6 | 0 | 1 | 13 | 73 |
| 21 | >200 | >200 | >200 | >200 | 87 | 0 | 0 | 1 |
| 22 | >200 | >200 | >200 | >200 | 57 | 2 | 1 | 3 |
| 25 | >200 | >200 | >200 | >200 | >200 | >200 | >200 | >200 |
| 26 | >200 | >200 | >200 | >200 | >200 | >200 | >200 | >200 |
| 27 | >200 | >200 | >200 | >200 | 174 | 160 | >200 | >200 |
| 28 | >200 | >200 | >200 | >200 | >200 | >200 | >200 | >200 |
| 29 | >200 | >200 | 107 | >200 | >200 | >200 | >200 | >200 |
| 30 | >200 | >200 | 69 | >200 | >200 | >200 | >200 | >200 |
| 31 | >200 | >200 | >200 | >200 | 8 | 0 | 10 | 65 |
| 32 | >200 | >200 | >200 | >200 | 6 | 0 | 6 | 55 |
| 33 | >200 | >200 | >200 | >200 | 17 | 0 | 0 | 16 |
| 34 | >200 | >200 | >200 | >200 | 4 | 0 | 0 | 13 |
| 35 | >200 | >200 | 194 | 17 | 0 | 0 | 9 | 66 |
| 36 | >200 | >200 | >200 | >200 | 14 | 0 | 2 | 60 |
| 37 | >200 | >200 | >200 | >200 | 124 | 198 | >200 | >200 |
| 38 | >200 | >200 | >200 | >200 | >200 | >200 | >200 | >200 |
| 39 | >200 | 84 | 52 | 6 | 4 | 1 | 25 | 26 |
| 40 | >200 | >200 | >200 | >200 | >200 | >200 | >200 | >200 |
| 41 | >200 | 118 | 1 | 1 | 1 | 1 | 1 | 4 |
| 42 | >200 | >200 | >200 | >200 | >200 | >200 | >200 | >200 |
| 43 | >200 | >200 | 194 | 176 | 195 | >200 | >200 | >200 |
| 44 | >200 | >200 | >200 | 21 | 20 | 52 | >200 | >200 |
| 45 | >200 | >200 | >200 | 188 | 48 | 42 | 134 | >200 |
| 46 | >200 | >200 | >200 | >200 | >200 | 169 | 197 | >200 |
| 47 | >200 | >200 | >200 | 168 | 87 | 118 | >200 | >200 |
| 48 | >200 | >200 | >200 | >200 | 177 | >200 | >200 | >200 |
| 49 | >200 | >200 | 27 | >200 | >200 | >200 | >200 | >200 |
| 50 | >200 | >200 | 183 | 161 | 132 | 73 | 62 | 21 |
| 51 | >200 | >200 | >200 | >200 | >200 | >200 | >200 | >200 |
| 52 | >200 | >200 | >200 | >200 | >200 | >200 | >200 | >200 |
| 53 | >200 | >200 | >200 | >200 | >200 | >200 | >200 | >200 |
| 54 | >200 | >200 | >200 | 100 | 150 | >200 | >200 | >200 |
| 55 | >200 | >200 | >200 | >200 | 146 | 102.5 | 108.5 | 146 |
| 56 | >200 | >200 | >200 | >200 | >200 | >200 | >200 | >200 |
| 57 | >200 | >200 | >200 | >200 | >200 | >200 | 121 | 80 |
| 58 | >200 | >200 | >200 | >200 | >200 | >200 | >200 | >200 |
| 59 | >200 | >200 | >200 | >200 | >200 | >200 | >200 | >200 |
| 60 | >200 | >200 | >200 | >200 | >200 | >200 | >200 | >200 |
| 61 | >200 | >200 | >200 | >200 | >200 | 81 | 50 | 48 |
| 62 | >200 | >200 | >200 | >200 | >200 | >200 | >200 | >200 |
| 63 | >200 | >200 | >200 | 1 | 2 | 75 | >200 | >200 |
| 64 | >200 | >200 | >200 | >200 | 189 | 91 | 136 | >200 |
| 65 | >200 | >200 | >200 | >200 | >200 | 176 | 96 | 89 |
| 66 | >200 | >200 | >200 | >200 | 155 | 46 | 77 | 144 |
| 67 | >200 | >200 | >200 | >200 | 166 | 15 | 24 | 60 |
| 68 | >200 | >200 | >200 | >200 | 170 | 17 | 6 | 7 |
| 69 | >200 | >200 | >200 | >200 | 158 | 6 | 2 | 24 |
| 70 | >200 | >200 | >200 | >200 | 69 | 32 | 52 | 89 |
| 71 | >200 | >200 | >200 | >200 | 156 | 37 | 27 | 26 |
| 72 | >200 | >200 | >200 | 168 | 130 | 126 | 165 | >200 |
| 73 | >200 | >200 | >200 | >200 | >200 | 155 | 169 | >200 |
| 74 | >200 | >200 | >200 | >200 | >200 | >200 | >200 | >200 |
| 75 | >200 | >200 | >200 | >200 | 193 | >200 | >200 | >200 |
| 76 | >200 | >200 | >200 | 45 | 1 | 4 | 104 | >200 |
| 77 | >200 | >200 | >200 | 185 | 23 | 5 | 33 | 94 |
| 78 | >200 | >200 | >200 | >200 | 122 | 92 | 79 | |
| 79 | >200 | >200 | >200 | >200 | >200 | >200 | >200 | >200 |
| 80 | >200 | >200 | >200 | >200 | >200 | >200 | >200 | >200 |
| 81 | >200 | >200 | >200 | >200 | >200 | >200 | >200 | >200 |

TABLE 12-continued

| Example # | Solubility (µM) | | | | | | | |
|---|---|---|---|---|---|---|---|---|
| | pH 3.0 | pH 4.0 | pH 5.0 | pH 6.0 | pH 6.5 | pH 7.0 | pH 7.5 | pH 8.0 |
| 82 | >200 | >200 | >200 | >200 | >200 | >200 | >200 | >200 |
| 83 | >200 | >200 | >200 | >200 | >200 | >200 | >200 | >200 |
| 84 | >200 | >200 | >200 | >200 | >200 | >200 | >200 | >200 |
| 85 | >200 | >200 | >200 | 185 | 64 | 22 | 47 | 109 |
| 86 | >200 | >200 | >200 | >200 | >200 | >200 | >200 | >200 |
| 87 | >200 | >200 | >200 | >200 | >200 | >200 | >200 | >200 |
| 88 | >200 | >200 | >200 | >200 | >200 | >200 | >200 | >200 |
| 89 | >200 | >200 | >200 | >200 | >200 | >200 | >200 | >200 |
| 90 | >200 | >200 | >200 | >200 | >200 | >200 | >200 | >200 |
| 91 | >200 | >200 | >200 | >200 | >200 | >200 | >200 | >200 |
| 92 | >200 | >200 | >200 | >200 | >200 | >200 | >200 | >200 |
| 93 | >200 | >200 | >200 | >200 | 84 | 74 | 163 | >200 |
| 94 | >200 | >200 | >200 | >200 | >200 | 138 | >200 | >200 |
| 95 | >200 | >200 | >200 | >200 | 16 | 2 | 11 | 51 |
| 96 | >200 | >200 | >200 | >200 | >200 | >200 | >200 | >200 |
| 97 | >200 | >200 | >200 | >200 | >200 | >200 | >200 | >200 |
| 98 | >200 | >200 | >200 | 85 | 1 | 1 | 1 | 1 |
| 99 | >200 | >200 | >200 | 2 | 1 | 1 | 1 | 1 |
| 100 | >200 | >200 | >200 | >200 | 28 | 9 | 30 | 95 |
| 101 | >200 | >200 | >200 | >200 | >200 | >200 | >200 | >200 |
| 102 | >200 | >200 | >200 | >200 | 198 | >200 | >200 | >200 |
| 103 | >200 | >200 | >200 | >200 | >200 | 199 | >200 | >200 |
| 104 | >200 | >200 | >200 | >200 | >200 | >200 | >200 | >200 |
| 105 | >200 | >200 | >200 | >200 | 152 | >200 | >200 | >200 |
| 106 | >200 | >200 | >200 | >200 | >200 | >200 | >200 | >200 |
| 107 | >200 | >200 | >200 | 49 | 4 | 27 | 174 | >200 |
| 108 | >200 | >200 | >200 | 193 | >200 | >200 | >200 | >200 |
| 109 | >200 | >200 | >200 | >200 | >200 | >200 | >200 | >200 |
| 110 | >200 | >200 | >200 | 1 | 1 | 1 | 1 | 1 |
| 111 | >200 | >200 | >200 | 2 | 1 | 1 | 1 | 3 |
| 112 | >200 | >200 | >200 | >200 | 161 | 23 | 4 | 2 |
| 113 | >200 | >200 | >200 | >200 | >200 | >200 | 188 | 124 |
| 114 | >200 | >200 | >200 | >200 | 73 | 14 | 31 | 79 |
| 115 | >200 | >200 | >200 | >200 | 73 | 22 | 46 | 115 |
| 116 | >200 | >200 | >200 | >200 | 120 | 44 | 79 | 173 |
| 117 | >200 | >200 | >200 | >200 | >200 | >200 | >200 | >200 |
| 118 | >200 | >200 | >200 | >200 | 105 | 37 | 57 | 117 |
| 119 | >200 | >200 | >200 | 32 | 3 | 13 | 114 | >200 |
| 120 | >200 | >200 | >200 | >200 | >200 | >200 | >200 | 197 |
| 121 | >200 | >200 | >200 | 155 | 127 | 54 | 157 | 117 |
| 122 | >200 | >200 | >200 | >200 | >200 | >200 | >200 | >200 |
| 123 | >200 | >200 | >200 | >200 | >200 | >200 | >200 | >200 |
| 124 | >200 | >200 | >200 | >200 | >200 | >200 | >200 | >200 |
| 125 | >200 | >200 | >200 | >200 | >200 | >200 | >200 | >200 |
| 127 | >200 | >200 | >200 | >200 | >200 | >200 | >200 | >200 |
| 128 | >200 | >200 | >200 | >200 | 114 | 140 | >200 | >200 |
| 129 | >200 | >200 | >200 | >200 | 194 | >200 | >200 | >200 |
| 130 | >200 | >200 | >200 | >200 | >200 | >200 | >200 | >200 |
| 131 | >200 | 172 | 150 | 25 | 6 | 4 | 4 | 3 |
| 132 | >200 | >200 | >200 | >200 | 198 | 142 | 169 | >200 |
| 133 | >200 | >200 | 107 | 1 | 1 | 1 | 1 | 1 |
| 134 | >200 | >200 | >200 | 3 | 1 | 2 | 3 | 2 |
| 135 | >200 | >200 | >200 | >200 | >200 | >200 | >200 | >200 |
| 136 | >200 | >200 | >200 | >200 | >200 | >200 | >200 | >200 |
| 137 | >200 | >200 | >200 | 192 | >200 | >200 | >200 | >200 |
| 138 | >200 | >200 | >200 | >200 | >200 | >200 | >200 | >200 |
| 139 | >200 | >200 | >200 | >200 | >200 | >200 | >200 | >200 |
| 140 | >200 | >200 | 104 | 2 | 1 | 1 | 1 | 1 |
| 141 | >200 | >200 | >200 | 84 | 3 | 2 | 1 | 1 |
| 142 | >200 | >200 | 185 | 118 | 1 | 1 | 1 | 1 |
| 143 | >200 | >200 | >200 | 75 | 122 | 165 | >200 | >200 |
| 144 | >200 | >200 | >200 | 47 | 2 | 1 | 1 | 1 |
| 145 | >200 | >200 | >200 | 178 | >200 | >200 | >200 | >200 |
| 146 | >200 | >200 | >200 | >200 | >200 | >200 | >200 | >200 |
| 147 | >200 | >200 | >200 | 1 | 1 | 1 | 1 | 1 |
| 148 | >200 | >200 | >200 | 51 | 19 | 1 | 1 | 1 |
| 150 | >200 | >200 | >200 | >200 | 163 | >200 | >200 | >200 |
| 151 | >200 | >200 | >200 | >200 | >200 | >200 | >200 | >200 |
| 155 | >200 | >200 | >200 | >200 | >200 | >200 | >200 | >200 |
| 157 | >200 | >200 | >200 | >200 | >200 | >200 | >200 | >200 |
| 158 | >200 | >200 | >200 | >200 | >200 | >200 | >200 | >200 |
| 159 | >200 | >200 | >200 | >200 | >200 | >200 | >200 | >200 |
| 160 | >200 | >200 | >200 | >200 | >200 | >200 | >200 | >200 |
| 161 | >200 | >200 | >200 | >200 | >200 | >200 | >200 | >200 |
| 162 | >200 | >200 | >200 | >200 | >200 | >200 | >200 | >200 |
| 163 | >200 | >200 | >200 | >200 | >200 | >200 | >200 | >200 |
| 164 | >200 | >200 | >200 | >200 | >200 | >200 | >200 | >200 |
| 166 | >200 | >200 | >200 | >200 | >200 | >200 | >200 | >200 |
| 167 | >200 | >200 | >200 | >200 | >200 | >200 | >200 | >200 |
| 168 | >200 | >200 | >200 | >200 | >200 | >200 | >200 | >200 |
| 169 | >200 | >200 | >200 | >200 | >200 | >200 | >200 | >200 |
| 170 | >200 | >200 | 186 | >200 | >200 | >200 | >200 | 188 |
| 171 | >200 | >200 | >200 | >200 | >200 | >200 | >200 | >200 |
| 177 | >200 | >200 | >200 | >200 | >200 | >200 | >200 | >200 |
| 178 | >200 | >200 | >200 | >200 | >200 | >200 | >200 | >200 |

The amylin derivatives were tested for physical stability in the ThT assay (Assay (III)) and the data given in Table 13.

TABLE 13

| Example # | ThT pH 4.0 lag time (h) | ThT pH 4.0 recovery (%) |
|---|---|---|
| 1 | 11 | 0 |
| 5 | 4.4 | 0 |
| 6 | 14 | 0 |
| 7 | 0 | 0 |
| 9 | >45 | 57 |
| 11 | 7.4 | 3 |
| 12 | >45 | 50 |
| 15 | 4.7 | 2 |
| 17 | 30.3 | 9 |
| 20 | 1.7 | 0 |
| 21 | 1 | 89 |
| 22 | 2.7 | 14 |
| 25 | 2.7 | 0 |
| 26 | 2 | 0 |
| 27 | 12.3 | 26 |
| 28 | 9.3 | 0 |
| 29 | 3 | 0 |
| 30 | 4.7 | 0 |
| 31 | >45 | 94 |
| 32 | >45 | 94 |
| 33 | 10 | 86 |
| 34 | 13 | 94 |
| 35 | 1.3 | 50 |
| 36 | 1.3 | 18 |
| 37 | >45 | 87 |
| 38 | >45 | 94 |
| 39 | 0 | 0 |
| 40 | 7 | 2 |
| 41 | 0 | 0 |
| 42 | 7.3 | 2 |
| 43 | 0 | 4 |
| 44 | 10.6 | 3 |
| 45 | 36.7 | 37 |
| 46 | 27.9 | 48.2 |
| 47 | 6 | 8 |
| 48 | 9 | 8 |
| 49 | 0 | 7 |
| 50 | >45 | 85 |
| 51 | 28.7 | 73 |
| 52 | >45 | 92.3 |
| 53 | >45 | 96.2 |
| 54 | 23 | 42 |
| 55 | 37 | 90.6 |
| 56 | 16 | 35 |
| 57 | >45 | 100 |
| 58 | >45 | 97 |
| 59 | >45 | 97 |
| 60 | 10 | 13 |
| 61 | >45 | 100 |
| 62 | 30 | 53 |
| 63 | 2 | 100 |
| 64 | 6 | 8 |
| 65 | >45 | 100 |
| 66 | >45 | 92 |

TABLE 13-continued

| Example # | ThT pH 4.0 lag time (h) | ThT pH 4.0 recovery (%) |
|---|---|---|
| 67 | >45 | 88 |
| 68 | >45 | 93 |
| 69 | >45 | 94 |
| 70 | >45 | 85 |
| 71 | >45 | 97 |
| 72 | 10.3 | 57 |
| 73 | >45 | 100 |
| 74 | >45 | 96 |
| 75 | 28 | 0 |
| 76 | >45 | 100 |
| 77 | >45 | 93 |
| 78 | >45 | 100 |
| 79 | 16 | 35 |
| 80 | 3 | 7 |
| 81 | 24 | 50 |
| 82 | 14 | 27 |
| 83 | >45 | 97 |
| 84 | 25.6 | 100 |
| 85 | >45 | 100 |
| 86 | 5 | 3.4 |
| 87 | 25 | 85 |
| 88 | >45 | 87 |
| 89 | >45 | 91 |
| 90 | >45 | 93 |
| 91 | 29 | 0 |
| 92 | 15.3 | 1.6 |
| 93 | 19 | 0 |
| 94 | 11.3 | 97 |
| 95 | >45 | 89 |
| 96 | >45 | 92 |
| 97 | 1.7 | 0 |
| 98 | 2.6 | 30 |
| 99 | 1.7 | 0 |
| 100 | 26 | 92 |
| 101 | >45 | 98 |
| 102 | 3.1 | 2 |
| 103 | 1.3 | 2 |
| 104 | 23 | 3 |
| 105 | 26 | 48 |
| 106 | 9.7 | 2 |
| 107 | 19 | 24 |
| 108 | 2.7 | 0 |
| 109 | 6.3 | 2.4 |
| 110 | 1.7 | 0 |
| 111 | >45 | 4 |
| 112 | >45 | 100 |
| 113 | >45 | 88 |
| 114 | >45 | 89 |
| 115 | >45 | 88 |
| 116 | >45 | 92 |
| 117 | >45 | 92 |
| 118 | >45 | 81 |
| 119 | >45 | 86 |
| 120 | 22 | 86 |
| 121 | 0.3 | 2.2 |
| 122 | 0.7 | 2.6 |
| 123 | 8.7 | 2.3 |
| 124 | >45 | 9.3 |
| 125 | 19 | 2.3 |
| 126 | 10 | 0 |
| 127 | 6 | 15 |
| 128 | >45 | 96 |
| 129 | 24 | 0 |
| 130 | >45 | 93 |
| 131 | 0.3 | 18 |
| 132 | >45 | 100 |
| 133 | >45 | 37 |
| 134 | >45 | 23 |
| 135 | >45 | 100 |
| 136 | >45 | 100 |
| 137 | 29 | 23 |
| 138 | 1.3 | 5 |
| 139 | 23.6 | 31 |
| 140 | 0 | 6 |
| 141 | 0 | 10 |
| 142 | 0 | 25 |
| 143 | 6 | 0 |
| 144 | 1.3 | 25 |
| 145 | >45 | 91 |
| 146 | >45 | 87 |
| 147 | 1 | 11 |
| 148 | 18 | 5 |
| 150 | >45 | 83 |
| 151 | 9 | 68 |
| 156 | >45 | 99 |
| 161 | >45 | 96 |
| 162 | >45 | 98 |
| 163 | >45 | 95 |
| 164 | >45 | 95 |
| 166 | 1.3 | 2 |
| 170 | >45 | 94 |

The amylin derivatives were tested with respect to their effect in the Food Intake assay (Assay (I)) and the results shown in Table 14

TABLE 14

| Example # | Food intake reduction 0-24 h 30 nmol/kg (%) | Food intake reduction 24-48 h 30 nmol/kg (%) | Food intake reduction 0-24 h 3 nmol/kg (%) | Food intake reduction 24-48 h 3 nmol/kg (%) |
|---|---|---|---|---|
| 1 | 93 | 92 | 50 | 45 |
| 3 | | | 37 | 32 |
| 7 | | | 53 | 46 |
| 9 | | | 39 | 32 |
| 10 | | | 50 | 40 |
| 11 | 87 | 92 | | |
| 12 | 70 | 45 | | |
| 14 | | | 27 | 8 |
| 15 | | | 56 | 59 |
| 17 | | | 40 | 22 |
| 18 | | | 40 | 32 |
| 22 | | | 26 | 5 |
| 26 | | | 46 | 39 |
| 27 | | | 56 | 53 |
| 28 | | | 39 | 36 |
| 29 | | | 15 | 5 |
| 37 | | | 24 | 0 |
| 38 | | | 16 | 0 |
| 42 | | | 45 | 5 |
| 46 | | | 54 | 27 |

TABLE 14-continued

| Example # | Food intake reduction 0-24 h 30 nmol/kg (%) | Food intake reduction 24-48 h 30 nmol/kg (%) | Food intake reduction 0-24 h 3 nmol/kg (%) | Food intake reduction 24-48 h 3 nmol/kg (%) |
|---|---|---|---|---|
| 50 |  |  | 30 | 8 |
| 52 |  |  | 62 | 74 |
| 53 |  |  | 40 | 28 |
| 55 | 88 | 90 | 58 | 40 |
| 56 |  |  | 46 | 21 |
| 57 |  |  | 17 | 0 |
| 59 |  |  | 59 | 27 |
| 71 |  |  | 10 | 0 |
| 73 |  |  | 29 | 2 |
| 84 |  |  | 68 | 67 |
| 87 |  |  | 66 | 47 |
| 89 |  |  | 42 | 23 |
| 96 |  |  | 69 | 89 |
| 101 |  |  | 70 | 90 |
| 117 |  |  | 50 | 35 |
| 120 |  |  | 53 | 2 |

The half life of the amylin derivatives of the inventions were tested in mini pigs as described in Assay (IX) and the data are given in Table 15.

TABLE 15

| Example # | PK minipig i.v. T½ (hours) |
|---|---|
| 11 | 106 |
| 27 | 90 |
| 52 | 105 |
| 53 | 98 |
| 55 | 73 |
| 57 | 68 |
| 59 | 59 |
| 96 | 107 |

Abbreviations

Some of the abbreviations used in the Examples are as follows:

Acm: acetamidomethyl
HATU: (O-(7-azabenzotriazol-1-yl)-1,1,3,3-tetramethyluronium hexafluorophosphate)
HBTU: 2-(1H-Benzotriazol-1-yl-)-1,1,3,3 tetramethyluronium hexafluorophosphate
Fmoc: 9H-fluoren-9-ylmethoxycarbonyl
Boc: tert butyloxycarbonyl
Mtt: 4-methyltrityl
DCM: dichloromethane
TIPS: triisopropylsilane
TFA: trifluoroacetic acid
NMP: 1-Methyl-pyrrolidin-2-one
HOAt: 1-Hydroxy-7-azabenzotriazole
DIC: Diisopropylcarbodiimide
Trt: triphenylm ethyl Assays In the following examples reference is made to the following Assays:

Assay (I)—Experimental protocol for efficacy testing on appetite using an ad libitum fed rat model
ASSAY (II)a—Functional assay—Human calcitonin and amylin receptor assay
ASSAY (II)b—Functional assay—Rat calcitonin and rat amylin receptor assays
ASSAY (III)—ThT fibrillation assays for the assessment of physical stability of protein formulations
ASSAY (IV)—Determination of solubility
ASSAY (V)—Determination of binding to the human amylin receptor
ASSAY (VI)—Determination of the binding to the rat amylin receptor
ASSAY (VII)—Determination of binding to the human calcitonin receptor
ASSAY (VIII)—Determination of binding to the rat calcitonin receptor
ASSAY (IX)—pK Determination of T½ in mini-pig
ASSAY (X)—pK Determination of T½ in rat
ASSAY (I)—Experimental Protocol for Efficacy Testing on Appetite Using an Ad Libitum Fed Rat Model Sprague Dawley (SD) rats from Taconic Europe, Denmark are used for the experiments. The rats have a body weight 200-250 g at the start of experiment. The rats arrive at least 10-14 days before start of experiment to allow acclimatization to experimental settings. During this period the animals are handled at least 2 times. After arrival rats are housed individually for one week in a reversed light/dark phase (meaning that lights are off during daytime and on during nighttime) for two weeks. Since rats are normally active and eat their major part of their daily food intake during the dark period, rats are dosed in the morning right before lights are turned off. This set-up results in the lowest data variation and highst test sensitivity. The experiment is conducted in the rats' home cages and rats have free access to food and water througout the acclimatization period and the experiment period. Each dose of derivative is tested in a group of 5-8 rats. A vehicle group of 6-8 rats is included in each set of testing. Rats are dosed once according to body weight with a 0.01-3 mg/kg solution administered intraperitoneally (ip), orally (po) or subcutaneously (sc). The time of dosing is recorded for each group. After dosing, the rats are returned to their home cages, where they then have access to food and water. The food consumption is recorded individually continuously by on-line registration or manually every hour for 7 hours, and then after 24 h and sometimes 48 h. At the end of the experimental session, the animals are euthanised.

The individual data are recorded in Microsoft excel sheets. Outliers are excluded after applying the Grubbs statistical evaluation test for outliers, and the result is presented graphically using the GraphPad Prism program.

ASSAY (II)—Functional Assays
Assay (II)a—Human Calcitonin and Amylin Receptor Assay
1. Luciferase Assay Outline Activation of calcitonin and amylin (coexpression of calcitonin receptor and receptor activity modifying proteins (RAMP)) receptors lead to increased intracellular concentrations of cAMP. Consequently, transcription is activated by promoters containing multiple copies of the cAMP response element (CRE). It is thus possible to measure amylin activity by the use of a CRE luciferase reporter gene introduced into BHK cells also expressing calcitonin or amylin receptors.

2. Construction of Calcitonin (a)—and amylin 3(a)—Receptor/CRE-luc Cell Line.

A BHK570 cell line was stably transfected with the human calcitonin receptor and a CRE-responsive luciferase reporter gene. The cell line was further transfected with RAMP-3, using standard methods. This turns the calcitonin receptor into an amylin 3(a) receptor. Methotrexate, Neomycin, and Hygromycin are selection markers for luciferase, the calcitonin receptor, and RAMP-3, respectively.

3. Luciferase Assays

To perform activity assays, BHK calcitonin (a) receptor- or amylin 3(a)-receptor/CRE-luc cells were seeded in white 96 well culture plates at a density of about 20.000 cells/well. The cells were in 100 µl growth medium (DMEM with 10% FBS, 1% Pen/Strep, 1 mM Na-pyruvate, 250 nM Methotrexate, 500 µg/ml Neomycin, and 400 µg/ml Hygromycin). After incubation overnight at 37° C. and 5% $CO_2$, the growth medium was replaced by 50 µl/well assay medium (DMEM (without phenol red), Glutamax™, 10% FBS, and 10 mM Hepes, pH 7.4). Further, 50 µl/well of standard or sample in assay buffer were added. After 3 hours incubation at 37° C. and 5% $CO_2$, the assay medium with standard or sample were removed and replaced by 100 µl/well PBS. Further, 100 µl/well LucLite™ was added. The plates were sealed and incubated at room temperature for 30 minutes. Finally, luminescence was measured on a TopCounter (Packard) in SPC (single photon counting) mode.

Assay (II)b—Rat Calcitonin and Rat Amylin Receptor Assays
cAMP Assay Outline

Activation of calcitonin and amylin (coexpression of calcitonin receptor and receptor activity modifying proteins (RAMP)) receptors lead to increased intracellular concentrations of cAMP. In order to quantify the cAMP levels in transiently transfected cells the Adenylyl Cyclase Activation FlashPlate® Assay from Perkin Elmer was used. The basic principle of the FlashPlate® Assay is a competition between radioactive and non-radioactive cAMP generated by the cells for a fixed number of binding sites.

Construction of Rat Calcitonin(a)—and Rat Amylin 3(a)—Receptor Cells.

BHK tk'ts 13 cells were transiently transfected with either rat calcitonin (a) receptor or rat amylin 3 (a) receptor (rat calcitonin(a) receptor+ rat RAMP3) using FuGENE® 6 (Roche), according to the manufacturers recommendations.

cAMP Assay 24 hours after transient transfection the cells (rat calcitonin (a)—or rat amylin 3(a)—receptor cells) were added (100.000 cells/well) to the 96 well FlashPlates® with samples or standard in FlashPlate stimulation buffer with IBMX and incubated for 30 min. Detection mix was created according to manufacturers protocol and scintillation measured after 3 h of incubation on TopCounter™ (Packard).

ASSAY (III)—ThT Fibrillation Assays for the Assessment of Physical Stability of Protein Formulations Low physical stability of a polypeptide may lead to amyloid fibril formation, which is observed as well-ordered, thread-like macromolecular structures in the sample eventually resulting in gel formation. This has traditionally been measured by visual inspection of the sample. However, that kind of measurement is very subjective and depending on the observer. Therefore, the application of a small molecule indicator probe is much more advantageous. Thioflavin T (ThT) is such a probe and has a distinct fluorescence signature when binding to fibrils [Naiki et al. (1989) Anal. Biochem. 177, 244-249; LeVine (1999) Methods. Enzymol. 09, 274-284].

The time course for fibril formation can be described by a sigmoidal curve with the following expression [Nielsen et al. (2001) Biochemistry 40, 6036-6046]:

$$F = f_i + m_i t + \frac{f_f + m_f t}{1 + e^{-[(t-t_0)/\tau]}} \qquad \text{Eq. (1)}$$

Here, F is the ThT fluorescence at the time t. The constant $t_0$ is the time needed to reach 50% of maximum fluorescence. The two important parameters describing fibril formation are the lag-time calculated by $t_0 - 2T$ and the apparent rate constant $k_{app} = 1/\tau$.

Formation of a partially folded intermediate of the polypeptide is suggested as a general initiating mechanism for fibrillation. Few of those intermediates nucleate to form a template onto which further intermediates may assembly and the fibrillation proceeds. The lag-time corresponds to the interval in which the critical mass of nucleus is built up and the apparent rate constant is the rate with which the fibril itself is formed.

Sample Preparation

Samples were prepared freshly before each assay. Each sample composition is described in each example. The pH of the sample was adjusted to the desired value using appropriate amounts of concentrated NaOH and $HClO_4$ or HCl. Thioflavin T was added to the samples from a stock solution in $H_2O$ to a final concentration of 1 µM.

Sample aliquots of 200 µl were placed in a 96 well microtiter plate (Packard OptiPlate™-96, white polystyrene). Usually, four or eight replica of each sample (corresponding to one test condition) were placed in one column of wells. The plate was sealed with Scotch Pad (Qiagen).

Incubation and Fluorescence Measurement

Incubation at given temperature, shaking and measurement of the ThT fluorescence emission were done in a Fluoroskan Ascent FL fluorescence platereader or Varioskan platereader (Thermo Labsystems). The temperature was adjusted to 37° C. The orbital shaking was adjusted to 960 rpm with an amplitude of 1 mm in all the presented data. Fluorescence measurement was done using excitation through a 444 nm filter and measurement of emission through a 485 nm filter.

Each run was initiated by incubating the plate at the assay temperature for 10 min. The plate was measured every 20 minutes for a desired period of time. Between each measurement, the plate was shaken and heated as described.

Data Handling

The measurement points were saved in Microsoft Excel format for further processing and curve drawing and fitting was performed using GraphPad Prism. The background emission from ThT in the absence of fibrils was negligible. The data points are typically a mean of four or eight samples and shown with standard deviation error bars. Only data obtained in the same experiment (i.e. samples on the same plate) are presented in the same graph ensuring a relative measure of fibrillation between experiments.

The data set may be fitted to Eq. (1). However, since full sigmodial curves in this case are not always achieved during the measurement time, the degree of fibrillation is expressed as ThT fluorescence tabulated as the mean of the samples and shown with the standard deviation at various time points.

Measurement of Initial and Final Concentrations

The polypeptide concentration in each of the tested formulations were measured both before application in the ThT fibrillation assay ("Initial") and after completion of the ThT fibrillation ("After ThT assay"). Concentrations were determined by reverse HPLC methods using a pramlintide standard as a reference. Before measurement after completion 150 µl was collected from each of the replica and transferred to an Eppendorf tube. These were centrifuged at 30000 G for 40 mins. The supernatants were filtered through a 0.22 µm filter before application on the HPLC system.

ASSAY (IV) Determination of Solubility

The polypeptide was dissolved in water at ~500 nmol/ml and mixed 1:1 with a series of buffers (100 mM glycylglycine pH 3.0, 100 mM glycylglycine pH 4.0, 100 mM glycylglycine pH 5.0, 100 mM bistrispropane pH 6.0, 100 mM bistrispropane pH 6.5, 100 mM bistrispropane pH 7.0, 100 mM bistrispropane pH 7.5, 100 mM bistrispropane pH 8.0). After 18 hours at room temperature the samples were centrifuged and the polypeptide concentration determined by UPLC.

ASSAY (V)—Determination of Binding to the Human Amylin Receptor

The binding assay was performed using scintillation proximity assay (SPA) beads (RPNQ0001) from PerkinElmer and cell membranes from the Amylin 3(a)/CRE-luc cells (as described in Assay (II)) were used. Membranes were prepared in the following way; the cells were rinsed with PBS and incubated with Versene for approximately 5 min before harvesting. The cells were flushed with PBS and the cell-suspension was centrifuged for 5 min at 1000 rpm. Cells were homogenized (ultrathurrax) in a buffer containing 20 mM Na-HEPES and 10 mM EDTA (pH 7.4) and centrifuged at 20.000 rpm for 15 min. The resulting pellet was resuspended, homogenized and centrifuged (20.000 rpm, 15 min) in a buffer containing 20 mM Na-HEPES and 0.1 mM EDTA (pH 7.4, buffer 2). The resulting pellet was resuspended in buffer 2 and protein concentration was measured (BCA protein Assay, Pierce). The homogenate was kept cold during the whole procedure. The membranes were kept at −80° C. until use. The assay was performed in a 384 well Optiplate (PerkinElmer) in a total volume of 40 ul. Membranes were mixed with SPA beads. Final concentration of membranes 35 ng/µL final and SPA beads was 0.05 mg/well. Test-compounds were dissolved in DMSO and further diluted in assay buffer (50 mM Hepes, pH 7.4, 1 mM CaCl$_2$, 5 mM MgCl$_2$, 0.1% OA and 0.02% Tween20). Radioligand $^{125}$I-rat amylin (NEX448 PerkinElmer) was dissolved in assay buffer and added to the Optiplate at a final concentration of 50 µM/well (approx. 20.000 cpm/10 ul). The final mixture was incubated with shaking at 400 rpm for 120 min at 25° C. prior to centrifugation (1500 rpm, 10 min). Samples were analyzed on TopCounter™ (Packard). The IC$_{50}$ was calculated using (one site binding competition analysis) GraphPad Prism5 as a measure of receptor affinity.

ASSAY (VI)—Determination of the Binding to the Rat Amylin Receptor

The assay was performed as described above (Assay (V) Determination of binding to the human amylin receptor) with the exception that we used membranes prepared from BHK tk'ts 13 cells that were transiently transfected with the rat calcitonin receptor rat RAMP 3 at an equimolar ratio (1:2). The BHK tk'ts 13 cells were transiently transfected with rat calcitonin receptor using FuGENE® 6 (Roche), according to the manufacturer's recommendations. Cells were grown in DMEM with 10% FBS and 1% Pen/Strep. Approximately 48 hours after transfection, the cells were harvested and membranes were prepared.

ASSAY (VII)—Determination of Binding to the Human Calcitonin Receptor

The binding assay was performed using scintillation proximity assay (SPA) beads (RPNQ0001) from PerkinElmer and cell membranes prepared from a BHK tk'ts 13 cell line was stably transfected with the human calcitonin receptor and a CRE-responsive luciferase reporter gene. Membranes were prepared in the following way; the cells were rinsed with PBS and incubated with Versene for approximately 5 min before harvesting. The cells were flushed with PBS and the cell-suspension was centrifuged for 5 min at 1000 rpm. Cells were homogenized (Ultrathurrax) in a buffer containing 20 mM Na-HEPES and 10 mM EDTA (pH 7.4) and centrifuged at 20.000 rpm for 15 min. The resulting pellet was resuspended, homogenized and centrifuged (20.000 rpm, 15 min) in a buffer containing 20 mM Na-HEPES and 0.1 mM EDTA (pH 7.4, buffer 2). The resulting pellet was resuspended in buffer 2 and protein concentration was measured (BCA protein Assay, Pierce). The homogenate was kept cold during the whole procedure. The membranes were kept at −80° C. until use. Assay was performed in a 384 well Optiplate (PerkinElmer) in a total volume of 40u1. Membranes were mixed with SPA beads. Final concentration of membranes 35 ng/µL final and Final concentration of SPA beads was 0.05 mg/well. Test-compounds were dissolved in DMSO and further diluted in assay buffer (50 mM Hepes, pH 7.4, 1 mM CaCl2, 5 mM MgCl$_2$, 0.1% OA and 0.02% Tween20). Radioligand $^{125}$I-Calcitonin (NEX422 PerkinElmer) was dissolved in assay buffer and added to the Optiplate at a final concentration of 75 µM/well (approx. 30.000 cpm/10 ul). The final mixture was incubated for 120 min with shaking at 400 rpm at 25° C. prior to centrifugation (1500 rpm, 10 min). Samples were analyzed on TopCounter™ (Packard). The $10_{50}$ was calculated using (one site binding competition analysis) GraphPad Prism5 as a measure of receptor affinity.

ASSAY (VIII)—Determination of Binding to the Rat Calcitonin Receptor

The assay was performed as described above (Assay (VII)—Determination of binding to the human calcitonin receptor) with the exception that we used membranes prepared from BHK tk'ts 13 cells that were transiently transfected with the rat calcitonin receptor. The BHK tk'ts 13 cells were transiently transfected with rat calcitonin receptor using FuGENE® 6 (Roche), according to the manufacturer's recommendations. Cells were grown in DMEM with 10% FBS and 1% Pen/Strep. Approximately 48 hours after transfection, the cells were harvested and membranes were prepared.

ASSAY (IX)—pK—Determination of TY2 in mini-pig

T½ is the terminal half-life=$\ln 2/\lambda_z$ of a compound in plasma. $\lambda_z$ is the first order rate constant associated with the terminal (log-linear) portion of the plasma concentration-time curve and is estimated by linear regression of time vs. log concentration.

T½ values of the amylin analogues of the invention is determined by pharmacokinetic studies in male Göttingen mini-pigs from Ellegaard Göttingen Minipigs ApS and the principles of laboratory animal care are followed.

An acclimatisation period of approximately 6-10 days was allowed before the animals entered the study. At start of the acclimatisation period the mini-pigs were about 5 to 12 months old and in the weight range of 7-35 kg. The mini-pigs had two central venous catheters inserted which were used for blood sampling.

The studies were conducted in an animal room which was illuminated to give a cycle of approx 12 hours light and 12 hours darkness. The animals were housed individually.

The animals had free access to domestic quality drinking water during the study, but were typically fasted from overnight before dosing until approx 6-12 hours after dosing. The animals were weighed on arrival and on the days of dosing.

In the present studies the test substances were administered subcutaneously in approx 2 nmol/kg dose. The animals received a single subcutaneous injection. The subcutaneous injection was given on the right side of the neck, approximately 5-7 cm from the ear and 7-9 cm from the middle of the neck. The injections were given with a stopper on the needle, allowing approx 0.5 cm of the needle to be introduced. Each test substance was given to typically three but in some cases two or four animals.

A full plasma concentration-time profile, employing 12-16 sampling points, was obtained from each animal. In example blood samples were collected according to the following schedule: After subcutaneous administration:
  Predose (0), 0.5, 1, 2, 4, 6, 8, 12, 24, 48, 72, 96, 120, 168 and 240 hours after injection.
  In some cases also additional blood samples up to 288 hours post injection were taken.

At each sampling time, 0.5 to 2 ml of blood was drawn from each animal. The blood samples were taken via the central venous catheter.

The blood samples were collected into EDTA test tubes (i.e. Sarstedt Micro tube 1.3 mL K3E). Blood samples were kept on ice for max 20 min. before centrifugation. Plasma was separated using centrifugation (i.e. at 4° C., 10 min., 1500G) and was immediately transferred to Micronic tubes. Approximately 200 µl plasma was transferred to each Micronic tube. The plasma was stored at −20° C. until assayed. The plasma samples were assayed for the content of amylin using an ELISA assay.

The plasma concentration-time profiles were analysed by a non-compartmental pharmacokinetic analysis (NCA) using WinNonlin Professional 5.0 (Pharsight Inc., Mountain View, Calif., USA). NCA was performed using the individual plasma concentration-time profiles from each animal. T½ is the terminal half-life=ln2/$\lambda_z$ and was determined from $\lambda_z$ the first order rate constant associated with the terminal (log-linear) portion of the curve, estimated by linear regression of time vs. log concentration.

ELISA Plasma Assay for Amylin Quantification

The human amylin ELISA is a monoclonal antibody-based sandwich immunoassay for determining amylin levels in human plasma. The capture antibody recognizes human amylin, amylin acid (deamidated amylin), a 1-20 fragment of amylin, but not reduced amylin. The detection antibody binds to reduced or unreduced human amylin but not amylin acid and is complexed with streptavidin-alkaline phosphatase. The substrate, 4-methylumbelliferyl phosphate, is applied to the completed sandwich and the fluorescent signal, monitored at 355 nm/460 nm, is proportional to the amount of amylin present in the sample.

MS-Method for Amylin Quantification

40 µl plasma is diluted with 120 µl 66.67% EtOH+1% HCOOH and mixed. Centrifuged for 20 min. at 13000 rpm, 4° C. The supernatant is analyzed by an LC-MS method on a Sciex API 3000 and quantitated with a standard made up in plasma ASSAY (X)—pK—Determination of TY2 in Rat T½ is the terminal half-life=ln2/$\lambda_z$ of a compound in plasma. $\lambda_z$ is the first order rate constant associated with the terminal (log-linear) portion of the plasma concentration-time curve and is estimated by linear regression of time vs. log concentration.

T½ values of the amylin analogues of the invention is determined by pharmacokinetic studies in Sprague Dawley male rats, from Taconic Europe and the principles of laboratory animal care are followed.

An acclimatisation period of approximately 7 days was allowed before the animals entered the study. At start of the acclimatisation period the rats were in the weight range of 300-400 g. The rats had permanent catheters inserted in a. carotis which were used for blood sampling.

The studies were conducted in an animal room which was illuminated to give a cycle of approx 12 hours light and 12 hours darkness. The animals were housed individually due to the catheters and had food and water ad lib. The animals were weighed on the days of dosing.

In the present studies the test substances were administered subcutaneously in approx 20 nmol/kg dose. The animals received a single subcutaneous injection to the neck using a 25 G needle with syringe. Each test substance was given to typically three but in some cases two or four animals.

A full plasma concentration-time profile, employing 8-10 sampling points, was obtained from each animal. In example blood samples were collected according to the following schedule: After subcutaneous administration:
  Predose (0), 0.5, 1, 1.5, 2, 4, 6, 12, 24, 48 and 72 hours after injection.

At each sampling time, 0.08 to 0.10 ml of blood was drawn from each animal. The blood samples were taken via the catheter.

The blood samples were collected into EDTA test tubes. Blood samples were kept on ice for max 20 min. before centrifugation. Plasma was separated using centrifugation (i.e. at 4° C., 10 min., 1500 G) and was immediately transferred to Micronic tubes or PCR plates. Approximately 40 µl plasma was transferred and was stored at −20° C. until assayed. The plasma samples were assayed for the content of amylin using an ELISA assay.

The plasma concentration-time profiles were analysed by a non-compartmental pharmacokinetic analysis (NCA) using WinNonlin Professional 5.0 (Pharsight Inc., Mountain View, Calif., USA). NCA was performed using the individual plasma concentration-time profiles from each animal. T½ is the terminal half-life=ln2/A, and was determined from $A_z$ the first order rate constant associated with the terminal (log-linear) portion of the curve, estimated by linear regression of time vs. log concentration.

Preparations

The polypeptide sequences were prepared according to the below-mentioned polypeptide synthesis and the compounds as presented in the Tables (e.g. Table 10) were prepared according to the below-mentioned synthesis.

One method of polypeptide synthesis was by Fmoc chemistry on a microwave-based Liberty polypeptide synthesizer (CEM Corp., North Carolina). The resin was Tentage! S RAM with a loading of about 0.25 mmol/g or PAL-Chem-Matrix with a loading of about 0.43 mmol/g. The coupling chemistry was DIC/HOAt in NMP using amino acid solutions of 0.3 M in NMP and a molar excess of 6-8 fold. Coupling conditions was 5 minutes at up to 70° C. Deprotection was with 5% piperidine in NMP at up to 70° C. The protected amino acids used were standard Fmoc-amino acids (supplied from e.g. Anaspec or Novabiochem) dissolved at 0.3 M in NMP containing 0.3 M HOAt.

Another method of polypeptide synthesis was by Fmoc chemistry on a Prelude polypeptide synthesizer (Protein Technologies, Arizona). The resin was Tentagel S RAM with a loading of about 0.25 mmol/g or PAL-Chem Matrix with a loading of about 0.43 mmol/g. The coupling chemistry was DIC/HOAt in NMP using amino acid solutions of 0.3 M in NMP and a molar excess of 6-8 fold. Coupling conditions was single or double couplings for 1 or 2 hours at room temperature. Deprotection was with 20% piperidine in NMP. The protected amino acids used were standard Fmoc-amino acids (supplied from e.g. Anaspec or Novabiochem) dissolved at 0.3 M in NMP containing 0.3 M HOAt.

Another method of polypeptide synthesis was on an Applied Biosystems 433 polypeptide synthesizer in 0.25 mmol or 1.0 mmol scale using the manufacturer supplied FastMoc UV protocols which employ HBTU or HATU mediated couplings in NMP, and UV monitoring of the deprotection of the Fmoc protection group. The starting resin used for the synthesis of the polypeptide amides was Rink-Amide resin. The protected amino acid derivatives used were standard Fmoc-amino acids (supplied from e.g. Anaspec, or Novabiochem) supplied in preweighed cartridges suitable for the ABI433A synthesizer.

When a chemical modification of a lysine side chain was desired, the lysine was incorporated as Lys(Mtt) and the N-terminal amino acid was either incorporated into the sequence as a Boc-amino acid or, if the N-terminal amino acid was incorporated as an Fmoc-amino acid, the Fmoc group was removed and the N-terminal was protected by treatment with 6 equivalents of Boc-carbonate and 6 equivalents of DIPEA in NMP for 30 minutes. The resin was washed with NMP and DCM and the Mtt group was removed by suspending the resin in neat hexafluoroisopropanol for 20 minutes followed by washing with DCM and NMP. The chemical modification of the lysine was performed by adding one or more of the building blocks listed below by the same methods as used for the polypeptide synthesis, i.e. by one or more automated steps on the Liberty or the ABI 433 or by one or more manual coupling steps at room temperature. After synthesis the resin was washed with DCM and dried, and the polypeptide was cleaved from the resin by a 2 hour treatment with TFA/TIPS/water (92.5/5/2.5 or 95/2.5/2.5) followed by precipitation with 4 volumes of diethylether, further washing with diethylether and drying. If the polypeptide contained cysteines protected with Acm groups, the polypeptide was redissolved in water at 2-5 mg/ml, pH adjusted to below 4, and the disulfide bridge formed by treatment with 4 eq. of iodine (2% w/v in methanol) for 15 minutes. Alternatively, the disulfide bridge was formed on the resin by using Trt as the protecting group for cysteine and treating with 10 equivalents of iodine in NMP for 1 hour. In this case the crude polypeptide was purified directly after cleavage and diethylether precipitation.

Purification: The crude polypeptide was purified by semi-preparative HPLC on a 20 mm×250 mm column packed with either 5μ or 7μ C-18 silica. Polypeptide solutions were pumped onto the HPLC column and precipitated polypeptides were dissolved in 5 ml 50% acetic acid $H_2O$ and diluted to 20 ml with $H_2O$ and injected on the column which then was eluted with a gradient of 40-60% $CH_3CN$ in 0.1% TFA 10 ml/min during 50 min at 40° C. The polypeptide containing fractions were collected. The purified polypeptide was lyophilized after dilution of the eluate with water.

For analysis of HPLC-fractions and final product RP-HPLC analysis was performed using UV detection at 214 nm and e.g. a Vydac 218TP54 4.6 mm×250 mm 5μ C-18 silica column (The Separations Group, Hesperia, USA) and eluted at e.g. 1 ml/min at 42° C. Most often one of four different elution conditions was used:

A1: Equilibration of the column with a buffer consisting of 0.1 M $(NH_4)_2SO_4$, which was adjusted to pH 2.5 with concentrated $H_2SO_4$ and elution by a gradient of 0% to 60% $CH_3CN$ in the same buffer during 50 min.

B1: Equilibration of the column with 0.1% $TFA/H_2O$ and elution by a gradient of 0% $CH_3CN/0.1\%$ $TFA/H_2O$ to 60% $CH_3CN/0.1\%$ $TFA/H_2O$ during 50 min.

B6: Equilibration of the column with 0.1% $TFA/H_2O$ and elution by a gradient of 0% $CH_3CN/0.1\%$ $TFA/H_2O$ to 90% $CH_3CN/0.1\%$ $TFA/H_2O$ during 50 min.

Alternatively the RP-HPLC analysis was performed using UV detection at 214 nm and a Symmetry300, 3.6 mm×150 mm, 3.5μ C-18 silica column (Waters) which was eluted at 1 ml/min at 42° C.

B4: Equilibration of the column with 0.05% $TFA/H_2O$ and elution by a gradient of 5% $CH_3CN/0.05\%$ $TFA/H_2O$ to 95% $CH_3CN/0.05\%$ $TFA/H_2O$ during 15 min.

The identity of the polypeptide was confirmed by MALDI-MS on a Bruker Microflex.

The polypeptides prepared are shown in Table 10 (presented earlier):

Observations

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law).

All headings and sub-headings are used herein for convenience only and should not be construed as limiting the invention in any way.

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The citation and incorporation of patent documents herein is done for convenience only and does not reflect any view of the validity, patentability, and/or enforceability of such patent documents.

This invention includes all modifications and equivalents of the subject matter recited in the claims appended hereto as permitted by applicable law.

SEQUENCE LISTING

SEQ ID NO: 1

Lys-Cys-Asn-Thr-Ala-Thr-Cys-Ala-Thr-Gln-Arg-Leu-Ala-Asn-Phe-Leu-Val-His-Ser-Ser-Asn-Asn-Phe-Gly-Ala-Ile-Leu-Ser-Ser-Thr-Asn-Val-Gly-Ser-Asn-Thr-Tyr

SEQUENCE LISTING

SEQ ID NO: 2
Lys-Cys-Asn-Thr-Ala-Thr-Cys-Ala-Thr-Gln-Arg-Leu-Ala-Asn-Phe-Leu-Val-His-Ser-Ser-Asn-Asn-Phe-Gly-Pro-Ile-Leu-Pro-Pro-Thr-Asn-Val-Gly-Ser-Asn-Thr-Tyr

SEQ ID NO: 3
$Xaa_1$-Cys-$Xaa_3$-Thr-Ala-Thr-Cys-Ala-Thr-Gln-Arg-Leu-Ala-$Xaa_{14}$-Phe-Leu-$Xaa_{17}$-$Xaa_{18}$-Ser-Ser-$Xaa_{21}$-$Xaa_{22}$-Phe-Gly-Pro-$Xaa_{26}$-Leu-Pro-Pro-Thr-$Xaa_{31}$-Val-Gly-Ser-$Xaa_{35}$-Thr-Pro

---

The invention claimed is:

1. A polypeptide comprising SEQ ID NO:3:

Formula (I)                                  (SEQ ID No: 3)
$Xaa_1$-Cys-$Xaa_3$-Thr-Ala-Thr-Cys-Ala-Thr-Gln-Arg-Leu- Ala-$Xaa_{14}$-Phe-Leu-$Xaa_{17}$-$Xaa_{18}$-Ser-Ser-$Xaa_{21}$-$Xaa_{22}$-

Phe-Gly-Pro-$Xaa_{26}$-Leu-Pro-Pro-Thr-$Xaa_{31}$-Val-Gly-

Ser-$Xaa_{35}$-Thr-Pro;

wherein $Xaa_1$ is deleted or independently selected from Ala, Cys, Glu, Gly, His, Arg, Ser and Lys;

$Xaa_3$ is independently selected from Gly, His, Arg, Ser and Asn;

$Xaa_{14}$ is independently selected from Glu and Asn;

$Xaa_{17}$ is independently selected from His, Arg, Lys and Val;

$Xaa_{18}$ is independently selected from Arg, Lys and His;

$Xaa_{21}$ is independently selected from Ala, Lys, Gln, Ser and Asn;

$Xaa_{22}$ is independently selected from Glu, Gln, Ser, Thr and Asn;

$Xaa_{26}$ is independently selected from Pro, Arg and Ile;

$Xaa_{31}$ is independently selected from Ser, Glu, Asp and Asn; and $Xaa_{35}$ is independently selected from His, Arg, Lys, Asp, Gln and Glu;

and wherein the C-terminal may optionally be derivatized.

2. The polypeptide according to claim 1 wherein $Xaa_{14}$ is glutamic acid.

3. The polypeptide according to claim 1 wherein $Xaa_{17}$ is arginine.

4. The polypeptide according to claim 1, wherein $Xaa_{14}$ is glutamic acid, and $Xaa_{17}$ is arginine.

5. The polypeptide according to claim 1 wherein at least one substituent is attached to at least one amino acid residue of said polypeptide.

6. The polypeptide according to claim 5 wherein the substituent group is selected from the group consisting of C20diacid, C20diacid-γGlu, C20diacid-γGlu-γGlu, C20diacid-γGlu-γGlu-γGlu, C20diacid-OEG, C20diacid-γGlu-OEG, C20diacid-γGlu-OEG-OEG, C18diacid-γGlu, C16diacid-γGlu, and C14diacid-γGlu.

7. The polypeptide according to claim 5 wherein a substituent is attached to the α-amino group of the N-terminal amino acid residue or to a Lys residue.

8. A polypeptide selected from the group consisting of

N-alpha-[(S)-4-Carboxy-4-(19-carboxynonadecanoylamino)butyryl]-Gly-[His1,Glu14,Arg17,Pro37]-pramlintide, N-alpha-[(S)-4-Carboxy-4-(19carboxynonadecanoylamino)butyryl]-[His1,Glu14,Arg17,Pro37]-pramlintide, N-alpha-[(S)-4-Carboxy-4-(19carboxynonadecanoylamino)butyryl]-[Gly1,Glu14,Arg17,Pro37]-pramlintide, N-alpha-[(S)-4-Carboxy-4-(19carboxynonadecanoy-
lamino)butyryl]-[Arg1,Glu14,His17,Pro37]-pramlint-
ide
N-alpha-[(S)-4-Carboxy-4-(19carboxynonadecanoy-
lamino)butyryl]-Gly-[Arg1,Glu14,His17,Pro37]-pram-
lintide,
N-alpha-[(S)-4-Carboxy-4-(19carboxynonadecanoy-
lamino)butyryl]-[Glu14,Arg17,Pro37]-pramlintide,
N-alpha-[(S)-4-Carboxy-4-(19carboxynonadecanoy-
lamino)butyryl]-[Glu14,His17,Gln21,Pro37]-pramlint-
ide,
N-alpha-[(S)-4-Carboxy-4-(19carboxynonadecanoy-
lamino)butyryl]-[Glu14,His17,Pro37]-pramlintide,
N-alpha-[(S)-4-Carboxy-4-(19carboxynonadecanoy-
lamino)butyryl]-[Lys11,Glu14,His17,Pro37]-pramlint-
ide,
N-alpha-[(S)-4-Carboxy-4-(19carboxynonadecanoy-
lamino)butyryl]-Glu-Arg-[Glu1,Glu14,Arg17,Pro37]-
pramlintide,
N-alpha-[(S)-4-Carboxy-4-(19carboxynonadecanoy-
lamino)butyryl]-[Glu14,Arg18,Ser21,Ser22,Ser28,
Ser29,Asp31,Asp35,Pro37]-pramlintide,
N-alpha-[(S)-4-Carboxy-4-(19carboxynonadecanoy-
lamino)butyryl]-[Glu14,His17,Gln21,Gln35,Pro37]-
pramlintide,
N-alpha-[(S)-4-Carboxy-4-(19carboxynonadecanoy-
lamino)butyryl]- [Glu14,His17,Thr21,Pro37]-pramlint-
ide,
N-alpha-[(S)-4-Carboxy-4-(19carboxynonadecanoy-
lamino)butyryl]-[Glu14,His17,Gln35,Pro37]-pramlint-
ide,
N-alpha-[(S)-4-Carboxy-4-(19carboxynonadecanoy-
lamino)butyryl]-Glu-Arg-[Glu1,Glu14,Arg17,Gln21,
Pro37]-pramlintide,
N-alpha-[(S)-4-Carboxy-4-(19carboxynonadecanoy-
lamino)butyryl]-Glu-Arg-[Glu1,Glu14,Arg17,Gln21,
Gln35,Pro37]-pramlintide,
N-alpha-[(S)-4-Carboxy-4-(19carboxynonadecanoy-
lamino)butyryl]-Glu-Arg-[Glu1,Glu14,Arg17,Gln21,
Gln31,Gln35,Pro37]-pramlintide, and
N-alpha-[(S)-4-Carboxy-4-(19carboxynonadecanoy-
lamino)butyryl]-Glu-Arg-[Glu1,Glu14,Arg17,Gln21,
Gln22,Gln31,Gln35,Pro37]-pramlintide.

9. A method of treating, type 2 diabetes, or obesity comprising administering the polypeptide of claim 1 to a subject in need thereof.

10. A pharmaceutical composition comprising the polypeptide of claim 1 and a pharmaceutically acceptable excipient.

11. A process for preparing a pharmaceutical composition comprising mixing the polypeptide of claim 1 with at least one pharmaceutically acceptable excipient.

* * * * *

UNITED STATES PATENT AND TRADEMARK OFFICE
CERTIFICATE OF CORRECTION

PATENT NO.         : 9,029,325 B2
APPLICATION NO.    : 14/038265
DATED              : May 12, 2015
INVENTOR(S)        : Lauge Schaeffer et al.

It is certified that error appears in the above-identified patent and that said Letters Patent is hereby corrected as shown below:

In the Claims:

At column 130, claim number 1, beginning at line number 40, please delete "and wherein the C terminal may optionally be derivatized".

At column 131, claim number 8, beginning at line number 9, please amend as follows:

N-alpha-[(S)-4-Carboxy-4-(19-carboxynonadecanoylamino)butyryl]-[Glu14,His17,Gln21,Pro37]-pramlintide, At column 131, claim number 8, beginning at line number 22, please amend as follows:

N-alpha-[(S)-4-Carboxy-4-(19-carboxynonadecanoylamino)butyryl]-[Glu14,His17,Gln21,Gln35,Pro37]-pramlintide, At column 132, claim number 8, beginning at line number 1, please amend as follows:

N-alpha-[(S)-4-Carboxy-4-(19-carboxynonadecanoylamino)butyryl]-[Glu14,His17,Gln35,Pro37]-pramlintide, N-alpha-[(S)-4-Carboxy-4-(19-carboxynonadecanoylamino)butyryl]-Glu-Arg-[Glu1,Glu14,Arg17,Gln21,Pro37]-pramlintide, Signed and Sealed this
First Day of March, 2016

Michelle K. Lee
*Director of the United States Patent and Trademark Office*

N-alpha-[(S)-4-Carboxy-4-(19-carboxynonadecanoylamino)butyryl]-Glu-Arg-[Glu1,Glu14,Arg17,Gln21,Gln35,Pro37]-pramlintide, N-alpha-[(S)-4-Carboxy-4-(19-carboxynonadecanoylamino)butyryl]-Glu-Arg-[Glu1,Glu14,Arg17,Gln21,Gln31,Gln35,Pro37]-pramlintide, and N-alpha-[(S)-4-Carboxy-4-(19-carboxynonadecanoylamino)butyryl]-Glu-Arg-[Glu1,Glu14,Arg17,Gln21,Gln22,Gln31,Gln35,Pro37]-pramlintide.

SEQUENCE LISTING

<160> NUMBER OF SEQ ID NOS: 3

<210> SEQ ID NO 1
<211> LENGTH: 37
<212> TYPE: PRT
<213> ORGANISM: homo sapiens

<400> SEQUENCE: 1

Lys Cys Asn Thr Ala Thr Cys Ala Thr Gln Arg Leu Ala Asn Phe Leu
1               5                   10                  15

Val His Ser Ser Asn Asn Phe Gly Ala Ile Leu Ser Ser Thr Asn Val
            20                  25                  30

Gly Ser Asn Thr Tyr
        35

<210> SEQ ID NO 2
<211> LENGTH: 37
<212> TYPE: PRT
<213> ORGANISM: ARTIFICIAL
<220> FEATURE:
<223> OTHER INFORMATION: synthetic

<400> SEQUENCE: 2

Lys Cys Asn Thr Ala Thr Cys Ala Thr Gln Arg Leu Ala Asn Phe Leu
1               5                   10                  15

Val His Ser Ser Asn Asn Phe Gly Pro Ile Leu Pro Pro Thr Asn Val
            20                  25                  30

Gly Ser Asn Thr Tyr
        35

<210> SEQ ID NO 3
<211> LENGTH: 37
<212> TYPE: PRT
<213> ORGANISM: ARTIFICIAL
<220> FEATURE:
<223> OTHER INFORMATION: synthetic
<220> FEATURE:
<221> NAME/KEY: Misc_Feature
<222> LOCATION: (1)..(1)
<223> OTHER INFORMATION: Xaa1 is deleted or independently selected from
      Ala, Cys, Glu, Gly, His, Arg, Ser and Lys;
<220> FEATURE:
<221> NAME/KEY: Misc_Feature
<222> LOCATION: (3)..(3)
<223> OTHER INFORMATION: Xaa3 is independently selected from Gly, His,
      Arg, Ser and Asn;
<220> FEATURE:
<221> NAME/KEY: Misc_Feature
<222> LOCATION: (14)..(14)
<223> OTHER INFORMATION: Xaa14 is independently selected from Glu and
      Asn;
<220> FEATURE:
<221> NAME/KEY: Misc_Feature
<222> LOCATION: (17)..(17)

```
<223> OTHER INFORMATION: Xaa17 is independently selected from His, Arg,
      Lys and Val;
<220> FEATURE:
<221> NAME/KEY: Misc_Feature
<222> LOCATION: (18)..(18)
<223> OTHER INFORMATION: Xaa18 is independently selected from Arg, Lys
      and His;
<220> FEATURE:
<221> NAME/KEY: Misc_Feature
<222> LOCATION: (21)..(21)
<223> OTHER INFORMATION: Xaa21 is independently selected from Ala, Lys,
      Gln, Ser and Asn;
<220> FEATURE:
<221> NAME/KEY: Misc_Feature
<222> LOCATION: (22)..(22)
<223> OTHER INFORMATION: Xaa22 is independently selected from Glu, Gln,
      Ser, Thr and Asn;
<220> FEATURE:
<221> NAME/KEY: Misc_Feature
<222> LOCATION: (26)..(26)
<223> OTHER INFORMATION: Xaa26 is independently selected from Pro, Arg
      and Ile;
<220> FEATURE:
<221> NAME/KEY: Misc_Feature
<222> LOCATION: (31)..(31)
<223> OTHER INFORMATION: Xaa31 is independently selected from Ser, Glu,
      Asp and Asn;
<220> FEATURE:
<221> NAME/KEY: Misc_Feature
<222> LOCATION: (35)..(35)
<223> OTHER INFORMATION: Xaa35 is independently selected from His, Arg,
      Lys, Asp, Gln and Glu;

<400> SEQUENCE: 3

Xaa Cys Xaa Thr Ala Thr Cys Ala Thr Gln Arg Leu Ala Xaa Phe Leu
1               5                   10                  15

Xaa Xaa Ser Ser Xaa Xaa Phe Gly Pro Xaa Leu Pro Pro Thr Xaa Val
            20                  25                  30

Gly Ser Xaa Thr Pro
        35
```